(12) United States Patent
Gallagher et al.

(10) Patent No.: US 9,605,027 B2
(45) Date of Patent: Mar. 28, 2017

(54) POLYPEPTIDES THAT BOUND TO IL-23 RECEPTOR AND INHIBIT BINDING OF IL-23 AND CELL SIGNALING THEREOF

(71) Applicants: Grant Gallagher, Milltown, NJ (US); Raymond Yu, East Brunswick, NJ (US); Jonathan Brazaitis, Parlin, NJ (US)

(72) Inventors: Grant Gallagher, Milltown, NJ (US); Raymond Yu, East Brunswick, NJ (US); Jonathan Brazaitis, Parlin, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 14/922,630

(22) Filed: Oct. 26, 2015

(65) Prior Publication Data
US 2016/0039878 A1 Feb. 11, 2016

Related U.S. Application Data

(63) Continuation-in-part of application No. 13/771,205, filed on Feb. 20, 2013, now Pat. No. 8,724,186, which is a continuation-in-part of application No. 13/523,286, filed on Jun. 14, 2012, now Pat. No. 8,946,150.

(60) Provisional application No. 61/520,710, filed on Jun. 14, 2011.

(51) Int. Cl.

| | |
|---|---|
| C07K 7/64 | (2006.01) |
| C07K 7/06 | (2006.01) |
| H04N 1/10 | (2006.01) |
| C07K 14/435 | (2006.01) |
| A61K 38/12 | (2006.01) |
| A61K 38/00 | (2006.01) |
| H04N 1/193 | (2006.01) |

(52) U.S. Cl.
CPC .............. *C07K 7/64* (2013.01); *C07K 7/06* (2013.01); *H04N 1/1013* (2013.01); *A61K 38/00* (2013.01); *A61K 38/12* (2013.01); *C07K 14/435* (2013.01); *H04N 1/193* (2013.01); *H04N 2201/0081* (2013.01); *H04N 2201/0446* (2013.01)

(58) Field of Classification Search
None
See application file for complete search history.

(56) References Cited

U.S. PATENT DOCUMENTS

2010/0190710 A1* 7/2010 Chemtob ........... C07K 14/4703
514/1.1

OTHER PUBLICATIONS

Parham et al, The Journal of Immunology, 2002, vol. 168, pp. 5699-5708.*
Kuchar et al, Proteins; 2014; vol. 82, pp. 975-989.*

* cited by examiner

*Primary Examiner* — Joanne Hama
*Assistant Examiner* — Fozia Hamud
(74) *Attorney, Agent, or Firm* — Siu K. Lo

(57) ABSTRACT

The present invention relates to novel linear and cyclic polypeptides that bind to IL-23 receptor and inhibit the binding of IL-23 to its corresponding receptor and cell signaling thereof. The novel polypeptides of the present invention has a core structure of $WX_1X_2X_3W$, where W is tryptophan, and $X_1$, $X_2$ and $X_3$ are amino acids, with the proviso that when one of $X_1$, $X_2$ or $X_3$ is W, the remaining two of $X_1$, $X_2$ or $X_3$ cannot be W. Preferred core structures include WVDYW or WQDYW. The present invention relates a composition containing the novel polypeptides (linear or cyclic), and use of same in inhibiting cell functions including production of IL-22 and IL-17F from immune cells as well as in treating IL-23 associated human diseases including, for example, inflammatory bowel diseases, psoriasis and Crohn's disease, ulcerative colitis and multiple sclerosis.

13 Claims, 68 Drawing Sheets

Figure 2

| Peptide number | SEQ ID number | Peptide sequence |
|---|---|---|
| 52 (65,71,74,77) | 1 | A M T W E D W W L Y G R |
| 60 (68) | 2 | N S D H W Y A Y W L I N |
| 61 | 3 | G F A K Q W H V D A N D |
| 66 (70,72) | 4 | E P T W Q W Y W G Q Y S |
| 75 | 5 | N H G S A W Q D Y Y L K |
| 79 | 6 | H W Q V P T G N H L W S |

Figure 4

| Peptide number | SEQ ID number | Peptide sequence | | | | | | | | | |
|---|---|---|---|---|---|---|---|---|---|---|---|
| 1 | 7 | S | G | A | S | W | V | Q | Y | W | V | Q | R |
| 2 | 8 | T | E | N | W | W | T | M | V | P | R | W | M |
| 3 | 9 | D | Q | E | R | W | L | S | Y | F | L | G | T |
| 4 (12,26,28) | 10 | A | E | T | P | S | W | Y | N | Y | W | M | N |
| 5 (16,31) | 11 | N | W | T | S | Q | L | H | T | G | I | S | T |
| 6 | 12 | M | P | D | W | H | A | F | Y | L | Q | A | Q |
| 7 | 13 | Q | S | D | T | W | M | T | Y | W | K | H | H |
| 9 | 14 | N | W | A | T | Y | W | Q | L | R | H | Q | T |
| 10 | 15 | A | S | W | E | M | Y | W | A | T | S | Y | N |
| 13 | 16 | Y | S | W | E | W | Y | A | T | R | F | V | Q |
| 14 | 17 | G | W | K | D | Y | W | T | T | F | Q | L | R |
| 15 | 18 | D | S | D | W | R | W | F | W | E | N | H | W |
| 18 | 19 | S | T | W | Q | E | Y | Y | D | V | W | Q | K |
| 19 | 20 | N | W | I | D | W | W | T | Q | S | E | K | H |
| 20 (21) | 21 | S | A | L | S | W | E | H | Y | W | R | K | H |
| 22 | 22 | A | V | W | Q | N | Y | W | N | E | Q | L | Y |
| 23 | 23 | A | M | T | W | E | D | W | W | L | Y | G | R |
| 24 | 24 | G | W | K | D | Y | W | T | T | F | Q | L | R |
| 25 | 25 | A | W | Q | D | V | W | K | M | H | N | K | V |
| 27 | 26 | D | D | W | M | Q | Y | W | R | Q | Q | V | R |
| 29 | 27 | E | P | F | A | W | H | A | Y | W | V | R | N |
| 30 | 28 | H | D | W | Q | T | Y | W | V | T | R | E | R |
| 32 | 29 | T | S | W | Q | S | F | W | H | H | H | N | T |

Phage ELISA

Figure 6

| Peptide NO. | SEQ ID NO. | Peptide sequence | | | | | | | | | | | OD$_{450}$ |
|---|---|---|---|---|---|---|---|---|---|---|---|---|---|
| 1 | 7 | S | G | A | S | W | V | Q | Y | W | V | Q | R | 0.419 |
| 2 | 8 | T | E | N | W | W | T | M | V | P | R | W | M | 0.350 |
| 3 | 9 | D | Q | E | R | W | L | S | Y | F | L | G | T | 0.314 |
| 4 | 10 | A | E | T | P | S | W | Y | N | Y | W | M | N | 0.396 |
| 5 | 11 | N | W | T | S | Q | L | H | T | G | I | S | T | 0.385 |
| 6 | 12 | M | P | D | W | H | A | F | Y | L | Q | A | Q | 0.260 |
| 7 | 13 | Q | S | D | T | W | M | T | Y | W | K | H | H | 0.414 |
| 8 | | Empty phage | | | | | | | | | | | | 0.017 |
| 9 | 14 | N | W | A | T | Y | W | Q | L | R | H | Q | T | 0.253 |
| 10 | 15 | A | S | W | E | M | Y | W | A | T | S | Y | N | 0.400 |
| 11 | | Empty phage | | | | | | | | | | | | 0.022 |
| 12 | 10 | A | E | T | P | S | W | Y | N | Y | W | M | N | 0.367 |
| 13 | 16 | Y | S | W | E | W | Y | A | T | R | F | V | Q | 0.351 |
| 14 | 17 | G | W | K | D | Y | W | T | T | F | Q | L | R | 0.383 |
| 15 | 18 | D | S | D | W | R | W | F | W | E | N | H | W | 0.376 |
| 16 | 11 | N | W | T | S | Q | L | H | T | G | I | S | T | 0.415 |

Figure 7

Sequence Analysis: Frequency

| Peptide No. | SEQ ID NO. | Peptide sequence | | | | | | | | | | | Frequency |
|---|---|---|---|---|---|---|---|---|---|---|---|---|---|
| 1  | 7  | S | G | A | S | W | V | Q | Y | W | V | Q | R | 1 |
| 2  | 8  | T | E | N | W | W | T | M | V | P | R | W | M | 1 |
| 3  | 9  | D | Q | E | R | W | L | S | Y | F | L | G | T | 1 |
| 4  | 10 | A | E | T | P | S | W | Y | N | Y | W | M | N | 4 |
| 6  | 12 | M | P | D | W | H | A | F | Y | L | Q | A | Q | 1 |
| 7  | 13 | Q | S | D | T | W | M | T | Y | W | K | H | H | 1 |
| 9  | 14 | N | W | A | T | Y | W | Q | L | R | H | Q | T | 1 |
| 10 | 15 | A | S | W | E | M | Y | W | A | T | S | Y | N | 1 |
| 13 | 16 | Y | S | W | E | W | Y | A | T | R | F | V | Q | 1 |
| 14 | 17 | G | W | K | D | Y | W | T | T | F | Q | L | R | 2 |
| 15 | 18 | D | S | D | W | R | W | F | W | E | N | H | W | 1 |
| 16 | 11 | N | W | T | S | Q | L | H | T | G | I | S | T | 3 |
| 18 | 19 | S | T | W | Q | E | Y | Y | D | V | W | Q | K | 1 |
| 19 | 20 | N | W | I | D | W | W | T | Q | S | E | K | H | 1 |
| 20 | 21 | S | A | L | S | W | E | H | Y | W | R | K | H | 2 |
| 22 | 22 | A | V | W | Q | N | Y | W | N | E | Q | L | Y | 1 |
| 23 | 23 | A | M | T | W | E | D | W | W | L | Y | G | R | 6 |
| 25 | 25 | A | W | Q | D | V | W | K | M | H | N | K | V | 1 |
| 27 | 26 | D | D | W | M | Q | Y | W | R | Q | Q | V | R | 1 |
| 29 | 27 | E | P | F | A | W | H | A | Y | W | V | R | N | 1 |
| 30 | 28 | H | D | W | Q | T | Y | W | V | T | R | E | R | 1 |
| 32 | 29 | T | S | W | Q | S | F | W | H | H | H | N | T | 1 |
| 60 | 2  | N | S | D | H | W | Y | A | Y | W | L | I | N | 2 |
| 61 | 3  | G | F | A | K | Q̄ | W | H | V | D̄ | A | N | D | 1 |
| 66 | 4  | E | P | T | W | Q | W̄ | Y | W | G | Q | Y | S | 3 |
| 75 | 5  | N | H | G | S̄ | A | W | Q | D̄ | Y | Y | L | K | 1 |
| 79 | 6  | H | W | Q | V | P | T̄ | G | N | H | L | W | S | 1 |

Figure 8

Sequence Analysis: $\underline{W}X_1X_2X_3\underline{W}$ motif

| Peptide No. | SEQ ID NO. | Peptide sequence |
|---|---|---|
| 1 | 7 | - S G A S W V Q Y W V Q R - - - |
| 4 (12,26,28) | 10 | A E T P S W Y N Y W M N - - - - |
| 7 | 13 | - Q S D T W M T Y W K H H - - - |
| 9 | 14 | - - - - N W A T Y W Q L R H Q T |
| 10 | 15 | - - - A S W E M Y W A T S Y N - |
| 14 | 17 | - - - - G W K D Y W T T F Q L R |
| 15 | 18 | - - D S D W R W F W E N H W - - |
| 19 | 20 | - - - - N W I D W W T Q S E K H |
| 20 (21) | 21 | - S A L S W E H Y W R K H - - - |
| 22 | 22 | - - - A V W Q N Y W N E Q L Y - |
| 23 (52,65,71,74,77) | 23 | - - A M T W E D W W L Y G R - - |
| 24 | 24 | - - - - G W K D Y W T T F Q L R |
| 25 | 25 | - - - - A W Q D V W K M H N K V |
| 27 | 26 | - - - D D W M Q Y W R Q Q V R - |
| 29 | 27 | - E P F A W H A Y W V R N - - - |
| 30 | 28 | - - - H D W Q T Y W V T R E R - |
| 32 | 29 | - - - T S W Q S F W H H H N T - |
| 60 (68) | 2 | - N S D H W Y A Y W L I N - - - |
| 66 (70,72) | 4 | - - E P T W Q W Y W G Q Y S - - |

Figure 9

Sequence Analysis:

$WX_1X_2WW$

| Peptide No. | SEQ ID NO. | Peptide sequence |
|---|---|---|
| 19 | 20 | - - N W I D W W T Q S E K H |
| 23 | 23 | A M T W E D W W L Y G R - - |
| (52,65,71,74,77) | | |

$WWX_nW$

| | | |
|---|---|---|
| 2 | 8 | T E N W W T M V P R W M |

$WX_nW; n \neq 3$

| | | |
|---|---|---|
| 13 | 16 | Y S W E W Y A T R F V Q |
| 18 | 19 | S T W Q E Y Y D V W Q K |
| 79 | 6 | H W Q V P T G N H L W S |

One "W"

| | | |
|---|---|---|
| 3 | 9 | D Q E R W L S Y F L G T |
| 5 | 11 | N W T S Q L H T G I S T |
| (16,31) | | |
| 6 | 12 | M P D W H A F Y L Q A Q |
| 61 | 3 | G F A K Q W H V D A N D |
| 75 | 5 | N H G S A W Q D Y Y L K |

*In vitro* binding assay

*In vitro* binding assay

Competitive ELISA

Cellular signaling

Cellular signaling: Dose response of peptide #1

Competitive ELISA

Competitive ELISA - Dose response

| Peptide number | SEQ ID number | Peptide sequence |
|---|---|---|
| 1   | 44 | S G A S W V Q Y W V Q R |
| 1.1 | 45 | S G A S F V Q Y W V Q R |
| 1.2 | 46 | S G A S W V Q Y F V Q R |
| 1.3 | 47 | S G A S F V Q Y F V Q R |

*In vitro* binding assay

| Peptide No. | SEQ ID NO. | Peptide sequence |
|---|---|---|
| 1   | 44 | S G A S W V Q Y W V Q R |
| 1.1 | 45 | S G A S F V Q Y W V Q R |
| 1.2 | 46 | S G A S W V Q Y F V Q R |
| 1.3 | 47 | S G A S F V Q Y F V Q R |

Figure 21
Flow cytometry: IL-23R expression
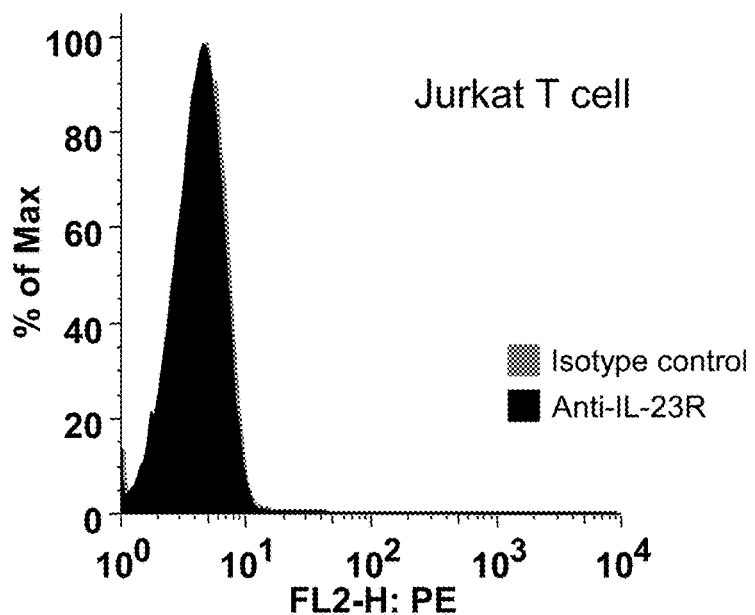
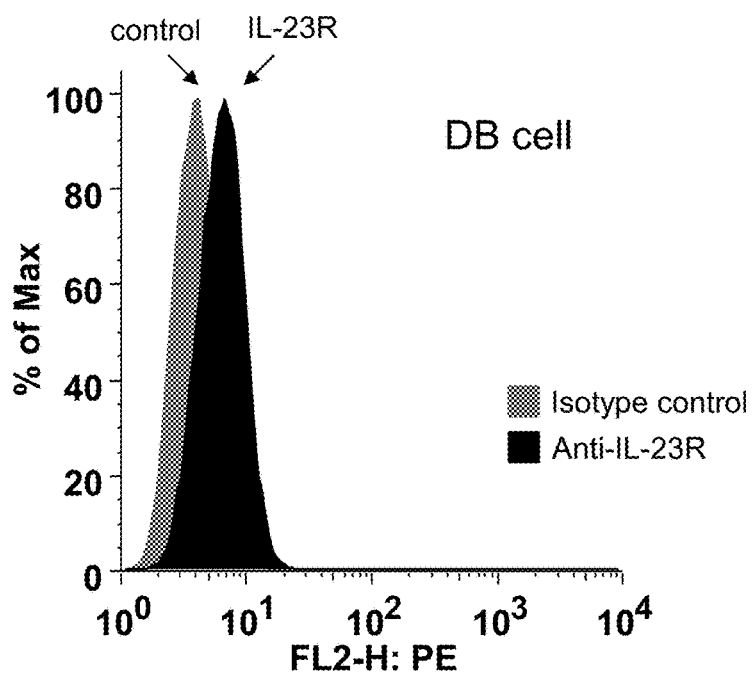

Flow cytometry: Peptide specificity

Flow cytometry: IL-23R knockdown by siRNA

Figure 25

Mean Fluorescence Intensity (MFI)

| Staining | Percentage decrease of MFI by IL-23R siRNA |
|---|---|
| Anti-IL23R | 25% |
| Peptide #1-Fc | 25.6% |

N.D.: Not Determined

| Peptide number | SEQ ID number | Peptide sequence |
|---|---|---|
| 23 | 23 | A M T W E D W W L Y G R |
| 23.1 | 56 | M T W E D W W L Y |
| 23.2 | 57 | G A A M T W E D W W L Y G R G A |
| 23.3 | 58 | V G A A M T W E D W W L Y G R G A L |

| Peptide number | SEQ ID number | Peptide sequence |
|---|---|---|
| 1 | 7 | S G A S W V Q Y W V Q R |
| 1.7 | 59 | S G A S W W Q Y V V Q R |
| 1.8 | 60 | S G A S W V W Y Q V Q R |
| 1.9 | 61 | S G A S W V Q W Y V Q R |
| 1.10 | 62 | S G A W S V Q Y V W Q R |
| 1.11 | 63 | S G W S A V Q Y Q V W R |
| 1.12 | 64 | W G A S S V Q Y R V Q W |

| Peptide number | SEQ ID number | Peptide sequence |
|---|---|---|
| 9   | 14 | N W A T Y W Q L R H Q T |
| 9.1 | 65 | N W W T Y A Q L R H Q T |
| 9.2 | 66 | N W A W Y T Q L R H Q T |
| 9.3 | 67 | N W A T Y L Q W R H Q T |
| 9.4 | 68 | N W A T Y H Q L R W Q T |
| 9.5 | 69 | N W A T Y Q Q L R H W T |

| Peptide number | SEQ ID number | Peptide sequence |
|---|---|---|
| 1 | 7 | S G A S W V Q Y W V Q R |
| 1.15 | 72 | S G A S W L Q Y W V Q R |
| 1.16 | 73 | S G A S W V N Y W V Q R |
| 1.17 | 74 | S G A S W V Q F W V Q R |

N.D.: Not Determined

| Peptide number | SEQ ID number | Peptide sequence |
|---|---|---|
| 1 | 7 | S G A S W V Q Y W V Q R |
| 1.18 | 75 | S G A W W V Q Y W V Q R |
| 1.19 | 76 | S G A S W V Q Y W W Q R |
| 1.20 | 77 | S G W W W V Q Y W V Q R |
| 1.21 | 78 | S G A S W V Q Y W W W R |

N.D.: Not Determined

| Peptide number | SEQ ID number | Peptide sequence |
|---|---|---|
| 1 | 7 | S G A S W V Q Y W V Q R |
| 1.24 | 81 | A S S A W V Q Y W V Q R |
| 1.25 | 82 | S G A S W V Q Y W Y E E |

| Peptide number | SEQ ID number | Peptide sequence |
|---|---|---|
| 23 | 23 | A M T W E D W W L Y G R |
| 23.4 | 83 | A M T W D D W W L Y G R |
| 23.5 | 84 | A M T W E E W W L Y G R |

| Peptide number | SEQ ID number | Peptide sequence |
|---|---|---|
| 23 | 23 | A M T W E D W W L Y G R |
| 23.6 | 85 | A M T W Q D W W L Y G R |
| 23.7 | 86 | A M T W E N W W L Y G R |
| 23.8 | 87 | A M T W Q N W W L Y G R |

| Peptide number | SEQ ID number | Peptide sequence |
|---|---|---|
| 23 | 23 | A M T W E D W W L Y G R |
| 23.9 | 88 | A M T W E K W W L Y G R |
| 23.10 | 89 | A M T W K D W W L Y G R |
| 23.11 | 90 | A M T W K K W W L Y G R |

Figure 39

| Peptide number | SEQ ID number | Peptide sequence |
|---|---|---|
| 23 | 23 | A M T W E D W W L Y G R |
| 23.15 | 126 | A M T W Q D Y W L Y G R |

| Peptide number | Competitive ELISA IC$_{50}$ |
|---|---|
| 23 | 0.85 μM |
| 23.15 | 0.56 μM |

| Peptide number | SEQ ID number | Peptide sequence |
|---|---|---|
| 23.15 | 126 | A M T W Q D Y W L Y G R |
| 23.16 | 127 |    M T W Q D Y W L Y |
| 23.17 | 128 |       T W Q D Y W L |
| 23.18 | 129 |          W Q D Y W |

Competitive ELISA

Figure 41

| Peptide number | SEQ ID number | Peptide sequence |
|---|---|---|
| 23.15 | 126 | A M T W Q D Y W L Y G R |
| 23.19 | 130 | C A M T W Q D Y W L Y G R C |

| Peptide number | Competitive ELISA $IC_{50}$ |
|---|---|
| 23.15 | 0.56 μM |
| 23.19 | 0.39 μM |

| Peptide number | SEQ ID number | Peptide sequence |
|---|---|---|
| 23.19 | 130 | C A M T W Q D Y W L Y G R C |
| 23.20 | 131 | C M T W Q D Y W L Y C |
| 23.21 | 132 | C T W Q D Y W L C |
| 23.22 | 133 | C W Q D Y W C |

Figure 43

| Peptide number | Competitive ELISA IC$_{50}$ |
|---|---|
| 23.15 | 0.56 µM |
| 23.15-Fc | 0.009 µM |

Figure 45

| Peptide number | DB cells - STAT3-Luc IC$_{50}$ |
|---|---|
| 23.19 | 2.5 μM |
| 23.15-Fc | 2 μM |

Competitive ELISA - Mouse

Figure 47

Competitive ELISA - Mouse

| Peptide number | Competitive ELISA $IC_{50}$ |
|---|---|
| 23.15 | 50 μM |
| 23.19 | 12.5 μM |
| 23.15-Fc | 1 μM |

ECD: Extra-Cellular Domain
ICD: Intra-Cellular Domain

Figure 49

IL-23 p19 subunit

Signal peptide

MLGSRAVMLL LLLPWTAQGR AVPGGSSPAW TQCQQLSQKL
              ↖W1              ↖W2
CTLAWSAHPL VGHMDLREEG DEETTNDVPH IQCGDGCDPQ
    ↖W3
GLRDNSQFCL QRIHQGLIFY EKLLGSDIFT GEPSLLPDSP

VGQLHASLLG LSQLLQPEGH HWETQQIPSL SPSQPWQRLL
                            ↖W4           ↖W5
LRFKILRSLQ AFVAVAARVF AHGAATLSP

SEQ ID NO: 176

Figure 50
Secreted level of cytokines
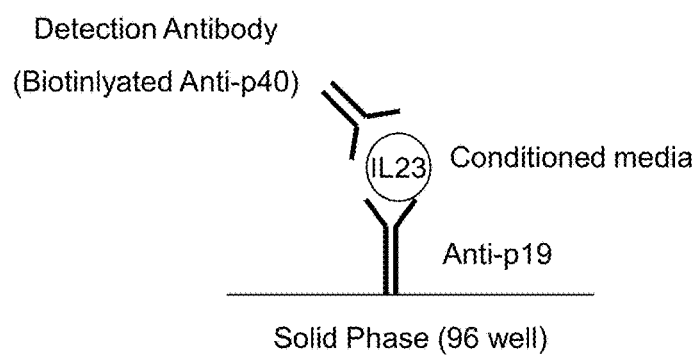
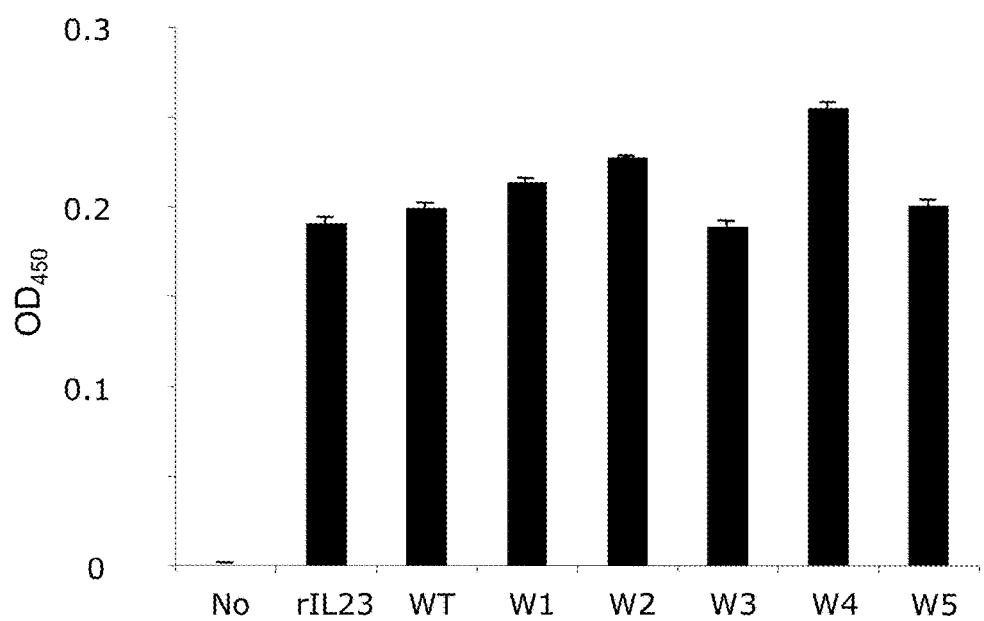

Competition Assay

Figure 55

| Peptide number | SEQ ID number | Peptide sequence |
|---|---|---|
| 23.15 | 126 | A M T W Q D Y W L Y G R |
| Library | 148 | X X X W X X Y W X X X |

Figure 57

>Targeted PEPTIDE Library (SEQ ID NO. 149)
GAAATTAATACGACTCACTATAGGGAGACCACAACGGTTTCCCTCTAGAAATAATTTTGTT
TAACTTTAAGAAGGAGATATACCAATG<u>NNKNNKNNKTGGNNKNNKTACTGGNNKNNKNNKN
NK</u>gagggtggcggtactaaacctcctgagtacggtgatacacctattccggctatactta
tatcaaccctctcgacggcacttatccgcctggtactgagcaaaacccgctaatcctaat
ccttctcttgaggagtctcagcctcttaatactttcatgtttcagaataataggttccgaa
ataggcaggggcattaactgtttatacgggcactgttactcaaggcactgaccccgttaa
aacttattaccagtacactcctgtatcatcaaaagccatgtatgacgcttactggaacggt
aaattcagagactgcgctttccattctggctttaatgaggatccattcgtttgtgaatatc
aaggccaatcgtctgacctgcctcaacctcctgtcaatgctggcggcggctctggtggtgg
ttctggtggcggctctgagggtggtggctctgagggtggcggttctgagggtggcggctct
gagggaggcggttccggtggtggctctggttccggtgatttgattatgaaaagatggcaa
acgctaataaggggctatgaccgaaaatgccgatgaaaacgcgctacagtctgacgctaa
aggcaaacttgattctgtcgctactgattacggtgctTTTTCTACTCCTGTTTGGATTTCT
CAAGCTCAAGGTATTCGTGCTGGTCCTTGATGAATA

Figure 59

8th Round of Selection

| Peptide number | SEQ ID number | Peptide sequence |
|---|---|---|
| >1  | 152 | MMTWQDYWLANV |
| >2  | 153 | KMTWVDYWLKNC |
| >3  | 153 | KMTWVDYWLKNC |
| >4  | 154 | KLTWEMYWLMSL |
| >5  |     | Bad sequencing |
| >6  | 155 | IKTWEWYWMKSQ |
| >7  | 156 | MKTWVDYWLETQ |
| >8  | 157 | KMTWVDYWLRNC |
| >9  | 158 | KKTWTEYWLENQ |
| >10 | 153 | KMTWVDYWLKNC |
| >11 | 159 | SKTWEWYWMNRD |
| >12 | 153 | KMTWVDYWLKNC |
| >13 | 160 | TYDWTYYWLMNS |
| >14 | 161 | NLTWEIYWLRSQ |
| >15 | 162 | LKTWIDYWIASQ |
| >16 | 155 | IKTWEWYWMKSQ |
| >17 | 163 | RLTWVDYWLASR |
| >18 | 164 | MKTWQDYWLANR |
| >19 | 153 | KMTWVDYWLKNC |
| >20 | 165 | NELWMWYWINSA |
| >21 | 162 | LKTWIDYWIASQ |
| >22 | 166 | TNTWMIYWWINQ |
| >23 | 153 | KMTWVDYWLKNC |
| >24 | 156 | MKTWVDYWLETQ |

Figure 60

8th Round of Selection

| Peptide number | SEQ ID number | Peptide sequence | Frequency |
|---|---|---|---|
| >1 | 152 | MMTWQDYWLANV | 1 |
| >2 | 153 | KMTWVDYWLKNC | 6 |
| >4 | 154 | KLTWEMYWLMSL | 1 |
| >6 | 155 | IKTWEWYWMKSQ | 2 |
| >7 | 156 | MKTWVDYWLETQ | 2 |
| >8 | 157 | KMTWVDYWLRNC | 1 |
| >9 | 158 | KKTWTEYWLENQ | 1 |
| >11 | 159 | SKTWEWYWMNRD | 1 |
| >13 | 160 | TYDWTYYWLMNS | 1 |
| >14 | 161 | NLTWEIYWLRSQ | 1 |
| >15 | 162 | LKTWIDYWIASQ | 2 |
| >17 | 163 | RLTWVDYWLASR | 1 |
| >18 | 164 | MKTWQDYWLANR | 1 |
| >20 | 165 | NELWMWYWINSA | 1 |
| >22 | 166 | TNTWMIYWWINQ | 1 |

Figure 61

8th Round of Selection

| Group | Peptide number | SEQ ID number | Peptide sequence | Frequency |
|---|---|---|---|---|
| Group A | >2 | 153 | KMTWVDYWLKNC | 6 |
| | >8 | 157 | KMTWVDYWLRNC | 1 |
| | >7 | 156 | MKTWVDYWLETQ | 2 |
| | >17 | 163 | RLTWVDYWLASR | 1 |
| Group B | >1 | 152 | MMTWQDYWLANV | 1 |
| | >18 | 164 | MKTWQDYWLANR | 1 |
| Group C | >4 | 154 | KLTWEMYWLMSL | 1 |
| | >6 | 155 | IKTWEWYWMKSQ | 2 |
| | >9 | 158 | KKTWTEYWLENQ | 1 |
| | >11 | 159 | SKTWEWYWMNRD | 1 |
| | >13 | 160 | TYDWTYYWLMNS | 1 |
| | >14 | 161 | NLTWEIYWLRSQ | 1 |
| | >15 | 162 | LKTWIDYWIASQ | 2 |
| | >20 | 165 | NELWMWYWINSA | 1 |
| | >22 | 166 | TNTWMIYWWINQ | 1 |

Figure 63

| Peptide number | SEQ ID number | Peptide sequence | Cell-free Competitive ELISA $IC_{50}$ (nM) |
|---|---|---|---|
| Linear peptide | | | |
| 2 | 153 | KMTWVDYWLKNC | 34.6 ± 13.3 |
| 7 | 156 | MKTWVDYWLETQ | 58.0 ± 1.3 |
| Cyclic peptide | | | |
| 2HT AA | 177 | AKMTWVDYWLKNCA | 8.1 ± 04.1 |
| 7 CC | 178 | CMKTWVDYWLETQC | 45.8 ± 00.0 |
| 7HT AA | 179 | AMKTWVDYWLETQA | 30.0 ± 00.0 |

Figure 64

| Peptide number | SEQ ID number | Peptide sequence | Cell-based DB-Luc IC$_{50}$ (nM) |
|---|---|---|---|
| Linear peptide | | | |
| 2 | 153 | KMTWVDYWLKNC | 2243.0 ± 908.0 |
| 7 | 156 | MKTWVDYWLETQ | 2342.5 ± 490.0 |
| Cyclic peptide | | | |
| 2HT AA | 177 | AKMTWVDYWLKNCA | 341.8 ± 44.3 |
| 7HT AA | 179 | AMKTWVDYWLETQA | 2184.5 ± 02.1 |

| Peptide number | SEQ ID number | Peptide sequence | $IC_{50}$ (nM) |
|---|---|---|---|
| 2HT AA | 177 | AKMTWVDYWLKNCA | 338.6 ± 163.2 |

| Peptide number | SEQ ID number | Peptide sequence | $IC_{50}$ (nM) |
|---|---|---|---|
| 2HT AA | 177 | AKMTWVDYWLKNCA | 337.5 ± 113.5 |

… continued

```
                        SEQUENCE LISTING

<160> NUMBER OF SEQ ID NOS: 181

<210> SEQ ID NO 1
<211> LENGTH: 12
<212> TYPE: PRT
<213> ORGANISM: Homo sapiens

<400> SEQUENCE: 1

Ala Met Thr Trp Glu Asp Trp Trp Leu Tyr Gly Arg
1               5                   10

<210> SEQ ID NO 2
<211> LENGTH: 12
<212> TYPE: PRT
<213> ORGANISM: Homo sapiens

<400> SEQUENCE: 2

Asn Ser Asp His Trp Tyr Ala Tyr Trp Leu Ile Asn
1               5                   10

<210> SEQ ID NO 3
<211> LENGTH: 12
<212> TYPE: PRT
<213> ORGANISM: Homo sapiens

<400> SEQUENCE: 3

Gly Phe Ala Lys Gln Trp His Val Asp Ala Asn Asp
1               5                   10

<210> SEQ ID NO 4
<211> LENGTH: 12
<212> TYPE: PRT
<213> ORGANISM: Homo sapiens

<400> SEQUENCE: 4

Glu Pro Thr Trp Gln Trp Tyr Trp Gly Gln Tyr Ser
1               5                   10

<210> SEQ ID NO 5
<211> LENGTH: 12
<212> TYPE: PRT
<213> ORGANISM: Homo sapiens

<400> SEQUENCE: 5

Asn His Gly Ser Ala Trp Gln Asp Tyr Tyr Leu Lys
1               5                   10

<210> SEQ ID NO 6
<211> LENGTH: 12
<212> TYPE: PRT
```

-continued

<213> ORGANISM: Homo sapiens

<400> SEQUENCE: 6

His Trp Gln Val Pro Thr Gly Asn His Leu Trp Ser
1               5                   10

<210> SEQ ID NO 7
<211> LENGTH: 12
<212> TYPE: PRT
<213> ORGANISM: Homo sapiens

<400> SEQUENCE: 7

Ser Gly Ala Ser Trp Val Gln Tyr Trp Val Gln Arg
1               5                   10

<210> SEQ ID NO 8
<211> LENGTH: 12
<212> TYPE: PRT
<213> ORGANISM: Homo sapiens

<400> SEQUENCE: 8

Thr Glu Asn Trp Trp Thr Met Val Pro Arg Trp Met
1               5                   10

<210> SEQ ID NO 9
<211> LENGTH: 12
<212> TYPE: PRT
<213> ORGANISM: Homo sapiens

<400> SEQUENCE: 9

Asp Gln Glu Arg Trp Leu Ser Tyr Phe Leu Gly Thr
1               5                   10

<210> SEQ ID NO 10
<211> LENGTH: 12
<212> TYPE: PRT
<213> ORGANISM: Homo sapiens

<400> SEQUENCE: 10

Ala Glu Thr Pro Ser Trp Tyr Asn Tyr Trp Met Asn
1               5                   10

<210> SEQ ID NO 11
<211> LENGTH: 12
<212> TYPE: PRT
<213> ORGANISM: Homo sapiens

<400> SEQUENCE: 11

Asn Trp Thr Ser Gln Leu His Thr Gly Ile Ser Thr
1               5                   10

<210> SEQ ID NO 12
<211> LENGTH: 12
<212> TYPE: PRT
<213> ORGANISM: Homo sapiens

<400> SEQUENCE: 12

Met Pro Asp Trp His Ala Phe Tyr Leu Gln Ala Gln
1               5                   10

<210> SEQ ID NO 13
<211> LENGTH: 12
<212> TYPE: PRT
<213> ORGANISM: Homo sapiens

<400> SEQUENCE: 13

Gln Ser Asp Thr Trp Met Thr Tyr Trp Lys His His
1               5                   10

<210> SEQ ID NO 14
<211> LENGTH: 12
<212> TYPE: PRT
<213> ORGANISM: Homo sapiens

<400> SEQUENCE: 14

Asn Trp Ala Thr Tyr Trp Gln Leu Arg His Gln Thr
1               5                   10

<210> SEQ ID NO 15
<211> LENGTH: 12
<212> TYPE: PRT
<213> ORGANISM: Homo sapiens

<400> SEQUENCE: 15

Ala Ser Trp Glu Met Tyr Trp Ala Thr Ser Tyr Asn
1               5                   10

<210> SEQ ID NO 16
<211> LENGTH: 12
<212> TYPE: PRT
<213> ORGANISM: Homo sapiens

<400> SEQUENCE: 16

Tyr Ser Trp Glu Trp Tyr Ala Thr Arg Phe Val Gln
1               5                   10

<210> SEQ ID NO 17
<211> LENGTH: 12
<212> TYPE: PRT
<213> ORGANISM: Homo sapiens

<400> SEQUENCE: 17

Gly Trp Lys Asp Tyr Trp Thr Thr Phe Gln Leu Arg
1               5                   10

<210> SEQ ID NO 18
<211> LENGTH: 12
<212> TYPE: PRT
<213> ORGANISM: Homo sapiens

<400> SEQUENCE: 18

Asp Ser Asp Trp Arg Trp Phe Trp Glu Asn His Trp
1               5                   10

<210> SEQ ID NO 19
<211> LENGTH: 12
<212> TYPE: PRT
<213> ORGANISM: Homo sapiens

<400> SEQUENCE: 19

Ser Thr Trp Gln Glu Tyr Tyr Asp Val Trp Gln Lys
1               5                   10

<210> SEQ ID NO 20
<211> LENGTH: 12
<212> TYPE: PRT
<213> ORGANISM: Homo sapiens

<400> SEQUENCE: 20

Asn Trp Ile Asp Trp Trp Thr Gln Ser Glu Lys His
1               5                   10

<210> SEQ ID NO 21
<211> LENGTH: 12
<212> TYPE: PRT
<213> ORGANISM: Homo sapiens

<400> SEQUENCE: 21

Ser Ala Leu Ser Trp Glu His Tyr Trp Arg Lys His
1               5                   10

<210> SEQ ID NO 22
<211> LENGTH: 12
<212> TYPE: PRT
<213> ORGANISM: Homo sapiens

<400> SEQUENCE: 22

Ala Val Trp Gln Asn Tyr Trp Asn Glu Gln Leu Tyr
1               5                   10

<210> SEQ ID NO 23
<211> LENGTH: 12
<212> TYPE: PRT
<213> ORGANISM: Homo sapiens

<400> SEQUENCE: 23

Ala Met Thr Trp Glu Asp Trp Trp Leu Tyr Gly Arg
1               5                   10

<210> SEQ ID NO 24
<211> LENGTH: 12
<212> TYPE: PRT
<213> ORGANISM: Homo sapiens

<400> SEQUENCE: 24

Gly Trp Lys Asp Tyr Trp Thr Thr Phe Gln Leu Arg
1               5                   10

<210> SEQ ID NO 25
<211> LENGTH: 12
<212> TYPE: PRT
<213> ORGANISM: Homo sapiens

<400> SEQUENCE: 25

Ala Trp Gln Asp Val Trp Lys Met His Asn Lys Val
1               5                   10

<210> SEQ ID NO 26
<211> LENGTH: 12
<212> TYPE: PRT
<213> ORGANISM: Homo sapiens

<400> SEQUENCE: 26

Asp Asp Trp Met Gln Tyr Trp Arg Gln Gln Val Arg
1               5                   10

<210> SEQ ID NO 27
<211> LENGTH: 12
<212> TYPE: PRT
<213> ORGANISM: Homo sapiens

<400> SEQUENCE: 27

Glu Pro Phe Ala Trp His Ala Tyr Trp Val Arg Asn
1               5                   10

```
<210> SEQ ID NO 28
<211> LENGTH: 12
<212> TYPE: PRT
<213> ORGANISM: Homo sapiens

<400> SEQUENCE: 28

His Asp Trp Gln Thr Tyr Trp Val Thr Arg Glu Arg
1               5                   10

<210> SEQ ID NO 29
<211> LENGTH: 12
<212> TYPE: PRT
<213> ORGANISM: Homo sapiens

<400> SEQUENCE: 29

Thr Ser Trp Gln Ser Phe Trp His His His Asn Thr
1               5                   10

<210> SEQ ID NO 30
<211> LENGTH: 44
<212> TYPE: DNA
<213> ORGANISM: Homo sapiens

<400> SEQUENCE: 30
catggttagt ggtgcttcgt gggttcagta ttgggttcag cgga            44

<210> SEQ ID NO 31
<211> LENGTH: 44
<212> TYPE: DNA
<213> ORGANISM: Homo sapiens

<400> SEQUENCE: 31
gatctccgct gaacccaata ctgaacccac gaagcaccac taac            44

<210> SEQ ID NO 32
<211> LENGTH: 44
<212> TYPE: DNA
<213> ORGANISM: Homo sapiens

<400> SEQUENCE: 32
catggttgct gagacgccta gttggtataa ttattggatg aata            44

<210> SEQ ID NO 33
<211> LENGTH: 44
<212> TYPE: DNA
<213> ORGANISM: Homo sapiens

<400> SEQUENCE: 33
gatctattca tccaataatt ataccaacta ggcgtctcag caac            44

<210> SEQ ID NO 34
<211> LENGTH: 44
<212> TYPE: DNA
<213> ORGANISM: Homo sapiens

<400> SEQUENCE: 34
catggttcag tcggatacgt ggatgacgta ttggaagcat cata            44

<210> SEQ ID NO 35
<211> LENGTH: 44
<212> TYPE: DNA
<213> ORGANISM: Homo sapiens
```

<400> SEQUENCE: 35
gatctatgat gcttccaata cgtcatccac gtatccgact gaac          44

<210> SEQ ID NO 36
<211> LENGTH: 44
<212> TYPE: DNA
<213> ORGANISM: Homo sapiens

<400> SEQUENCE: 36
catggttgcg tcttgggaga tgtattgggc tacgtcgtat aata          44

<210> SEQ ID NO 37
<211> LENGTH: 44
<212> TYPE: DNA
<213> ORGANISM: Homo sapiens

<400> SEQUENCE: 37
gatctattat acgacgtagc ccaatacatc tcccaagacg caac          44

<210> SEQ ID NO 38
<211> LENGTH: 44
<212> TYPE: DNA
<213> ORGANISM: Homo sapiens

<400> SEQUENCE: 38
catggttaat tggactagtc agcttcatac ggggatttcg acta          44

<210> SEQ ID NO 39
<211> LENGTH: 44
<212> TYPE: DNA
<213> ORGANISM: Homo sapiens

<400> SEQUENCE: 39
gatctagtcg aaatccccgt atgaagctga ctagtccaat taac          44

<210> SEQ ID NO 40
<211> LENGTH: 44
<212> TYPE: DNA
<213> ORGANISM: Homo sapiens

<400> SEQUENCE: 40
catggttgct gtgtggcaga attattggaa tgagcagttg tata          44

<210> SEQ ID NO 41
<211> LENGTH: 44
<212> TYPE: DNA
<213> ORGANISM: Homo sapiens

<400> SEQUENCE: 41
gatctataca actgctcatt ccaataattc tgccacacag caac          44

<210> SEQ ID NO 42
<211> LENGTH: 44
<212> TYPE: DNA
<213> ORGANISM: Homo sapiens

<400> SEQUENCE: 42
catggttacg tcttggcagt cttttttggca tcatcataat acta          44

<210> SEQ ID NO 43
<211> LENGTH: 44
<212> TYPE: DNA
<213> ORGANISM: Homo sapiens

<400> SEQUENCE: 43
gatctagtat tatgatgatg ccaaaaagac tgccaagacg taac            44

<210> SEQ ID NO 44
<211> LENGTH: 12
<212> TYPE: PRT
<213> ORGANISM: Homo sapiens

<400> SEQUENCE: 44

Ser Gly Ala Ser Trp Val Gln Tyr Trp Val Gln Arg
1               5                   10

<210> SEQ ID NO 45
<211> LENGTH: 12
<212> TYPE: PRT
<213> ORGANISM: Homo sapiens

<400> SEQUENCE: 45

Ser Gly Ala Ser Phe Val Gln Tyr Trp Val Gln Arg
1               5                   10

<210> SEQ ID NO 46
<211> LENGTH: 12
<212> TYPE: PRT
<213> ORGANISM: Homo sapiens

<400> SEQUENCE: 46

Ser Gly Ala Ser Trp Val Gln Tyr Phe Val Gln Arg
1               5                   10

<210> SEQ ID NO 47
<211> LENGTH: 12
<212> TYPE: PRT
<213> ORGANISM: Homo sapiens

<400> SEQUENCE: 47

Ser Gly Ala Ser Phe Val Gln Tyr Phe Val Gln Arg
1               5                   10

<210> SEQ ID NO 48
<211> LENGTH: 44
<212> TYPE: DNA
<213> ORGANISM: Homo sapiens

<400> SEQUENCE: 48
gatctccgct gaacccaata ctgaacaaac gaagcaccac taac            44

<210> SEQ ID NO 49
<211> LENGTH: 44
<212> TYPE: DNA
<213> ORGANISM: Homo sapiens

<400> SEQUENCE: 49
catggttagt ggtgcttcgt gggttcagta ttttgttcag cgga            44

<210> SEQ ID NO 50
<211> LENGTH: 44
<212> TYPE: DNA
<213> ORGANISM: Homo sapiens

<400> SEQUENCE: 50
gatctccgct gaacaaaata ctgaacccac gaagcaccac taac            44

<210> SEQ ID NO 51
<211> LENGTH: 44
<212> TYPE: DNA
<213> ORGANISM: Homo sapiens

<400> SEQUENCE: 51
catggttagt ggtgcttcgt tgttcagta ttttgttcag cgga       44

<210> SEQ ID NO 52
<211> LENGTH: 44
<212> TYPE: DNA
<213> ORGANISM: Homo sapiens

<400> SEQUENCE: 52
gatctccgct gaacaaaata ctgaacaaac gaagcaccac taac       44

<210> SEQ ID NO 53
<211> LENGTH: 9
<212> TYPE: PRT
<213> ORGANISM: Homo sapiens

<400> SEQUENCE: 53

Ala Ser Trp Val Gln Tyr Trp Val Gln
1               5

<210> SEQ ID NO 54
<211> LENGTH: 16
<212> TYPE: PRT
<213> ORGANISM: Homo sapiens

<400> SEQUENCE: 54

Gly Ala Ser Gly Ala Ser Trp Val Gln Tyr Trp Val Gln Arg Gly Ala
1               5                   10                  15

<210> SEQ ID NO 55
<211> LENGTH: 18
<212> TYPE: PRT
<213> ORGANISM: Homo sapiens

<400> SEQUENCE: 55

Val Gly Ala Ser Gly Ala Ser Trp Val Gln Tyr Trp Val Gln Arg Gly
1               5                   10                  15

Ala Leu

<210> SEQ ID NO 56
<211> LENGTH: 9
<212> TYPE: PRT
<213> ORGANISM: Homo sapiens

<400> SEQUENCE: 56

Met Thr Trp Glu Asp Trp Trp Leu Tyr
1               5

<210> SEQ ID NO 57
<211> LENGTH: 16
<212> TYPE: PRT
<213> ORGANISM: Homo sapiens

<400> SEQUENCE: 57

Gly Ala Ala Met Thr Trp Glu Asp Trp Trp Leu Tyr Gly Arg Gly Ala
1               5                   10                  15

<210> SEQ ID NO 58

-continued

```
<211> LENGTH: 18
<212> TYPE: PRT
<213> ORGANISM: Homo sapiens

<400> SEQUENCE: 58

Val Gly Ala Ala Met Thr Trp Glu Asp Trp Trp Leu Tyr Gly Arg Gly
1               5                   10                  15

Ala Leu

<210> SEQ ID NO 59
<211> LENGTH: 12
<212> TYPE: PRT
<213> ORGANISM: Homo sapiens

<400> SEQUENCE: 59

Ser Gly Ala Ser Trp Trp Gln Tyr Val Val Gln Arg
1               5                   10

<210> SEQ ID NO 60
<211> LENGTH: 12
<212> TYPE: PRT
<213> ORGANISM: Homo sapiens

<400> SEQUENCE: 60

Ser Gly Ala Ser Trp Val Trp Tyr Gln Val Gln Arg
1               5                   10

<210> SEQ ID NO 61
<211> LENGTH: 12
<212> TYPE: PRT
<213> ORGANISM: Homo sapiens

<400> SEQUENCE: 61

Ser Gly Ala Ser Trp Val Gln Trp Tyr Val Gln Arg
1               5                   10

<210> SEQ ID NO 62
<211> LENGTH: 12
<212> TYPE: PRT
<213> ORGANISM: Homo sapiens

<400> SEQUENCE: 62

Ser Gly Ala Trp Ser Val Gln Tyr Val Trp Gln Arg
1               5                   10

<210> SEQ ID NO 63
<211> LENGTH: 12
<212> TYPE: PRT
<213> ORGANISM: Homo sapiens

<400> SEQUENCE: 63

Ser Gly Trp Ser Ala Val Gln Tyr Gln Val Trp Arg
1               5                   10

<210> SEQ ID NO 64
<211> LENGTH: 12
<212> TYPE: PRT
<213> ORGANISM: Homo sapiens

<400> SEQUENCE: 64

Trp Gly Ala Ser Ser Val Gln Tyr Arg Val Gln Trp
1               5                   10

<210> SEQ ID NO 65
```

```
<211> LENGTH: 12
<212> TYPE: PRT
<213> ORGANISM: Homo sapiens

<400> SEQUENCE: 65

Asn Trp Trp Thr Tyr Ala Gln Leu Arg His Gln Thr
1               5                   10

<210> SEQ ID NO 66
<211> LENGTH: 12
<212> TYPE: PRT
<213> ORGANISM: Homo sapiens

<400> SEQUENCE: 66

Asn Trp Ala Trp Tyr Thr Gln Leu Arg His Gln Thr
1               5                   10

<210> SEQ ID NO 67
<211> LENGTH: 12
<212> TYPE: PRT
<213> ORGANISM: Homo sapiens

<400> SEQUENCE: 67

Asn Trp Ala Thr Tyr Leu Gln Trp Arg His Gln Thr
1               5                   10

<210> SEQ ID NO 68
<211> LENGTH: 12
<212> TYPE: PRT
<213> ORGANISM: Homo sapiens

<400> SEQUENCE: 68

Asn Trp Ala Thr Tyr His Gln Leu Arg Trp Gln Thr
1               5                   10

<210> SEQ ID NO 69
<211> LENGTH: 12
<212> TYPE: PRT
<213> ORGANISM: Homo sapiens

<400> SEQUENCE: 69

Asn Trp Ala Thr Tyr Gln Gln Leu Arg His Trp Thr
1               5                   10

<210> SEQ ID NO 70
<211> LENGTH: 12
<212> TYPE: PRT
<213> ORGANISM: Homo sapiens

<400> SEQUENCE: 70

Ser Gly Ala Ser Trp Asn Leu Ala Trp Val Gln Arg
1               5                   10

<210> SEQ ID NO 71
<211> LENGTH: 12
<212> TYPE: PRT
<213> ORGANISM: Homo sapiens

<400> SEQUENCE: 71

Ser Gly Ala Ser Trp Leu Asn Phe Trp Val Gln Arg
1               5                   10

<210> SEQ ID NO 72
<211> LENGTH: 12
<212> TYPE: PRT
```

<213> ORGANISM: Homo sapiens

<400> SEQUENCE: 72

Ser Gly Ala Ser Trp Leu Gln Tyr Trp Val Gln Arg
1               5                   10

<210> SEQ ID NO 73
<211> LENGTH: 12
<212> TYPE: PRT
<213> ORGANISM: Homo sapiens

<400> SEQUENCE: 73

Ser Gly Ala Ser Trp Val Asn Tyr Trp Val Gln Arg
1               5                   10

<210> SEQ ID NO 74
<211> LENGTH: 12
<212> TYPE: PRT
<213> ORGANISM: Homo sapiens

<400> SEQUENCE: 74

Ser Gly Ala Ser Trp Val Gln Phe Trp Val Gln Arg
1               5                   10

<210> SEQ ID NO 75
<211> LENGTH: 12
<212> TYPE: PRT
<213> ORGANISM: Homo sapiens

<400> SEQUENCE: 75

Ser Gly Ala Trp Trp Val Gln Tyr Trp Val Gln Arg
1               5                   10

<210> SEQ ID NO 76
<211> LENGTH: 12
<212> TYPE: PRT
<213> ORGANISM: Homo sapiens

<400> SEQUENCE: 76

Ser Gly Ala Ser Trp Val Gln Tyr Trp Trp Gln Arg
1               5                   10

<210> SEQ ID NO 77
<211> LENGTH: 12
<212> TYPE: PRT
<213> ORGANISM: Homo sapiens

<400> SEQUENCE: 77

Ser Gly Trp Trp Trp Val Gln Tyr Trp Val Gln Arg
1               5                   10

<210> SEQ ID NO 78
<211> LENGTH: 12
<212> TYPE: PRT
<213> ORGANISM: Homo sapiens

<400> SEQUENCE: 78

Ser Gly Ala Ser Trp Val Gln Tyr Trp Trp Trp Arg
1               5                   10

<210> SEQ ID NO 79
<211> LENGTH: 12
<212> TYPE: PRT
<213> ORGANISM: Homo sapiens

<400> SEQUENCE: 79

Thr Ala Gly Thr Trp Val Gln Tyr Trp Val Gln Arg
1               5                   10

<210> SEQ ID NO 80
<211> LENGTH: 12
<212> TYPE: PRT
<213> ORGANISM: Homo sapiens

<400> SEQUENCE: 80

Ser Gly Ala Ser Trp Val Gln Tyr Trp Leu Asn Lys
1               5                   10

<210> SEQ ID NO 81
<211> LENGTH: 12
<212> TYPE: PRT
<213> ORGANISM: Homo sapiens

<400> SEQUENCE: 81

Ala Ser Ser Ala Trp Val Gln Tyr Trp Val Gln Arg
1               5                   10

<210> SEQ ID NO 82
<211> LENGTH: 12
<212> TYPE: PRT
<213> ORGANISM: Homo sapiens

<400> SEQUENCE: 82

Ser Gly Ala Ser Trp Val Gln Tyr Trp Tyr Glu Glu
1               5                   10

<210> SEQ ID NO 83
<211> LENGTH: 12
<212> TYPE: PRT
<213> ORGANISM: Homo sapiens

<400> SEQUENCE: 83

Ala Met Thr Trp Asp Asp Trp Trp Leu Tyr Gly Arg
1               5                   10

<210> SEQ ID NO 84
<211> LENGTH: 12
<212> TYPE: PRT
<213> ORGANISM: Homo sapiens

<400> SEQUENCE: 84

Ala Met Thr Trp Glu Glu Trp Trp Leu Tyr Gly Arg
1               5                   10

<210> SEQ ID NO 85
<211> LENGTH: 12
<212> TYPE: PRT
<213> ORGANISM: Homo sapiens

<400> SEQUENCE: 85

Ala Met Thr Trp Gln Asp Trp Trp Leu Tyr Gly Arg
1               5                   10

<210> SEQ ID NO 86
<211> LENGTH: 12
<212> TYPE: PRT
<213> ORGANISM: Homo sapiens

<400> SEQUENCE: 86

```
Ala Met Thr Trp Glu Asn Trp Trp Leu Tyr Gly Arg
1               5                   10
```

<210> SEQ ID NO 87
<211> LENGTH: 12
<212> TYPE: PRT
<213> ORGANISM: Homo sapiens

<400> SEQUENCE: 87

```
Ala Met Thr Trp Gln Asn Trp Trp Leu Tyr Gly Arg
1               5                   10
```

<210> SEQ ID NO 88
<211> LENGTH: 12
<212> TYPE: PRT
<213> ORGANISM: Homo sapiens

<400> SEQUENCE: 88

```
Ala Met Thr Trp Glu Lys Trp Trp Leu Tyr Gly Arg
1               5                   10
```

<210> SEQ ID NO 89
<211> LENGTH: 12
<212> TYPE: PRT
<213> ORGANISM: Homo sapiens

<400> SEQUENCE: 89

```
Ala Met Thr Trp Lys Asp Trp Trp Leu Tyr Gly Arg
1               5                   10
```

<210> SEQ ID NO 90
<211> LENGTH: 12
<212> TYPE: PRT
<213> ORGANISM: Homo sapiens

<400> SEQUENCE: 90

```
Ala Met Thr Trp Lys Lys Trp Trp Leu Tyr Gly Arg
1               5                   10
```

<210> SEQ ID NO 91
<211> LENGTH: 12
<212> TYPE: PRT
<213> ORGANISM: Homo sapiens

<400> SEQUENCE: 91

```
Ala Met Thr Trp Glu Asp Tyr Trp Leu Tyr Gly Arg
1               5                   10
```

<210> SEQ ID NO 92
<211> LENGTH: 12
<212> TYPE: PRT
<213> ORGANISM: Homo sapiens

<400> SEQUENCE: 92

```
Ala Met Thr Trp Glu Asn Phe Trp Leu Tyr Gly Arg
1               5                   10
```

<210> SEQ ID NO 93
<211> LENGTH: 12
<212> TYPE: PRT
<213> ORGANISM: Homo sapiens

<400> SEQUENCE: 93

```
Ala Met Thr Trp Glu Asn Ala Trp Leu Tyr Gly Arg
1               5                   10
```

```
<210> SEQ ID NO 94
<211> LENGTH: 5
<212> TYPE: PRT
<213> ORGANISM: Homo sapiens

<400> SEQUENCE: 94

Trp Val Gln Tyr Trp
1               5

<210> SEQ ID NO 95
<211> LENGTH: 5
<212> TYPE: PRT
<213> ORGANISM: Homo sapiens

<400> SEQUENCE: 95

Trp Tyr Asn Tyr Trp
1               5

<210> SEQ ID NO 96
<211> LENGTH: 5
<212> TYPE: PRT
<213> ORGANISM: Homo sapiens

<400> SEQUENCE: 96

Trp Met Thr Tyr Trp
1               5

<210> SEQ ID NO 97
<211> LENGTH: 5
<212> TYPE: PRT
<213> ORGANISM: Homo sapiens

<400> SEQUENCE: 97

Trp Ala Thr Tyr Trp
1               5

<210> SEQ ID NO 98
<211> LENGTH: 5
<212> TYPE: PRT
<213> ORGANISM: Homo sapiens

<400> SEQUENCE: 98

Trp Glu Met Tyr Trp
1               5

<210> SEQ ID NO 99
<211> LENGTH: 5
<212> TYPE: PRT
<213> ORGANISM: Homo sapiens

<400> SEQUENCE: 99

Trp Lys Asp Tyr Trp
1               5

<210> SEQ ID NO 100
<211> LENGTH: 5
<212> TYPE: PRT
<213> ORGANISM: Homo sapiens

<400> SEQUENCE: 100

Trp Glu His Tyr Trp
1               5
```

```
<210> SEQ ID NO 101
<211> LENGTH: 5
<212> TYPE: PRT
<213> ORGANISM: Homo sapiens

<400> SEQUENCE: 101

Trp Gln Asn Tyr Trp
1               5

<210> SEQ ID NO 102
<211> LENGTH: 5
<212> TYPE: PRT
<213> ORGANISM: Homo sapiens

<400> SEQUENCE: 102

Trp Gln Asp Val Trp
1               5

<210> SEQ ID NO 103
<211> LENGTH: 5
<212> TYPE: PRT
<213> ORGANISM: Homo sapiens

<400> SEQUENCE: 103

Trp Met Gln Tyr Trp
1               5

<210> SEQ ID NO 104
<211> LENGTH: 5
<212> TYPE: PRT
<213> ORGANISM: Homo sapiens

<400> SEQUENCE: 104

Trp His Ala Tyr Trp
1               5

<210> SEQ ID NO 105
<211> LENGTH: 5
<212> TYPE: PRT
<213> ORGANISM: Homo sapiens

<400> SEQUENCE: 105

Trp Gln Thr Tyr Trp
1               5

<210> SEQ ID NO 106
<211> LENGTH: 5
<212> TYPE: PRT
<213> ORGANISM: Homo sapiens

<400> SEQUENCE: 106

Trp Gln Ser Phe Trp
1               5

<210> SEQ ID NO 107
<211> LENGTH: 5
<212> TYPE: PRT
<213> ORGANISM: Homo sapiens

<400> SEQUENCE: 107

Trp Tyr Ala Tyr Trp
1               5

<210> SEQ ID NO 108
<211> LENGTH: 5
```

<212> TYPE: PRT
<213> ORGANISM: Homo sapiens

<400> SEQUENCE: 108

Trp Glu Asp Tyr Trp
1               5

<210> SEQ ID NO 109
<211> LENGTH: 5
<212> TYPE: PRT
<213> ORGANISM: Homo sapiens

<400> SEQUENCE: 109

Trp Glu Asp Phe Trp
1               5

<210> SEQ ID NO 110
<211> LENGTH: 5
<212> TYPE: PRT
<213> ORGANISM: Homo sapiens

<400> SEQUENCE: 110

Trp Glu Asp Ala Trp
1               5

<210> SEQ ID NO 111
<211> LENGTH: 5
<212> TYPE: PRT
<213> ORGANISM: Homo sapiens

<400> SEQUENCE: 111

Trp Leu Gln Tyr Trp
1               5

<210> SEQ ID NO 112
<211> LENGTH: 5
<212> TYPE: PRT
<213> ORGANISM: Homo sapiens

<400> SEQUENCE: 112

Trp Leu Asn Tyr Trp
1               5

<210> SEQ ID NO 113
<211> LENGTH: 5
<212> TYPE: PRT
<213> ORGANISM: Homo sapiens

<400> SEQUENCE: 113

Trp Asn Leu Ala Trp
1               5

<210> SEQ ID NO 114
<211> LENGTH: 5
<212> TYPE: PRT
<213> ORGANISM: Homo sapiens

<400> SEQUENCE: 114

Trp Leu Asn Phe Trp
1               5

<210> SEQ ID NO 115
<211> LENGTH: 5
<212> TYPE: PRT
<213> ORGANISM: Homo sapiens

```
<400> SEQUENCE: 115

Trp Arg Trp Phe Trp
1               5

<210> SEQ ID NO 116
<211> LENGTH: 5
<212> TYPE: PRT
<213> ORGANISM: Homo sapiens

<400> SEQUENCE: 116

Trp Glu Asp Trp Trp
1               5

<210> SEQ ID NO 117
<211> LENGTH: 5
<212> TYPE: PRT
<213> ORGANISM: Homo sapiens

<400> SEQUENCE: 117

Trp Ile Asp Trp Trp
1               5

<210> SEQ ID NO 118
<211> LENGTH: 5
<212> TYPE: PRT
<213> ORGANISM: Homo sapiens

<400> SEQUENCE: 118

Trp Asp Asp Trp Trp
1               5

<210> SEQ ID NO 119
<211> LENGTH: 5
<212> TYPE: PRT
<213> ORGANISM: Homo sapiens

<400> SEQUENCE: 119

Trp Glu Glu Trp Trp
1               5

<210> SEQ ID NO 120
<211> LENGTH: 5
<212> TYPE: PRT
<213> ORGANISM: Homo sapiens

<400> SEQUENCE: 120

Trp Gln Asp Trp Trp
1               5

<210> SEQ ID NO 121
<211> LENGTH: 5
<212> TYPE: PRT
<213> ORGANISM: Homo sapiens

<400> SEQUENCE: 121

Trp Glu Asn Trp Trp
1               5

<210> SEQ ID NO 122
<211> LENGTH: 5
<212> TYPE: PRT
<213> ORGANISM: Homo sapiens

<400> SEQUENCE: 122
```

Trp Gln Asn Trp Trp
1               5

<210> SEQ ID NO 123
<211> LENGTH: 5
<212> TYPE: PRT
<213> ORGANISM: Homo sapiens

<400> SEQUENCE: 123

Trp Glu Lys Trp Trp
1               5

<210> SEQ ID NO 124
<211> LENGTH: 5
<212> TYPE: PRT
<213> ORGANISM: Homo sapiens

<400> SEQUENCE: 124

Trp Lys Asp Trp Trp
1               5

<210> SEQ ID NO 125
<211> LENGTH: 5
<212> TYPE: PRT
<213> ORGANISM: Homo sapiens

<400> SEQUENCE: 125

Trp Lys Lys Trp Trp
1               5

<210> SEQ ID NO 126
<211> LENGTH: 12
<212> TYPE: PRT
<213> ORGANISM: Homo sapiens

<400> SEQUENCE: 126

Ala Met Thr Trp Gln Asp Tyr Trp Leu Tyr Gly Arg
1               5                   10

<210> SEQ ID NO 127
<211> LENGTH: 9
<212> TYPE: PRT
<213> ORGANISM: Homo sapiens

<400> SEQUENCE: 127

Met Thr Trp Gln Asp Tyr Trp Leu Tyr
1               5

<210> SEQ ID NO 128
<211> LENGTH: 7
<212> TYPE: PRT
<213> ORGANISM: Homo sapiens

<400> SEQUENCE: 128

Thr Trp Gln Asp Tyr Trp Leu
1               5

<210> SEQ ID NO 129
<211> LENGTH: 5
<212> TYPE: PRT
<213> ORGANISM: Homo sapiens

<400> SEQUENCE: 129

Trp Gln Asp Tyr Trp

<210> SEQ ID NO 130
<211> LENGTH: 14
<212> TYPE: PRT
<213> ORGANISM: Homo sapiens

<400> SEQUENCE: 130

Cys Ala Met Thr Trp Gln Asp Tyr Trp Leu Tyr Gly Arg Cys
1               5                   10

<210> SEQ ID NO 131
<211> LENGTH: 11
<212> TYPE: PRT
<213> ORGANISM: Homo sapiens

<400> SEQUENCE: 131

Cys Met Thr Trp Gln Asp Tyr Trp Leu Tyr Cys
1               5                   10

<210> SEQ ID NO 132
<211> LENGTH: 9
<212> TYPE: PRT
<213> ORGANISM: Homo sapiens

<400> SEQUENCE: 132

Cys Thr Trp Gln Asp Tyr Trp Leu Cys
1               5

<210> SEQ ID NO 133
<211> LENGTH: 7
<212> TYPE: PRT
<213> ORGANISM: Homo sapiens

<400> SEQUENCE: 133

Cys Trp Gln Asp Tyr Trp Cys
1               5

<210> SEQ ID NO 134
<211> LENGTH: 32
<212> TYPE: DNA
<213> ORGANISM: Homo sapiens

<400> SEQUENCE: 134
catgacctgg caggactact ggctgtacgg ca                                32

<210> SEQ ID NO 135
<211> LENGTH: 32
<212> TYPE: DNA
<213> ORGANISM: Homo sapiens

<400> SEQUENCE: 135
tggaccgtcc tgatgaccga catgccgtct ag                                32

<210> SEQ ID NO 136
<211> LENGTH: 24
<212> TYPE: DNA
<213> ORGANISM: Homo sapiens

<400> SEQUENCE: 136
gccaccatgc tggggagcag agct                                         24

<210> SEQ ID NO 137
<211> LENGTH: 48

```
<212> TYPE: DNA
<213> ORGANISM: Homo sapiens

<400> SEQUENCE: 137
tcagtgatga tggtggtgat gtccgctgcc gggactcagg gttgctgc        48

<210> SEQ ID NO 138
<211> LENGTH: 33
<212> TYPE: DNA
<213> ORGANISM: Homo sapiens

<400> SEQUENCE: 138
ctgttgctgc tgcccggtac agctcagggc aga                        33

<210> SEQ ID NO 139
<211> LENGTH: 33
<212> TYPE: DNA
<213> ORGANISM: Homo sapiens

<400> SEQUENCE: 139
tctgccctga gctgtaccgg gcagcagcaa cag                        33

<210> SEQ ID NO 140
<211> LENGTH: 33
<212> TYPE: DNA
<213> ORGANISM: Homo sapiens

<400> SEQUENCE: 140
ggcagcagcc ctgccggtac tcagtgccag cag                        33

<210> SEQ ID NO 141
<211> LENGTH: 33
<212> TYPE: DNA
<213> ORGANISM: Homo sapiens

<400> SEQUENCE: 141
ctgctggcac tgagtaccgg cagggctgct gcc                        33

<210> SEQ ID NO 142
<211> LENGTH: 33
<212> TYPE: DNA
<213> ORGANISM: Homo sapiens

<400> SEQUENCE: 142
ctctgcacac tggccggtag tgcacatcca cta                        33

<210> SEQ ID NO 143
<211> LENGTH: 33
<212> TYPE: DNA
<213> ORGANISM: Homo sapiens

<400> SEQUENCE: 143
tagtggatgt gcactaccgg ccagtgtgca gag                        33

<210> SEQ ID NO 144
<211> LENGTH: 33
<212> TYPE: DNA
<213> ORGANISM: Homo sapiens

<400> SEQUENCE: 144
cctgagggtc accacggtga gactcagcag att                        33

<210> SEQ ID NO 145
```

```
<211> LENGTH: 33
<212> TYPE: DNA
<213> ORGANISM: Homo sapiens

<400> SEQUENCE: 145
aatctgctga gtctcaccgt ggtgaccctc agg                                    33

<210> SEQ ID NO 146
<211> LENGTH: 33
<212> TYPE: DNA
<213> ORGANISM: Homo sapiens

<400> SEQUENCE: 146
agtcccagcc agccaggtca gcgtctcctt ctc                                    33

<210> SEQ ID NO 147
<211> LENGTH: 33
<212> TYPE: DNA
<213> ORGANISM: Homo sapiens

<400> SEQUENCE: 147
gagaaggaga cgctgacctg gctggctggg act                                    33

<210> SEQ ID NO 148
<211> LENGTH: 12
<212> TYPE: PRT
<213> ORGANISM: Homo sapiens
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid

<400> SEQUENCE: 148

Xaa Xaa Xaa Trp Xaa Xaa Tyr Trp Xaa Xaa Xaa Xaa
1               5                   10

<210> SEQ ID NO 149
<211> LENGTH: 829
<212> TYPE: DNA
<213> ORGANISM: Homo sapiens
<220> FEATURE:
<221> NAME/KEY: k
<222> LOCATION: (1)..(829)
<223> OTHER INFORMATION: 'k' is a 't' or 'g'
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
```

```
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t

<400> SEQUENCE: 149
gaaattaata cgactcacta tagggagacc acaacggttt ccctctagaa ataattttgt    60
ttaactttaa gaaggagata taccaatgnn knnknnktgg nnknnktact ggnnknnknn   120
knnkgagggt ggcggtacta aacctcctga gtacggtgat acacctattc cgggctatac   180
ttatatcaac cctctcgacg gcacttatcc gcctggtact gagcaaaacc ccgctaatcc   240
taatccttct cttgaggagt ctcagcctct taatactttc atgtttcaga ataataggtt   300
ccgaaatagg caggggggcat taactgttta tacgggcact gttactcaag gcactgaccc   360
cgttaaaact tattaccagt acactcctgt atcatcaaaa gccatgtatg acgcttactg   420
gaacggtaaa ttcagagact gcgctttcca ttctggcttt aatgaggatc cattcgtttg   480
tgaatatcaa ggccaatcgt ctgacctgcc tcaacctcct gtcaatgctg gcggcggctc   540
tggtggtggt tctggtggcg gctctgaggg tggtggctct gagggtggcg gttctgaggg   600
tggcggctct gagggaggcg gttccggtgg tggctctggt tccggtgatt ttgattatga   660
aaagatggca aacgctaata agggggctat gaccgaaaat gccgatgaaa acgcgctaca   720
gtctgacgct aaaggcaaac ttgattctgt cgctactgat tacggtgctt tttctactcc   780
tgtttggatt tctcaagctc aaggtattcg tgctggtcct tgatgaata              829

<210> SEQ ID NO 150
<211> LENGTH: 5
<212> TYPE: PRT
<213> ORGANISM: Homo sapiens

<400> SEQUENCE: 150

Trp Val Asp Tyr Trp
1               5

<210> SEQ ID NO 151
<211> LENGTH: 5
<212> TYPE: PRT
<213> ORGANISM: Homo sapiens

<400> SEQUENCE: 151

Trp Gln Asp Tyr Trp
1               5

<210> SEQ ID NO 152
<211> LENGTH: 12
<212> TYPE: PRT
<213> ORGANISM: Homo sapiens

<400> SEQUENCE: 152

Met Met Thr Trp Gln Asp Tyr Trp Leu Ala Asn Val
```

```
1               5                   10
```

<210> SEQ ID NO 153
<211> LENGTH: 12
<212> TYPE: PRT
<213> ORGANISM: Homo sapiens

<400> SEQUENCE: 153

```
Lys Met Thr Trp Val Asp Tyr Trp Leu Lys Asn Cys
1               5                   10
```

<210> SEQ ID NO 154
<211> LENGTH: 12
<212> TYPE: PRT
<213> ORGANISM: Homo sapiens

<400> SEQUENCE: 154

```
Lys Leu Thr Trp Glu Met Tyr Trp Leu Met Ser Leu
1               5                   10
```

<210> SEQ ID NO 155
<211> LENGTH: 12
<212> TYPE: PRT
<213> ORGANISM: Homo sapiens

<400> SEQUENCE: 155

```
Ile Lys Thr Trp Glu Trp Tyr Trp Met Lys Ser Gln
1               5                   10
```

<210> SEQ ID NO 156
<211> LENGTH: 12
<212> TYPE: PRT
<213> ORGANISM: Homo sapiens

<400> SEQUENCE: 156

```
Met Lys Thr Trp Val Asp Tyr Trp Leu Glu Thr Gln
1               5                   10
```

<210> SEQ ID NO 157
<211> LENGTH: 12
<212> TYPE: PRT
<213> ORGANISM: Homo sapiens

<400> SEQUENCE: 157

```
Lys Met Thr Trp Val Asp Tyr Trp Leu Arg Asn Cys
1               5                   10
```

<210> SEQ ID NO 158
<211> LENGTH: 12
<212> TYPE: PRT
<213> ORGANISM: Homo sapiens

<400> SEQUENCE: 158

```
Lys Lys Thr Trp Thr Glu Tyr Trp Leu Glu Asn Gln
1               5                   10
```

<210> SEQ ID NO 159
<211> LENGTH: 12
<212> TYPE: PRT
<213> ORGANISM: Homo sapiens

<400> SEQUENCE: 159

```
Ser Lys Thr Trp Glu Trp Tyr Trp Met Asn Arg Asp
1               5                   10
```

<210> SEQ ID NO 160
<211> LENGTH: 12
<212> TYPE: PRT
<213> ORGANISM: Homo sapiens

<400> SEQUENCE: 160

Thr Tyr Asp Trp Thr Tyr Tyr Trp Leu Met Asn Ser
1               5                   10

<210> SEQ ID NO 161
<211> LENGTH: 12
<212> TYPE: PRT
<213> ORGANISM: Homo sapiens

<400> SEQUENCE: 161

Asn Leu Thr Trp Glu Ile Tyr Trp Leu Arg Ser Gln
1               5                   10

<210> SEQ ID NO 162
<211> LENGTH: 12
<212> TYPE: PRT
<213> ORGANISM: Homo sapiens

<400> SEQUENCE: 162

Leu Lys Thr Trp Ile Asp Tyr Trp Ile Ala Ser Gln
1               5                   10

<210> SEQ ID NO 163
<211> LENGTH: 12
<212> TYPE: PRT
<213> ORGANISM: Homo sapiens

<400> SEQUENCE: 163

Arg Leu Thr Trp Val Asp Tyr Trp Leu Ala Ser Arg
1               5                   10

<210> SEQ ID NO 164
<211> LENGTH: 12
<212> TYPE: PRT
<213> ORGANISM: Homo sapiens

<400> SEQUENCE: 164

Met Lys Thr Trp Gln Asp Tyr Trp Leu Ala Asn Arg
1               5                   10

<210> SEQ ID NO 165
<211> LENGTH: 12
<212> TYPE: PRT
<213> ORGANISM: Homo sapiens

<400> SEQUENCE: 165

Asn Glu Leu Trp Met Trp Tyr Trp Ile Asn Ser Ala
1               5                   10

<210> SEQ ID NO 166
<211> LENGTH: 12
<212> TYPE: PRT
<213> ORGANISM: Homo sapiens

<400> SEQUENCE: 166

Thr Asn Thr Trp Met Ile Tyr Trp Trp Ile Asn Gln
1               5                   10

<210> SEQ ID NO 167

```
<211> LENGTH: 82
<212> TYPE: DNA
<213> ORGANISM: Homo sapiens
<220> FEATURE:
<221> NAME/KEY: 'k'
<222> LOCATION: (1)..(82)
<223> OTHER INFORMATION: 'k' is a 't' or 'g'
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 167
taactttaag aaggagatat accaatgnnk nnknnktggn nknnktactg gnnknnknnk      60
nnkgagggtg gcggtactaa ac                                              82

<210> SEQ ID NO 168
<211> LENGTH: 85
<212> TYPE: DNA
<213> ORGANISM: Homo sapiens

<400> SEQUENCE: 168
gaaattaata cgactcacta tagggagacc acaacggttt ccctctagaa ataattttgt      60
ttaactttaa gaaggagata tacca                                           85

<210> SEQ ID NO 169
<211> LENGTH: 79
<212> TYPE: DNA
<213> ORGANISM: Homo sapiens

<400> SEQUENCE: 169
tattcatcaa ggaccagcac gaataccttg agcttgagaa atccaaacag gagtagaaaa      60
atcgatagca gcaccgtaa                                                  79

<210> SEQ ID NO 170
<211> LENGTH: 44
<212> TYPE: DNA
<213> ORGANISM: Homo sapiens
```

```
<400> SEQUENCE: 170
catggttagt ggtgcttcgt ttgttcagta ttgggttcag cgga          44

<210> SEQ ID NO 171
<211> LENGTH: 8
<212> TYPE: PRT
<213> ORGANISM: Homo sapiens

<400> SEQUENCE: 171

Leu Pro Asp Glu Val Thr Cys Val
1               5

<210> SEQ ID NO 172
<211> LENGTH: 8
<212> TYPE: PRT
<213> ORGANISM: Homo sapiens

<400> SEQUENCE: 172

Thr Glu Glu Glu Gln Gln Tyr Leu
1               5

<210> SEQ ID NO 173
<211> LENGTH: 8
<212> TYPE: PRT
<213> ORGANISM: Homo sapiens

<400> SEQUENCE: 173

Lys Lys Tyr Leu Val Trp Val Gln
1               5

<210> SEQ ID NO 174
<211> LENGTH: 9
<212> TYPE: PRT
<213> ORGANISM: Homo sapiens

<400> SEQUENCE: 174

Met Glu Glu Ser Lys Gln Leu Gln Leu
1               5

<210> SEQ ID NO 175
<211> LENGTH: 8
<212> TYPE: PRT
<213> ORGANISM: Homo sapiens

<400> SEQUENCE: 175

Asp Tyr Lys Asp Asp Asp Asp Lys
1               5

<210> SEQ ID NO 176
<211> LENGTH: 189
<212> TYPE: PRT
<213> ORGANISM: Homo sapiens

<400> SEQUENCE: 176

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
        50                  55                  60
```

```
Thr Asn Asp Val Pro His Ile Gln Cys Gly Asp Gly Cys Asp Pro Gln
 65                  70                  75                  80

Gly Leu Arg Asp Asn Ser Gln Phe Cys Leu Gln Arg Ile His Gln Gly
                 85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Gly Gln Leu His Ala Ser Leu
            115                 120                 125

Leu Gly Leu Ser Gln Leu Leu Gln Pro Glu Gly His His Trp Glu Thr
        130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 177
<211> LENGTH: 14
<212> TYPE: PRT
<213> ORGANISM: Homo sapiens

<400> SEQUENCE: 177

```
Ala Lys Met Thr Trp Val Asp Tyr Trp Leu Lys Asn Cys Ala
1               5                   10
```

<210> SEQ ID NO 178
<211> LENGTH: 14
<212> TYPE: PRT
<213> ORGANISM: Homo sapiens

<400> SEQUENCE: 178

```
Cys Met Lys Thr Trp Val Asp Tyr Trp Leu Glu Thr Gln Cys
1               5                   10
```

<210> SEQ ID NO 179
<211> LENGTH: 14
<212> TYPE: PRT
<213> ORGANISM: Homo sapiens

<400> SEQUENCE: 179

```
Ala Met Lys Thr Trp Val Asp Tyr Trp Leu Glu Thr Gln Ala
1               5                   10
```

<210> SEQ ID NO 180
<211> LENGTH: 20
<212> TYPE: DNA
<213> ORGANISM: Rattus norvegicus

<400> SEQUENCE: 180
ggctcctgtg aaacaaccat                                            20

<210> SEQ ID NO 181
<211> LENGTH: 20
<212> TYPE: DNA
<213> ORGANISM: Rattus norvegicus

<400> SEQUENCE: 181
acagaaatgc cctggttttg                                            20

POLYPEPTIDES THAT BOUND TO IL-23 RECEPTOR AND INHIBIT BINDING OF IL-23 AND CELL SIGNALING THEREOF

CROSS-REFERENCE TO RELATED APPLICATIONS

The present application is a Continuation-In-Part of U.S. application Ser. No. 13/771,305, (now U.S. Pat. No. 9,169,292)filed Feb. 20, 2013, which is a Continuation-In-Part of U.S. application Ser. No. 13/523,286, filed Jun. 14, 2012 (now U.S. Pat. No. 8,946,150), which claims the benefit of priority under 35 U.S.C. §119(e) to U.S. Provisional Application No. 61/520,710 filed Jun. 14, 2011, the disclosures of which are hereby incorporated by reference in their entirety.

FIELD OF THE INVENTION

The present invention relates to novel polypeptides (linear and cyclic) that bind to IL-23 receptor and inhibit the binding of IL-23 to its corresponding receptor and cell signaling thereof. The present invention also relates to compositions containing the novel polypeptides, and use of same to treat IL-23 associated human diseases including, for example, inflammatory bowel diseases, psoriasis and Crohn's disease.

BACKGROUND OF THE INVENTION

Overt production of inflammatory cytokines such as IL-23 has been implicated in a number of diseases including multiple sclerosis, asthma, rheumatoid arthritis, inflammatory bowel diseases, Crohn's disease and psoriasis. Over 10 million people in the United States are affected by these IL-23 mediated diseases. Systemic levels of IL-23 are found to be associated with rheumatoid arthritis. (Melis, et al., *Ann. Rheum. Dis.,* 69: 618-623, 2010). IL-23 gene knock-out mice are found to be resistant to development of many inflammatory diseases, indicating a crucial role of IL-23 in the pathogenesis of the disorders. (Langowski, et al., *Nature,* 442:7101, 2006). Single nucleotide polymorphisms in the IL-23 receptor genes have been associated with psoriasis. (Capon et al., *Hum. Genet.* 122:201-6, 2007). A single nucleotide polymorphism in the IL-23 receptor gene has been found to be associated with Crohn's disease and inflammatory bowel diseases. (Duerr, et al., *Science,* 314: 1461-1463, 2006).

At a structural level, cytokine IL-23 is a heterodimeric cytokine that consists of two subunits (i.e., p19 and p40). The mature p19 subunit contains 170 amino acid residues in a 4 α-helix bundle, and the mature p40 subunit contains 306 amino acid residues consisting of three sequentially arranged β-strands. (Oppmann, et al., *Immunity* 13 (5): 715-725, 2000). Binding of IL-23 to its corresponding receptor (i.e., IL-23R) mediates cell signaling. For example, binding of IL-23 to IL-23R stimulates the production of IL-17, which is a key inflammatory mediator. IL-23R is a heterodimeric receptor consisting of an IL-23Rα subunit and an IL-12Rβ1 subunit. (Parham, et al., *J. Immunol.,* 168:5699-5708, 2002). Interestingly, the IL-12Rβ1 subunit is shared with the IL-12 receptor.

Several researchers have reported using anti-IL-23 antibodies or IL-23 agonists in an attempt to disrupt IL-23 signaling. These studies shed light on the potential clinical applications in treating IL-23 related diseases. For example, U.S. Pat. No. 7,790,862 discloses the use of anti-p19 antibodies. Anti-p19 polyclonal antibodies reduced IL-17A and IL-17F production in a murine splenocyte assay. These authors purported that such anti-p19 antibodies may have utility in treating inflammatory diseases and cancer. U.S. Pat. No. 7,282,204 discloses the use of anti-p19 and anti-p40 antibodies. The authors claimed that anti-p19 antibodies reduced cancer volume in skin tumors, while anti-p40 antibodies provoked weight gain as to reduce cachexia. U.S. Patent Publication No. 2010/0166767 discloses the use of humanized anti-IL-23R antibodies. The authors determined the equilibrium dissociation constant for the created humanized anti-human IL-23R antibodies (i.e., $K_d$ of Hum20D7 is 131 pM). U.S. Pat. No. 7,575,741 discloses the generation of an IL-23 fusion protein comprising the p19 subunit linked to the p40 subunit. The fusion protein is found to have property of enhancing wound healing in various mouse models.

The use of anti-p40 antibodies in inhibiting IL-23 activity, however, has many drawbacks. In particular, because the p40 subunit is shared by the IL-23 and IL-12 cytokines, anti-p40 antibodies may have the unintended consequence of inhibiting IL-12, demonstrating their non-specific effects (See, e.g., Oppmann, et al., *Immunity* 13:715-725, 2000; Cua, et al., *Nature* 421:744-748, 2003). Similarly, knocking out the p40 subunit has the dual affect of knocking out both IL-23 and IL-12.

Antibody-based approaches to inhibit IL-23R mediated signaling have additional shortcomings. First, it is recognized that antibody therapy often elicits an adverse immune response to the foreign administered antibodies during treatment. Second, repeated administration of antibodies (e.g., rodent-derived antibodies) potentially leads to fatal anaphylactic responses and suffer from loss in therapeutic efficacy and potency. Third, use of chimeric antibodies (i.e., antibodies in which mouse variable regions are fused with human constant regions) still possesses unwanted immunogenicity, albeit they may attenuate some anaphylactic responses. Fourth, while use of humanized antibodies (i.e., antibodies generated by grafting rodent CDR loops to human frameworks) may remedy the immunogenicity issues, preparation of humanized antibodies often leads to less effective antibodies (i.e., reduced antibody binding activity).

Although the amino acid sequence of IL-23R is known, there has been no report relating to the crystallization study of the molecular structure of IL-23R. Relying on the linear amino acid sequence with the aid of computer modeling, Chemtob et al. generated peptides that correspond to the hinge regions within the D1, D2 and D3 of the IL-23R. These authors disclosed in the U.S. Patent Publication 2010/0190710 ('710 application) that their IL-23R based polypeptides (e.g., LPDEVTCV,(SEQ ID NO: 171), TEEQQYL, (SEQ ID NO: 172),KKYLVWVQ (SEQ ID NO: 173), and MEESKQLQL (SEQ ID NO: 174) may represent potential antagonists of IL-23R. In particular, the '710 application discloses certain polypeptides can inhibit IL-23R mediated cell signaling (i.e., STAT3 phosphorylation). They reported using polypeptides that mimic IL-23R and function as IL-23R antagonists.

There is a continuing need for the discovery of novel linear or cyclic polypeptides that inhibit IL-23 mediated cell signaling and diseases. The present inventors report herein, using a novel phage display approach, the identification of novel polypeptides that can bind to IL-23R. There is also disclosed the structure of these polypeptides, its compositions and methods of treatment using same in inhibiting binding of IL-23 to its receptor thereof and the subsequent cell signaling events. The novel polypeptides have utility in clinical application in the treatment of IL-23 mediated immuno-diseases.

SUMMARY OF THE INVENTION

The present invention provides the discovery of therapeutic peptides (screened with a phage display library method) that are capable of inhibiting the binding of IL-23 to its corresponding receptor thereof. The therapeutic peptides have clinical application in the treatment of IL-23 associated immunological diseases including, in particular, Crohn's disease and inflammatory bowel diseases.

The peptides according to this invention are useful in methods and compositions for the treatment of IL-23 associated diseases. Targeting of IL-23 or the IL-23 receptor (i.e., the IL-23 axis) with the present peptides thus represents a novel therapeutic approach for autoimmune diseases including psoriasis, inflammatory bowel disease, rheumatoid arthritis and multiple sclerosis.

In another aspect, the present invention provides an isolated polypeptide having a core structure of $WX_1X_2X_3W$. The $X_1$, $X_2$, and $X_3$ are amino acid residues, with the proviso that when one of $X_1$, $X_2$ or $X_3$ is W, the remaining $X_1$, $X_2$ or $X_3$ cannot be W. The polypeptides of the present invention are characterized by its ability to inhibit the binding of IL-23 to IL-23 receptor and the IL-23-mediated signaling. For example, the polypeptides are effective in binding to IL-23R as evidenced by flow cytometry and immunoprecipitation with a soluble IL-23R (i.e., Δ9). The polypeptides are also effective in blocking IL-23 mediated signaling in cells as evidenced by the phosphor-STAT3 levels.

In one aspect, the $X_3$ in the $WX_1X_2X_3W$ core structure of the polypeptides is an aromatic amino acid, such as Y, W or F. Preferably, the $X_3$ is Y.

In one embodiment, the $WX_1X_2YW$ core structure provides an isolated polypeptide that has an amino acid sequence of SEQ NO: 2, SEQ ID NO: 4, SEQ ID NO: 7, SEQ ID NO: 10, SEQ ID NO: 13, SEQ ID NO: 14, SEQ ID NO: 15, SEQ ID NO: 17, SEQ ID NO: 21, SEQ ID NO: 22, SEQ ID NO: 24, SEQ ID NO: 26, SEQ ID NO: 27 and SEQ ID NO: 28, SEQ NO: 54, SEQ ID NO: 55, SEQ ID NO: 72, SEQ ID NO: 73, SEQ ID NO: 76, SEQ ID NO: 79, SEQ ID NO: 80, SEQ ID NO: 81, SEQ ID NO: 82, SEQ ID NO: 91, and SEQ ID NO: 126.

In another embodiment, the present invention provides an isolated polypeptide that contains a core structure which has an amino acid sequence of $WX_1X_2YW$, wherein $WX_1X_2YW$ is WVQYW (SEQ ID NO: 94), WYNYW (SEQ ID NO: 95), WMTYW (SEQ ID NO: 96), WATYW (SEQ ID NO: 97), WEMYW (SEQ ID NO: 98), WKDYW (SEQ ID NO: 99), WEHYW (SEQ ID NO: 100), WQNYW (SEQ ID NO: 101), WMQYW (SEQ ID NO: 103), WHAYW (SEQ ID NO: 104), WQTYW (SEQ ID NO: 105), WYAYW (SEQ ID NO: 107), WEDYW (SEQ ID NO: 108), WLQYW (SEQ ID NO: 111), and WLNYW (SEQ ID NO: 112).

In another aspect, the present invention provides an isolated polypeptide having a core structure of $WX_1X_2WW$.

In one embodiment, the present invention provides an isolated polypeptide that has an amino acid sequence of SEQ ID NO: 1, SEQ ID NO: 20, SEQ NO: 57, SEQ ID NO: 58, SEQ ID NO: 83, SEQ ID NO: 84, SEQ ID NO: 85, SEQ ID NO: 86, SEQ ID NO: 87, SEQ ID NO: 88, SEQ ID NO: 89, and SEQ ID NO: 90.

In another embodiment, the present invention provides an isolated polypeptide that contains a core structure which has an amino acid sequence of $WX_1X_2WW$, wherein $WX_1X_2WW$ is WEDWW (SEQ ID NO: 116), WIDWW (SEQ ID NO: 117), WDDWW (SEQ ID NO: 118), WEEWW (SEQ ID NO: 119), WQDWW (SEQ ID NO: 120), WENWW (SEQ ID NO: 121), WQNWW (SEQ ID NO: 122), WEKWW (SEQ ID NO: 123), WKDWW (SEQ ID NO: 124), and WKKWW (SEQ ID NO: 125).

In another aspect, the present invention provides an isolated polypeptide having a core structure of $WX_1X_2FW$.

In one embodiment, the present invention provides an isolated polypeptide that has an amino acid sequence of SEQ NO: 18, SEQ ID NO: 29, SEQ ID NO: 71, SEQ ID NO: 74, SEQ ID NO: 92, SEQ ID NO: 106, SEQ ID NO: 109, SEQ ID NO: 114, and SEQ ID NO: 115.

In another aspect, the present invention provides an isolated polypeptide having a core structure of $WWX_2X_3W$.

In one embodiment, the present invention provides an isolated polypeptide that has an amino acid sequence of SEQ ID NO: 102, SEQ ID NO: 110, and SEQ ID NO: 113.

In another aspect, the present invention provides an isolated polypeptide that is a cyclic polypeptide through a disulfide bond between two cysteine residues located at the N-terminus and the C-terminus.

In another aspect, the present invention provides an isolated polypeptide that is a cyclic polypeptide through a peptide bond between two amino acids (i.e., the alpha carboxyl of one amino acid residue at one terminus to the alpha amine of another amino acid residue at the other terminus).

In one embodiment, the present invention provides an isolated cyclic polypeptide that has an amino acid sequence of SEQ ID NO: 130 and SEQ ID NO: 131.

In one embodiment, the present invention provides an isolated cyclic polypeptide that has an amino acid sequence of SEQ ID NO: 177, SEQ ID NO: 178 and SEQ ID NO: 179.

In one embodiment, the present invention provides an isolated polypeptide that has an amino acid sequence of SEQ ID NO: 3, SEQ ID NO: 5, SEQ ID NO: 19, SEQ ID NO: 25, SEQ ID NO: 70, and SEQ ID NO: 93. The isolated polypeptide is capable of inhibiting the binding of IL-23 to IL-23 receptor and IL-23-mediated signaling.

In another aspect, the present invention provides an isolated polypeptide having a core structure of $WX_1X_2X_3W$. Preferably, the isolated polypeptide is 12 amino acids in length.

In another aspect, the present invention provides an isolated polypeptide of 9-18 amino acids in length. The isolated polypeptide comprises a core structure having an amino acid sequence of $WX_1X_2X_3W$, wherein W is tryptophan, $X_1$, $X_2$ and $X_3$ are amino acids, with the proviso that when one of $X_1$, $X_2$ or $X_3$ is W, the remaining $X_1$, $X_2$ or $X_3$ cannot be W. The isolated polypeptide binds to soluble recombinant human IL-23R and inhibits binding between IL-23 and its corresponding receptor thereof.

In another aspect, the present invention provides an isolated polypeptide having a length of 9-18 amino acids. The polypeptide comprises a core structure having an amino acid sequence of $WX_1X_2WW$ or $WWX_2X_3W$ where W is tryptophan and $X_1$, $X_2$ and $X_3$ are amino acids.

In one embodiment, the present invention provides an isolated polypeptide having a core structure of WEDWW (SEQ ID NO: 116), WIDWW (SEQ ID NO: 117), WDDWW (SEQ ID NO: 118), WEEWW (SEQ ID NO: 119), WQDWW (SEQ ID NO: 120), WENWW (SEQ ID NO: 121), WQNWW (SEQ ID NO: 122), WEKWW (SEQ ID NO: 123), WKDWW (SEQ ID NO: 124) or WKKWW (SEQ ID NO: 125).

In another aspect, the present invention provides an isolated polypeptide having a length of 9-18 amino acids. The polypeptide comprises a core structure having an amino acid sequence of WX$_1$X$_2$X$_3$W, wherein W is tryptophan and X$_1$, X$_2$ and X$_3$ are amino acids, with the proviso that when one of X$_1$, X$_2$ or X$_3$ is W, the remaining X$_1$, X$_2$ or X$_3$ cannot be W. The isolated polypeptide binds to soluble recombinant human IL-23R and inhibits binding between IL-23 and its receptor.

The present invention further provides the discovery of therapeutic peptides (using ribosome display screening) that are capable of inhibiting the binding of IL-23 to its corresponding receptor thereof. The therapeutic peptides have clinical application in the treatment of IL-23 associated immunological diseases including, in particular, Crohn's disease and inflammatory bowel diseases.

In another aspect, the present invention provides an isolated polypeptide having a length of 9-18 amino acids. The polypeptide comprises a core structure having an amino acid sequence of WX$_1$X$_2$YW, where W is tryptophan and X$_1$ and X$_2$ are amino acids. The isolated polypeptide binds to soluble recombinant human IL-23R and inhibits binding between IL-23 and its receptor.

In one embodiment, the present invention provides an isolated polypeptide having a core structure of WVDYW (SEQ ID NO: 150), WQDYW (SEQ ID NO: 151).

In one embodiment, the present invention provides an isolated polypeptide that has an amino acid sequence of SEQ ID NO: 3, SEQ ID NO: 5, SEQ ID NO: 19, SEQ ID NO: 25, SEQ ID NO: 70, and SEQ ID NO: 93. The isolated polypeptide is capable of inhibiting the binding of IL-23 to IL-23 receptor and IL-23-mediated signaling.

In another aspect, the present invention provides isolated polypeptides that inhibit IL-23 mediated cell signaling.

In one embodiment, the present invention provides a method of using an isolated polypeptide to inhibit cell functions including production and release of IL-22 in a cell. Preferably, the isolated polypeptide is a cyclic polypeptide (e.g., SEQ ID NO: 177, SEQ ID NO: 178, and SEQ ID NO: 179). Preferably, the cell is a peripheral blood mononuclear cell.

In one embodiment, the present invention provides a method of using an isolated polypeptide to inhibit cell functions including production and release of IL-17F from a Th17 cell. Preferably, the isolated polypeptide is a cyclic polypeptide (e.g., SEQ ID NO: 177, SEQ ID NO: 178, and SEQ ID NO: 179). Preferably, the Th17 cell is a splenocyte.

In another aspect, the present invention provides a pharmaceutical composition comprising the isolated polypeptides disclosed in this application, together with a pharmaceutically acceptable carrier. In one embodiment, the isolated polypeptides are cyclized. In one preferred embodiment, the cyclized polypeptides are SEQ ID NO: 177, SEQ ID NO: 178 and SEQ ID NO: 179.

In another aspect, the present invention provides a method of inhibiting the binding of IL-23 to IL-23 receptor on a cell and IL-23 mediated signaling thereof, comprising the steps of: a) providing a cell in need of treatment; and b) exposing the cell to an isolated polypeptide of the present invention.

In another aspect, the present invention provides a method of treating IL-23 associated diseases, comprising the steps of: a) identifying a human suspected of suffering an IL-23 associated disease; and b) administering a composition containing polypeptides of the present invention in an effective amount to block IL-23 binding to its receptor and subsequent cell signaling thereof.

BRIEF DESCRIPTION OF THE DRAWINGS

FIG. 2 depicts the amino acid sequences of six (6) novel types of polypeptides obtained following screening of the Phage Display Library with the Δ9-Flag protein. Note that some of these polypeptides have the same repeated amino acid sequences (e.g., polypeptide nos. 52, 65, 71, 74 and 77). The tryptophan residues within the polypeptides are highlighted.

FIG. 4 depicts the amino acid sequences of twenty-two (22) novel types of polypeptides obtained after screening of the Phage Display Library with the IL-23R/Fc fusion protein. Note that some of these polypeptides have the same repeated amino acid sequences (e.g., polypeptide nos. 4, 12, 26 and 28). Polypeptide no. 23 (in the IL-23R/Fc fusion protein assay) has the same amino acid sequence as polypeptide no. 52 (in the Δ9-Flag protein assay). The tryptophan residues within the polypeptides are highlighted.

FIG. 6 depicts the binding between the phages bearing some of the screened polypeptide sequences (i.e., polypeptide nos. 1, 2, 3, 4, 5, 6, 7, 9, 10, 12, 13, 14, 15 and 16) with the IL-23R/Fc fusion protein in the Phage ELISA. The degree of binding is reflected by OD$_{450}$, which is provided in the figure. Phages that did not express polypeptide sequences (i.e., empty phage) served as a negative control.

FIG. 7 depicts all of the screened polypeptides obtained after the Phage Display Screening (using both the Δ9-Flag protein assay and the IL-23R/Fc fusion protein assay). (See, FIGS. 1 and 3). A total of twenty-seven (27) novel polypeptides and their amino acid sequences are listed. The frequency of polypeptides having the repeated amino acid sequences is provided. The tryptophan residues within the 27 polypeptides are highlighted.

FIG. 8 depicts Sequence Analysis of the eighteen (18) unique polypeptide sequences obtained after Phage Display Screening (using both the Δ9-Flag protein assay and the IL-23R/Fc fusion protein assay). Sequence Analysis reveals the core structure of WX$_1$X$_2$X$_3$W. The sequences were aligned at tryptophan (W) residues to demonstrate the presence of the core structure within the polypeptide sequences.

FIG. 9 depicts the Sequence Analysis of eleven (11) polypeptides obtained after Phage Display Screening (using both the Δ9-Flag protein assay and the IL-23R/Fc fusion protein assay). Note that two (2) polypeptides have the core structure of WXnWW, one (1) polypeptide has the core structure of WWXnW, and five (5) polypeptides have one (1) tryptophan (W) within the amino acid sequences.

FIG. 21 depicts the cell surface expression of IL-23R on Jurkat T cells and DB cells using Flow Cytometry. Cells were stained with isotype control or anti-IL-23R antibodies. Significant increase in fluorescence was observed in DB cells, but not in Jurkat T cells indicating IL-23R on DB cells.

FIG. 25 depicts a parallel reduction between IL-23R expression and polypeptide binding. siRNA was used to reduce IL-23R expression on DB cells. IL-23R expression and binding of polypeptide no. 1-Fc fusion protein were monitored by Flow Cytometry.

FIG. 39 depicts the $IC_{50}$ values of polypeptide on its ability to inhibit binding of IL-23 to its receptor. IL-23 binding to its receptor was monitored by Competitive ELISA.

FIG. 41 depicts the $IC_{50}$ values of polypeptide on its ability to inhibit binding of IL-23 to its receptor. IL-23 binding to its receptor was monitored by Competitive ELISA.

FIG. 43 depicts the $IC_{50}$ values of polypeptide and peptide-Fc fusion protein on its ability to inhibit binding of IL-23 to its receptor. IL-23 binding to its receptor was monitored by Competitive ELISA.

FIG. 45 depicts the $IC_{50}$ values of polypeptide and peptide-Fc fusion protein on its ability to inhibit binding of IL-23 to its receptor. IL-23 binding to its receptor was monitored by cell-based assay using the DB cells stably transfected with STAT3-Luc reporter construct.

FIG. 47 depicts the $IC_{50}$ values of polypeptides and peptide-Fc fusion protein on its ability to inhibit binding of mouse IL-23 to mouse IL-23R. Mouse IL-23 binding to its receptor was monitored by Competitive ELISA.

FIG. 49 depicts the amino acid sequence of p19 subunit of IL-23 cytokine The position of tryptophan residue is highlighted in the figure. Totally, five (5) tryptophan residues are found in the p19 subunit of IL-23 cytokine FIG. 50 depicts the ELISA to measure the secreted level of IL-23 cytokines from the cells transfected with IL-23 expression constructs. Recombinant IL-23 (rIL-23) is used as positive control.

FIG. 55 depicts the sequence of inhibitory peptide no. 23.15 (SEQ ID NO: 126), for the IL-23R pathway. This peptide no. 23.15 (SEQ ID NO: 126) binds to IL-23 receptor and inhibits the binding of IL-23 cytokine to its receptor. The underlined residues, tryptophan (W) and tyrosine (Y), and their spacing are important to the peptide activity. Based on this information, targeted library was generated. The sequence of targeted peptide library was illustrated in the figure.

FIG. 57 depicts the DNA sequence of targeted peptide library for the ribosomal display screening. The underlined represents the DNA sequence of the 12 amino acid peptide library.

FIG. 59 depicts the peptide sequences after $8^{th}$ round of selection. Twenty-four (24) independent clones were picked and analyzed.

FIG. 60 depicts the frequency of peptides after $8^{th}$ round of selection.

FIG. 61 depicts the grouping of peptides. The identified peptides were classified into three (3) groups, Groups A, B, and C, based on the sequence of the core motif "$WX_1X_2YW$." Groups A and B contain "WVDYW" core (SEQ ID NO: 150) and "WQDYW" core (SEQ ID NO: 151) respectively. Group C represents peptides containing other core sequences.

FIG. 63 depicts the $IC_{50}$ values of the polypeptides' ability to inhibit the binding of IL-23 to its receptor. IL-23 binding to its receptor was monitored by competitive ELISA.

FIG. 64 depicts the $IC_{50}$ values of the polypeptides' ability to inhibit the binding of IL-23 to its receptor. IL-23 binding to its receptor was monitored by cell-based assay using the DB cells stably transfected with STAT3-Luc reporter construct.

Figure 68:
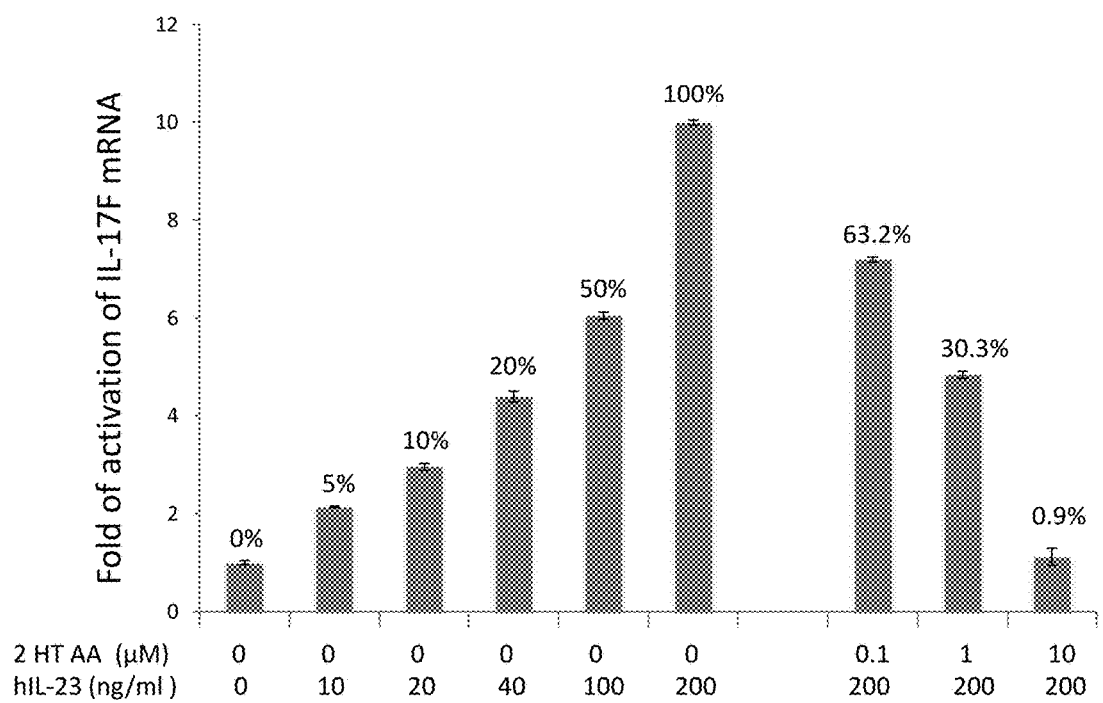

FIG. 68 depicts the dose-response curve of cyclic polypeptide no. 2HT AA (SEQ ID NO: 177) to inhibit mRNA expression of IL-17F upon IL-23 stimulation in the rat splenocytes and a summary of its $IC_{50}$ value.

DETAILED DESCRIPTION OF THE INVENTION

The present invention can be better understood from the following description of preferred embodiments, taken in conjunction with the accompanying drawings. It should be apparent to those skilled in the art that the described embodiments of the present invention provided herein are merely exemplary and illustrative and not limiting.

Definitions:

As used herein, the term "IL-23" refers to Interleukin-23. IL-23 is a heterodimeric cytokine consisting of two subunits; namely, p19 (IL-23 alpha subunit) (nucleotide sequence— NCBI NM_016584; protein sequence—NCBI NP 057668), and p40 (IL-12 beta subunit) (nucleotide sequence—NCBI NM_002187; protein sequence—NCBI NP_002187).

As used herein, the term "IL-23R" refers to the interleukin-23 receptor. IL-23R is composed of two (2) subunits: namely, IL-23Rα (mRNA sequence NCBI-NM_144701, protein sequence NCBI NP_653302) and IL-12Rβ1 (mRNA and protein sequences NCBI-NM_005535). The IL-23Rα gene is located on chromosome 1p31.3. The full-length translated IL-23R protein is a type I cytokine receptor. Human IL-12β1, when partnered with human IL-12β2, forms a different interleukin receptor (i.e., IL-12 receptor).

As used herein, the term "Δ9" refers to the naturally-occurring truncated IL-23Rα resulting from IL-23Rα gene splicing. For purposes of this application, "Δ9 variant", "Δ9 isoform", and "Δ9 protein" are used interchangeably to refer to this particular naturally-occurring truncated IL-23Rα protein. The Δ9 protein has 348 amino acids plus eight (8) novel amino acid sequences unique to Δ9 protein (i.e., a total of 356 amino acids). The signal sequence (i.e., 1-23 amino acids) on the immature Δ9 protein (located inside the cells) is cleaved before the mature Δ9 protein is released outside of the cells. The mature Δ9 therefore has a total of 333 amino acids (i.e., 24-356). For purposes of this application, therefore, the term "Δ9" is intended to include both of these two (2) forms. The immature Δ9 (i.e., containing 1-23 signal peptide and amino acid residues 24-348 and the eight (8) novel amino acid sequence) has an amino acid sequence set forth in SEQ ID NO: 126.

As used herein, the term "IL-23 mediated cell signaling" refers to a detectable biological activity after IL-23 binding to the IL-23 receptor and includes, for example, STAT3 phosphorylation and the stimulation of chemokines, cytokines or pro-inflammatory molecules.

As used herein, the term "IL-23 associated disease" refers to a disease condition that results from abnormal activity of IL-23 or its receptor and includes, for example, inflammatory bowel diseases, Crohn's disease, ulcerative colitis, psoriasis, multiple sclerosis, and the like.

As used herein, the term "amino acid" refers to a molecule containing an amine group, a carboxylic acid group and a side-chain that varies between different amino acids. Amino acids are the structural units that make up proteins. Twenty-two amino acids are naturally incorporated into polypeptides and are called natural amino acids. Non-natural amino acids refers to those amino acids that are not found in proteins (for example carnitine, GABA, and L-DOPA), or are not produced directly and in isolation by standard cellular machinery (for example, hydroxyproline and selenomethionine). Got purposes of this application, amino acids may include non-naturally occurring amino acids including, for example, lanthionine, 2-aminoisobutyric acid, dehydroalanine, gamma-aminobutyric acid, and the like.

As used herein, "amino acid" may be represented by either the full name of the amino acid, standard three-letter code, or standard single-letter code as below: A=Ala; C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr.

As used herein, the term "polypeptide" refers to an amino acid chain comprising two or more amino acids. The terms "protein", "polypeptide", and "peptide" are used synonymously in this application.

As used herein, the term "core structure" refers to an amino acid sequence that is present in many of the isolated polypeptides screened using a Phage Display Library and human IL-23R in the present invention. The core structure comprises two tryptophan (W) residues separated by amino acid residues. An example of a core structure is $WX_1X_2X_3W$ (W=tryptophan and $X_1$, $X_2$ and $X_3$ are amino acid residues). Another example of a core structure is $WX_1X_2X_3 X_4X_5X_6W$ (W=tryptophan and $X_1$, $X_2$, $X_3$, $X_4$, $X_5$, and $X_6$ are amino acid residues). All of the screened isolated polypeptides have the ability to (i) bind human IL-23R, (ii) inhibit IL-23 binding to IL-23R and (iii) inhibit the IL-23 mediated subsequent cellular signaling thereof.

As used herein, the term "isolated" refers to polypeptides that are essentially free of other substances with which they may be found in vivo or as a result of being produced synthetically.

As used herein, the term "FLAG" refers to a protein tag that can be added to a protein using recombinant DNA technology. The peptide sequence of the FLAG-tag is: N-DYKDDDDK-C(1,012 Da). The insertion of a FLAG permits the protein to be isolated by affinity chromatography; for example, separating a recombinant over-expressed protein from a wild-type protein expressed by a host organism. FLAG can also be used in the isolation of protein complexes. Inserting a FLAG-tag to a protein also allows one to purify the protein with an antibody against the FLAG sequence. Examples are cellular localization studies by immunofluorescence or detection by SDS PAGE protein electrophoresis.

As used herein, the term "cyclic polypeptide" refers to a polypeptide chain whose amino and carboxyl termini are themselves linked together with a peptide bond or a disulfide bond to form a circular chain. In the case of a peptide bond, the linkage is between the alpha carboxyl of one amino acid residue at one terminus to the alpha amine of another amino acid residue at the other terminus. In the case of a disulfide bond, the linkage is between one cysteine at one terminus and another cysteine at another terminus; the formation of a disulfide bond occurs between the two cysteines (i.e., formation of a cystine). For purposes of this application, cyclic polypeptides may also include linkage other than a peptide bond such as non-alpha amide linkage, thioether linkage between Trp and Cys residues.

As used herein, the term "Phage Display Screening" refers to a method for studying protein-peptide interactions that uses bacteriophages that have been genetically engineered to express a set of peptides on their outer surface. Phage Display was originally invented by George P. Smith in 1985. Smith demonstrated the display of peptides on filamentous phage by fusing the peptide of interest on to gene3 of filamentous phage. The connection between genotype and phenotype enables large libraries of proteins (i.e., a phage display library) to be screened and amplified in a process called in vitro selection or bio-panning.

The term "inhibit" refers to a decrease of a biological activity. For purposes of this application, biological activity includes IL-23 cell signaling.

As used herein, the term "treat" or "treatment" as used within the context of the present invention are meant to include therapeutic as well as prophylactic treatments for the diseases. Thus, for example, it includes the administration of the peptides prior to or following the onset of the IL-23 associated diseases thereby preventing clinical signs of the IL-23 associated diseases. As another example, administration of the peptides after clinical manifestation of the diseases to combat the symptoms of the IL-23 associated disease comprises "treatment" of the diseases. Those "in need of treatment" include humans who already having the IL-23 associated diseases.

As used herein, the term "ELISA" refers to "Enzyme-Linked ImmunoSorbent Assay" and is a biochemical technique used in detecting the presence of antibody or antigen in a sample.

As used herein, the term "Competitive ELISA" refers to an ELISA performed using two ligands for a target molecule to determine relative signal and binding affinities of the two ligands.

As used herein, the term "STAT3" (also known as signal transducer and activator of transcription 3) (NCBI Accession No. NP_003141) refers to the transcription factor which in humans is encoded by the STAT3 gene.

As used herein, the term "$IC_{50}$" refers to half maximal inhibitory concentration ($IC_{50}$). $IC_{50}$ is a measure of the effectiveness of a compound in inhibiting biological or biochemical function. This quantitative measure indicates how much of a particular drug or other substance is needed to inhibit a given biological process by half.

As used herein, the term "cyclic peptides" or cyclic polypeptides" refer to polypeptide chains wherein the amino termini and carboxyl termini, amino termini and side chain, carboxyl termini and side chain, or side chain and side chain are linked with a covalent bond that generates a ring. A cyclic peptide can be created by a disulfide bond between two cysteine residues located at the N-terminus and the C-terminus or by a peptide bond between two amino acids (i.e., the alpha carboxyl of one amino acid residue at one terminus to the alpha amine of another amino acid residue at the other terminus).

As used herein, the term "IL-22" refers to Interleukin-22 (NCBI NM_020525). IL-22 is an α-helical cytokine IL-22 has important functions in host defense at mucosal surfaces as well as in tissue repair. It is unique as a cytokine that is produced by immune cells, including T-helper (Th) cell subsets and innate lymphocytes, but acts only on non-hematopoietic stromal cells. IL-22 binds to a heterodimeric cell surface receptor (IL-22R) composed of subunits IL-10R2 (NCBI NM_000628) and IL-22R1 (NCBI NM_181310). IL-22R is expressed on epithelial cells, keratinocytes, hepatocytes, and pancreatic islets and it is absent on immune cells.

As used herein, the term "IL-17F" refers to Interleukin-17F (NCBI NM_052872) IL-17F is a cytokine that is expressed by activated T cells, and has been shown to stimulate the production of several other cytokines, including IL6, IL8, granulocyte colony-stimulating factor, and can regulate cartilage matrix turnover. IL-17F also stimulates PBMC and T-cell proliferation and inhibits angiogenesis and CSF2/GM_CSF. IL-17F also induces endothelial cells to produce IL2, TGFB1/TGFB, and monocyte chemoattractant protein-1.

As used herein, the term "Th17 cell" refers to a subset of T helper cells that produce IL-17. Th17 cells create inflammation and tissue injury in autoimmune diseases and allergen-induced airway responses.

As used herein, the term "PBMC" refers to peripheral blood mononuclear cells. PBMC is any blood cell having a round nucleus (e.g., lymphocytes, monocytes and macrophages). PBMCs are a critical component in the immune system to fight infection.

As used herein, the term "splenocyte" refers to different white blood cell types in the spleen or purified from splenic tissue.

As noted above, the present invention is generally directed to compositions and methods for treatment of IL-23 mediated diseases in human. In one aspect, the composition includes polypeptides that inhibit binding of IL-23 to its corresponding receptor and inhibit its cellular activation thereof.

In accordance with the present invention, the present inventors used a Phage Display Screening Assay. A phage library containing a large collection of peptides (i.e., containing approximately $1 \times 10^{11}$ pfu random peptide sequences) was screened based on binding ability towards IL-23R. In this study, we used a phage library that displayed 12-mer polypeptides. The phage library was screened using soluble IL-23R to identify polypeptides of interest (i.e., those that would bind to IL-23R). One skilled in the art would recognize that the polypeptides displayed on the phage surface are not limited to 12-mer in length. Indeed, the polypeptides of the present invention would encompass various amino acid lengths insofar as they possess the binding ability towards IL-23R. Exemplary amino acid lengths include, but not limited to, 14-mer, 16-mer, 18-mer and the like.

In order to screen polypeptides with respect to its ability to bind IL-23R, we used a soluble form of IL-23R. In one embodiment, Phage Display Screening was conducted using a Δ9 IL-23R protein (i.e., IL-23R lacking a transmembrane domain, and thus render the receptor soluble). A particular Δ9 IL-23R protein used in the assay is the soluble IL-23R protein that has an amino acid sequence set forth in SEQ ID NO: 126. This particular Δ9 protein is a soluble form of IL-23R that lacks the trans-membrane domain. To screen the bound polypeptides that bind to soluble IL-23R, the IL-23R is coupled to a Flag protein (SEQ ID NO: 128). Anti-Flag affinity gel (e.g., agarose) is then used to capture the random polypeptides that interact with Δ9 IL-23R-Flag (which is precipitated by an anti-Flag affinity agarose) (See, FIG. 1).

The polypeptides of the present invention are screened and selected based on a unique function that is equally shared by all the screened polypeptides; that is, they bind to IL-23R. In one embodiment, the polypeptides of the present invention bind specifically to IL-23R that is integrally expressed on a cell membrane (i.e., IL-23R having a transmembrane domain). In another embodiment, the polypeptides of the present invention bind specifically to a soluble IL-23R (e.g., IL-23R lacking a transmembrane domain). Binding of the polypeptides to IL-23R (either membrane bound IL-23R or soluble IL-23R) may be determined using a binding assay specifically designed to detect the binding between a polypeptide and the IL-23R.

In one embodiment, binding of polypeptides to IL-23R can be determined using an IL-23R expressing cell. An exemplary IL-23R expressing cell may include a cell line that is stably transfected with IL-23R cDNA.

In another embodiment, soluble IL-23R may be employed to develop a binding assay with a polypeptide. An exemplary soluble IL-23R includes, but not limited to, Δ9 protein. Another exemplary soluble IL-23R is IL-23R coupled with Fc (i.e., fusion protein).

Other binding assays known to the art may be used to assess the binding of a polypeptide with IL-23R. One exemplary assay is immunoprecipitation. One skilled in the art would recognize that an immunoprecipitation assay often involves the use of a bead (e.g., agarose beads) to immunoprecipitate a polypeptide of interest. To better detect the binding in an immunoprecipitation assay, polypeptides are often labeled with a radioactive agent or a fluorescent compound.

Using the Flag protein approach, we have identified a total of 13 polypeptides (i.e., peptide nos. 52, 60, 61, 65, 68, 70, 71, 72, 74, 75, 77 and 79) (See, FIG. 2). Based on many of these polypeptides having overlapping and identical amino acid sequences (e.g., peptide nos. 52=65=71, and 60=68) (See, FIG. 2), we have identified a total of six (6) novel peptide sequences.

In another embodiment, Phage Display Screening was conducted using a different soluble IL-23R. A particular soluble IL-23R used in our study is IL-23R-Fc chimera. This particular IL-23R has the full-length IL-23R amino acid sequence, but coupled with an Fc region of human $IgG_1$. To screen the bound polypeptides that bind to soluble IL-23R, the IL-23R is coupled with the Fc (i.e., Fc fusion protein). A protein A sepharose is then used to capture the random polypeptides that interact with the IL-23R-Fc fusion protein (which is precipitated by a protein-A sepharose).

Using the IL-23R-Fc chimera protein approach, we have identified a total of 29 polypeptides (i.e., peptide nos. 1, 2, 3, 4, 5, 6, 7, 9, 10, 12, 13, 14, 15, 16, 18, 19, 20, 21, 22, 23, 24, 25, 26, 27, 28, 29, 30, 31 and 32) (See, FIG. 4). Because some of these polypeptides have overlapping and identical amino acid sequences (e.g., peptide nos. 5=16=31, 20=21, and 4=12=26=28) (See, FIG. 4), there are a total of 23 novel peptide sequences.

It is noted that one (1) polypeptide sequence was identified both in the Flag protein approach and in the IL-23R-Fc chimera protein approach.

Accordingly, using soluble IL-23R (i.e., both Flag protein approach and IL-23R-Fc chimera protein approach) in a Phage Display Screening assay, we have identified a total of 28 novel polypeptides that bound IL-23. It is noted that the Flag protein approach generates fewer polypeptides in comparison to the IL-23R-Fc chimera approach. This may be attributed to the finding that the Flag protein approach has yielded a higher background (i.e., anti-Flag and Flag may provide non-specific screening—that is, a false positive result). Many of the screened polypeptides in fact were due to Flag sequences. On the other hand, the use of IL-23R-Fc chimera in our Phage Display Screening provides optimal results.

The polypeptides of the present invention may be made by synthetic methods. Preferably, solid phase synthesis techniques may be used to prepare the present polypeptides. Suitable techniques are well known in the art. For example, Merrifield, Chem. Polypeptides, pages 335-361 (Katsoyannis and Panayotis editors) (1973); Merrifield, J. Am. Chem. Soc., Volume 85, page 2149 (1963); Davis et al., Biochem. Intl., Volume 10, pages 394-414 (1985); Stewart and Young, Solid Phase Peptide Synthesis (1969); U.S. Pat. No. 3,941, 763; Finn et al., The Proteins (3d edition), Volume 2, pages 105-253 (1976). Solid phase synthesis is the preferred technique for making individual polypeptides because of its cost-effectiveness.

In one embodiment, the present invention provides modifications of inhibitory polypeptides such as cyclic polypeptide or Fc coupled polypeptides. The modification can protect therapeutic peptides from proteolytic enzymes, increase stability as well as enhance circulation time of the peptides. Thus, the modified polypeptides possess an enhanced biological activity of the therapeutic molecule. The techniques for protein modification and Fc fusion proteins are known to one skilled in the art. (See, for example, WO 00/24782 which describes fusion proteins comprising Fc antibody domains linked to biologically active peptides and their use as pharmaceutical agents).

In one embodiment, the modified polypeptide is cyclic. For example, the polypeptide may be modified to contain two Cys residues at the C-terminus and N-terminus, which could cyclize by disulfide bond formation. The cyclization of linear peptides to obtain cyclized polypeptides having the core structure according to the present invention can be carried out by various methods known to the person skilled in the art.

In one embodiment, the inhibitory polypeptides are coupled to the "Fc" domain of an antibody. Antibodies contain two functionally independent parts, a variable domain known as "Fab", which binds antigen, and a constant domain known as "Fc", which functions as complement activation and binds to the Fc receptor present on the phagocytic cells (e.g., macrophages). Because of its size, an Fc domain generally has a long serum half-life as compared to that of a Fab which is short-lived. (See, Capon et al., Nature, Volume 337, pages 525-31 (1989)). The Fc domain may be fused to the N-terminus or C-terminus of the polypeptide or at both the N- and C-termini. The coupling of a polypeptide (linear or cyclic) to an Fc can provide longer half-life and offers additional advantages of Fc receptor binding and protein A binding. Preferably, the immunoglobulin source of the native Fc is of human origin (to avoid antibody-antigen reaction during human therapeutic application of the polypeptides). Preferably, the Fc may be $IgG_1$ and $IgG_2$. One example of a native Fc is a disulfide-bonded dimer resulting from papain digestion of an IgG. (See, Ellison et al., Nucleic Acids Res., Volume 10, pages 4071-4079 (1982).

In one embodiment, the modified polypeptides may be synthesized by well-known organic chemistry techniques. Alternatively, the modified peptides of the invention may be made in transformed host cells using recombinant DNA techniques. To do so, a recombinant DNA molecule coding for the peptide is prepared. Methods of preparing such DNA molecules are well known in the art. See, generally, Watson et al., Molecular Biology of the Gene, Volumes I and II, The Benjamin/Cummings Publishing Company, Inc., Menlo Park, Calif. (1987); Sambrook et al., Molecular Cloning, A Laboratory Manual, Cold Spring Harbor Laboratory Press, Cold Spring Harbor, N.Y. (1989)). These references are herein entirely incorporated by reference. In one embodiment, a vector capable of expressing the peptides or modified peptides in an appropriate host. The vector comprises the DNA molecule that codes for the peptides or modified peptides operatively linked to appropriate expression control sequences. Expression control sequences include promoters, activators, enhancers, operators, ribosomal binding sites, start signals, stop signals, cap signals, polyadenylation signals, and other signals involved with the control of transcription or translation. The resulting vector having the DNA molecule thereon is used to transform an appropriate host. This transformation may be performed using methods well known in the art. Preferably, microbial hosts include bacteria such as *Escherichia* (*E. coli*) and the like. Preferred strains of *Escherichia coli* includes, for example, HB101, (ATCC NO. 33694) DH5α, DH10, and MC1061 (ATCC NO. 53338)).

The present invention provides a total of twenty-eight (28) novel amino acid sequences (screened and isolated from our Phage Display library) that exhibit the ability to bind to IL-23R. The screened polypeptides are shown to have the ability to bind IL-23R.

For purposes of this application, the polypeptides can be linear or cyclic. Preferably, the polypeptides are cyclic. The present invention also provides methods of using the polypeptides or pharmaceutical compositions of the inventive peptides in the treatment of IL-23 associated diseases. The present polypeptides are capable of binding to IL-23R and blocking the IL-23 mediated cell signaling. The therapeutic application of the polypeptides (linear or cyclic) includes treatment of immunological diseases where overt production of IL-23 is a key feature. For example, the polypeptides can be used to suppress immunological responses in a cell or human diseases such as Crohn's disease and inflammatory bowel diseases as well as in general inflammation such as arthritis, rheumatic diseases, lupus, osteoarthritis, inflammatory bowel disorders, psoriasis, and the like. The peptides of the invention also have therapeutic value for the prevention of immunological diseases often characterized by IL-23.

The present invention also relates to the use of one or more of the peptide of the present invention in the manufacture of a medicament for the treatment of a disorder such as any one of those mentioned above.

Amino acid sequences of the screened polypeptides were determined by sequencing. When the amino acid sequences of the screened polypeptides are aligned, many polypeptides exhibit a unique feature of an amino acid sequence (which we called a "core structure"). Based on the presence of the unique feature, the screened polypeptides can be categorized into two (2) general classes.

The first class of the screened polypeptides encompasses novel polypeptides that share a core structure of amino acids. This class occupies about seventy-five percent (82%) (23/28) of the total screened polypeptides. All of the polypeptides possess a core structure that contains an amino acid motif comprising two (2) tryptophan (W) residues separated by a few amino acids. For example, the two (2) tryptophan (W) residues are separated by one (1), three (3), six (6) or eight (8) amino acids.

In one embodiment, the core structure is composed of two (2) tryptophan (W) residues separated by one (1) amino acid residue (i.e., $WX_1W$) where $X_1$ is an amino acid other than tryptophan. An example of this core structure includes SEQ ID NO: 16 (peptide no. 13).

In another embodiment, the core structure is composed of two (2) tryptophan (W) residues separated by three (3) amino acid residues (i.e., $WX_1X_2X_3W$) where $X_1$, $X_2$ and $X_3$ are three (3) separate amino acids. Examples of this core structure include SEQ ID NO: 1 (peptide no. 23, 52, 65, 71, 74, 77); SEQ ID NO: 2 (peptide no. 60, 68); SEQ ID NO: 4 (peptide no. 66, 70, 72); SEQ ID NO: 7 (peptide no. 1); SEQ ID NO: 10 (peptide no. 4, 12, 26, 28); SEQ ID NO: 13 (peptide no. 7); SEQ ID NO: 14 (peptide no. 9); SEQ ID NO: 15 (peptide no. 10); SEQ ID NO: 17 (peptide no. 14); SEQ ID NO: 18 (peptide no. 15); SEQ ID NO: 20 (peptide no. 19); SEQ ID NO: 21 (peptide no. 20, 21); SEQ ID NO: 22 (peptide no. 22); SEQ ID NO: 23 (peptide no. 23, 52, 65, 71, 74, 77); SEQ ID NO: 24 (peptide no. 24); SEQ ID NO: 25 (peptide no. 25); SEQ ID NO: 26 (peptide no. 27); SEQ ID NO: 27 (peptide no. 29); SEQ ID NO: 28 (peptide no. 30); or SEQ ID NO: 29 (peptide no. 32).

In another embodiment, the core structure is composed of two (2) tryptophan (W) residues separated by six (6) amino acid residues (i.e., $WX_1X_2X_3X_4X_5X_6W$, where $X_1$, $X_2$, $X_3$, $X_4$, $X_5$, and $X_6$ are six (6) separate amino acids. Examples of this core structure include SEQ ID NO: 8 (peptide no. 2) and SEQ ID NO: 19 (peptide no. 18).

In another embodiment, the core structure is composed of two (2) tryptophan (W) residues separated by eight (8) amino acid residues (i.e., $WX_1X_2X_3X_4X_5X_6X_7$, $X_8W$, where $X_1$, $X_2$, $X_3$, $X_4$, $X_5$, $X_6$, $X_7$, and $X_8$ are eight (8) separate amino acids. Examples of this core structure include SEQ ID NO: 6 (peptide no. 79).

Polypeptides that include the core structure (e.g., $WX_1W$, $WX_1X_2X_3W$, $WX_1X_2X_3X_4X_5X_6W$, and the like) have the ability to bind IL-23R and inhibit IL-23 notwithstanding the remainder of the polypeptide sequence.

The second class of the screened polypeptides encompasses novel polypeptides that do not contain a recognizable core structure, despite having a similar ability to bind to IL-23R (as compared to the first class of polypeptides). This class occupies eighteen (18) percent (18%) (5/28) of the total screened polypeptides. Examples of these polypeptide include SEQ ID NO: 3 (peptide no. 61); SEQ ID NO: 5 (peptide no. 75); SEQ ID NO: 9 (peptide no. 3); SEQ ID NO: 11 (peptide no. 5, 16, 31); SEQ ID NO: 12 (peptide no. 6).

The novel polypeptides were tested for their ability to inhibit IL-23 using a Competitive ELISA. In such an assay, IL-23R/Fc fusion protein was immobilized on a solid support. In this instance, the solid support was a 96-well plate, but the support may be any support that is typically used for an ELISA. The novel polypeptide and IL-23 were allowed to compete for binding to the immobilized IL-23R/Fc fusion protein. IL-23 that bound to IL-23R-Fc was detected using biotinylated anti-p40 antibody. The bound anti-p40 antibody was detected using streptavidin-horseradish peroxidase (HRP) and a tetramethylbenzidine (TMB) substrate was added to measure peroxidase activity. The color was measured at optical density (OD) $450_{nm}$. The color intensity was directly proportional to the amount of the bound IL-23 protein. The Competitive ELISA demonstrated that the novel polypeptides inhibit IL-23 binding to IL-23R. (See, FIG. 16.)

It was found that the novel peptides could effectively inhibit the biological effects of IL-23 binding to IL-23R. It is recognized that the protein STAT3 is phosphorylated in response to IL-23 binding to IL-23R. Phosphorylation of STAT3 (i.e., formation of pSTAT3) results in the production of IL-17 and IL-17F, which, in turn, produce the inflammatory response associated with diseases including, but not limited to, psoriasis, irritable bowel disease, Crohn's disease and ulcerative colitis. Thus, it is generally recognized that reduced levels of STAT3 phosphorylation indicate decreased levels of IL-23 mediated cell signaling and correspondingly, will result in reduced inflammation levels.

pSTAT3 levels in the cell lysate of DB cells that were treated with the novel synthetic polypeptide (i.e., polypeptide no. 1 (SEQ ID NO: 7), 7 (SEQ ID NO: 13), 16 (SEQ ID NO: 11)) and IL-23 was measured using polyclonal rabbit anti-p-STAT3 antibodies (Cell Signaling Technology, Beverly, Mass.). Polypeptide nos. 1 and 7, which had previously been shown to bind strongly to IL-23R and inhibit IL-23, reduced pSTAT3 levels in cell lysates. Polypeptide no. 16, which demonstrated limited ability to bind to IL-23R and inhibit IL-23, did not show perceptible pSTAT3 reduction when pSTAT3 levels were measured by Western blot. Polypeptide nos. 1 (SEQ ID NO: 7) and 7 (SEQ ID NO: 13) both belong to the first class of polypeptides that include a core structure composed of two (2) tryptophan (W) residues separated by three (3) amino acid residues (i.e., $WX_1X_2X_3W$). Polypeptide no. 16 (SEQ ID NO: 11) belongs to the second class of polypeptides that do not include a recognizable core structure.

Evaluation of IL-23 mediated cell signaling activity need not be limited to measuring pSTAT3 and STAT3 levels. The inhibition of other components of the IL-23 signaling pathway (e.g., the Jak-STAT signaling cascade) may also be used to determine if a polypeptide is inhibiting IL-23 mediated cell signaling. For example, IL-23 mediated cell signaling can be assessed by determining translocation of STAT3 to the nucleus, activity of the IL-17A and IL-17F genes, or the differentiation of Th17 cells. These cell signaling assays are well known in the art and one of ordinary skill in the art would be able to optimize the assays for its application to the present invention.

It is noted that polypeptides that include the core structure may tolerate some variations and still possess its ability to bind IL-23R and inhibit IL-23 mediated cell signaling thereof. It is intended that the present invention encompasses variants that still possess the biological activity of binding to IL-23R and inhibits its subsequent cell signaling. Accordingly, polypeptides of the present invention retain their biological activity notwithstanding the position of the core structure (e.g., $WX_1X_2X_3W$) within the length of the polypeptide.

In one embodiment, the present invention encompasses polypeptides that contain the core structure insofar as they inhibit binding and signaling of IL-23R. It is found that the location of the core structure may vary within the polypeptide without affecting the ability of the polypeptide to bind IL-23R and inhibit IL-23. For example, in some instances (e.g., peptide nos. 9, 10, 19, 22, 24, 25, 30, 32), the core structure is located nearer the amino terminus of the polypeptide. In other instances (e.g., peptide nos. 4, 12, 26, 28), the core structure is located nearer the carboxy terminus of the polypeptide. In yet other instances (e.g., peptide no. 7, 14, 18, 20, 21, 23, 29, 52, 60, 65, 66, 68, 70, 71, 72, 74, 77, 79), the core structure is centrally located within the polypeptide. The present invention encompasses all of these polypeptides containing the core structure, regardless its location.

In another embodiment, the present invention is directed to polypeptides that have an overall length of twelve (12) amino acid residues. In our initial screening, it was found that certain polypeptides having twelve (12) amino acid residues are effective at binding IL-23R and inhibiting IL-23. It is noted that polypeptides of varying amino acid lengths are functionally equivalent in the binding assays and Competitive ELISA described herein. In one embodiment, polypeptides that include a core structure and have an overall length of nine (9) amino acids bind to IL-23R and inhibit IL-23 (see, e.g., SEQ ID NO: 56 (peptide no. 23.1)). In one embodiment, polypeptides that include a core structure and have an overall length of sixteen (16) amino acids bind to IL-23R and inhibit IL-23 (see, e.g., SEQ ID NO: 54 (peptide no. 1.5) and SEQ ID NO: 57 (peptide no. 23.2), respectively). In one embodiment, polypeptides that include a core structure and have an overall length of eighteen (18) amino acids bind to IL-23R and inhibit IL-23 (see, e.g., SEQ ID NO: 55 (peptide no. 1.6) and SEQ ID NO: 58 (peptide no. 23.3)). Accordingly, the overall amino acid length of the polypeptide (having a core structure) may vary insofar as the polypeptide can function to inhibit binding of IL-23R and IL-23 cell signaling. Preferably, the overall amino acid length of the polypeptide covers from nine (9) to eighteen (18) amino acids. Preferably, the overall amino acid length of the polypeptide is twelve (12) amino acids.

Polypeptides of the present invention may be modified, for example, substitution, deletion, or addition of amino acids that have minimal influence on the inhibiting activity towards IL-23R binding and cell signaling thereof. In the present invention, it should be noted that substitution of either tryptophan (W) on each side of the core structure destroys the polypeptide's functionality (i.e., its ability to bind IL-23R and inhibit IL-23). Exemplary of such substitution includes polypeptides of SEQ ID NOs: 45-47. Insofar as the two (2) tryptophan (W) residues are present in the polypeptide (i.e., the core structure is present), the polypeptides are found to tolerate some amino acid changes throughout the other parts of the polypeptide sequence.

In one embodiment, the present invention provides polypeptides that include a change of amino acid residues in and outside the two (2) tryptophan core structure. One of skilled in the art would conveniently determine the optimal changes in the amino acid residues yet still possess the ability to inhibit binding to IL-23R and cell signaling thereof.

A "conservative substitution" is one in which an amino acid is substituted for another amino acid that has similar properties, such that one skilled in the art of peptide chemistry would expect the secondary structure and hydropathic nature of the polypeptide to be substantially unchanged. In generally, the following groups of amino acid represent conservative changes: (1) ala, pro, gly, glu, asp, gln, asn, ser, thr; (2) cys, ser, try, thr; (3) val, ile, leu, met, ala, phe; (4) lys, arg, his; and (5) phe, tyr, trp, his.

The amino acids that are present inside the core structure (e.g., $X_1X_2X_3$ within the $WX_1X_2X_3W$ motif) or flanking the core structure (e.g., outside the $WX_1X_2X_3W$ motif) include any of the standard twenty-two (22) amino acid residues in their L- or D-form. They may also be a non-standard amino acid notwithstanding the amino acids that are not found in proteins (for example, carnitine, GABA, and L-DOPA), or are not produced directly and in isolation by standard cellular machinery (for example, hydroxyproline and selenomethionine).

In the present invention, a predominant polypeptide group is that the two (2) tryptophan residues are separated by a few amino acid residues (e.g., $WX_1X_2X_3W$, $WX_1X_2X_3$, $X_4W$, and the like). In one exemplary embodiment, the present invention provides a polypeptide having a core structure of $WX_1X_2X_3W$, where $X_1$ is W. In another exemplary embodiment, the present invention provides a polypeptide having a core structure of $WX_1X_2X_3W$, where $X_2$ is W. In yet another exemplary embodiment, the present invention provides a polypeptide having a core structure of $WX_1X_2X_3W$, where $X_3$ is an aromatic amino acid residue (i.e., tryptophan, tyrosine or phenylalanine) Preferably, $X_3$ is tryptophan. However, it should be noted that when one of $X_1$, $X_2$ or $X_3$ is tryptophan, the remainder of $X_1$, $X_2$ or $X_3$ cannot be tryptophan.

A non-limiting exemplary list of the core structures that bind to IL-23R and inhibit IL-23 include: WVQYW (SEQ ID NO: 94), WYNYW (SEQ ID NO: 95), WMTYW (SEQ ID NO: 96), WATYW (SEQ ID NO: 97), WEMYW (SEQ ID NO: 98), WKDYW (SEQ ID NO: 99), WEHYW (SEQ ID NO: 100), WQNYW (SEQ ID NO: 101), WQDVW (SEQ ID NO: 102), WMQYW (SEQ ID NO: 103), WHAYW (SEQ ID NO: 104), WQTYW (SEQ ID NO: 105), WQSFW (SEQ ID NO: 106), WYAYW (SEQ ID NO: 107), WEDYW (SEQ ID NO: 108), WEDFW (SEQ ID NO: 109), WEDAW (SEQ ID NO: 110), WLQYW (SEQ ID NO: 111), WLNYW (SEQ ID NO: 112), WNLAW (SEQ ID NO: 113), WLNFW(SEQ ID NO: 114), WRWFW (SEQ ID NO: 115), WEDWW (SEQ ID NO: 116), WIDWW (SEQ ID NO: 117), WDDWW (SEQ ID NO: 118), WEEWW (SEQ ID NO: 119), WQDWW (SEQ ID NO: 120), WENWW (SEQ ID NO: 121), WQNWW (SEQ ID NO: 122), WEKWW (SEQ ID NO: 123), WKDWW (SEQ ID NO: 124), and WKKWW (SEQ ID NO: 125).

According to preferred aspects of the present invention, the peptide is a cyclic peptide. In one preferred embodiment, the cyclic peptide is SEQ ID NO: 130 or SEQ ID NO: 131. In another preferred embodiment, the cyclic peptide is SEQ ID NO: 177, SEQ ID NO: 178 or SEQ ID NO: 179.

It is surprising to discover the core structure of our novel polypeptides that possess the ability to bind to IL-23R and effectively inhibit IL-23. Contrary to what would be expected, the amino acid sequences of the core structure of the present polypeptides do not correspond to any sequence within IL-23 or within IL-23R. The biological activity of the novel peptides suggests that the present polypeptides function equivalently to IL-23 subunit p19 but lack the ability to activate IL-23R signaling pathways. Despite the knowledge of the crystallographic structure of IL-23, the purported receptor interaction sites of IL-23 do not show any amino acid sequence that resemble or is homologous to the core structure (e.g., $WX_1X_2X_3W$) of the present invention. (See, e.g., Lupardus, et al., *J. Mol. Bio.,* 382:931-41, 2008). BLAST data further demonstrate that there is no significant similarity between the core structure (e.g., $WX_1X_2X_3W$) and the linear amino acid sequence of p19. Given the dissimilarity in amino acid sequence, one of ordinary skill in the art would not have predicted or expected the present polypeptides to bind IL-23R.

The present inventors also surprised to discover that the present polypeptides are not limited (by and large) to any specific amino acid sequence provided that the polypeptide includes a core structure. The present polypeptides all exhibit the same biological properties (i.e., inhibit IL-23R binding and IL-23 cell signaling). This holds true whether amino acid changes are "conservative" or "drastic."

One skilled in the art would recognize that there are several methods of determining whether an amino acid substitution is "conservative" or "drastic." Amino acids are generally divided into families based on the properties of their side chains. Aspartate and glutamate are acidic. Lysine, arginine, and histidine are basic. Glycine, alanine, valine, leucine, isoleucine, proline, phenylalanine, methionine, and tryptophan are hydrophobic. Asparagine, glutamine, cysteine, serine, threonine, and tyrosine are neutral and hydrophilic. Phenylalanine, tryptophan, and tyrosine also are classified as aromatic. These classes typically convey variant properties on polypeptides according to the characteristics of the amino acid side chain.

The hydropathic index of amino acids is a method for assessing whether an amino acid change is "conservative" or "drastic." Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

One standard method for assessing whether a change is "conservative" or "drastic" amino acids is based on hydrophilicity. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4).

A "conservative" amino acid substitution involves substitution of a native amino acid residue with a normative residue such that there is little or no effect on the polarity or charge of the amino acid residue at that position or substitution of one amino acid residue with another amino acid residue having the same or a similar hydropathic or hydrophilicity score. As used herein, a "drastic" amino acid substitution involves a substitution where there is a change in the polarity or charge of the amino acid residue at that position or substitution of one amino acid residue with another amino acid residue having a different hydropathic or hydrophilicity score.

It is generally believed that a conservative amino acid substitution is not expected to alter biological activity. Kyte, et al., *J. Mol. Biol.,* 157: 105-131 (1982). Conversely, a drastic amino acid substitution is expected to alter biological activity. Contrary to what one of skill in the art would expect, the present inventors found functional equivalency between polypeptide sequences that include a core structure (e.g., $WX_1X_2X_3W$), even when drastic amino acid changes are made.

The novel polypeptides of the present invention may be synthesized by methods known in the art. For example, polypeptides can be prepared using solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., Solid Phase Peptide Synthesis: A Practical Approach (IRL Press 1989), Fields and Colowick, "Solid-Phase Peptide Synthesis," Methods in Enzymology Volume 289 (Academic Press 1997), and Lloyd-Williams et al., Chemical Approaches to the Synthesis of Peptides and Proteins (CRC Press, Inc. 1997)). Variations in total chemical synthesis strategies, such as "native chemical ligation" and "expressed protein ligation" are also standard (see, for example, Dawson et al., Science 266:776 (1994), Hackeng et al., Proc. Nat'l Acad. Sci. USA 94:7845 (1997)).

Cyclic polypeptides are often desirable (as compared to their linear counterparts), in part, because of the stability (i.e., cyclic polypeptides are less accessible by enzymatic digestion). Because of more rigid structures, cyclic polypeptides may display higher activity as compared to those of their linear counterparts (See, for example, SEQ ID NO: 153 v. SEQ ID NO: 177; FIG. 64). Another additional benefit of cyclization may relate to the fact that cyclic polypeptides mimic active peptides of their protein secondary structures, such as protein loops, or helices.

Preparation of cyclic polypeptides is generally known by one skilled in the art. There are many existing synthetic protocols for making cyclic peptides. Two commonly protocols include the so-called "Cys-Cys" (CC) cyclization and the "Head-to-Tail" (HT) cyclization. In either case, amino acids may be added to the active sequence for the sole purpose of facilitating cyclization. Other cyclization methods may also be suitable for preparation of cyclic peptides, for example, thioether chemistry and azide-alkyne cycloaddition chemistry.

Cys-Cys cyclization is the result of forming a disulphide (S—S) bond between the thiol side chains of two cystiene residues in a peptide. Usually, these cysteine residues are present at the N-terminus and C-terminus respectively of the peptide. Alternatively, one or other cysteines may be present internally of the peptide. Cys-Cys cyclization is a straightforward method of cyclizating a peptide, but the resulting peptide may be unstable under certain reducing conditions (which break the S—S bond), resulting in re-linearization of the peptide.

Head-to-Tail cyclization results in a more stable cyclic peptide. Chemically, the process is known as "Amide-Bond cyclization." While Head-to-Tail cyclization is commonly applied to backbone residues. This cyclizes the residues at the N-terminus and at the C-terminus of the peptide. In some instances, amino a side chains may also be used, in which case cyclization may involve internal residues.

Polypeptides of the present invention (linear or cyclic) can be purified or isolated after synthesis. Protein purification methods are well known in the art, and are described, for example in Deutscher, et al. (ed., 1990, In: *Guide to Protein Purification*, Harcourt Brace Jovanovich, San Diego).

In one aspect, the present invention is directed to a pharmaceutical composition comprising a novel polypeptide of the present invention, and a pharmaceutical acceptable carrier. The present composition is believed to reduce activation of cells implicated in the IL-23 mediated inflammatory response. The present composition is thus useful and has practical utility in preventing and treating IL-23 mediated diseases. Such composition may be administered to a mammal (e.g., human) to inhibit binding of IL23R (by IL-23) and cell signaling thereof. The present composition aids to prevent, ameliorate or treat the symptoms of IL-23 mediated inflammatory disorders. The present composition is useful in treating IL-23 mediated diseases including, but not limited to, psoriasis, rheumatoid arthritis, and inflammatory bowel diseases (IBD) such as ulcerative colitis and Crohn's disease and the like.

In one aspect, the present invention provides a pharmaceutical composition comprising a novel polypeptide (e.g., cyclic peptide) of the present invention to treat IBD. IBD is known to include two common autoimmune diseases in humans—Crohn's disease and ulcerative colitis. These autoimmune diseases share many of the same physiological, mechanistic, immune, inflammatory and genetic features, as well as common treatment strategies (such as TNF withdrawal therapy). An important immunological mechanism common to both Crohn's disease and ulcerative colitis is the pathological role of Th17 cells. It is generally believed by medical researchers and physicians that treatment strategies that prevent the development of Th17 cells will prevent their ability to promote inflammatory diseases and disorders, such as IBD.

Without being bound by a theory, it is generally believed that while many cell-types contribute to the pathology of IBD (including, such as, epithelial cells, myeloid cells, B-cells, other T-cells, and the like), Th17 cells are central to the process and pivotal to the pathological actions of the other cells involved.

Th17 cells are a population of CD4+ T-cells whose function is to promote antigen-specific inflammation in barrier tissues such as bowel tissues, skin tissues and airway tissues. Th17 cells are characterized as using their ability to secrete cytokines to promote the secretion of inflammatory mediators (such as TNF and IL) in these tissues. Illustrative cytokines that are commonly secreted by Th17 cells include, but not limited to, IL-17A, IL-17F, IL-22, IL-26 and IFNγ. These cytokines are generally recognized as signatures of Th17 activity in humans and other mammals.

Development of Th17 cells is dependent on the action of IL-23. Th17 cell precursors become functionally mature Th17 cells when they receive IL-23 signals. Upon stimulation with IL-23, Th17 signature cytokines illustrated above are secreted from mature Th17 cells. Thus, blocking IL-23 signaling is a valuable therapeutic strategy in Th17 cell-mediated diseases, particularly IBD. In fact, the blocking of IL-23 signaling may also be benefit in other diseases such as psoriasis and multiple sclerosis.

Accordingly, the present inventors have screened a set of novel peptides that function to prevent IL-23 from binding to the IL-23 receptor, thus blocking the IL-23 signaling. The present novel peptides are shown to bind to the IL-23 receptor and prevent its natural ligand (i.e., IL-23) from binding to the IL-23 receptor. Without being bound by a theory, the present inventors discovered that the present novel peptides bind to the IL-23 receptor and prevent it from interacting with the p19 component of the IL-23 heterodimer. Because the present peptides are unable to mimic the IL-23 signaling, they represent unique and useful IL-23 antagonists by blocking IL-23 binding to IL-23 receptor. According, the present invention provides a means of using a novel peptide in blocking IL-23 signaling and has therapeutically utility in Th17-dependent diseases such as IBD.

One aspect of the present peptides' function is the ability to prevent IL-23 from binding to an isolated IL-23 receptor protein. Another aspect is the ability to bind to the cell surface receptor. Yet another aspect is to prevent the induction of IL23-dependent cell signaling. A further aspect is the ability to prevent the generation of IL-17A mRNA in isolated human CD4+ T-cells. We observed that both linear and cyclised peptides were effective. Preferred cyclized peptides can be based on linear peptides containing amino acid sequence in Peptide No. 2 (SEQ ID NO: 153) (i.e., KMTWVDYWLKNC) or Peptide No. 7 (SEQ ID NO: 156) (i.e., MKTWVDYWLETQ). The resulting cyclic peptides include, for example, SEQ ID NOs: 177, 178 and 179.

In one embodiment, the present inventors illustrate, in exemplary cyclized peptides (SEQ ID Nos: 177, 178 and 179) that these peptides antagonize IL-23 in a mixed population of human peripheral blood mononuclear cells by blocking IL-17F mRNA production. The peptides exhibit a dose-dependent inhibition on IL-17F mRNA with an $IC_{50}$~300 nM.

In another embodiment, the present inventors illustrate that the cyclized peptides (SEQ ID Nos: 177, 178 and 179) effectively antagonizing IL-23 in a mixed population of lymphoid cells from isolated spleens in rat. The peptides exhibit a dose-dependent inhibition on IL-17F mRNA production and IL-17F protein secretion with an $IC_{50}$~300 nM.

In another embodiment, the present inventors illustrate that the cyclized peptides (SEQ ID Nos: 177, 178 and 179) effectively antagonizing IL-23 in a mixed population of lymphoid cells from isolated spleens in rat. The peptides exhibit a dose-dependent inhibition on IL-22 protein secretion with an $IC_{50}$~300 nM.

In sum, the present inventors demonstrate that the invented peptides are able to antagonize multiple IL-23-dependent functions in mixed leukocyte populations, both in human and non-human species with equivalent efficacy (IC50). Together, the present invention provides a therapeutic application for the invented peptides to treat IL-23-dependent diseases. By blocking IL-23 cell signaling and inhibiting subsequent cytokine actions (e.g., IL-17F production), the invented peptides have therapeutic applications in the treatment of IL-23 dependent Th17 disorders such as IBD, psoriasis and multiple sclerosis.

In one aspect, the present invention provides a method of preparing a pharmaceutical composition that contains a novel polypeptide of the present invention and a pharmaceutically acceptable excipient.

Pharmaceutically acceptable excipients are known in the art (see, e.g., Remington's Pharmaceutical Sciences and U.S. Pharmacopeia: National Formulary, Mack Publishing Company, Easton, Pa. (1984)), including methods of combining an active ingredient (e.g., novel polypeptide) with the pharmaceutical acceptable excipient. Formulation of the therapeutic agents (i.e., novel polypeptides) may be prepared by mixing with physiologically acceptable excipients, or stabilizers in the form of, e.g., lyophilized powders, slurries, aqueous solutions or suspensions (see, e.g., Hardman, et al. (2001) Goodman and Gilman's *The Pharmacological Basis of Therapeutics*, McGraw-Hill, New York, N.Y.; Gennaro (2000) Remington: *The Science and Practice of Pharmacy*, Lippincott, Williams, and Wilkins, New York, N.Y.; Avis, et al. (eds.) (1993) Pharmaceutical Dosage Forms: Parenteral Medications, Marcel Dekker, N.Y.; Lieberman, et al. (eds.) (1990) Pharmaceutical Dosage Forms: Tablets, Marcel Dekker, N.Y.; Lieberman, et al. (eds.) (1990) Pharmaceutical Dosage Forms: Disperse Systems, Marcel Dekker, N.Y.; Weiner and Kotkoskie (2000) Excipient Toxicity and Safety, Marcel Dekker, Inc., New York, N.Y.).

In another aspect, the present invention provides a method of treating IL-23 mediated immunological diseases by administering to a human a pharmaceutical composition comprising the novel polypeptides. The suitable route of administration may include injection or infusion by intravenous, intramuscular, or by sustained release systems. The pharmaceutical compositions containing novel peptides may additionally contain other active ingredients such as anti-infective agents, antibiotics, or anti-IL-23R antibodies and the like. After diagnosing suffering from an IL-23 associated disease (e.g., IBD, Crohn's disease, ulcerative colitis, psoriasis, multiple sclerosis, and the like), a patient may be administered a pharmaceutical composition comprising the novel polypeptides. The present claimed polypeptides, upon administration into a patient in need of inhibition of IL-23, can suppress the progression of the disease by inhibiting the IL-23 mediated cell signaling. In one embodiment, the present invention provides a method of inhibiting the production of IL-17F in a Th17 cell in a human by exposing the claimed pharmaceutical composition containing the novel peptides (i.e., after administration into the human). In another embodiment, the present invention provides a method inhibiting the production of IL-17F in a splenycyte in a human by exposing the claimed pharmaceutical composition containing the novel peptides (i.e., after administration into the human). In yet another embodiment, the present invention provides a method of inhibiting the production of IL-22 in a mononuclear cell in a human by exposing the claimed pharmaceutical composition containing the novel peptides (i.e., after administration into the human).

Effective amounts of the present composition for a particular patient may vary depending on factors such as the condition being treated, the overall health of the patient, the method route and dose of administration and the severity of side affects (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK). It will be apparent to those of ordinary skill in the art that the therapeutic effective amount of the inventive peptides of this invention will depend, inter alia, upon many factors such as the administration schedule, the unit dose of peptide administered, whether the peptide is administered in combination with other therapeutic agents, the immune status and health of the patient, the therapeutic activity of the peptide administered and the judgment of the treating physician. An effective dose protocol can be conveniently devised by one of ordinary skill in the art. (See, e.g., Yang, et al., *New Engl. J. Med.* 349:427-434, 2003; Herold, et al., *New Engl. J. Med.* 346:1692-1698, 2002; and Portielji, et al., *Cancer Immunol. Immunother.* 52:133-144, 2003).

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1

Phage Display Screening—Identification of Novel Polypeptides that Bind to IL-23 Receptor (IL-23R)

IL-23R is composed of 629 amino acids, whose sequence (accession no. NM 144701.2) has been reported by Oppmann et al. (Immunity 13 (5), 715-725, 2000). To date, no crystallization structure has been reported for IL-23R; and its three dimensional structure remains unknown. Chemtob et al. relied on the linear amino acid sequence of IL-23R and created peptides corresponding to portions of the IL-23R. Using this rational drug design approach, these authors reported several IL-23R antagonists and an IL-23R agonist. The purported amino acid structure for the IL-23R antagonists includes LPDEVTCV (SEQ ID NO: 171), TEEQQYL (SEQ ID NO 172), KKYLVWVQ (SEQ ID NO: 173) and MEESKQLQL (SEQ ID NO. 174). Because these synthetic polypeptides are based on the IL-23R, they were reported to act as an antagonist in blocking IL-23 binding to IL-23R and subsequent cell signaling.

In this study, we chose a different approach. Instead of a rational drug design based on a computer generated model, we used a random peptide approach using a Phage Display Screening. This novel approach was adopted to maximize the chances to identify novel polypeptides that bind to IL-23R (i.e., our screened polypeptides do not have corresponding IL-23R amino acid sequence; rather, our screen polypeptides are expected to mimic IL-23 and bind to IL-23R).

The present inventors have identified polypeptides that share common core structures. These polypeptides function to inhibit binding of IL-23 to IL-23R and to inhibit cell signaling of IL23R. These polypeptides also bind to IL-23R. It is surprising to note that our screened polypeptides do not resemble that of IL-23 when the amino acid sequence is considered. Beyer et al. and Lupardus et al. have reported the crystallized structure for IL-23. Comparison of the purported crystallized structure unexpectedly reveals little, if any, similarity between our screened polypeptides and portions of the IL-23.

Figure 1:
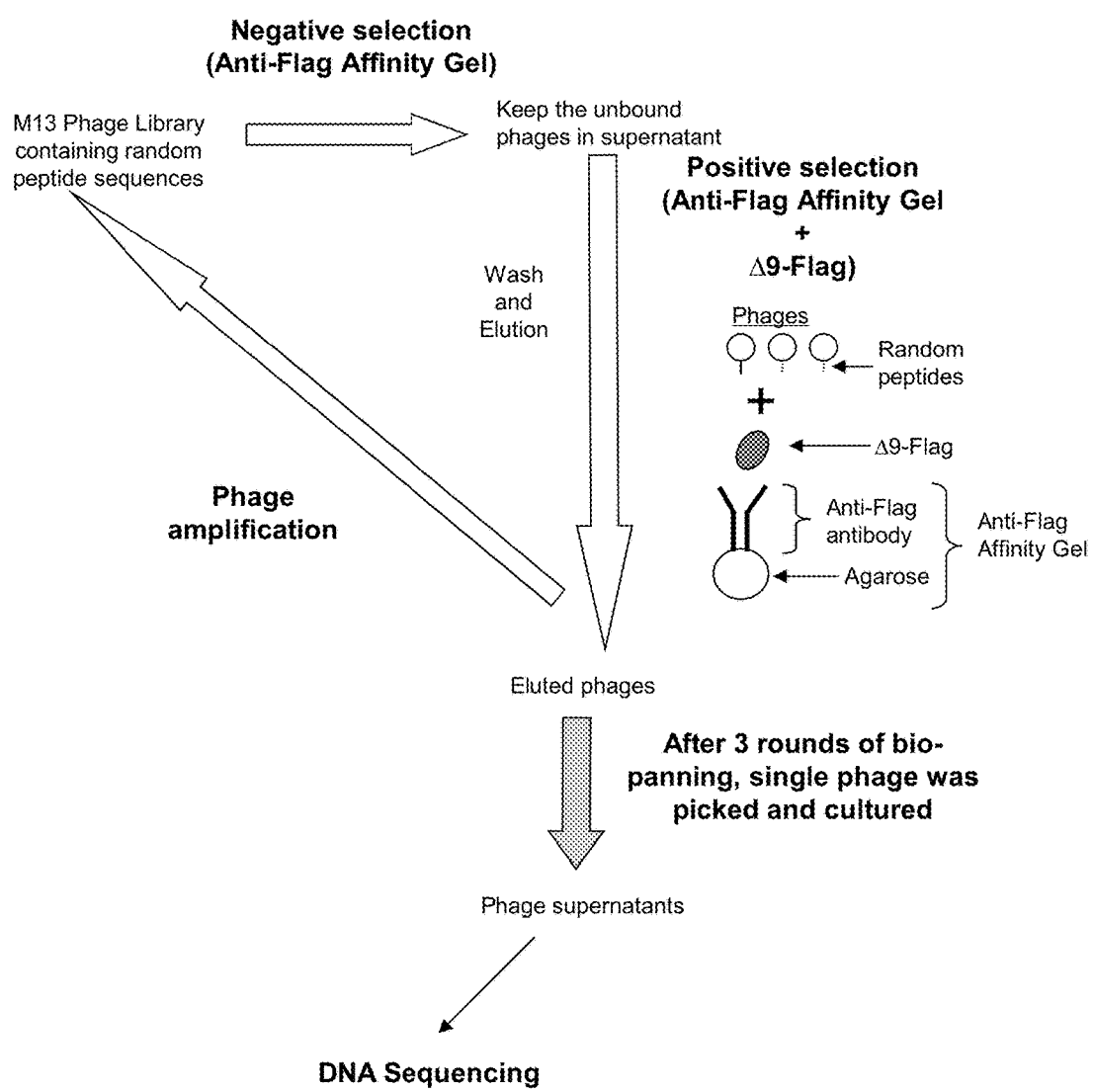
FIG. 1 depicts a schematic diagram of the Phage Display Screening. In this screening assay, a M13 phage library displaying random 12-mer peptide sequences was screened to identify polypeptides that bind to a soluble recombinant splice variant of IL-23 receptor lacking the exon 9 domain (i.e., Δ9) that is coupled to a Flag (i.e., Δ9-Flag protein).
Figure 3:
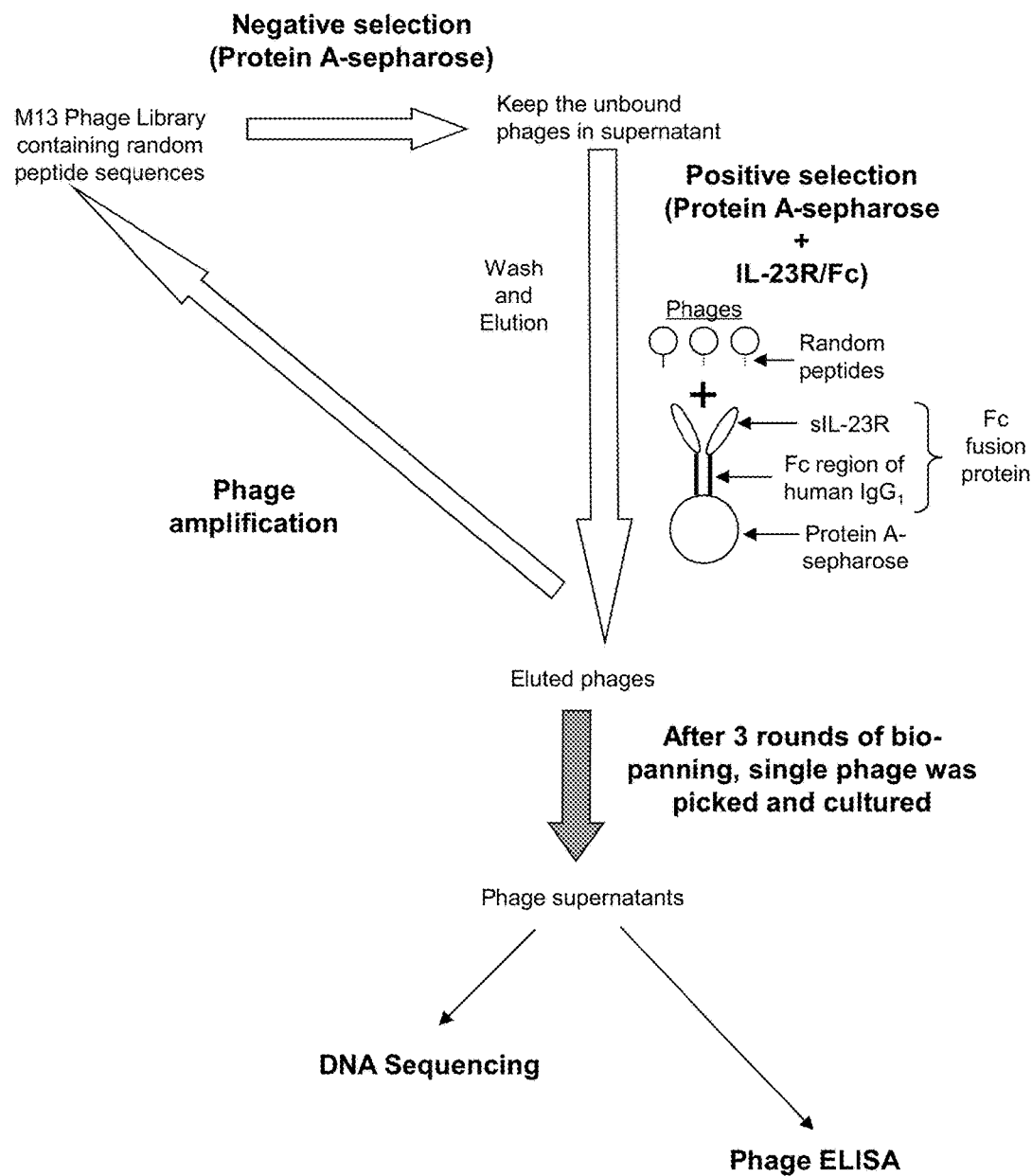
FIG. 3 depicts a schematic diagram of the Phage Display Screening. In this screening assay, a M13 phage library displaying random 12-mer peptide sequences was screened to identify polypeptides that bind to a full-length soluble recombinant IL-23 receptor (i.e., IL-23R) that is coupled to a Fc (i.e., IL-23R/Fc fusion protein).

In the present Phage Display Screening, the assay essentially involves four steps (See, FIGS. 1 and 3). First, we prepared random polypeptide sequences with the help of a phage library. Second, we developed a screening assay that discriminate and select polypeptides that bind to IL-23R. To this end, our screening assay employs two soluble forms of IL-23R—namely, a soluble recombinant Δ9 form of IL-23R (i.e., Δ9-Flag) and a soluble recombinant IL-23R form (having the entire extracellular domain, but lacking the transmembrane domain and intracellular domain) coupled to a Fc (sIL-23-Fc fusion protein). Third, we amplified the bound phages. Fourth, we sequenced the bound polypeptides to obtain their amino acid sequence.

The details of the Phage Display Screening are described as follows:

A) Phage Display Library Expressing Random Peptide Sequences

A phage library displaying approximately $1\times10^{11}$ pfu random 12-mer peptide sequences was prepared (obtained from New England BioLabs (Ipswich, Mass.) (Cat. No. E8110S)). The phage library was then used in our Phage Display Screening. To identify and select phages that express peptide sequences that were bound, we employed bio-panning. Two independent bio-panning assays were performed.

(i) Bio-Panning (Screening) Using a Soluble Recombinant Δ9 IL-23R (i.e., Δ9-Flag Screening)

In previous studies we had identified a soluble recombinant IL-23R lacking a domain (i.e., between the 349 amino acid residue to 629 amino acid residue) but possess an extra eight (8) amino acid residues (i.e., Δ9 protein) due to a messenger RNA splicing event. (See, Kan et al., Genes Immun. (7):631-9, 2008; Mancini G et al., Genes Immun. 2008 (6):566-9, 2008; and Yu et al., J. Immunol. 185(12): 7302-8, 2010). We had further shown that this particular soluble IL-23R variant (also known as Δ9 protein) functions equivalently as the full-length IL-23R in terms of its IL-23 binding activity. (See, Yu et al., J. Immunol. 185(12):7302-8, 2010).

In the initial bio-panning assay, phages were screened using purified Flag-tagged fusion protein containing the soluble recombinant Δ9 which contains the entire extracellular domain of IL-23R (i.e., Δ9-Flag) (See FIG. 1). After the phages were allowed to bind to Δ9-Flag, the phage-Δ9-Flag complexes were precipitated using anti-Flag affinity gel (Sigma, St. Louis, Mo.).

Data obtained using this Δ9-Flag screening revealed that this approach yielded a total of thirteen (13) polypeptides, indicating a need to improve efficiency. After sequence confirmation, many of the screened polypeptides were found to be the Flag sequence, in part because the anti-Flag antibody used in the screening process may also capture random peptides that resemble the Flag sequence.

A list of the novel polypeptides (i.e., six (6) polypeptides) (polypeptide nos. 52, 60, 61, 66, 75, and 79) (SEQ ID NOs: 1-6, respectively) screened using the Δ9-Flag screening approach is summarized in FIG. 2.

(ii) Bio-Panning (Screening) Using a Soluble Recombinant IL-23R (Containing the Entire Extracellular Domain but Lacking the Transmembrane and Intracellular Domains) (i.e., IL-23R/Fc Chimera Screening)

We improved the Phage Display Screening Assay. To avoid potential interaction between Flag and anti-Flag, we chose to use a different capturing reagent.

To this end, we planned to prepare a soluble recombinant IL-23R lacking the signal peptide sequence (i.e., 1-23 amino acids). This soluble recombinant IL-23R has the protein portion between the 24 amino acid residue to 353 amino acid residue. In contrast to the full-length IL-23R (1-629 amino acids in length), this soluble recombinant IL-23R lacks the transmembrane domain and cytoplasm domain (i.e., between the 354 amino acid residue to 629 amino acid residue). The soluble recombinant IL-23R may be coupled to a human $IgG_1$ Fc (i.e., between the 100 amino acid residue to 330 amino acid residue) and created an IL-23R/Fc chimera (i.e., IL-23R/Fc).

We obtained the IL-23R/Fc from a commercial source (i.e., R&D Systems, Minneapolis, Minn.; Cat. No. 1400-IR-050). To mediate capturing, we employed protein A sepharose to capture the Fc portion of the IL-23R/Fc. Such molecular device eliminates the binding between Flag and anti-Flag. (FIG. 3).

Using this IL-23R/Fc chimera screening approach, we obtained a total of twenty-two (22) unique polypeptides that bound to IL-23R, demonstrating an efficient screening.

A list of the novel polypeptides (i.e., 22 polypeptides) (polypeptides nos. 1, 2, 3, 4, 5, 6, 7, 9, 10, 13, 14, 15, 18, 19, 20, 22, 23, 24, 25, 27, 29, 30 and 32) (SEQ ID NOs: 7-29, respectively) screened using the IL-23R/Fc chimera screening approach is summarized in FIG. 4.

B) Elimination of Non-Specific Binding

To avoid non-specific binding, we performed a negative selection step. Either protein A sepharose or anti-Flag affinity gel was incubated with $1\times10^{11}$ pfu of phage display library at room temperature for 15 minutes. The mixture was centrifuged at 5,000 rpm for 2 minutes to separate the phages that bound non-specifically from unbound phages. The phages in the supernatant were then screened using either the Δ9-Flag followed by anti-flag agarose or the soluble recombinant IL-23R (containing the entire extracellular domain, but lacking both the transmembrane and intracellular domains) followed by Fc-protein A sepharose to obtain phages displaying sequences that bind to IL-23R (as detailed above).

C) Detection of IL-23R Binding (i) Using Δ9-Flag Followed by Anti-Flag Agarose

Phage-containing supernatant (300 μl) was incubated with anti-Flag affinity gel and Flag-tagged fusion protein containing the entire extracellular domain of IL-23R (Δ9-Flag) (FIG. 1). The mixture was incubated overnight at 4° C. with mixing. The mixture was centrifuged at 5,000 rpm for 2 minutes to precipitate the affinity gel-bound phages or sepharose bead-bound phages (i.e., phages displaying sequences that bound IL-23R). The supernatant was removed and the resin was washed ten times (10×) with 1 ml of 0.1% Tris-Buffered Saline Tween-20 (TBST).

(ii) Using Soluble Recombinant IL-23R (Containing the Entire Extracellular Domain, but Missing the Transmembrane and Intracellular Domains) Followed by Fc-Protein a Sepharose The second independent screening was performed by incubating the phage-containing supernatant (300 μl) with protein A sepharose (20 μl) and recombinant human IL-23R/Fc (10 μg) (FIG. 3). The mixture was incubated overnight at 4° C. with mixing. The mixture was centrifuged at 5,000 rpm for 2 minutes to precipitate the affinity gel-bound phages or sepharose bead-bound phages (i.e., phages displaying sequences that bound IL-23R). The supernatant was removed and the resin was washed ten times (10×) with 1 ml of 0.1% Tris-Buffered Saline Tween-20 (TBST).

D) Amplification of Binding Phages in E. coli

Phages that bound IL-23R were removed from the affinity gel or sepharose beads by adding 1 ml of glycine elution buffer (0.2 M glycine-HCl, pH 2.2, 0.1% BSA) to the resin and incubating the resin-buffer mixture for 10-minutes at room temperature. The resin was removed by centrifuging the mixture at 5,000 rpm for 2 minutes, which leaves the relevant phages in the supernatant. The eluted phages were neutralized by adding 150 µl of 1 M Tris-HCl, pH 9.1 to the supernatant.

Next, binding phages were amplified. Phages were introduced to an early-log 20 ml culture of E. coli ER2738. The mixture was incubated for 4.5 hours at 37° C. with shaking Following incubation, the culture was centrifuged at 12,000 rpm for 10 minutes to remove cell debris and E. coli cells. To precipitate the phages, the upper 80% of the supernatant was incubated overnight at 4° C. with 3 ml of 20% polyethylene glycol (PEG)/2.5 M NaCl. The solution was centrifuged at 12,000 rpm for 30 minutes to collect the precipitated phages. The supernatant was discarded. The pellet was re-suspended in 1 ml of TBS. 200 µl of 20% PEG/2.5 M NaCl was added to the supernatant and the mixture was incubated on ice for 1 hour. The solution was centrifuged at 12,000 rpm for 10 minutes and the pellet re-suspended in 200 µl of TBS.

The phage concentration in the amplified pool was measured by the phage titer on LB/IPTG/Xgal plates. The phage titer was determined by counting blue plaques. Two additional rounds of bio-panning were performed as described above. After 3 rounds of bio-panning, the eluted phages were subjected for titer before phage amplification.

Individual plaques (i.e., blue plaques) were randomly selected and amplified by adding the plaques to 1 ml of E. coli ER2738. The mixture was incubated at 37° C. with shaking for 5 hours. The cultures were centrifuged to remove cell debris and the pellets discarded. 500 µl of the supernatant (i.e. LB containing amplified individual phage identified after 3 around of bio-panning) was apportioned for DNA sequencing. The remaining supernatant volume was used in a phage ELISA.

Example 2

Sequencing of Phage DNA

DNA from the phages that bound to either Δ9-Flag or to IL-23R/Fc chimera was sequenced to determine the amino acid sequence of the polypeptides that bound IL-23R.

In this study, phages were precipitated from the 500 µl of supernatant obtained following the phage display assay. 200 µl of 20% PEG/2.5 M NaCl was added to the 500 µl phage-containing supernatant (1:2.5 volume to volume ratio of PEG/NaCl to supernatant). The mixture was incubated for 20 minutes at room temperature. Phages were collected by centrifuging at 12,000 rpm for 10 minutes. The supernatant was discarded and the pellet re-suspended in 100 µl iodide buffer (10 mM Tris-HCl (pH 8.0), 1 mM EDTA, 4 M sodium iodide). 250 µl ethanol was added and the solution incubated at room temperature for 20 minutes. The solution was centrifuged at 12,000 rpm for 10 minutes. The supernatant was discarded and the pellet was washed with 0.5 ml of cold 70% ethanol. After another centrifugation at 12,000 rpm for 10 minutes, the supernatant was discarded and the pellet, containing the phage DNA, was suspended in 20 µl TE buffer.

For DNA sequencing, we used Beckman Coulter GenomeLab DTCS Quick Start Kit (Cat. No. 60812) (Beckman Coulter, Fullerton, Calif.). The concentration of phage DNA was measured by the NanoDrop at $OD_{280}$. (NanoDrop Technologies inc, Wilmington, Del.). Approximately 150 ng of phage DNA was used for each sequencing reaction. 1 pmol of −96 GIII sequencing primer (20-mer), (supplied with New England BioLabs Ph.D.™ 12 Phage Display Peptide Library Kit, Ipswich, Mass.) was used for each reaction. The thermal cycling program was 20 seconds at 96° C., 20 seconds at 50° C., and 4 minutes at 60° C., for 30 cycles. Ethanol precipitation was performed according to the Beckman Coulter kit insert. DNA sequencing was performed using Beckman Coulter CEQ 8000.

Δ9-Flag Screening:

With respect to the Δ9-Flag screening, eighty (80) bound phages were selected and subject to DNA sequencing. Among the eight (80) bound phages, the DNA sequencing study reveals thirteen (13) polypeptides, of which six (6) of the polypeptides have novel amino acid sequences. FIG. 2 depicts the six (6) novel polypeptide amino acid sequences. The reminder DNA sequences (i.e., sixty-seven (67) phages) revealed that the bound phages contained the Flag sequence, and the data were discarded.

Analysis of the polypeptide sequence reveals that these novel polypeptides contain at least one (1) tryptophan (W) residue. Interestingly, three (3) of the six (6) polypeptide sequences (i.e., polypeptide nos. 52, 60, and 66) included a $WX_1X_2X_3W$ core structure.

IL-23R/Fc Chimera Screening:

With respect to the IL-23R/Fc chimera screening, thirty-two (32) bound phages were selected and subjected to DNA sequencing. Among these bound phages, DNA sequencing reveals twenty-nine (29) polypeptides, of which twenty-two (22) of the polypeptides have novel amino acid sequences. FIG. 4 depicts the twenty-two (22) sequences. Three (3) phages were empty (i.e., did not display a peptide sequence).

Analysis of the polypeptide sequence reveals that all twenty-two (22) of the phages expressing peptide sequences included at least one tryptophan (W) residue. Fifteen (15) of the twenty-two (22) polypeptide sequences (i.e., polypeptide nos. 1, 4, 7, 9, 10, 14, 15, 20, 22, 23, 25, 27, 29, 30 and 32) included a $WX_1X_2X_3W$ core structure.

Δ9-Flag and IL-23R/Fc Chimera Screening:

Of interest is the observation that one amino acid sequence obtained from the Δ9-Flag screening matches that of IL-23R/Fc chimera screening (i.e., polypeptide nos. 52, 65, 71, 74 and 77 from Δ9-Flag screening match the polypeptide no. 23 from IL-23R/Fc chimera screening). Accordingly, both Δ9-Flag screening and IL-23R/Fc chimera screening together yielded a total of twenty seven (27) novel polypeptides. A full list of all the sequences obtained using these two screening approaches is shown in FIG. 7 (See, Example 4 below).

Example 3

Validation of IL-23 Receptor Binding Peptides by Phage ELISA

To confirm the binding of phages isolated using IL-23R/Fc conjugated to protein A sepharose to IL-23R, we performed a phage ELISA. IL-23R/Fc was used to select peptide sequences from the phage stock obtained in our bio-panning assay. Sixteen (16) isolated phages were tested for their ability to bind IL-23R in the ELISA. Twelve (12) different polypeptide sequences were expressed on these sixteen (16) phages. Two empty phages (i.e., numbers 8 and 11) were run as controls.

Figure 5:
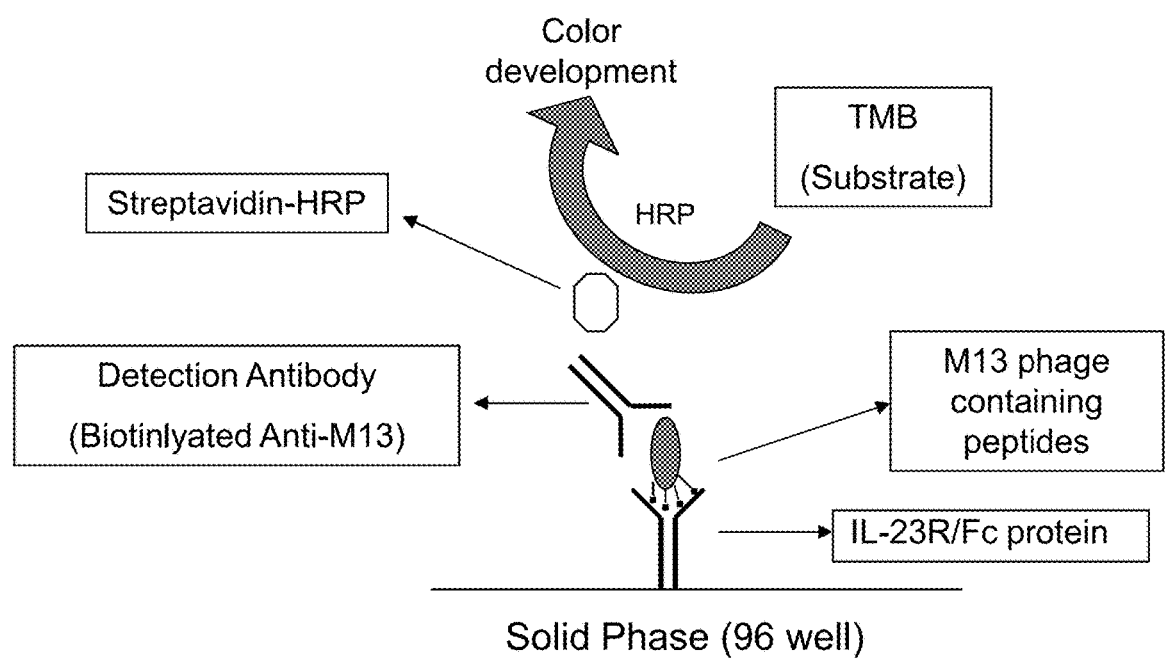
FIG. 5 depicts the schematic diagram showing a Phage ELISA. The phage ELISA was used to confirm the binding of M13 phage display polypeptide sequences to IL-23R/Fc fusion protein. The binding was detected using TMB substrate color development.

FIG. 5 provides a schematic depiction of the phage ELISA. To prepare the ELISA, microtiter plates were coated with 2 µg/ml of recombinant human IL-23R/Fc and incubated overnight at 4° C. The plates were blocked for 2 hours using 10% FBS/TBST at room temperature. 10 μl of 10×PBS was added to each well. 90 μl of M13 phage-containing LB media was also added. To permit phage binding to the IL-23R, the plate was incubated overnight at 4° C.

Bound phage was detected by adding 2 μg/ml of biotinylated anti-M13 antibody (Cat. No.: ab17269) (Abcam, Cambridge, Mass.). Streptavidin-horseradish peroxidase (HRP) was added to detect anti-M13 antibody bound to IL-23R bound phages. Peroxidase activity (representing the level of M13 captured onto plates) was measured by adding 100 μl of a tetramethylbenzidine (TMB) to each well. The color intensity was directly proportional to the amount of the bound M13 phage. Optical density was read at $450_{nm}$.

FIG. 6 shows the results of the phage ELISA. All twelve (12) of the phages which contained peptide sequences had higher OD values than the two (2) empty phages. The $OD_{450}$ data indicates that the twelve (12) polypeptides bind to IL-23R.

Example 4

Sequence Analysis of Identified Polypeptides

A total of twenty-seven (27) different polypeptide sequences were obtained from the Phage Display Screening assays. The screening with Δ9-Flag yielded six (6) novel polypeptide sequences. The screening with IL-23R/Fc chimera yielded twenty-two (22) novel polypeptide sequences. Altogether, the two approaches yielded a total of twenty seven (27) novel polypeptide sequences.

Interestingly, Δ9-Flag screening and the IL-23R/Fc chimera screening produced one (1) polypeptide sequence in common (i.e., polypeptide nos. 23 and 52), indicating that commonality of using the Δ9-Flag and IL-23R/Fc chimera approaches.

FIG. 7 depicts the twenty seven (27) sequences obtained from the Phage Display Screenings. Sequence analysis revealed that all twenty seven (27) polypeptide sequences contain at least one tryptophan (W) residue. Eighteen (18) of the twenty seven (27) sequences (66.7%) obtained through our Phage Display Screenings include the core structure $WX_1X_2X_3W$, indicating a crucial role of this core structure in peptide binding to IL-23R. Nine (9) of the twenty seven (27) sequences (33.3%) obtained through our Phage Display Screenings do not include the $WX_1X_2X_3W$ core structure.

FIG. 8 depicts the sequence alignment of eighteen (18) peptides that contained the core structure $WX_1X_2X_3W$. Sequence alignment further indicates that insofar as the $WX_1X_2X_3W$ core structure is present, it provides the polypeptide the ability to inhibit IL-23 binding. In other words, the location of the $WX_1X_2X_3W$ core structure within a polypeptide can vary, and still provides the polypeptide the ability to inhibit IL-23 binding. This finding is consistent with the hypothesis that it is the core structure that interacts with the binding domain between IL-23 and IL-23R, and the remainder feature of the polypeptides (e.g., length, amino acid residues, and relative position of the core structure, etc.) may only play a minor role, if any.

We also screened a minor portion of polypeptides (33.3%) containing a different core structure that is different from the $WX_1X_2X_3W$. FIG. 9 depicts the sequence alignment analysis of the nine (9) peptides, all of which do not contain the core structure $WX_1X_2X_3W$. Instead, these nine (9) peptides contain WWnW, WXnW and W.

FIG. 9 shows two (2) peptides that have a core structure of $WX_1X_2WW$. We interpret this core structure as one of the $WX_1X_2X_3W$, where $X_3$ is W. This finding is interesting and it suggests that the core structure of $WX_1X_2X_3W$ can tolerate two adjacent tryptophan (W) residues without destroying the ability of the polypeptide to inhibit IL-23 binding to IL-23R (e.g., $X_1$ and $X_2$ are simultaneously W, or $X_2$ and $X_3$ are simultaneously W). Our finding further indicates that the dual tryptophans (W) can be present on either side of the polypeptide.

A few of the selected polypeptides possess a single tryptophan (W). Because the presence of a single tryptophan is ubiquitous in many proteins, we believe that additional features within the polypeptides (e.g., neighboring amino acid residues) play a role in determining the polypeptide's ability to inhibit IL-23 binding to IL-23R.

Overall, the present study shows that $WX_1X_2X_3W$ is the major core structure of the polypeptides that bound to IL-23R and inhibit cell signaling thereof.

Example 5

Polypeptide Binding to IL-23R

The ability to bind to IL-23R is a property of the screened polypeptides obtained from our Phage Display Screening, because the screening assay is based on the ability of the polypeptides to bind to IL-23R. To further assess whether the polypeptides are physically bound to IL-23R, we performed immunoprecipitation assays using the extracellular domain of IL-23R (i.e., Δ9).

(i) Generation and Expression of Polypeptide-Fc Fusion Proteins

Polypeptide-Fc fusion proteins were obtained by designing expression constructs (i.e., polypeptide-Fc expression constructs) that expressed the amino acid sequence of interest fused to Fc.

Forward (F) and reverse (R) oligonucleotides corresponding to the desired peptide sequences were designed as set forth in Table 1.

TABLE 1

Oligonucleotide Sequences Used in Generating Polypeptide-Fc Fusion Proteins

| Polypeptide number | Dir | Oligonucleotide Sequence |
|---|---|---|
| 1 | F | C ATG GTT AGT GGT GCT TCG TGG GTT CAG TAT TGG GTT CAG CGG A (SEQ ID NO: 30) |
|  | R | GA TCT CCGCTGAACCCAATACTGA ACCCACGAAGCACCACTAAC (SEQ ID NO: 31) |
| 4 | F | C ATG GTT GCT GAG ACG CCT AGT TGG TAT AAT TAT TGG ATG AAT A (SEQ ID NO: 32) |
|  | R | GA TCT ATTCATCCAATAATTATAC CAACTAGGCGTCTCAGCAAC (SEQ ID NO: 33) |
| 7 | F | C ATG GTT CAGTCGGATACGTGGA TGACGTATTGGAAGCATCATA (SEQ ID NO: 34) |
|  | R | GA TCT ATGATGCTTCCAATACGTC ATCCACGTATCCGACTGAAC (SEQ ID NO: 35) |

TABLE 1-continued

Oligonucleotide Sequences Used in
Generating Polypeptide-Fc Fusion Proteins

| Polypeptide number | Dir | Oligonucleotide Sequence |
|---|---|---|
| 10 | F | C ATG GTT GCGTCTTGGGAGATGT ATTGGGCTACGTCGTATAATA (SEQ ID NO: 36) |
|  | R | GA TCT ATTATACGACGTAGCCCAA TACATCTCCCAAGACGCAAC (SEQ ID NO: 37) |
| 16 | F | C ATG GTT AATTGGACTAGTCAGC TTCATACGGGGATTTCGACTA (SEQ ID NO: 38) |
|  | R | GA TCT AGTCGAAATCCCCGTATGA AGCTGACTAGTCCAATTAAC (SEQ ID NO: 39) |
| 22 | F | C ATG GTT GCTGTGTGGCAGAATT ATTGGAATGAGCAGTTGTAT A (SEQ ID NO: 40) |
|  | R | GA TCT ATACAACTGCTCATTCCAA TAATTCTGCCACACAGCAAC (SEQ ID NO: 41) |
| 32 | F | C ATG GTT ACGTCTTGGCAGTCTT TTTGGCATCATCATAATACT A (SEQ ID NO: 42) |
|  | R | GA TCT AGTATTATGATGATGCCAA AAAGACTGCCAAGACGT AAC (SEQ ID NO: 43) |

Equal amounts of forward and reverse oligonucleotides were annealed into double strand form by incubating at 95° C. for 10 minutes. After the mixture cooled down to room temperature, 1 µl of double strand oligonucleotide was ligated with linearized Fc expression construct (Cat. No. ppfc2-mg2ae1) (InvivoGen, San Diego, Calif.). The linearized vector was prepared by treating the DNA with NcoI and BglII restriction enzymes. The ligated DNA was then transformed into Top10 competent cells (Invitrogen, Carlsbad, Calif.). The sequence of the expression constructs were verified by DNA sequencing. Fusion constructs were expressed by transfecting HEK-293T cells with 2 µg of polypeptide-Fc expression constructs.

We performed the immunoprecipitation using six (6) polypeptides that included the core structure $WX_1X_2X_3W$ (polypeptide nos. 1, 4, 7, 10, 22 and 32) and one polypeptide that included a single tryptophan (W) (polypeptide no. 16).

(ii) In Vitro Binding Assay—Polypeptide Binding to IL-23 Receptor

We next tested if the synthetic polypeptides we generated could bind IL-23R by performing an in vitro binding assay involving Fc-fusion protein and protein A bead (i.e., immunoprecipitation assay with Δ9).

Figure 10:
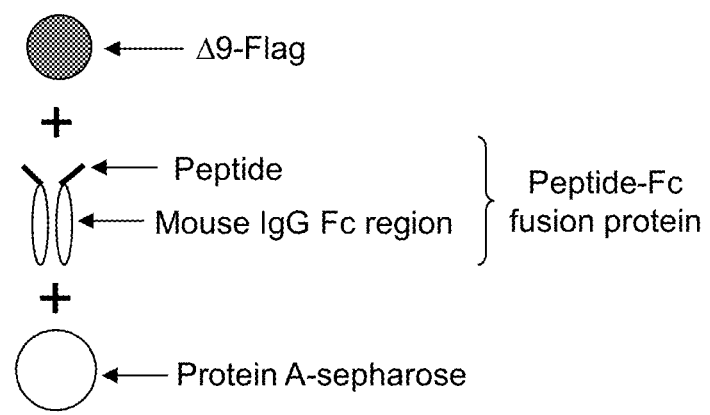
FIG. 10 depicts a schematic diagram of an in vitro binding assay where the components of the binding assay are shown. The in vitro assay is designed to confirm the binding interaction between screened polypeptides (having the unique amino acid sequences) and a soluble recombinant IL-23R (i.e., Δ9).
Figure 11:
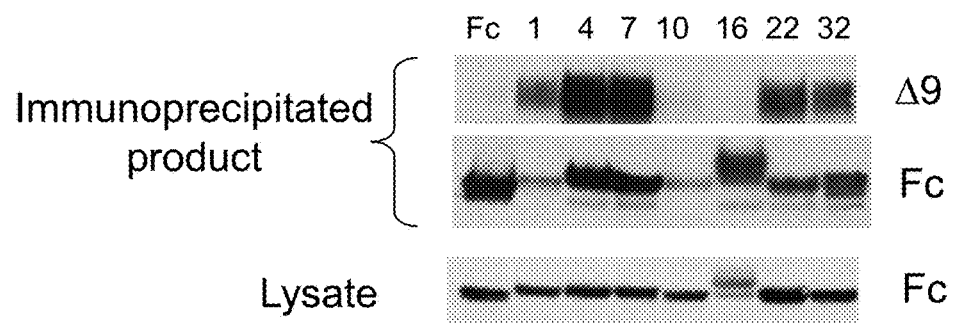
FIG. 11 depicts the immunoprecipitation results of an in vitro assay. The in vitro assay reveals binding of some of the screened polypeptides to soluble recombinant IL-23R (i.e., Δ9). Fc alone served as a negative control, and no immunoprecipitated product was observed with the Fc. Polypeptide nos. 1, 4, 7, 22 and 32 demonstrated avid binding to IL-23R in this immunoprecipitation assay, in contrast to the Fc control. Polypeptide nos. 10 and 16 exhibited minimal or no binding to IL-23R. Notably, polypeptide nos. 1, 4, 7, 22 and 32, each contain the core structure of $WX_1X_2X_3W$.
Figure 12:
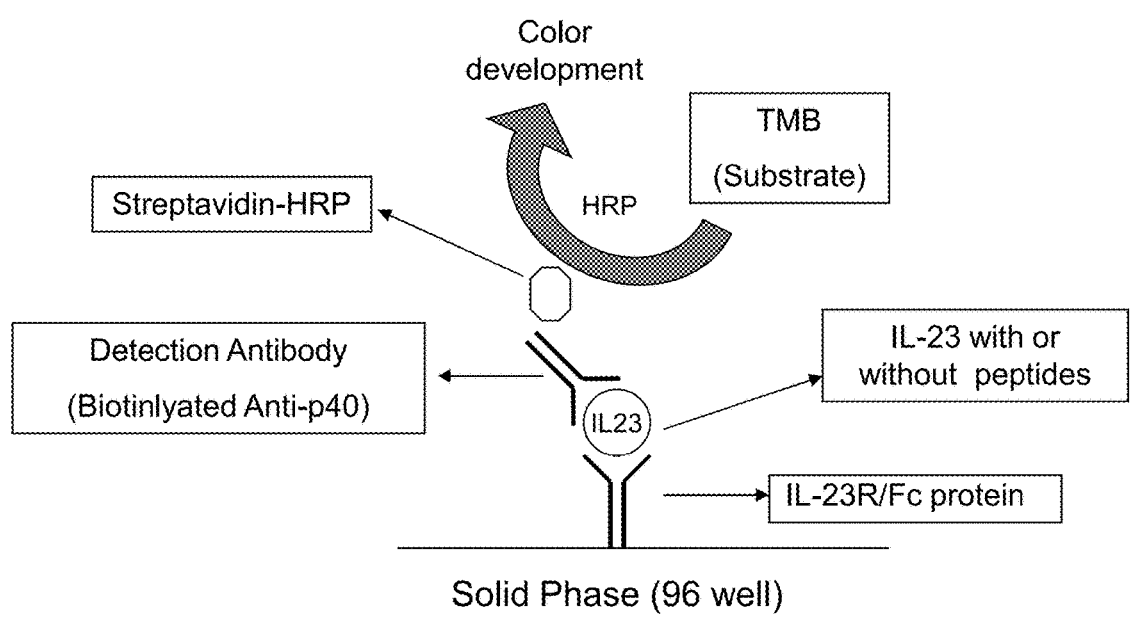
FIG. 12 depicts a schematic diagram of a Competitive ELISA. The competitive ELISA was used to examine the competitive inhibitory activity of the screened polypeptides against IL-23 binding towards IL-23R. Polypeptides used in this assay were synthesized and their amino acid sequences were based on the amino acid sequences of the screened polypeptides.
Figure 13:
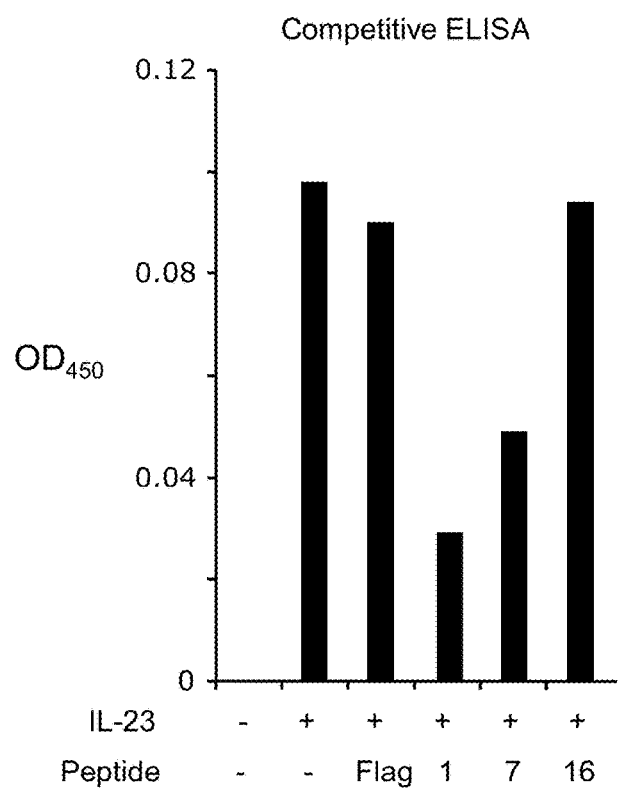
FIG. 13 depicts the results of the Competitive ELISA using synthetic polypeptide nos. 1, 7 and 16 in competition with IL-23. In this Competitive ELISA, the binding to IL-23R (i.e. Δ9-Flag protein) was observed. Polypeptide nos. 1 and 7 exhibited an inhibitory activity against IL-23 binding towards IL-23R; whereas polypeptide no. 16 exhibited minimal inhibitory activity. Note that the competitive ELISA data match that of the in vitro binding assay data (where polypeptide nos. 1 and 7, but not 16, bind to IL-23R). Polypeptides nos. 1 and 7 contain the $WX_1X_2X_3W$ motif whereas polypeptide no. 16 contains one (1) W.

FIG. 10 shows a schematic depiction of the preparation of the components for our immunoprecipation assay. 1 ml of cell culture medium that included polypeptide-Fc fusion protein was incubated with 20 µl of protein A sepharose at room temperature for 1 hour. 1 ml of Δ9 containing culture medium was added to the mixture (i.e., Fc proteins and protein A sepharose) which was incubated at 4° C. overnight with mixing. The mixture was centrifuged, the supernatant removed and the remaining protein A resin washed 5 times with 1 ml PBS to form a precipitate. The precipitated proteins were denatured by addition of sample loading buffer (Bio-Rad, Berkeley, Calif.) and run on 4-12% PAGE and transferred to Immun-Blot PVDF membrane. Membranes were blocked in 5% milk/TPBT at room temperature for 1 hour. Anti-Flag antibody (1:1000) (Sigma, St. Louis, Mo.) and anti-mouse antibody (1:3000) were used to detect the Δ9 and Fc proteins, respectively.

FIG. 11 shows the results of the immunoprecipitation assays. Five (5) of the six (6) polypeptides that included the core structure $WX_1X_2X_3W$ (i.e., polypeptide nos. 1, 4, 7, 22 and 32) bound to Δ9 in our immunoprecipitation assays. Binding to Δ9 was undetectable for polypeptide nos. 10 and 16 (which did not include the core structure $WX_1X_2X_3W$) and the control.

The immunoprecipitation assays confirmed that the polypeptides screened from the Phage Display Screening can bind to IL-23R. The majority of the polypeptides expressed the core structure $WX_1X_2X_3W$, indicating that this core structure is essential in IL-23R binding.

Example 6

Competitive ELISA—Inhibition of IL-23 Binding to its Receptor by Synthetic Polypeptides Immuno-precipitation studies established that polypeptides including the core structure can bind to IL-23R. In this next series of studies, we tested if the polypeptides could inhibit binding of IL-23R in the presence of IL-23 (i.e., could prevent IL-23 from binding to IL-23R). To do so, we performed the Competitive ELISA for IL-23R binding.

FIG. 12 is a schematic depiction of the Competitive ELISA. Recombinant human IL-23R-Fc (2 μg/ml) was coated onto microtiter plates as a capture reagent. IL-23 and polypeptides were added to compete for binding to the immobilized IL-23R-Fc. IL-23 that bound to IL-23R-Fc was detected using biotinylated anti-p40 antibody (1:250). The bound anti-p40 antibody was detected using streptavidin-horseradish peroxidase (HRP) (1:500) and 100 μl/well of a tetramethylbenzidine (TMB) substrate was added to measure peroxidase activity. The color was measured at optical density (OD) $450_{nm}$. (See, FIG. 12). The color intensity was directly proportional to the amount of the bound IL-23 protein.

Six (6) ELISA were performed. Polypeptide nos. 1 and 7 were examined by Competitive ELISA with IL-23. Both polypeptide no. 1 and polypeptide no. 7 include the core structure $WX_1X_2X_3W$. Polypeptide no. 16 (which included only a single tryptophan) was run as a negative control. The ELISA data is summarized in Table 2.

TABLE 2

Summary of Competitive ELISA Assays

| Competitor | ELISA 1 | ELISA 2 | ELISA 3 | ELISA 4 | ELISA 5 | ELISA 6 |
|---|---|---|---|---|---|---|
| IL-23 | None | 50 ng | 50 ng | 50 ng | 50 ng | 50 ng |
| Synthetic Peptide | None | None | Flag | No. 1 (100 μM) | No. 7 (100 μM) | No. 16 (100 μM) |

FIG. 13 depicts the results of our Competitive ELISA. As indicated by the reduction of peroxidase activity in the ELISA (compared to the control assays), polypeptide nos. 1 and 7 were found to compete against IL-23 and inhibited its binding to IL-23R. We had previously shown in immunoprecipitation that polypeptide nos. 1 and 7 could bind to IL-23R. Thus, these data together show that polypeptides including core structure $WX_1X_2X_3W$ not only bind to IL-23R, but inhibit the binding of IL-23 to IL-23R as well.

Example 7

Synthetic Polypeptides Inhibit the IL-23R Signaling Pathway in Cells

We examined if our polypeptides could inhibit IL-23R mediated cell signaling. DB cells (CRL-2289, ATCC, Manassas, Va.) were used in a cell based assay to study the effect of synthetic peptides on IL-23R mediated cell signaling. DB cells are human B cell lymphoma cell lines, which express IL-23R on their surface.

Activation of STAT3 by phosphorylation (p-STAT3) was used as a measurable indicator for the IL-23R mediated cell signaling in the DB cells. STAT3 is a transcription factor activated by IL-23 and phosphorylated in response to IL-23 binding to its receptor. Thus, higher relative levels of p-STAT3 to total p-STAT exist in cells where IL-23 has bound IL-23R. Conversely, when IL-23 cannot bind to IL-23R, STAT3 is not phosphoryated and cells exhibit a lower relative level of p-STAT3 to total p-STAT.

To determine the inhibitory affect of our peptides, we tested cell lysates for the expression level of p-STAT3 in response to IL-23 in the absence or the presence of synthetic polypeptide nos. 1, 7 or 16 and compared the p-STAT3 levels to total STAT3 levels.

DB cells ($3\times10^6$) were cultured in 1 ml of RPMI+10% FBS. The cells were pre-incubated with synthetic polypeptide (i.e., polypeptide nos. 1, 7, 16) (100 μM) for 30 minutes at 37° C. 30 ng/ml of IL-23 was added to the cells and incubated at 37° C. for an additional 20 minutes. Cells were washed with 1 ml of ice-cold PBS and lysed in 50 μl ProteoJET mammalian cell lysis reagent (Fermentas, Glen Burnie, Md.) with protease and phosphatase inhibitors (1 μl per 100 μl) (Sigma, St. Louis, Md.). Cell lysates were centrifuged at 12,000 rpm for 10 minutes. 10 μl of sample loading buffer (Bio-Rad, Berkeley, Calif.) was added to the supernatant. 35 μl of the mixture was run on 4-12% PAGE (Bio-Rad, Berkeley, Calif.). The proteins were transferred to an Immun-Blot PVDF membrane (Bio-Rad, Berkeley, Calif.) and then blocked in 5% milk/TPBT for 1 hour at room temperature. p-STAT3 was detected by probing the membrane with polyclonal rabbit anti-p-STAT3 antibodies (Cell Signaling Technology, Beverly, Mass.). After the membrane was stripped, STAT3 was detected using polyclonal rabbit anti-STAT3 antibodies (Cell Signaling Technology, Beverly, Mass.).

FIG. 14 shows the signaling results. Phosphorylated STAT3 was undetectable by immunoblot when DB cells were treated with polypeptide no. 1 or polypeptide no. 7. DB cells treated with polypeptide nos. 1 or 7 also demonstrated a reduced ratio of p-STAT3 to total STAT3.

We observed a decrease in the level of p-STAT3 as well as the ratio of p-STAT3 to total p-STAT in samples treated with our polypeptides. This data indicates that the polypeptides inhibited the activity of IL-23R and cell signaling in response to IL-23.

Example 8

Synthetic Peptide Number 1 Inhibits the IL-23R Signaling in a Concentration Dependent Manner We studied the dose response effect of our polypeptide (e.g., polypeptide no. 1). We examined IL-23R cell signaling activity using the level of p-STAT3 and the ratio of p-STAT3 to total STAT3 in DB cells.

DB cells were pre-incubated with varying amounts of polypeptide no. 1 (100 μM, 50 μM, 10 μM, 5 μM, or 1 μM) for 30 minutes at 37° C. To stimulate IL-23R, 30 ng/ml of IL-23 was added to the cells and the cells incubated for 20 minutes at 37° C. Cell lysates were prepared to examine the expression levels of p-STAT3 and total STAT3 as previously described.

As shown in FIG. 15, polypeptide no. 1 inhibited IL-23R cell signaling activity in a dose-dependent manner. The addition of 100 μM of polypeptide no. 1 completely inhibited phosphorylation of STAT3. The relative level of p-STAT3/STAT3 was ~0.3. p-STAT3 was more detectable when 50 μm of synthetic peptide no. 1 was added in our immunoprecipitation. This resulted in a relative level of p-STAT3/STAT3 of ~0.6. p-STAT3 was clearly detected in the assays in which 10 μM, 5 μM and 1 μM of synthetic peptide no. 1 was added. The relative p-STAT3/STAT3 level in each of those assays was greater than 1.5.

These results show that peptide no. 1 inhibits the effect IL-23 in cells in a concentration dependent manner.

Example 9

Competitive ELISA to Identify Peptides Showing Stronger Inhibitory Activity than Peptide No. 1

We extended our Competitive ELISA (FIG. 12 and Example 6) to include other polypeptides that were identified in Example 1. Totally, twenty-two (22) peptides were studied in this example. Sixteen (16) polypeptides (i.e., polypeptide nos. 1, 4, 7, 9, 14, 15, 19, 20, 22, 23, 25, 27, 29, 30, 32, 60) contained the core structure $WX_1X_2X_3W$. Six (6) polypeptides (i.e., polypeptide nos. 2, 16, 18, 61, 75, 79) did not contain the core structure $WX_1X_2X_3W$.

FIG. 16 depicts the result of the Competitive ELISA. Peptides containing non-$WX_1X_2X_3W$ motif showed similar inhibitory activity (as compared to that of peptide number 1). A number of peptides from the core structure $WX_1X_2X_3W$ group showed significant and better inhibitory activity compared to peptide number 1. These peptides included peptide number 9, 15, 20, 23, 27, 30 and 60. Peptide number 23 showed the best inhibitory activity among peptides.

Example 10

Dose Response of Polypeptides

We chose peptide number 1, 9, 23 and 27 to generate the dose-response curve in our competitive ELISA. We varied the concentrations of synthetic peptides (100 μM, 50 μM, 25 μM, 12.5 μM, 6.25 μM, 3.125 μM, 1.5625 μM or 0 μM) with fixed amount of IL-23 (50 ng/well) in the assay.

FIG. 17 depicts the results of the competitive ELISA. All peptides tested showed a concentration-dependent inhibition on IL-23 binding to IL-23R. The $IC_{50}$ (inhibitory concentrations of 50%) of peptide nos. 1, 9, 23 and 27 were calculated to be 6.25-12.5 μM, ~3 μM, 0-1.5625 μM and ~1.5625 μM respectively. Consistent with our observation (FIG. 16), peptide no. 23 has the lowest $IC_{50}$ value among other peptides. This result suggests that peptide no. 23 has the strongest inhibitory activity in our ELISA assay.

Example 11

Modification of the Core Structure by Removing Tryptophan Residues

We next sought to determine the importance of the tryptophan (i.e., W) residues in the consensus sequences we identified. To do so, we altered one or both of the tryptophan residues in our peptide sequences. The synthetic peptides were used in the competitive ELISA. The corresponding peptide-Fc fusion proteins were also constructed and used in our in vitro binding assay to examine its binding to IL-23R.

Figure 18:
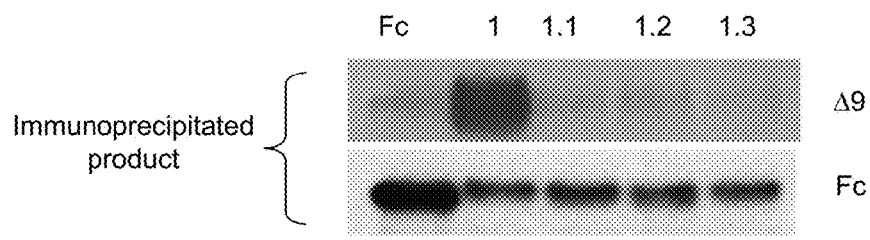
FIG. 18 depicts modified polypeptides used in an in vitro binding assay designed to determine the role of the $WX_1X_2X_3W$ core structure on polypeptide binding to IL-23R. The modified polypeptides (i.e., peptide nos. 1.1, 1.2, and 1.3) have the amino acid sequences designed based on the amino acid sequence of polypeptide no. 1. While polypeptide no. 1 demonstrated avid binding to soluble recombinant IL-23R in the immunoprecipitation assay, minimal immuno-precipitated products were observed for modified polypeptide nos. 1.1, 1.2 and 1.3 (similar to the Fc negative control).
Figure 19:
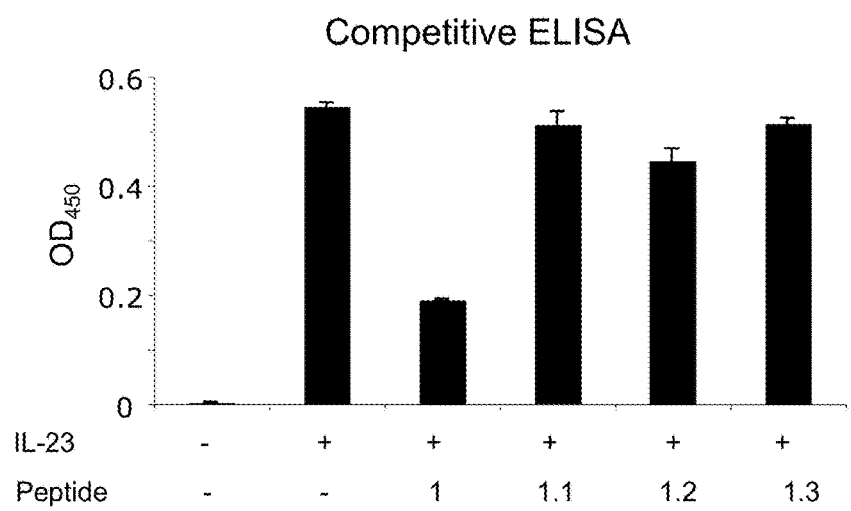
FIG. 19 depicts the modified polypeptides nos. 1.1, 1.2 and 1.3 used in the Competitive ELISA. While polypeptide no. 1 demonstrated avid binding to recombinant full-length IL-23R in the ELISA assay, minimal inhibition was observed for modified polypeptide nos. 1.1, 1.2 and 1.3 (inhibition effect similar to the negative control).
Figure 20:
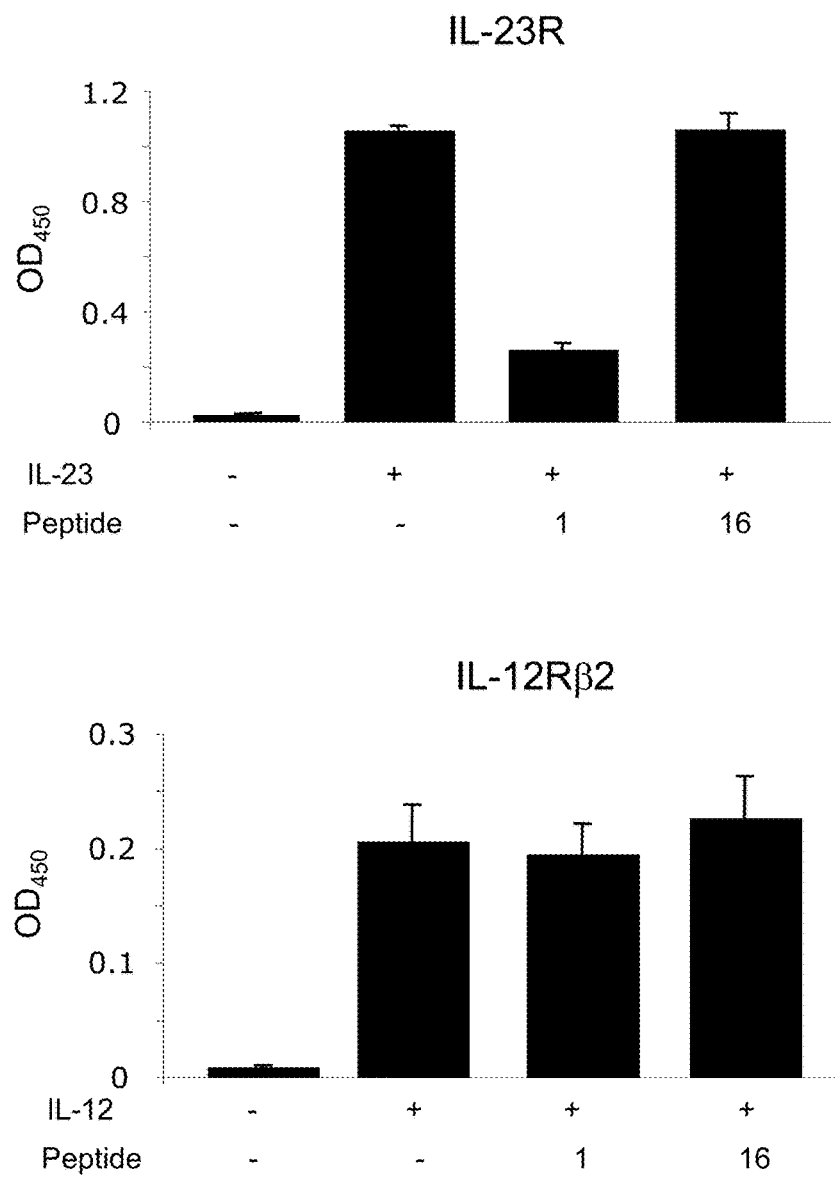
FIG. 20 depicts the peptide specificity for polypeptide no. 1. Competitive ELISA was used for both IL-23R and IL-12Rβ2. While polypeptide no. 1 exhibited inhibitory activity towards binding of IL-23 to IL-23R, this polypeptide had no inhibitory activity towards binding of IL-12 to IL-12Rβ2, indicating peptide specificity. Polypeptide no. 16 serves as a control, where this polypeptide had no inhibitory activity towards both IL-23 and IL-12 binding to their corresponding receptors.
Figure 22:
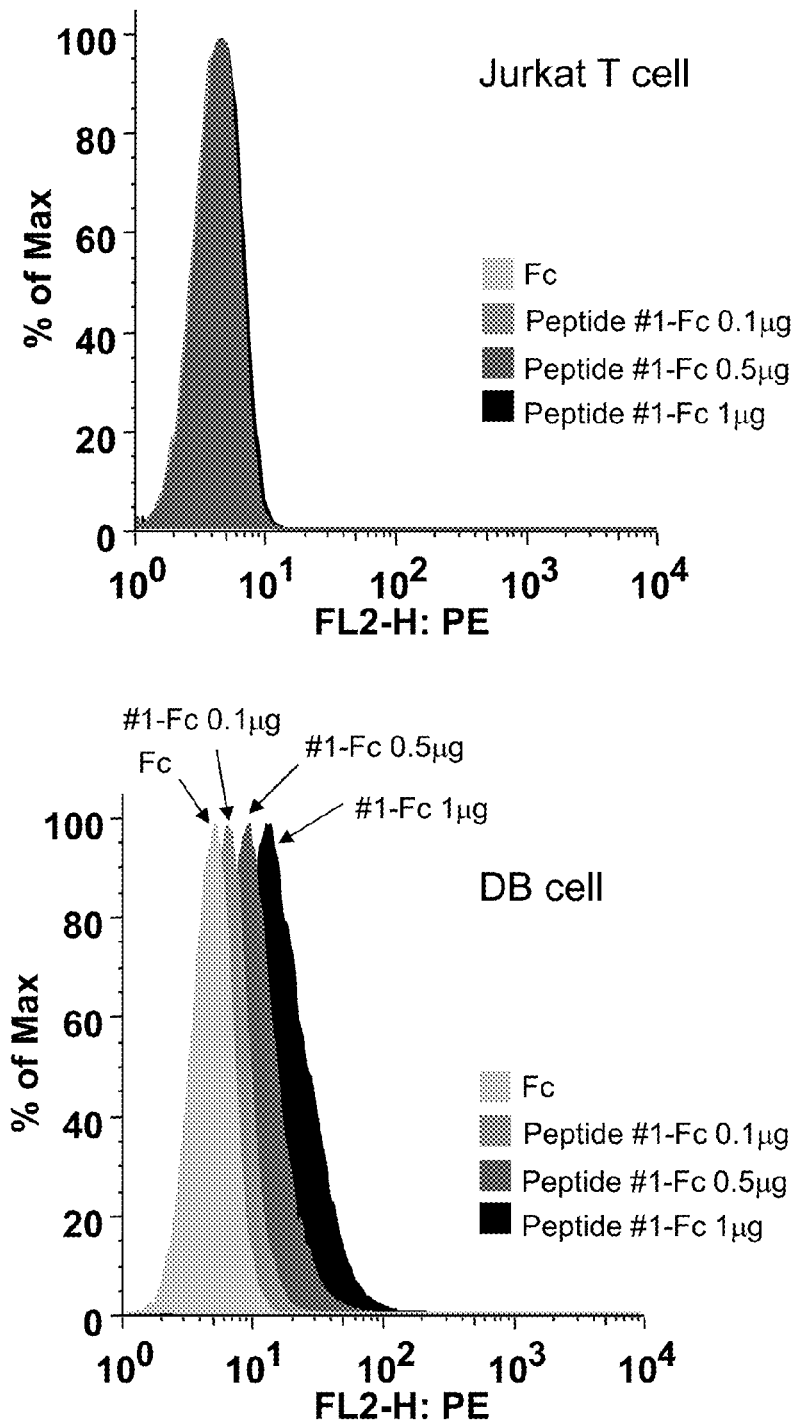
FIG. 22 depicts binding of peptide no. 1-Fc fusion with DB cells using Flow Cytometry. Increased fluorescence was observed in a dose dependent manner with varying concentrations of polypeptide no. 1-Fc fusion protein. The lack of fluorescence on Jurkat T cells indicates that the binding of polypeptide no. 1 is specific to cells expressing IL-23R.

We designed three alternative synthetic peptides based on the sequence of synthetic peptide no. 1. The peptide sequence of synthetic peptide no. 1 was modified at one or both of the tryptophan residues. This resulted in three (3) new synthetic peptide sequences designated as 1.1, 1.2 and 1.3 (collectively, "modified synthetic peptides"). The peptide sequences of synthetic peptide no. 1 and the modified synthetic peptides are depicted in FIG. 18 and Table 3.

TABLE 3

Amino Acid Sequence of Polypeptide Nos. 1, 1.1, 1.2 and 1.3

| Polypeptide No. | Peptide Sequence |
|---|---|
| 1 | SGASWVQYWVQR (SEQ ID NO: 44) |
| 1.1 | SGASFVQYWVQR (SEQ ID NO: 45) |
| 1.2 | SGASWVQYFVQR (SEQ ID NO: 46) |
| 1.3 | SGASFVQYFVQR (SEQ ID NO: 47) |

We designed forward (F) and reverse (R) oligonucleotide sequences corresponding to the desired peptide sequence for the construction of peptide-Fc fusion protein. The oligonucleotide sequences are set forth in Table 4.

TABLE 4

Oligonucleotide Sequences Used to Generate Synthetic Polypeptide Nos. 1, 1.1, 1.2 and 1.3

| Polypeptide No. | Dir. | Oligonucleotide Sequence |
|---|---|---|
| 1 | F | C ATG GTT AGT GGT GCT TCG TGG GTT CAG TAT TGG GTT CAG CGG A (SEQ ID NO: 30) |
|  | R | GA TCT CCGCTGAACCCAATACTG AACCCACGAAGCACCACTAAC (SEQ ID NO: 31) |
| 1.1 | F | C ATG GTT AGT GGT GCT TCG TTT GTT CAG TAT TGG GTT CAG CGG A (SEQ ID NO: 170) |
|  | R | GA TCT CCG CTG AAC CCA ATA CTG AAC AAA CGA AGC ACC ACT AAC (SEQ ID NO: 48) |
| 1.2 | F | C ATG GTT AGT GGT GCT TCG TGG GTT CAG TAT TTT GTT CAG CGG A (SEQ ID NO: 49) |
|  | R | GA TCT CCG CTG AAC AAA ATA CTG AAC CCA CGA AGC ACC ACT AAC (SEQ ID NO: 50) |
| 1.3 | F | C ATG GTT AGT GGT GCT TCG TTT GTT CAG TAT TTT GTT CAG CGG A (SEQ ID NO: 51) |
|  | R | GA TCT CCG CTG AAC AAA ATA CTG AAC AAA CGA AGC ACC ACT AAC (SEQ ID NO: 52) |

Equal amounts of forward and reverse oligonucleotides were annealed into double strand form by incubating at 95° C. for 10 minutes. After the mixture cooled down to room temperature, 1 μl of double strand oligonucleotides was ligated with linearized Fc expression construct (Cat. No. ppfc2-mg2ae1) (InvivoGen, San Diego, Calif.). The linearized vector was prepared by treating the DNA with NcoI and BglII restriction enzymes. The ligated DNA was then transformed into Top10 competent cells (Invitrogen, Carlsbad, Calif.). The sequence of the Fc expression constructs were verified by DNA sequencing.

After the peptide-Fc fusion constructs were prepared, we tested if the fusion proteins could bind extra-cellular region of IL-23R (i.e. Δ9). We performed an in vitro binding assay (i.e., immunoprecipitation assay) wherein we examined if the modified synthetic peptides could bind to Δ9. FIG. 10 depicts the components found in the in vitro binding assay.

Fusion constructs were expressed by transfecting HEK-293T cells with 2 μg of Fc expression constructs. 1 ml of cell culture medium was incubated with 20 μl of protein A sepharose at room temperature for 1 hour to precipitate the Fc proteins. 1 ml of Δ9 containing culture medium was added to the mixture (i.e. Fc proteins and protein A sepharose) and was incubated overnight with mixing at 4° C. The mixture was centrifuged and the supernatant was removed. The remaining protein A resin was then washed 5 times with 1M1 PBS. The proteins in the precipitate were then denatured by addition of sample loading buffer (Bio-Rad, Berkeley, Calif.).

The denatured proteins were subjected to 4-12% PAGE (Bio-Rad) and transferred to Immun-Blot PVDF membrane (Bio-Rad). Membranes were blocked in 5% milk/TPBT at room temperature for 1 hour. Anti-Flag antibody (1:1,000) (Sigma, St. Louis, Mo.) and anti-mouse antibody (1:3,000) were used to detect the Δ9 and Fc proteins respectively.

FIG. 18 shows the sequences of modified peptides and the result of the in vitro binding assay. Consistent with our previous results, synthetic polypeptide no. 1 bound Δ9. There was no detectable binding of the modified synthetic polypeptide sequence nos. 1.1, 1.2 or 1.3 to Δ9. In sum, eliminating one or both tryptophan residues present in polypeptide no. 1 abolished binding of peptide no. 1 to IL-23R.

We next performed a competitive ELISA (as shown in FIG. 12) using polypeptide no. 1 and our modified synthetic peptides (i.e., synthetic peptide nos. 1.1, 1.2 and 1.3) to test if the modified synthetic peptides could inhibit IL-23 binding to its receptor.

Six (6) ELISAs were performed. Control assays were performed in which (i) no IL-23 or peptide was added; (ii) IL-23 was added and peptide was not; and, (iii) IL-23 was added and peptide no. 1 was added. In each competitive assay, 50 μg of human IL-23 and 50 μM of the applicable modified peptide (either polypeptide no. 1.1, 1.2 or 1.3) were added to the wells and allowed to compete for binding to IL-23R. The relative amount of IL-23 bound to the IL-23 receptor was determined by reading optical density at 450 nm.

FIG. 19 shows the sequences of modified synthetic peptides and the results of the competitive ELISA. Optical density was zero in the negative control assay (i.e., no IL-23 and no peptide). Optical density was greater than 0.5 when IL-23 was added without any synthetic polypeptides. Optical density reduced to less than 0.2 when peptide no. 1 was added to compete with IL-23. Optical density increased to at least 0.4 in the assays where peptide no. 1.1, 1.2 or 1.3 was added to compete with IL-23. Thus, less IL-23 bound to IL-23R in the presence of polypeptide no. 1 in comparison to the amount of IL-23 that bound to IL-23R in the presence of polypeptide nos. 1.1, 1.2 or 1.3.

These results indicate an important role of the tryptophan residues in the core structure $WX_1X_2X_3W$ in binding to IL-23R and inhibiting IL-23R activity.

Example 12

Specificity of Synthetic Peptide No. 1 for IL-23R

Interleukin 23 (IL-23) belongs to the IL-12 family and is structurally similar to IL-12 in that the two cytokines share the p40 subunit. Mature IL-23 comprises of p19 and p40 subunits whereas IL-12 is composed of p35 and p40 subunits. IL-23 binds to a heterodimeric receptor (IL-23R), which is comprised of an IL-23a and an IL-12Rβ1 chain. IL-12Rβ1 is also a component of IL-12R complex. IL-12R comprises the IL-12Rβ1 and IL-12Rβ2 chains. It is desirable to specifically inhibit IL-23R while not inhibiting the activity associated with IL-12R.

To study the specificity of our synthetic peptides, we examined the effect of polypeptide no. 1 on IL-12R in a Competitive ELISA. Polypeptide no. 16 was run as a negative control.

Competitive ELISA were performed exactly the same as example 6 except the plate was coated with IL-12Rβ2 (2 μg/ml) or IL-23R (2 μg/ml). In addition, IL-12 (50 ng/well) and IL-23 (50 ng/well) was used in the plate coated with IL-12Rβ2 and IL-23R respectively. The rest of the experimental setup was the same as example 6.

FIG. 20 shows the results of the competitive ELISA between IL-23R and IL-12R. Consistent with our previous ELISA results, synthetic polypeptide no. 1 but not synthetic polypeptide no. 16 inhibited IL-23 binding to its receptor, IL-23R. However, none of the polypeptides inhibited IL-12 from binding to its receptor, IL-12R132.

These results indicate that the inhibitory effect of peptide no. 1 is specific for the IL-23R pathway.

Example 13

Examination of Cell Surface IL-23R Expression on Jurkat T Cell and DB Cell by Flow Cytometry We next performed Flow Cytometry to examine expression of IL-23R on two cell lines, Jurkat T cell and DB cell. Jurkat T cells and DB cells were stained with either isotype control antibodies (i.e., negative control) or anti-IL-23R antibodies.

In preparation for staining, cells were washed 2× with ice-cold PBS. 100 μl of blocking buffer (PBS+5% heat inactivated human serum) was added to re-suspend the cell pellet and the mixture was incubated for 30 minutes on ice. Antibodies (either control isotype antibody or biotinylated anti-IL-23R antibody) (0.5 μg/100 μl) were added and the mixture incubated for 30 minutes on ice followed by washing with ice-cold PBS for 3 times. The washed cells were re-suspended in 100 μl of blocking buffer containing 0.2 μl of streptavidin-PE (Cat. No. 554061BD) (Pharmingen, Phillipines) and were incubated on ice for 30 minutes followed by washing 1 ml PBS for 3 times. The cells were fixed in 1% of paraformaldehyde in PBS. The fixed cells were then acquired and analyzed in a Flow Cytometer.

FIG. 21 shows the results of our Flow Cytometry analysis of IL-23R on the cell surface of Jurkat T cell and DB cell. There was no difference in fluorescence levels when Jurkat T cells were stained with anti-IL-23R antibodies compared to Jurkat T cells stained with control antibodies. In contrast, DB cells stained with anti-IL-23R antibodies showed increased fluorescence as compared to DB cells stained with control antibodies. The fluorescence levels are proportional to the IL-23R level expressed on the cell surface.

These results indicate that IL-23R is expressed on DB cell surface but not on Jurkat T cell surface.

Example 14

Examination of Binding of Peptide No. 1 to Cell Surface by Flow Cytometry

We examined the affinity of peptide no. 1 to bind to IL-23R on the cell surface. Jurkat T cells (i.e., IL-23R negative cell) and DB cells (i.e., IL-23R positive cell) were incubated with peptide no. 1-Fc fusion protein that had been biotinylated to permit detection. In total, eight assays were performed. Four assays were performed in each cell line: (i) staining with biotinylated Fc (i.e., control); (ii) staining with 0.1 μg of biotinylated synthetic peptide no. 1-Fc chimera (no. 1-Fc); (iii) staining with 0.5 μg of biotinylated no. 1-Fc; and, (iv) staining with 1 μg of biotinylated no. 1-Fc.

HEK-293T cells cultured in DMEM+10% FBS were transfected with 10 μg of Fc expression constructs using FuGENE® HD (Roche Cat. No. 04709705001). The cells were washed with PBS. The culture medium was replaced with serum-free CD293 media (Cat. No. 11913019) (Invitrogen, Carlsbad, Calif.) 16 hours after transfection. The cultured media were collected 72 hours after the transfection and concentrated by using Amicon Ultra-15 Centrifugal Filter Unit with Ultracel-30 membrane (Cat. No. UFC903024) (Millipore, Billerica, Mass.). The Fc proteins were purified using the Protein A IgG purification kit (Cat. No. 44667) (Pierce, Rockford, Ill.). The quantity of purified Fc proteins was measured by $OD_{280}$.

Fc proteins were biotinylated using the EZ-Link® Micro Sulfo-NHS-Biotinylation Kit (Cat. No. 21925) (Pierce, Rockford, Ill.). 50 μg of purified Fc proteins in 200 ul of phosphate-buffered saline (PBS pH=7.4) were mixed with 2 μl of sulfo-NHS-biotin solution and incubated on ice for two hours. Excess biotin was removed by centrifuging at 1,000 g for 2 minutes using the Zeba Desalt Spin Column provided in the kit. The collected flow-through solution contained biotinylated Fc protein.

FIG. 22 shows the results of the Flow Cytometry experiment. Jurkat T cells did not demonstrate any increased fluorescence beyond control levels when stained with increasing concentrations of polypeptide no. 1-Fc. In contrast, DB cells showed increased fluorescence when stained with increasing concentrations of polypeptide no. 1-Fc. These results suggest that peptide no. 1 binds to IL-23R on present on cell surfaces and that it binds in a dose-dependent manner.

Example 15

Reduction of Cell Surface IL-23R by Addition of IL-23R siRNA

We examined if the binding of peptide no. 1 to cell surface IL-23R is reduced when IL-23R levels are reduced. siRNA was administered to diminish the expression level of IL-23R.

We performed four assays: (1) control siRNA (i.e., siRNA that would not bind to IL-23R RNA) stained with control antibodies; (2) control siRNA stained with anti-IL-23R antibodies; (3) IL-23R siRNA (i.e., siRNA specific for IL-23R RNA) stained with control antibodies; and, (4) IL-23R siRNA stained with anti-IL-23R antibodies.

DB cells (5×10⁶) were transfected with siRNA using Amaxa® Human T cell Nucleofector® Kit (Cat. No. VPA-1002) (Lonza, Allendale, N.J.). The control siRNA and human IL-23R siRNA were obtained from Thermo Scientific Dharmacon® (Cat. No. D-001810-01-05 (control) and L-007976-00 (IL-23R)) (Lafayette, Colo.). DB cells were precipitated by centrifugation at 200×g for 10 minutes. The cell pellet was re-suspended in 100 µl of Nucleofector® solution containing either control siRNA or IL23R siRNA. The cell and siRNA suspension were transferred into certified cuvette. The cuvette was inserted into the Nucleofector® Cuvette Holder and V-024 program was applied. 500 µl of the pre-equilibrated culture medium (RPMI+10% FBS) was gently added to the cuvette and was transferred into one well of a 12-well plate. The cells were incubated for 48 hours and were used in the Flow Cytometry experiment. The cells were stained with either isotype control antibodies or anti-IL23R antibodies as previously described.

Figure 23:
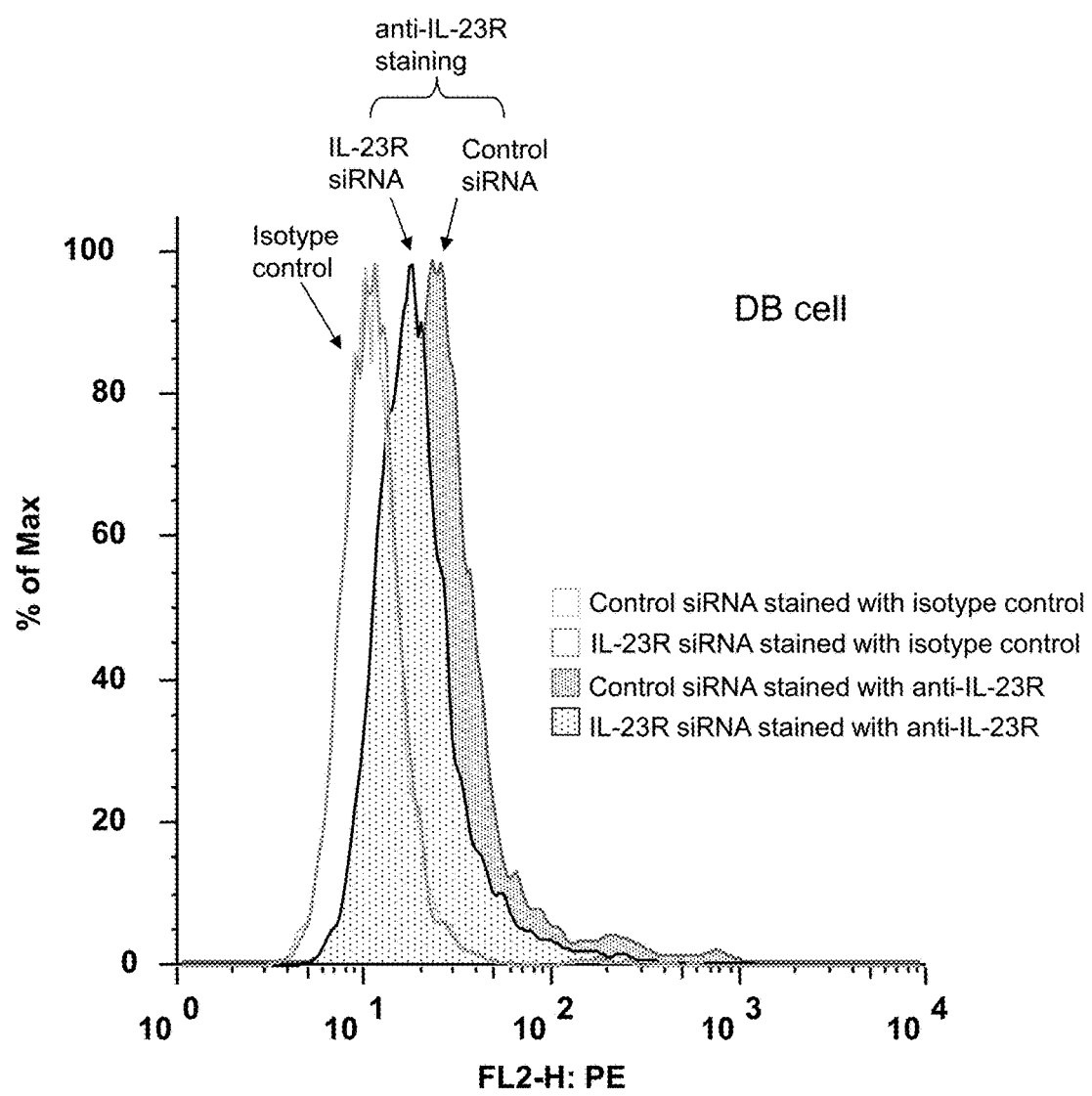
FIG. 23 depicts the knockdown of IL-23R on DB cells using siRNA against IL-23R. Flow Cytometry was used to monitor cell surface expression of IL-23R. Treatment of DB cells with an IL-23R siRNA reduces the IL-23R expression as evidenced by a reduction in fluorescence intensity.
Figure 24:
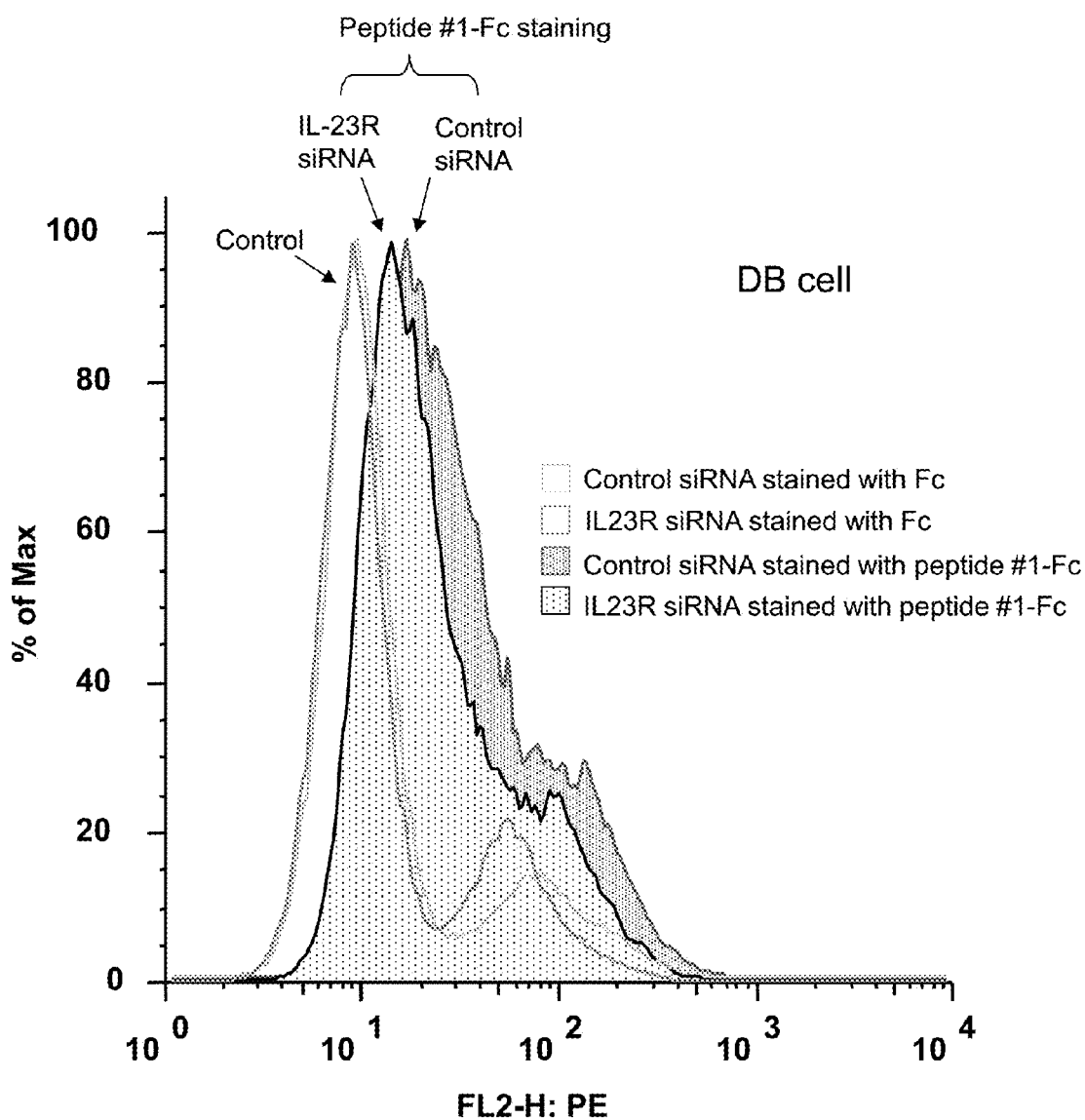
FIG. 24 depicts binding of peptide no. 1-Fc fusion protein with DB cells treated with an anti-IL-23R siRNA. siRNA treated DB cells were confirmed to have a reduced IL-23R expression as evidenced by Flow Cytometry. The concomitant reduction in polypeptide binding in the siRNA treated DB cells indicates the peptide specificity.
Figure 26:
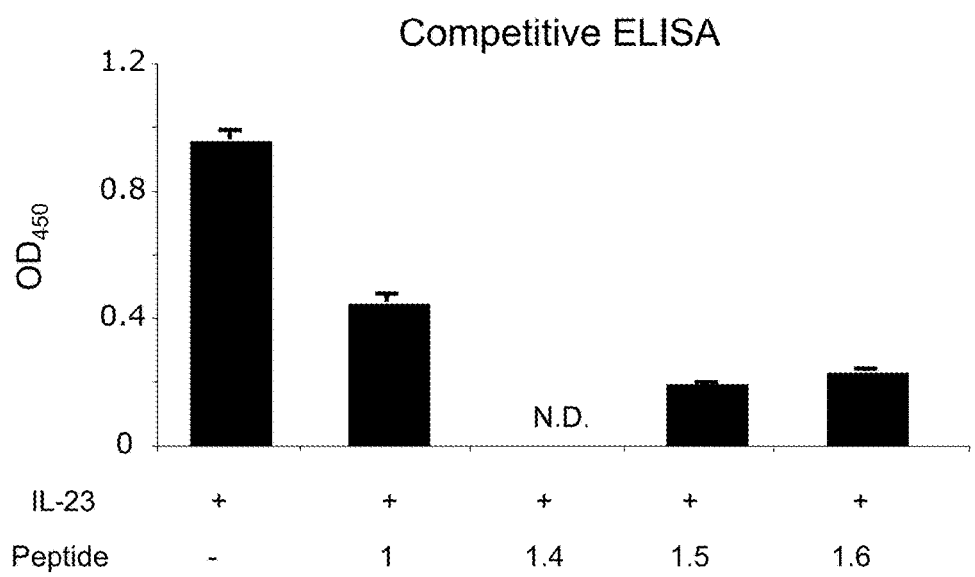
FIG. 26 depicts the effect of polypeptide modification on its ability to inhibit binding of IL-23 to its receptor. Polypeptide modification was achieved by altering the polypeptide length. IL-23 binding to its receptor was monitored by Competitive ELISA. With respect to polypeptide no. 1, reducing the total number of amino acid residues from twelve (12) to nine (9) decreased solubility (i.e., they formed precipitates and rendered the Competitive ELISA infeasible). Modified polypeptide nos. 1.5 and 1.6 exhibit an equal, if not stronger, inhibition toward IL-23 binding.
Figure 27:
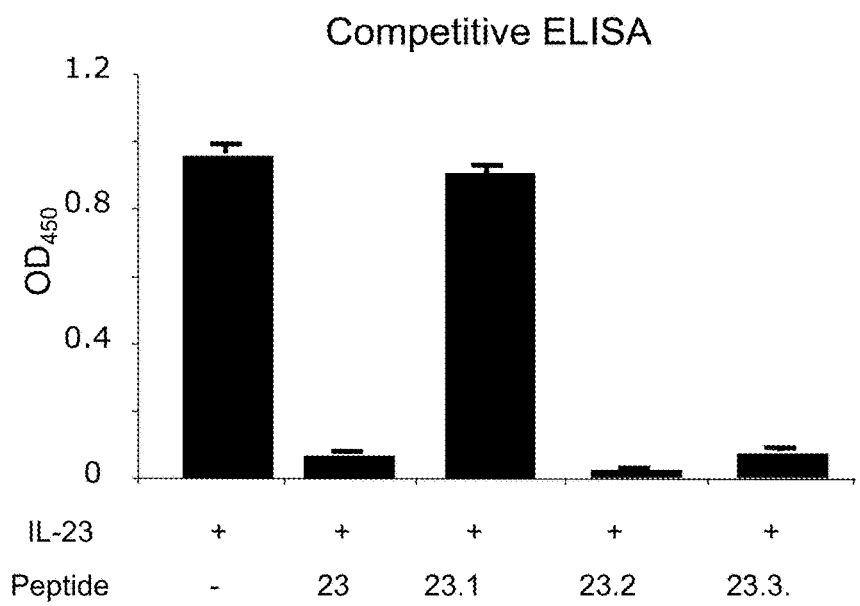
FIG. 27 depicts the effect of polypeptide modification on its ability to inhibit binding of IL-23 to its receptor. Polypeptide modification was achieved by altering the polypeptide length. IL-23 binding to its receptor was monitored by Competitive ELISA. With respect to polypeptide no. 23, reducing the total number of amino acid residues from twelve (12) to nine (9) did not alter its solubility. Modified polypeptide nos. 23.2 and 23.3 exhibit an equal, if not stronger, inhibition toward IL-23 binding.

FIG. 23 shows the cell surface expression of IL-23R after siRNA treatment by Flow Cytometry. Control siRNA treated cells stained with anti-IL-23R showed increased fluorescence in comparison to control siRNA treated cells stained with control antibodies. IL-23R siRNA treated cells stained with control antibodies demonstrated fluorescence levels comparable to those found with control siRNA treated cells stained with control antibodies (i.e., background staining level was the same between control siRNA or IL-23R siRNA treated cells). IL-23R siRNA treated cells stained with anti-IL-23R antibodies demonstrated decreased fluorescence levels when compared to control siRNA treated cells stained with anti-IL-23R antibodies.

These data show that IL-23R levels were reduced by the addition of IL-23R siRNA.

Example 16

Reduction of Synthetic Peptide Binding by Addition of IL-23R siRNA

We examined the effect of the IL-23R siRNA in DB cells and determined if it may affect the binding of polypeptide no. 1-Fc to DB cell IL-23 receptors.

We performed four assays: (1) control siRNA (i.e., siRNA not specific to IL-23R) stained with biotinylated Fc; (2) IL-23R siRNA stained with biotinylated Fc; (3) control siRNA stained with biotinylated polypeptide no. 1-Fc; and, (4) IL-23R siRNA stained with biotinylated polypeptide no. 1-Fc. Fc proteins were purified and biotinylated as set forth in Example 16.

FIG. 24 shows the results of our assay. Control siRNA treated cells and IL-23R siRNA treated cells showed no difference in fluorescence levels when stained with Fc (i.e., the background level of staining was not affected by siRNA treatment). In cells stained with polypeptide no. 1-Fc, IL-23R siRNA cells demonstrated decreased fluorescence in comparison to control siRNA cells. The degree of reduction in the mean fluorescence intensity (MFI) upon IL-23R siRNA treatment is summarized in the FIG. 25.

These data show that the addition of IL-23R siRNA reduces the amount of polypeptide no. 1 that is binding to the cells. Thus, given that IL-23R siRNA reduces the levels of IL-23R on the cells, the data suggests that polypeptide no. 1 binds to the cell surface through IL-23R.

Example 17

Polypeptide Modification—the Effect of Varying Polypeptide Length while Retaining the Core Structure We examined the effect of peptide length on IL-23 inhibition. Polypeptides with a total amino acid length of 9, 16 or 18 amino acids were prepared by deleting or adding amino acids to sequences of polypeptide nos. 1 or 23. Despite a change in the overall length of the polypeptide, the core structure of the polypeptide was retained.

The modified polypeptides were used in a Competitive ELISA with IL-23, which was performed in accordance with the procedure set forth in Example 6.

(i) Core Structure $WX_1X_2X_3W$-Polypeptide No. 1

We prepared three (3) polypeptides of various lengths based on the amino acid sequence of polypeptide no. 1. FIG. 26 and Table 5 show the sequence of the polypeptides we created.

TABLE 5

Amino Acid Sequences of Polypeptide Nos. 1, 1.4, 1.5 and 1.6

| Polypeptide No. | Polypeptide Sequence | |
|---|---|---|
| 1 | SGASWVQYWVQR | (SEQ ID NO: 7) |
| 1.4 | ASWVQYWVQ | (SEQ ID NO: 53) |
| 1.5 | GASGASWVQYWVQRGA | (SEQ ID NO: 54) |
| 1.6 | VGASGASWVQYWVQRGAL | (SEQ ID NO: 55) |

FIG. 26 shows the results of the Competitive ELISA. Polypeptide no. 1.4 formed a precipitate and could not be reliably assessed. Increasing polypeptide length from twelve (12) amino acids (as in polypeptide no. 1) to sixteen (16) amino acids (as in polypeptide no. 1.5) or eighteen (18) amino acids (as in polypeptide no. 1.6) did not diminish the ability of the polypeptides including the core structure $WX_1X_2X_3W$ from inhibiting the activity of IL-23.

(ii) Core Structure $WX_1X_2WW$-Polypeptide No. 23

We also prepared three (3) polypeptides of various lengths based on the amino acid sequence of polypeptide no. 23. FIG. 27 and Table 6 show the sequence of the polypeptides we created.

TABLE 6

Amino Acid Sequences of Polypeptide Nos. 23, 23.1, 23.2 and 23.3

| Polypeptide No. | Polypeptide Sequence | |
|---|---|---|
| 23 | AMTWEDWWLYGR | (SEQ ID NO: 23) |
| 23.1 | MTWEDWWLY | (SEQ ID NO: 56) |
| 23.2 | GAAMTWEDWWLYGRGA | (SEQ ID NO: 57) |
| 23.3 | VGAAMTWEDWWLYGRGAL | (SEQ ID NO: 58) |

FIG. 27 shows the results of the Competitive ELISA. Decreasing the total amino acid length from twelve (12) (as in polypeptide no. 23) to nine (9) (as in polypeptide no. 23.1)

did eliminate the ability of the polypeptides including the core structure $WX_1X_2WW$ from inhibiting the activity of IL-23. Likewise, increasing polypeptide length from twelve (12) amino acids to sixteen (16) amino acids (as in polypeptide no. 23.2) or eighteen (18) amino acids (as in polypeptide no. 23.3) did not diminish the ability of the polypeptides including the core structure $WX_1X_2WW$ from inhibiting the activity of IL-23.

These data show that if the core structure is retained and the length of the polypeptide is twelve (12) amino acids or longer, no adverse affect on inhibitory activity was noticed.

Example 18

Polypeptide Modification-Altering Tryptophan Positioning

We altered the number of amino acids between tryptophan residues (thereby destroying the core structure $WX_1X_2X_3W$) and tested the role of tryptophan spacing on inhibition of IL-23 binding to its receptor.

The modified polypeptides were used in a Competitive ELISA with IL-23. The Competitive ELISA was performed in accordance with the procedure set forth in Example 6.

(i) Modified Sequences Based Upon Polypeptide No. 1

Based on the sequence of polypeptide no. 1, we prepared six (6) modified polypeptides (polypeptide nos. 1.7, 1.8, 1.9, 1.10, 1.11 and 1.12) in which the number of amino acid residues between tryptophan residues was changed (i.e., they no longer included the core structure $WX_1X_2X_3W$). The FIG. 28 and Table 7 show the sequence of the modified polypeptides and polypeptide no. 1, on which the modified polypeptides were based.

TABLE 7

Amino Acid Sequences of Polypeptide Nos. 1, 1.7, 1.8, 1.9, 1.10, 1.11 and 1.12

| Polypeptide No. | Polypeptide Sequence |
|---|---|
| 1 | SGASWVQYWVQR (SEQ ID NO: 7) |
| 1.7 | SGASWWQYVVQR (SEQ ID NO: 59) |
| 1.8 | SGASWVWYQVQR (SEQ ID NO: 60) |
| 1.9 | SGASWVQWYVQR (SEQ ID NO: 61) |
| 1.10 | SGAWSVQYVWQR (SEQ ID NO: 62) |
| 1.11 | SGWSAVQYQVWR (SEQ ID NO: 63) |
| 1.12 | WGASSVQYRVQW (SEQ ID NO: 64) |

Figure 28:
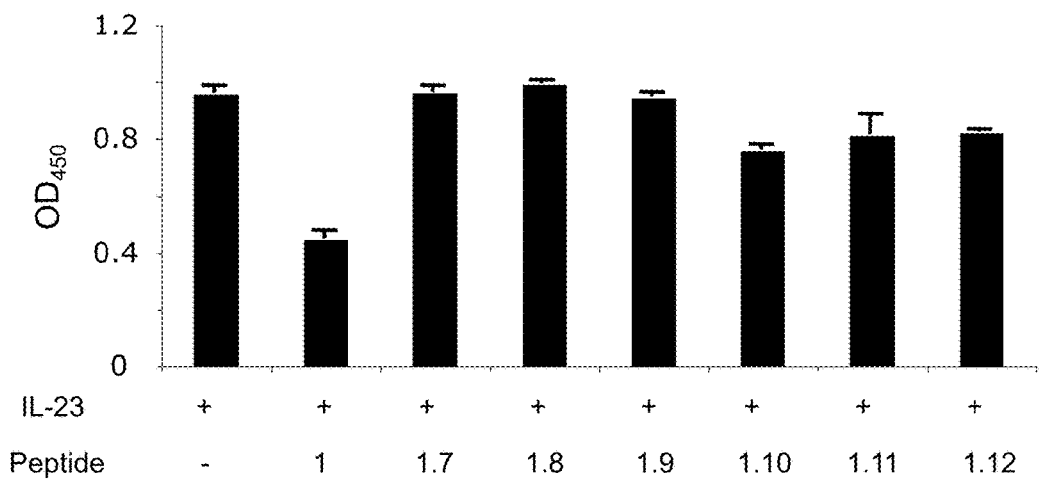
FIG. 28 depicts the effect of polypeptide modification on its ability to inhibit binding of IL-23 to its receptor. Polypeptide modification was achieved by altering the number of amino acids between the two (2) tryptophan (W) residues within the core structure of $WX_1X_2X_3W$. IL-23 binding to its receptor was monitored by Competitive ELISA. With respect to polypeptide no. 1, the core structure of $WX_1X_2X_3W$ provided optimal inhibition of IL-23 binding.

FIG. 28 shows the results of the Competitive ELISA that were performed. Modified polypeptides 1.7, 1.8, 1.9, 1.10, 1.11 and 1.12 did not demonstrate any inhibitory effect on IL-23 binding. This was the case when the number of amino acid residues between tryptophan residues was reduced (to zero (0), one (1) or two (2) amino acids in polypeptide nos. 1.7, 1.8 and 1.9, respectively) and when the number of amino acid residues between tryptophan residues was increased (to five (5), seven (7) or ten (10) amino acids in polypeptide nos. 1.10, 1.11 and 1.12, respectively).

These data suggest that the spacing between tryptophan residues, and specifically the core structure $WX_1X_2X_3W$, plays an influential role in the ability of a polypeptide to inhibit IL-23 binding to its receptor.

(ii) Modified Sequences Based Upon Polypeptide No. 9

Figure 29:
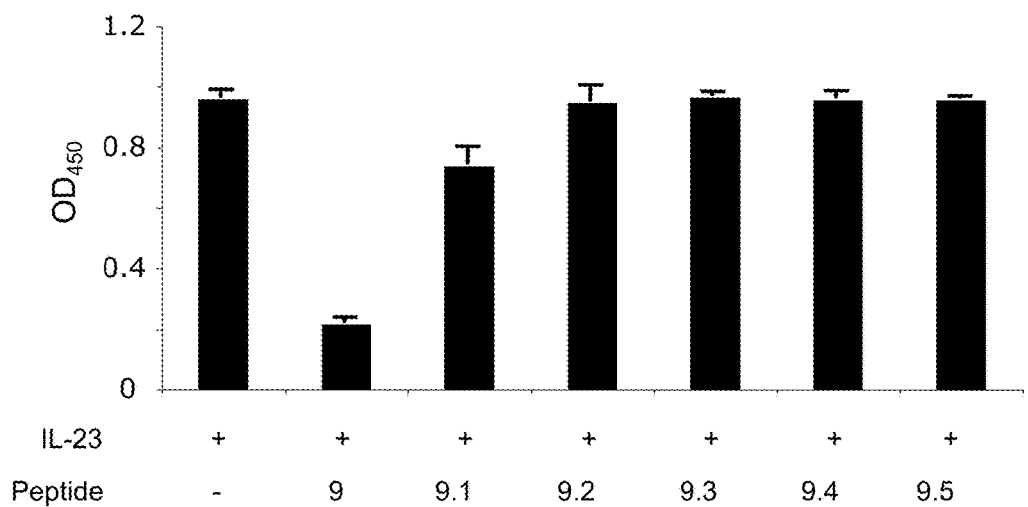
FIG. 29 depicts the effect of polypeptide modification on its ability to inhibit binding of IL-23 to its receptor. Polypeptide modification was achieved by altering the number of amino acids between the two (2) tryptophan (W) residues within the core structure of $WX_1X_2X_3W$. IL-23 binding to its receptor was monitored by Competitive ELISA. With respect to polypeptide no. 9, the core structure of $WX_1X_2X_3W$ provided optimal inhibition of IL-23 binding.

Using the amino acid sequence of polypeptide no. 9, we designed five (5) additional peptides (i.e., polypeptide nos. 9.1, 9.2, 9.3, 9.4 and 9.5) in which the number of amino acid residues between tryptophan residues was changed (i.e., they no longer included the core structure $WX_1X_2X_3W$). FIG. 29 and Table 8 show the sequence of the modified polypeptides and polypeptide no. 9, on which the modified polypeptides were based.

TABLE 8

Amino Acid Sequences of Polypeptide Nos. 9, 9.1, 9.2, 9.3, 9.4 and 9.5

| Polypeptide No. | Polypeptide Sequence |
|---|---|
| 9 | NWATYWQLRHQT (SEQ ID NO: 14) |
| 9.1 | NWWTYAQLRHQT (SEQ ID NO: 65) |
| 9.2 | NWAWYTQLRHQT (SEQ ID NO: 66) |
| 9.3 | NWATYLQWRHQT (SEQ ID NO: 67) |
| 9.4 | NWATYHQLRWQT (SEQ ID NO: 68) |
| 9.5 | NWATYQQLRHWT (SEQ ID NO: 69) |

FIG. 29 shows the results of the Competitive ELISA between the modified polypeptides and IL-23. Modified polypeptides 9.1, 9.2, 9.3, 9.4 and 9.5 did not demonstrate any inhibitory effect on IL-23 binding. This was the case when the number of amino acid residues between tryptophan residues was reduced (to zero (0) or one (1) amino acid residues in polypeptide nos. 9.1 and 9.2, respectively) and when the number of amino acid residues between tryptophan residues was increased (to five (5), seven (7) or eight (8) amino acids in polypeptide nos. 9.3, 9.4 and 9.5, respectively).

These data suggest that the spacing between tryptophan residues, and specifically the core structure $WX_1X_2X_3W$, plays an influential role in the ability of a polypeptide to inhibit IL-23 binding to its receptor.

Example 19

Polypeptide Modification—Altering Amino Acid Residues at $X_1X_2X_3$ within the Core Structure We examined the role of the three (3) amino acid residues (i.e., $X_1X_2X_3$) within the core structure $WX_1X_2X_3W$ on IL-23 inhibition. To do so, we substituted the amino acid residues by: (i) simultaneously substituting all three amino acid residues between the tryptophan (W) residues, or (ii) substituting (one at a time) of the three amino acid residues between the tryptophan (W) residues (i.e., substituting at one of $X_1$, $X_2$ or $X_3$).

Figure 30:
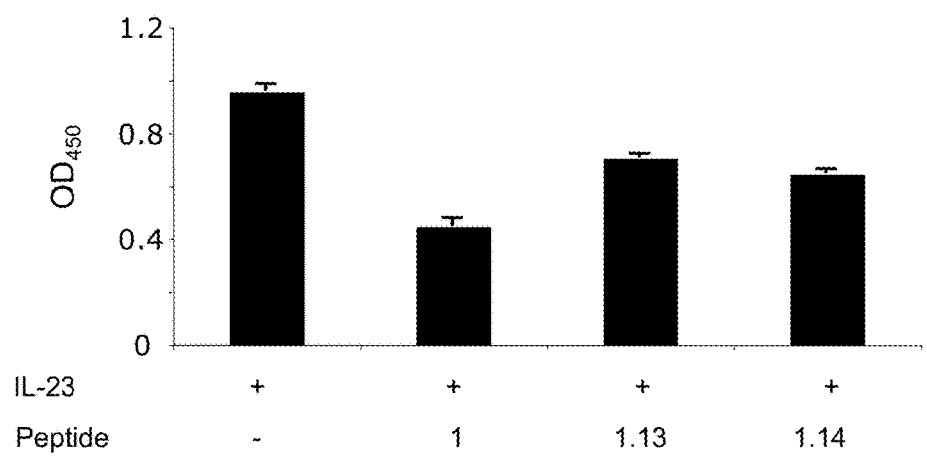
FIG. 30 depicts the effect of polypeptide modification on its ability to inhibit binding of IL-23 to its receptor. Polypeptide modification was achieved by simultaneous substitution of all three amino acids (i.e., $X_1X_2X_3$) spanning between the two (2) tryptophan (W) residues within the core structure of $WX_1X_2X_3W$. IL-23 binding to its receptor was monitored by Competitive ELISA. Polypeptide no. 1.13 represents a "drastic" amino acid substitution. Polypeptide no. 1.14 represents a "conservative" amino acid substitution. With respect to polypeptide no. 1, amino acid substitution did not abrogate the ability of the polypeptide to inhibit binding of IL-23 to its receptor.
Figure 31:
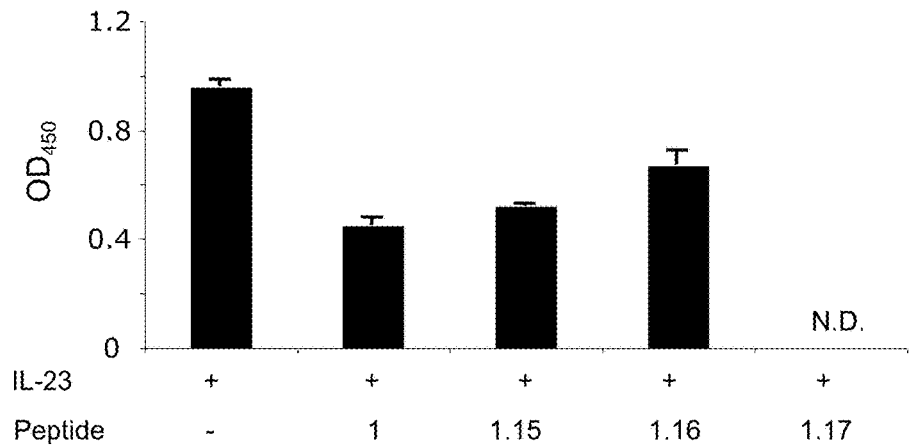
FIG. 31 depicts the effect of polypeptide modification on its ability to inhibit binding of IL-23 to its receptor. Polypeptide modification was achieved by gradual "conservative" substitution of the three amino acids (i.e., $X_1X_2X_3$) spanning between the two (2) tryptophan (W) residues within the core structure of $WX_1X_2X_3W$. IL-23 binding to its receptor was monitored by Competitive ELISA. With respect to polypeptide no. 1, amino acid substitution of the $X_1X_2$ did not abrogate the ability of the polypeptide to inhibit IL-23 binding to its receptor. Note that when $X_3$ is altered from tyrosine (Y) to phenylalanine (F), it rendered the polypeptide insoluble.

Using polypeptide no. 1 as a control, we prepared the modified polypeptides and studied the polypeptide modification (See, FIG. 30 and FIG. 31). The modified polypeptides were examined using a Competitive ELISA with IL-23, which was performed in accordance with the procedure set forth in Example 6.

(i) Simultaneous Substitution of all Three (3) Amino Acids

In this series of studies, we simultaneously substituted all three amino acid residues of polypeptide no. 1 while maintaining the remaining amino acid residues unchanged. We used two approaches: (i) drastic amino acid substitution change; and (ii) conservative amino acid substitution change.

In the drastic substitution change approach, the original amino acid residues were replaced by amino acids with different properties on the side chain. For example, an amino acid with a non-polar side chain was replaced with amino acid with polar uncharged side chain. An amino acid with aromatic side chain was changed to amino acid with aliphatic side chain. Polypeptide no. 1.13 was modified using the dramatic change approach. FIG. 30 and Table 9 show the sequence of polypeptide nos. 1, 1.13 and 1.14.

In the conservative change approach, the original amino acid residues were replaced by amino acids with the same properties on the side chain. For example, amino acid with a non-polar side chain was replaced with another amino acid with non-polar side chain. An amino acid with aromatic side chain was changed to another amino acid with aromatic side chain. Polypeptide no. 1.14 was modified by the conservative change approach. FIG. 30 and Table 9 show the sequence of polypeptide nos. 1, and 1.14.

TABLE 9

Amino Acid Sequences of Polypeptide Nos. 1, 1.13 and 1.14

| Polypeptide No. | Polypeptide Sequence |
|---|---|
| 1 | SGASWVQYWVQR (SEQ ID NO: 7) |
| 1.13 | SGASWNLAWVQR (SEQ ID NO: 70) |
| 1.14 | SGASWLNFWVQR (SEQ ID NO: 71) |

FIG. 30 shows the results of the Competitive ELISA. The results indicate that changing all three amino acid residues within the core structure $WX_1X_2X_3W$, either drastically or conservatively, did not eliminate the inhibitory capability of the modified polypeptides.

(ii) Gradual Substitution of Amino Acids

In this study, we changed the (3) three amino acid residues (i.e. VQY) of the polypeptide no. 1 in the core structure $WX_1X_2X_3W$ individually. The conservative change approach was applied in this study. Three (3) modified polypeptides based on the amino acid sequence of polypeptide no. 1 were generated (i.e., polypeptide nos. 1.12, 1.13 and 1.14). FIG. 31 and Table 10 show the sequence of the polypeptides we designed and the sequence of polypeptide no. 1.

TABLE 10

Amino Acid Sequences of Polypeptide Nos. 1, 1.15, 1.16 and 1.17

| Polypeptide No. | Polypeptide Sequence |
|---|---|
| 1 | SGASWVQYWVQR (SEQ ID NO: 7) |
| 1.15 | SGASWLQYWVQR (SEQ ID NO: 72) |
| 1.16 | SGASWVNYWVQR (SEQ ID NO: 73) |
| 1.17 | SGASWVQFWVQR (SEQ ID NO: 74) |

FIG. 31 shows the results of the Competitive ELISA. Polypeptide no. 1.17 formed a precipitate and therefore could not be assayed. Addition of phenylalanine (F) in place of tyrosine (Y) next to tryptophan (W) adversely affects the solubility of the polypeptide no. 1. The conservative change of valine (V) to leucine (L) (polypeptide no. 1.15) or glutamine (Q) to asparagine (N) (polypeptide no. 1.16) did not abolish the inhibitory activity of modified polypeptides.

We concluded that the amino acid residues $X_1X_2X_3$ within the core structure $WX_1X_2X_3W$ play only a limited, if any, role in a polypeptide's ability to inhibit IL-23 binding to its receptor. This observation is also consistent with the results obtained in our studies wherein we performed simultaneous substitution of all three (3) amino acid residues in the core structure $WX_1X_2X_3W$.

Example 20

Polypeptide Modification—Adding Tryptophan Residues Adjacent to Core Structure

Figure 32:
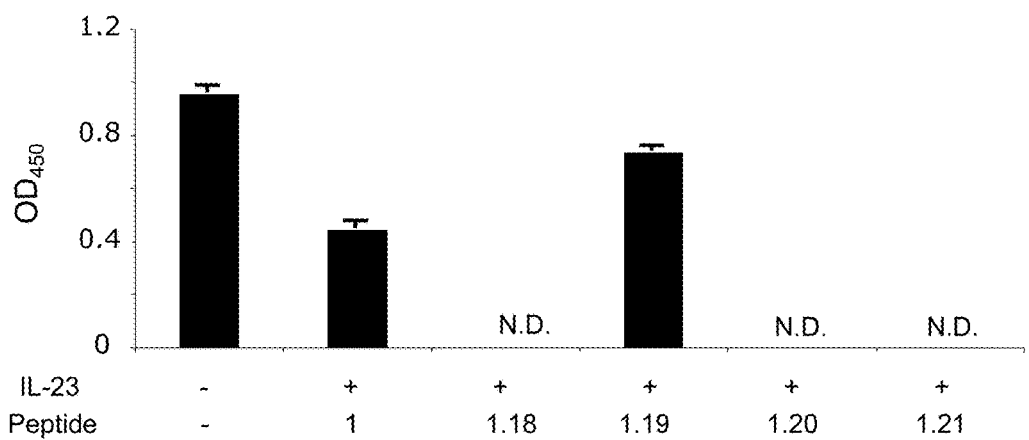
FIG. 32 depicts the effect of polypeptide modification on its ability to inhibit binding of IL-23 to its receptor. Polypeptide modification was achieved by addition of tryptophan (W) residue(s) adjacent to the $WX_1X_2X_3W$ core structure. IL-23 binding to its receptor was monitored by Competitive ELISA. Addition of one (1) tryptophan (W) residue is tolerated, with further addition increases the likelihood of insolubility.

We examined the role of tryptophan (W) on binding to IL-23R and inhibiting IL-23. We prepared modified polypeptides that included additional tryptophan (W) residues adjacent to, but outside of, the $WX_1X_2X_3W$ core structure. One (1) or two (2) tryptophan residues were added to either side of the $WX_1X_2X_3W$ core structure of polypeptide no. 1. FIG. 32 and Table 11 show the amino acid sequences of the modified polypeptides.

TABLE 11

Amino Acid Sequences of Polypeptide Nos. 1, 1.18, 1.19, 1.20 and 1.21

| Polypeptide No. | Polypeptide Sequence |
|---|---|
| 1 | SGASWVQYWVQR (SEQ ID NO: 7) |
| 1.18 | SGAWWVQYWVQR (SEQ ID NO: 75) |
| 1.19 | SGASWVQYWWQR (SEQ ID NO: 76) |
| 1.20 | SGWWWVQYWVQR (SEQ ID NO: 77) |
| 1.21 | SGASWVQYWWWR (SEQ ID NO: 78) |

The modified polypeptides were used in a Competitive ELISA with IL-23. The Competitive ELISA was performed in accordance with the procedure set forth in Example 6.

FIG. 32 show the results of the Competitive ELISA. Addition of extra tryptophan (W) residues adjacent to, and outside, the core structure $WX_1X_2X_3W$ did not abrogate the ability of polypeptide no. 1.19 to inhibit IL-23 binding to its receptor. However, polypeptide nos. 1.18, 1.20 and 1.21 were insoluble (and thus could not be tested in our Competitive ELISA).

Thus, it appears that additional tryptophan (W) residues adjacent to (but outside of) the $WX_1X_2X_3W$ core structure may attribute to solubility of the polypeptide (i.e., additional tryptophan (W) residues may adversely affect the solubility of the polypeptides).

Example 21

Polypeptide Modification—Altering Amino Acids Adjacent to the $WX_1X_2X_3W$ Core Structure We examined the contribution of the amino acids adjacent (on both sides) to the core structure $WX_1X_2X_3W$ of polypeptide no. 1 on the inhibitory properties of the polypeptides. We prepared several modified polypeptides based on the amino acid sequence of polypeptide no. 1. We maintained the core structure $WX_1X_2X_3W$ of the polypeptides, but changed the amino acid residues before (i.e., SGAS) or after (i.e., VQR) the $WX_1X_2X_3W$ core structure. (See, FIG. 33 and FIG. 34). We used both a conservative change approach and a drastic change approach in altering the amino acids for the modified polypeptides.

The modified polypeptides were examined in a Competitive ELISA, which was performed in accordance with the procedure set forth in Example 6.

(i) Conservative Chance of Adjacent Amino Acids

Figure 33:
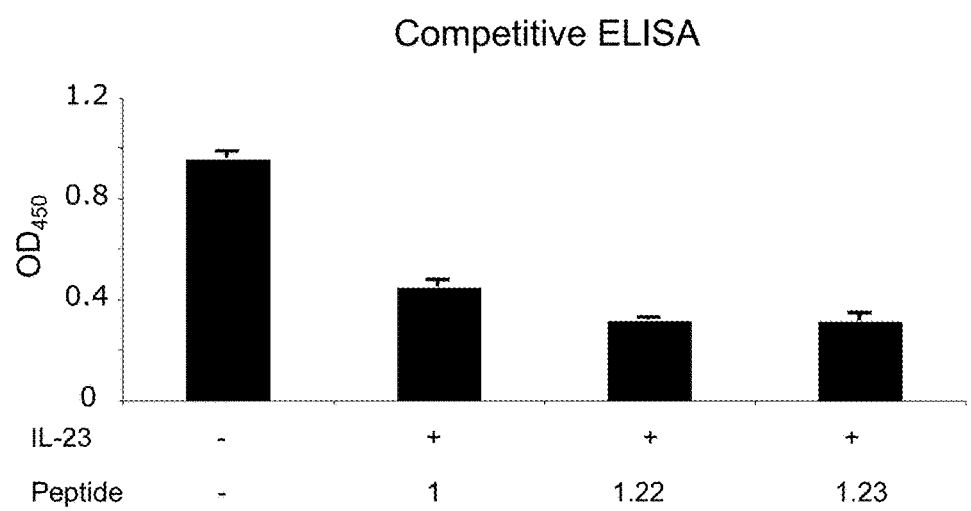
FIG. 33 depicts the effect of polypeptide modification on its ability to inhibit binding of IL-23 to its receptor. Polypeptide modification was achieved by substituting either side of the $WX_1X_2X_3W$ core structure with conservative amino acid residues. IL-23 binding to its receptor was monitored by Competitive ELISA. With respect to polypeptide no. 1, conservative amino acid substitution of the amino acids on either side of the core structure did not abrogate the ability of the polypeptides to inhibit IL-23 binding to its receptor.

Polypeptide nos. 1.19 and 1.20 were modified by the conservative change approach, in which the original amino acid residues were replaced by amino acids with the same properties on the side chain. FIG. 33 and Table 12 show the amino acid sequence of the polypeptides prepared using the conservative change approach.

TABLE 12

Amino Acid Sequences of Polypeptide Nos. 1, 1.22 and 1.23

| Polypeptide No. | Polypeptide Sequence | |
|---|---|---|
| 1 | SGASWVQYWVQR | (SEQ ID NO: 7) |
| 1.22 | TAGTWVQYWVQR | (SEQ ID NO: 79) |
| 1.23 | SGASWVQYWLNK | (SEQ ID NO: 80) |

FIG. 33 shows the results of the Competitive ELISA. Modified polypeptide nos. 1.22 and 1.23 demonstrated an equal inhibition of IL-23 binding to its receptor as compared to polypeptide no. 1.

This suggests that it is the core structure $WX_1X_2X_3W$ and not the surrounding amino acid residues that are responsible for binding to IL-23R and inhibiting IL-23.

(ii) Drastic Chance of Adjacent Amino Acids

Figure 34:
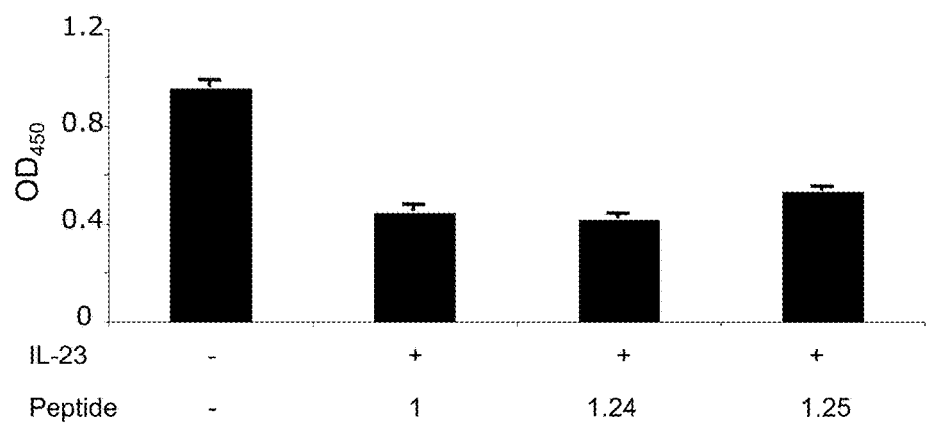
FIG. 34 depicts the effect of polypeptide modification on its ability to inhibit binding of IL-23 to its receptor. Polypeptide modification was achieved by drastic substitution of the amino acids on either side of the core structure $WX_1X_2X_3W$. IL-23 binding to its receptor was monitored by Competitive ELISA. With respect to polypeptide no. 1, drastic amino acid substitution of the amino acids adjacent to the core structure did not abrogate the ability of the polypeptides to inhibit IL-23 binding to its receptor.

Polypeptide nos. 1.24 and 1.25 were prepared by modifying polypeptide no. 1 according to a drastic change approach in which the original amino acid residues were replaced by amino acids with different properties on the side chain. FIG. 34 and Table 13 show the amino acid sequence of the polypeptides prepared using the drastic change approach.

TABLE 13

Amino Acid Sequences of Polypeptide Nos. 1, 1.24 and 1.25

| Polypeptide No. | Polypeptide Sequence | |
|---|---|---|
| 1 | SGASWVQYWVQR | (SEQ ID NO: 7) |
| 1.24 | ASSAWVQYWVQR | (SEQ ID NO: 81) |
| 1.25 | SGASWVQYWYEE | (SEQ ID NO: 82) |

FIG. 34 shows the results of the Competitive ELISA. Changing the amino acids located adjacent to, but outside of, the core structure $WX_1X_2X_3W$ did not abrogate the ability of polypeptide nos. 1.24 or 1.25 to inhibit IL-23 binding to its receptor in our ELISA. This data demonstrates that it is the core structure $WX_1X_2X_3W$ and not the surrounding amino acid residues that are responsible for binding to IL-23R and inhibiting IL-23.

Many polypeptides screened from our Phage Display Screening possess variations in amino acids adjacent to the $WX_1X_2X_3W$ core structure. Despite these amino acid variations, all exhibit the ability to bind to IL-23R as well as inhibiting IL-23R signaling. (See, FIG. 8). This suggests the $WX_1X_2X_3W$ core structure (and not the amino acids outside the core structure) is responsible for polypeptide binding to IL-23R as well as inhibition of IL-23 cell signaling thereof.

Example 22

Polypeptide Modification—Altering $X_3$ within the Core Structure of Polypeptide No. 23

Competitive ELISA studies indicate that polypeptide no. 23 may have the strongest inhibitory effect of all the polypeptides selected in our Phage Display Screening. (See FIG. 6). We noted that polypeptide no. 23 contains the core structure $WX_1X_2X_3W$. But, unlike the majority of the polypeptides selected, polypeptide no. 23 possesses a tryptophan (W) at $X_3$ instead of a tyrosine (Y). Further, polypeptide no. 23 contains the amino acid residue glutamate (E) at $X_1$ and the amino acid residue aspartate (D) at $X_2$. Among all the amino acids, aspartate (D) and glutamate (E) are the only two negatively charged residues.

In this series of studies, we examined the negatively charged amino acids inside the core structure on the inhibitory activity of polypeptide no. 23. To do so, we prepared several modified polypeptides based on the amino acid sequence of polypeptide no. 23. We modified polypeptide no. 23 by: (i) changing the negatively charged amino acid residues into different negatively charged residues (either D to E or E to D); (ii) changing the negatively charged amino acid residues into polar and uncharged residues; or (iii) changing the negatively charged amino acid residues to positively charged residues.

The modified polypeptides were studied in a Competitive ELISA with IL-23 which was performed in accordance with the procedure set forth in Example 6. Polypeptide no. 23 was run as a control.

Figure 35:
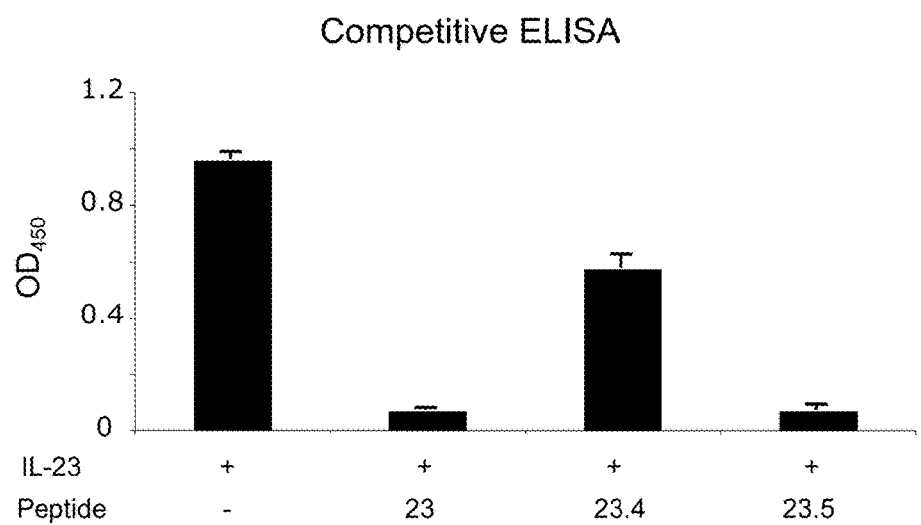
FIG. 35 depicts the effect of polypeptide modification on its ability to inhibit binding of IL-23 to its receptor. Polypeptide modification was achieved by substituting either one of the two amino acids (i.e., $X_1X_2$) within the $WX_1X_2WW$ core structure. IL-23 binding to its receptor was monitored by Competitive ELISA. With respect to polypeptide no. 23, single amino acid substitution of $X_1$ or $X_2$ did not abrogate the ability of the polypeptide to inhibit IL-23 binding to its receptor.

(i) Changing the Negatively Charged Amino Acid Residues into Another Negatively Charged Residue In this example, we changed the core structure of polypeptide no. 23 (i.e., WEDWW) into WDDWW (i.e., peptide no. 23.4) and WEEWW (i.e., peptide no. 23.5). The negative charge of the amino acids was preserved in these modified polypeptides. FIG. 35 and Table 14 show the amino acid sequence of the polypeptides we created using this approach.

TABLE 14

Amino Acid Sequence of Polypeptide Nos. 23, 23.4 and 23.5

| Polypeptide No. | Polypeptide Sequence | |
|---|---|---|
| 23 | AMTWEDWWLYGR | (SEQ ID NO: 23) |
| 23.4 | AMTWDDWWLYGR | (SEQ ID NO: 83) |
| 23.5 | AMTWEEWWLYGR | (SEQ ID NO: 84) |

FIG. 35 shows the results of the Competitive ELISA. Modified polypeptide nos. 23.4 and 23.5 were all effective at inhibiting IL-23 binding to its receptor. Thus, changing the amino acids while maintaining the charge did not abrogate the ability of the polypeptide to inhibit IL-23 binding to its receptor.

Figure 36:
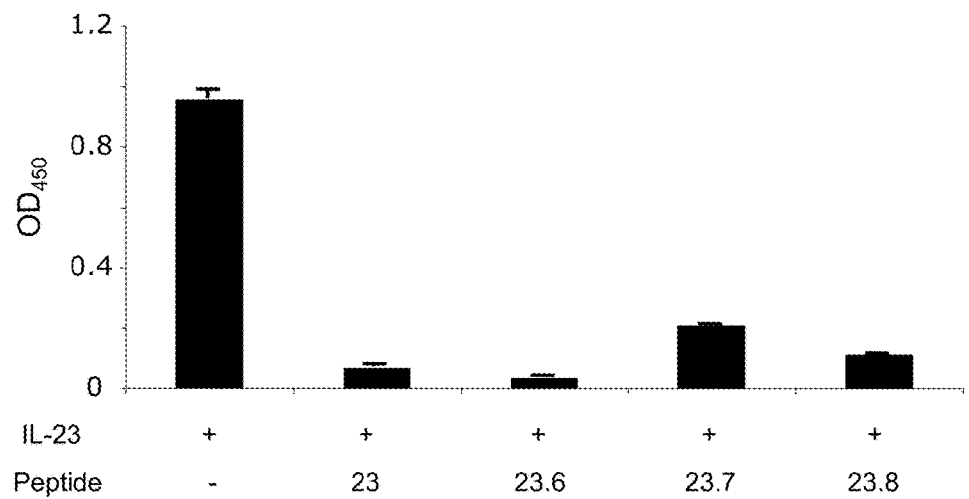
FIG. 36 depicts the effect of polypeptide modification on its ability to inhibit binding of IL-23 to its receptor. Polypeptide modification was achieved by substituting a negatively charged amino acid residues with a neutral amino acid residue. The charged amino acid residues are present within the $WX_1X_2WW$ core structure. With respect to polypeptide no. 23, amino acid substitution of $X_1$ or $X_2$ to alter its charge did not abrogate the ability of the polypeptide to inhibit IL-23 binding to its receptor.

(ii) Changing Negatively Charged Amino Acid Residues to Polar and/or Uncharged Amino Acid Residues We determined the effect of changing the negatively charged amino acids in the WEDWW motif of polypeptide no. 23 into polar and uncharged amino acids. We prepared three (3) modified polypeptides by changing aspartate (D) and glutamate (E) into asparagine (N) and glutamine (Q), respectively. FIG. 36 and Table 15 show the amino acid sequence of the polypeptides we prepared using this approach.

TABLE 15

Amino Acid Sequence of Polypeptide Nos. 23, 23.6, 23.7 and 23.8

| Polypeptide No. | Polypeptide Sequence | |
|---|---|---|
| 23 | AMTWEDWWLYGR | (SEQ ID NO: 23) |
| 23.6 | AMTWQDWWLYGR | (SEQ ID NO: 85) |
| 23.7 | AMTWENWWLYGR | (SEQ ID NO: 86) |
| 23.8 | AMTWQNWWLYGR | (SEQ ID NO: 87) |

FIG. 36 shows the results of the Competitive ELISA. Modified polypeptide nos. 23.6, 23.7 and 23.8 were all effective at inhibiting IL-23 binding to its receptor. Thus, even when the amino acids within the core structure were changed from negatively charged amino acids to polar and uncharged amino acids, the ability of the polypeptide to inhibit IL-23 binding to its receptor was not affected.

Figure 37:
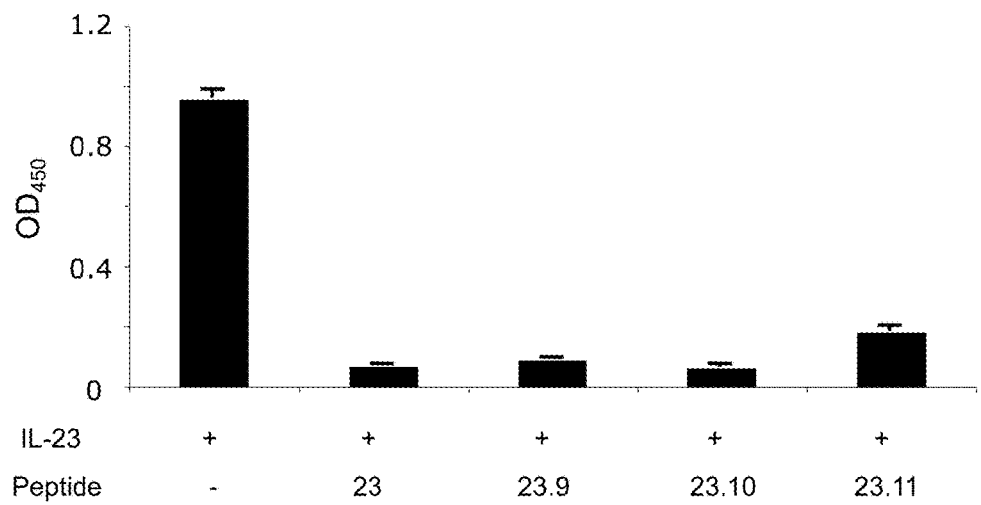
FIG. 37 depicts the effect of polypeptide modification on its ability to inhibit binding of IL-23 to its receptor. Polypeptide modification was achieved by substituting a negatively charged amino acid residue with a positively charged amino acid residue. The charged amino acid residues are present within the $WX_1X_2WW$ core structure. With respect to polypeptide no. 23, amino acid substitution of $X_1$ or $X_2$ to alter its charge did not abrogate the ability of the polypeptide to inhibit IL-23 binding to its receptor.

(iii) Changing Negatively Charged Amino Acid Residues to Positively Charged Amino Acid Residues Because the negatively charged residues in the WEDWW motif of peptide no. 23 could be substituted by the uncharged amino acids without major effect on its inhibitory activity, we examined whether these residues could be replaced by positively charged amino acids. We prepared three (3) modified polypeptides (i.e., polypeptide nos. 23.9, 23.10 and 23.11) in which either one or both of the negative amino acid residues were changed to positively charged lysine (K). FIG. 37 and Table 16 show the amino acid sequence of the polypeptides we created using this approach.

TABLE 16

Amino Acid Sequence of Polypeptide Nos. 23, 23.9, 23.10 and 23.11

| Polypeptide No. | Polypeptide Sequence | |
|---|---|---|
| 23 | AMTWEDWWLYGR | (SEQ ID NO: 23) |
| 23.9 | AMTWEKWWLYGR | (SEQ ID NO: 88) |
| 23.10 | AMTWKDWWLYGR | (SEQ ID NO: 89) |
| 23.11 | AMTWKKWWLYGR | (SEQ ID NO: 90) |

FIG. 37 shows the results of the Competitive ELISA. To our surprise, modified polypeptide nos. 23.9, 23.10 and 23.11 were all effective at inhibiting IL-23 binding to its receptor. Thus, even when the amino acids within the core structure were changed from negatively charged amino acids to positively charged amino acids, the ability of the polypeptide to inhibit IL-23 binding to its receptor was not abrogated.

In sum, the results of this example (Example 22 parts (i), (ii) and (iii)) suggest that the charge of the amino acid residues in the core structure does not appear to be an important determinant of the ability of a polypeptide to inhibit IL-23 binding to its receptor.

Example 23

Polypeptide Modification—Altering Tryptophan Residue Inside the WEDWW Motif of Polypeptide No. 23

Figure 38:
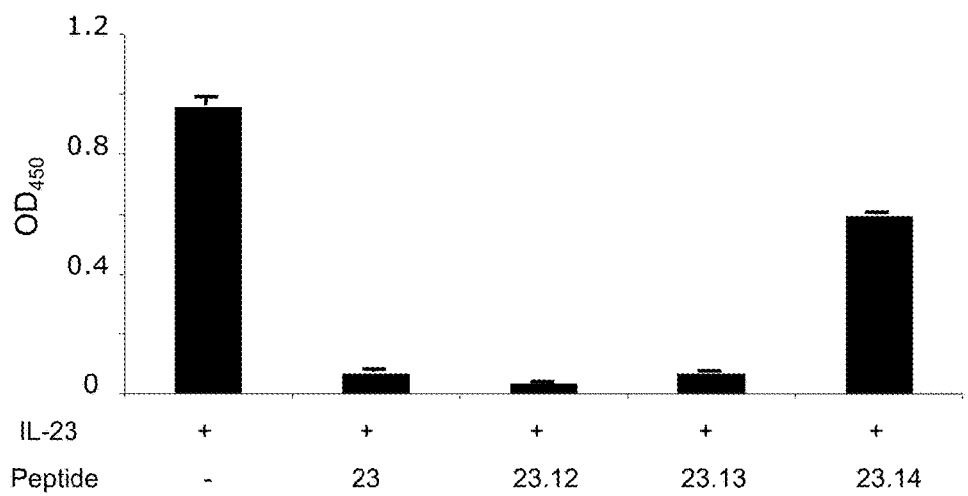
FIG. 38 depicts the effect of polypeptide modification on its ability to inhibit binding of IL-23 to its receptor. Polypeptide modification was achieved by substituting one of the tryptophan (W) residues present within the $WX_1X_2WW$ core structure with phenylalanine (F), tyrosine (Y) or alanine (A). With respect to polypeptide no. 23, the change did not abrogate the ability of the polypeptide to inhibit IL-23 binding to its receptor.
Figure 40:
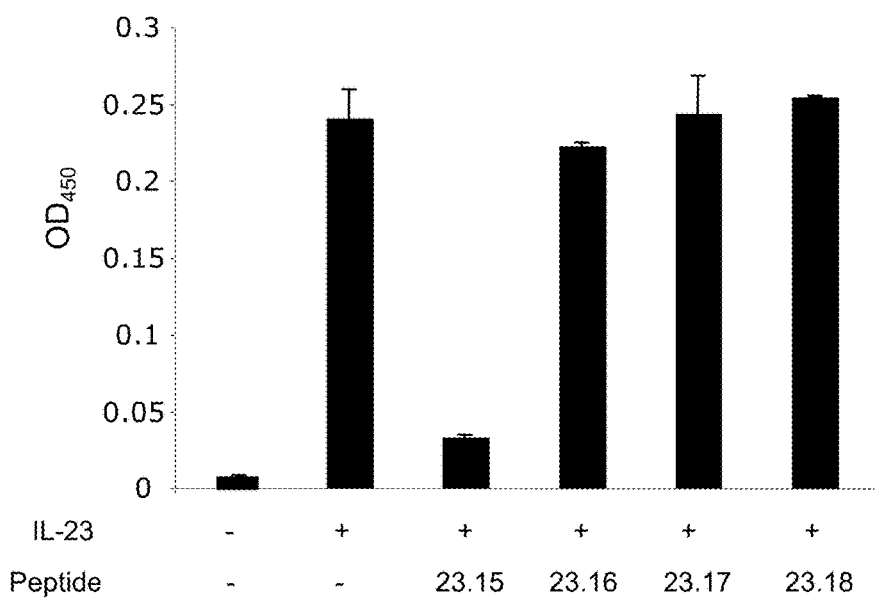
FIG. 40 depicts the effect of polypeptide modification on its ability to inhibit binding of IL-23 to its receptor. Polypeptide modification was achieved by altering the polypeptide length on the polypeptide no 23.12. IL-23 binding to its receptor was monitored by Competitive ELISA. With respect to polypeptide no. 23.15, reducing the total number of amino acid residues from twelve (12) to five (5) did not alter its solubility. Modified polypeptide nos. 23.16, 23.17 and 23.18 exhibit no inhibition toward IL-23 binding.

We examined the importance of tryptophan (W) residue inside the core structure $WX_1X_2X_3W$ (i.e., the W at $X_3$) of polypeptide no. 23. It is well recognized that tryptophan residue has an aromatic side chain. To examine the role of tryptophan at $X_3$, we prepared three (3) modified polypeptides. In modified polypeptide nos. 23.12 and 23.13, we changed tryptophan (W) to tyrosine (Y) and phenylalanine (F), respectively. Tyrosine (Y) and phenylalanine (F) both include, like tryptophan (W), an aromatic side chain. In modified polypeptide no. 23.14, tryptophan (W) was changed to the non-polar, aliphatic amino acid residue alanine (A). Table 17 and FIG. 38 show the amino acid sequences of the modified polypeptides.

TABLE 17

Amino Acid Sequence of Polypeptide Nos. 23, 23.12, 23.13 and 23.14

| Polypeptide No. | Polypeptide Sequence | |
|---|---|---|
| 23 | AMTWEDWWLYGR | (SEQ ID NO: 23) |
| 23.12 | AMTWEDYWLYGR | (SEQ ID NO: 91) |
| 23.13 | AMTWENFWLYGR | (SEQ ID NO: 92) |
| 23.14 | AMTWENAWLYGR | (SEQ ID NO: 93) |

The modified polypeptides were examined in the Competitive ELISA, which was performed in accordance with the procedure set forth in Example 6.

FIG. 38 shows the results of the Competitive ELISA. When compared to polypeptide no. 23, modified polypeptide nos. 23.12 and 23.13 appear at least as effective at inhibiting IL-23 binding to its receptor. Albeit lesser effective, the modified polypeptide 23.14 still inhibits IL-23 binding to its receptor.

In sum, it appears that polypeptides that include an aromatic amino acid at position $X_3$ of the core structure $WX_1X_2X_3W$, have a greater ability to inhibit IL-23 binding its receptor. This observation was consistent with our phage display screening result in which 30 out of 31 of the screened polypeptides (96.8%) contained an aromatic amino acid at position $X_3$ of the core structure. (See, FIG. 8).

Example 24

Polypeptide No. 23.15

The polypeptide no. 23 has the core structure of $WX_1X_2X_3W$, wherein $X_1$ is glutamate (E) $X_2$ is aspartate (D) and $X_3$ is tryptophan (W). Based on the observations made in Example 22 and Example 23, the $X_1$ and $X_3$ amino acid residues inside the core structure of polypeptide no. 23 may be glutamine (Q) and tyrosine (Y) respectively.

In this study, we continued to modify the polypeptide no. 23. We modified the polypeptide no. 23 with a new core structure having an amino acid sequence of "WQDYW." Table 18 and FIG. 38 show the amino acid sequences of the modified polypeptides.

TABLE 18

Amino Acid Sequence of Polypeptide Nos. 23 and 23.15

| Polypeptide No. | Polypeptide Sequence | |
|---|---|---|
| 23 | AMTWEDWWLYGR | (SEQ ID NO: 23) |
| 23.15 | AMTWQDYWLYGR | (SEQ ID NO: 126) |

The modified polypeptide was examined in the Competitive ELISA, which was performed in accordance with the procedure set forth in Example 6. The $IC_{50}$ value of polypeptides was calculated.

FIG. 39 shows the $IC_{50}$ value of polypeptides calculated from the Competitive ELISA experiment. When compared to polypeptide no. 23, the modified polypeptide no. 23.15 appears at least as effective at inhibiting IL-23 binding to its receptor.

Example 25

Polypeptide 23.15—Effect of Reducing Polypeptide Length while Retaining the Core Structure We chose the polypeptide no. 23.15 and used it to examine the effect of peptide length on IL-23 inhibition. Polypeptides having a total amino acid length of 5, 7 or 9 amino acids were prepared by deleting amino acids from the amino acid sequences of polypeptide no 23.15. Despite the varying length of the polypeptides, the core structure of the polypeptide remained WQDYW. FIG. 40 and Table 19 show the sequences of the polypeptides we created.

The modified polypeptides were used in a Competitive ELISA with IL-23, which was performed in accordance with the procedure set forth in Example 6.

TABLE 19

Amino Acid Sequences of Polypeptide Nos. 23.15, 23.16, 23.17 and 23.18

| Polypeptide No. | Polypeptide Sequence | |
|---|---|---|
| 23.15 | AMTWQDYWLYGR | (SEQ ID NO: 126) |
| 23.16 | MTWQDYWLY | (SEQ ID NO: 127) |
| 23.17 | TWQDYWL | (SEQ ID NO: 128) |
| 23.18 | WQDYW | (SEQ ID NO: 129) |

FIG. 40 shows the results of the Competitive ELISA. Reducing polypeptide length from twelve (12) amino acids (as in polypeptide no. 23.15) to nine (9) amino acids (as in polypeptide no. 23.16), seven (7) amino acids (as in polypeptide no. 23.17) or five (5) amino acids (as in polypeptide no. 23.18) eliminated the ability of the polypeptides including the core structure $WX_1X_2X_3W$ from inhibiting the activity of IL-23.

These data show that reducing the total amino acid length of the polypeptide with the core structure WQDYW has adverse effect on inhibitory activity.

Example 26

Polypeptide 23.15—Effect of Cyclic Peptide

Cyclic peptide includes a polypeptide on which the amino terminus and carboxyl terminus are themselves linked together with a peptide bond that forms a circular (i.e., cyclic) chain. Using the polypeptide no. 23.15, we generated the polypeptide no. 23.19, which is a cyclic peptide, by adding a cysteine residue on both side of polypeptide no. 23.15. A disulfide bond (i.e., a covalent bond) is formed by coupling the thiol group on the cysteine residue in a head-tail fashion (HT) to generate a cyclic peptide. Table 20 and FIG. 41 show the amino acid sequences of the cyclic polypeptide (i.e., polypeptide no. 23.19).

Cyclic peptide synthesis: We obtained the crude peptide following the method of solid phase synthesis with TRT resin. We placed the sample in aqueous solution of 0.5 mg/ml concentration and adjust the pH to 8.5, dropping 10 equivalent of $H_2O_2$, then the cyclization reaction start and be retained for one hour. After the detection and the reaction being confirmed completed, we separated the sample by HPLC (solute: acetonitrile (ACN) with 0.1% TFA+$H_2O$ with 0.1% TFA, C18 column). The desired sample obtained will be freeze-dried and HPLC verified (purity >90%).

TABLE 20

Amino Acid Sequences of Polypeptide Nos. 23 and 23.15

| Polypeptide No. | Polypeptide Sequence | |
|---|---|---|
| 23.15 | AMTWQDYWLYGR | (SEQ ID NO: 126) |
| 23.19 | CAMTWQDYWLYGRC | (SEQ ID NO: 130) |

The cyclic polypeptide was examined in the Competitive ELISA, which was performed in accordance with the procedure set forth in Example 6. The $IC_{50}$ value of polypeptides was calculated.

FIG. 41 shows the $IC_{50}$ value of polypeptides calculated from the Competitive ELISA experiment. When compared to polypeptide no. 23.15, the cyclic polypeptide no. 23.19 is equally effective in inhibiting IL-23 binding to its receptor.

Example 27

Cyclic Polypeptide 23.19—Effect of Reducing Polypeptide Length while Retaining the Core Structure of Cyclic Peptide We examined the effect of peptide length relating to the cyclic polypeptide 23.19 on IL-23 inhibition. Cyclic polypeptides with a total amino acid length of 7, 9, or 11 amino acids were prepared by deleting amino acids to sequences of polypeptide no 23.19. Despite varying the polypeptide length, the core structure of the cyclic polypeptide ("WQDYW") was retained. FIG. 42 and Table 21 show the amino acid sequence of the three cyclic polypeptides that we created prepared (i.e., 23.20, 23.21, and 23.22).

The modified polypeptides were used in a Competitive ELISA with IL-23, which was performed in accordance with the procedure set forth in Example 6.

TABLE 19

Amino Acid Sequences of Polypeptide Nos. 23.20, 23.21, and 23.22

| Polypeptide No. | Polypeptide Sequence | |
|---|---|---|
| 23.19 | CAMTWQDYWLYGRC | (SEQ ID NO: 130) |
| 23.20 | CMTWQDYWLYC | (SEQ ID NO: 131) |
| 23.21 | CTWQDYWLC | (SEQ ID NO: 132) |
| 23.22 | CWQDYWC | (SEQ ID NO: 133) |

Figure 42:
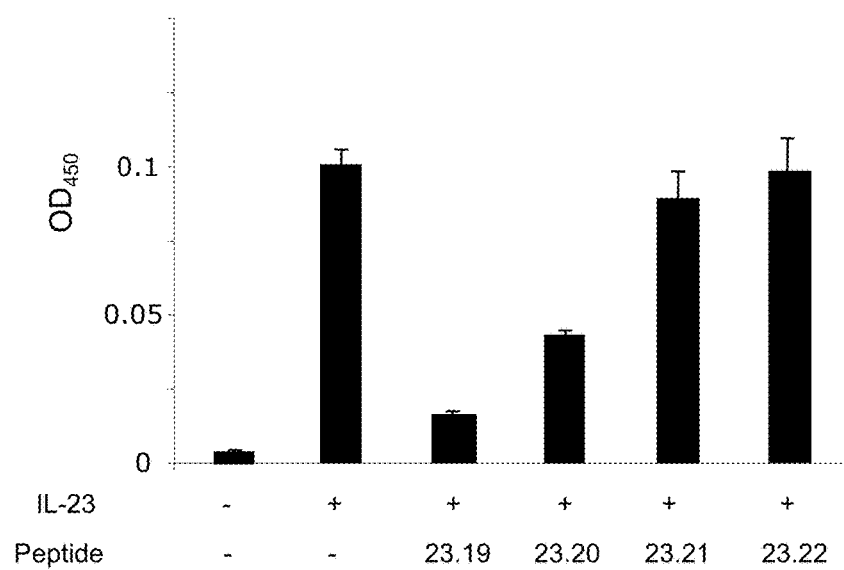
FIG. 42 depicts the effect of polypeptide modification on its ability to inhibit binding of IL-23 to its receptor. Polypeptide modification was achieved by altering the polypeptide length on the polypeptide no 23.19. IL-23 binding to its receptor was monitored by Competitive ELISA. With respect to polypeptide no. 23.15, reducing the total number of amino acid residues from fourteen (14) to seven (7) did not alter its solubility. Shortening of polypeptide gradually reduces the inhibition activity of polypeptide toward IL-23 binding.
Figure 44:
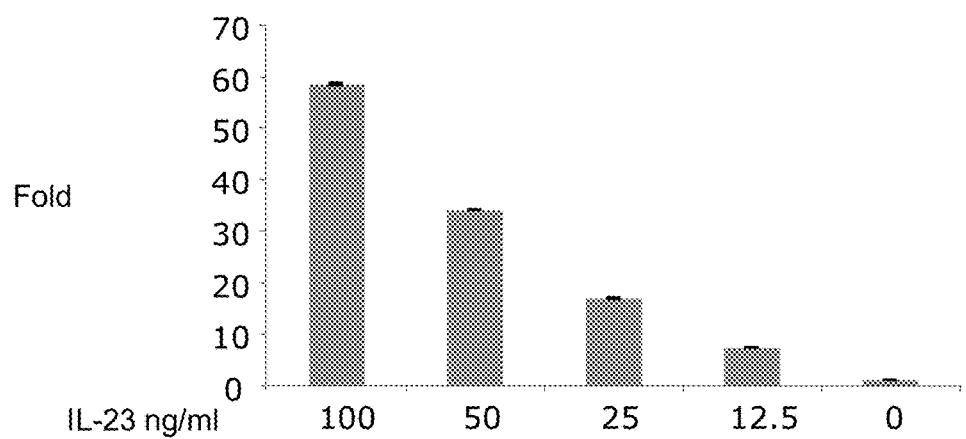
FIG. 44 depicts the IL-23 stimulation on the DB cells stably transfected with STAT3-Luc reporter construct. Luciferase activity is activated by IL-23 cytokine in a dose-dependent manner.

FIG. 42 shows the results of the Competitive ELISA. Reducing polypeptide length of the cyclic polypeptide no. 23.19 from fourteen (14) amino acids to eleven (11) amino acids (as in polypeptide no. 23.20) slightly decreases the ability of the cyclic polypeptide containing the core structure $WX_1X_2X_3W$ from inhibiting the activity of IL-23. In contrast, reducing polypeptide length of from fourteen (14) amino acids to nine (9) amino acids (as in polypeptide no. 23.21) or seven (7) amino acids (as in polypeptide no. 23.22) greatly reduced the ability of the cyclic polypeptides from inhibiting the activity of IL-23.

These data show that reducing the polypeptide length of the cyclic polypeptide (containing the "WQDYW" core structure) has an adverse effect on the inhibitory activity.

Example 28

Polypeptide 23.15-Fc Fusion Protein

Polypeptide no. 23.15-Fc fusion protein was obtained by designing expression constructs (i.e., polypeptide-Fc expression constructs) that expressed the amino acid sequence of interest fused to Fc.

Forward (F) and reverse (R) oligonucleotides corresponding to the desired peptide sequences were designed as set forth in Table 20.

TABLE 20

Oligonucleotide Sequences Used in Generating Polypeptide-Fc Fusion Proteins

| Polypeptide number | Dir | Oligonucleotide Sequence |
|---|---|---|
| 23.15 | F | C ATG ACC TGG CAG GAC TAC TGG CTG TAC GGC A (SEQ ID NO: 134) |
| | R | TGG ACC GTC CTG ATG ACC GAC ATG CCG TCT AG (SEQ ID NO: 135) |

Equal amounts of forward and reverse oligonucleotides were annealed into double strand form by incubating at 95° C. for 10 minutes. After the mixture cooled down to room temperature, 1 μl of double strand oligonucleotide was ligated with linearized Fc expression construct (Cat. No. ppfc2-mg2ae1) (InvivoGen, San Diego, Calif.). The linearized vector was prepared by treating the DNA with NcoI and BglII restriction enzymes. The ligated DNA was then transformed into Top10 competent cells (Invitrogen, Carlsbad, Calif.). The sequence of the expression constructs were verified by DNA sequencing. Fusion protein was expressed by transfecting HEK-293T cells with the polypeptide-Fc expression construct. We performed the purification using protein A-agarose bead to isolate #23.15-Fc fusion protein.

The isolated polypeptide no. 23.15-Fc fusion protein was used in a Competitive ELISA with IL-23, which was performed in accordance with the procedure set forth in Example 6. The $IC_{50}$ value of polypeptides was calculated.

FIG. 43 shows the results of the Competitive ELISA. Polypeptide 23.15 fused with the Fc protein (i.e., polypeptide no. 23.15-Fc fusion protein) did not eliminate the ability of the polypeptides including the core structure $WX_1X_2X_3W$ from inhibiting the activity of IL-23. Surprisingly, the polypeptide no. 23.15-Fc fusion protein performs better than the polypeptide no. 23.15 peptide in the competitive ELISA assay. The $IC_{50}$ value of the polypeptide no. 23.15-Fc fusion protein was 0.009 μM (See, FIG. 43).

These data show that fusing the polypeptide no. 23.15 to Fc protein increased its inhibitory activity.

Example 29

Cell Based Assay—$IC_{50}$ Values of Cyclic Polypeptide No. 23.19 and Polypeptide No. 23.15-Fc Fusion Protein (i) Generation of Cell Based Assay—DB Cells—STAT3-Luc In Example 13, we examined expression of IL-23R on the DB cells. In a flow cytometry assay, DB cells were stained with either isotype control antibodies or anti-IL-23R antibodies (Figure. 21). The results indicate that IL-23R is expressed on DB cell surface. In addition, we have successfully shown that DB cells respond to IL-23 stimulation in Example 7 (FIGS. 14 and 15). Activation of STAT3 by phosphorylation (p-STAT3) was detected when the DB cells were stimulated with IL-23 cytokine Based on these observations, DB cells were used to develop a cell-based assay to measure the inhibitory activity of cyclic polypeptides and polypeptide—Fc fusion protein.

The Cignal STAT3 reporter (SA Biosciences, CCS-9028L), designed to measure the transcriptional activity of STAT3 homodimers, was transiently transfected into the DB cells. The stably transfected STAT3-Luc reporter clone was selected using 200 ng/ml of Hygromycin B.

The stably transfected STAT3-Luc reporter DB cells ($0.5\times10^6$) were cultured in 100 μl of RPMI+10% FBS. IL-23 was added to the cells and incubated at 37° C. for 4 hours. Luciferase activity was measured using Dual-Glo luciferase assay system (Promega).

As depicted in FIG. 44, varying amounts of IL-23 (100 ng/mL to 12.5 ng/mL) (control includes 0 ng/mL IL-23) were added to the stably transfected DB-STAT3-Luc reporter cells. These cells were stimulated with IL-23 cytokine for 4 hours followed by the measurement of luciferase activity. IL-23 cytokine stimulates the STAT3 activity in a dose-dependent manner.

This result clearly demonstrates that the stably transfected DB-STAT-Luc reporter cells can be used as cell-based assay to measure the activity of IL-23R pathway upon IL-23 cytokine stimulation.

ii) Measurement of $IC_{50}$ Values of Cyclic polypeptide No. 23.19 and Polypeptide No. 23.15-Fc Fusion Protein The isolated cyclic polypeptide no. 23.15-Fc fusion protein and cyclic polypeptide no. 23.19 were used in a cell-based assay to measure the $IC_{50}$ values. The stably transfected STAT3-Luc reporter DB cells ($0.5 \times 10^6$) were cultured in 100 µl of RPMI+10% FBS. The cells were pre-incubated with different concentration of isolated cyclic polypeptide no. 23.15-Fc fusion protein or polypeptide no. 23.19 for 30 minutes at 37° C. 50 ng/ml of IL-23 was added to the cells and incubated at 37° C. for an additional 4 hours. Luciferase activity was measured using Dual-Glo luciferase assay system (Promega). The $IC_{50}$ values of isolated cyclic polypeptide no. 23.15-Fc fusion protein and cyclic polypeptide no. 23.19 are 2.5 µM and 2.5 µM respectively. The $IC_{50}$ values obtained from this cell-based assay are comparable to the $IC_{50}$ values obtained from the cell-free assay.

This result clearly demonstrates that both isolated cyclic polypeptide no. 23.15-Fc fusion protein and cyclic polypeptide no. 23.19 are active in the cell-based assay to inhibit the IL-23 signaling.

Example 30

Competitive Mouse ELISA—Inhibition of Mouse IL-23 Binding to Mouse IL-23R by Polypeptide No. 23.15, Cyclic Polypeptide No. 23.19 and the Isolated Polypeptide No. 23.15-Fc Fusion Protein In this study, we tested if the cyclic polypeptide no. 23.15, cyclic polypeptide no. 23.19 and the isolated polypeptide 23.15-Fc fusion protein could inhibit binding of mouse IL-23 to mouse IL-23R. Mouse IL-23 (p19 Gene Accession #: NM_031252; p40 Gene Accession #: NM_008352), the sequence of which is incorporated herein by reference. Mouse IL-23R (Gene Accession #: NM_144548), the sequence of which is incorporated herein by reference. To do so, we performed the Competitive ELISA.

Figure 46:
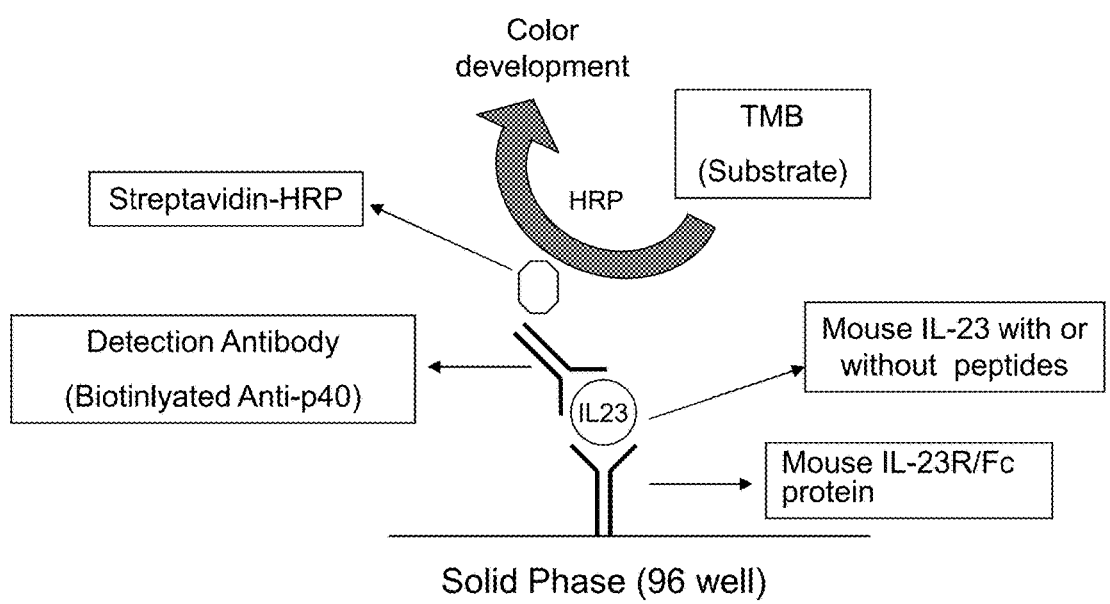
FIG. 46 depicts a schematic of a Competitive ELISA. The competitive ELISA was used to examine the competitive inhibitory activity of the polypeptides or peptide-Fc fusion protein against mouse IL-23 binding towards mouse IL-23R. Polypeptides used in this assay were synthesized and their amino acid sequences were based on the amino acid sequences of the polypeptides. Peptide-Fc fusion protein is an isolated protein.

FIG. 46 is a schematic depiction of the Competitive ELISA in mouse. Recombinant mouse IL-23R-Fc (2 µg/ml) was coated onto microtiter plates as a capture reagent. Mouse IL-23 and polypeptide or isolated peptide-Fc fusion protein were added to compete for binding to the immobilized mouse IL-23R-Fc. Mouse IL-23 that bound to mouse IL-23R-Fc was detected using biotinylated anti-p40 antibody (1:250). The bound anti-p40 antibody was detected using streptavidin-horseradish peroxidase (HRP) (1:500) and 100 µl/well of a tetramethylbenzidine (TMB) substrate was added to measure peroxidase activity. The color was measured at optical density (OD) $450_{nm}$. The color intensity was directly proportional to the amount of the bound mouse IL-23 protein.

The isolated polypeptide no. 23.15-Fc fusion protein, cyclic polypeptide no. 23.19 and polypeptide no. 23.15 were used in a Competitive ELISA with IL-23, which was performed in accordance with the procedure depicted in FIG. 46. The $IC_{50}$ values were calculated.

FIG. 47 depicts the results of our Competitive ELISA in mouse system. The isolated polypeptide no. 23.15-Fc fusion protein, cyclic polypeptide no. 23.19 and polypeptide no. 23.15 were used in a cell-free assay to measure the $IC_{50}$ values. The $IC_{50}$ values of isolated polypeptide no. 23.15-Fc fusion protein, cyclic polypeptide no. 23.19 and polypeptide no. 23.15 are 1 µM, 12.5 µM and 50 µM respectively.

This result clearly demonstrates that both isolated polypeptide no. 23.15-Fc fusion protein, cyclic polypeptide no. 23.19 and polypeptide no. 23.15 are active in the cell-free assay to inhibit the mouse IL-23 cytokine binding to mouse IL-23R, and that the polypeptide no. 23.15-Fc fusion protein exhibits the strongest inhibitory activity.

Example 31

Polypeptide No. 23.15-Fc Fusion Protein and IL-23 Cytokine Bind to the Same Region on IL-23R In all the above-mentioned examples, polypeptide and isolated polypeptide no. 23.15-Fc fusion protein not only bind to IL-23R but also block the IL-23 cytokine binding to IL-23R. This observation suggests that the polypeptides containing the core structure $WX_1X_2X_3W$ and IL-23 cytokine bind to the same region of IL-23R.

In this study, we examined which regions of IL-23R proteins were required for the binding to IL-23 and polypeptide no. 23.15-fc fusion protein. To do so, we generated a series of IL-23R deletion proteins as illustrated in the FIG. 48.

Figure 48:
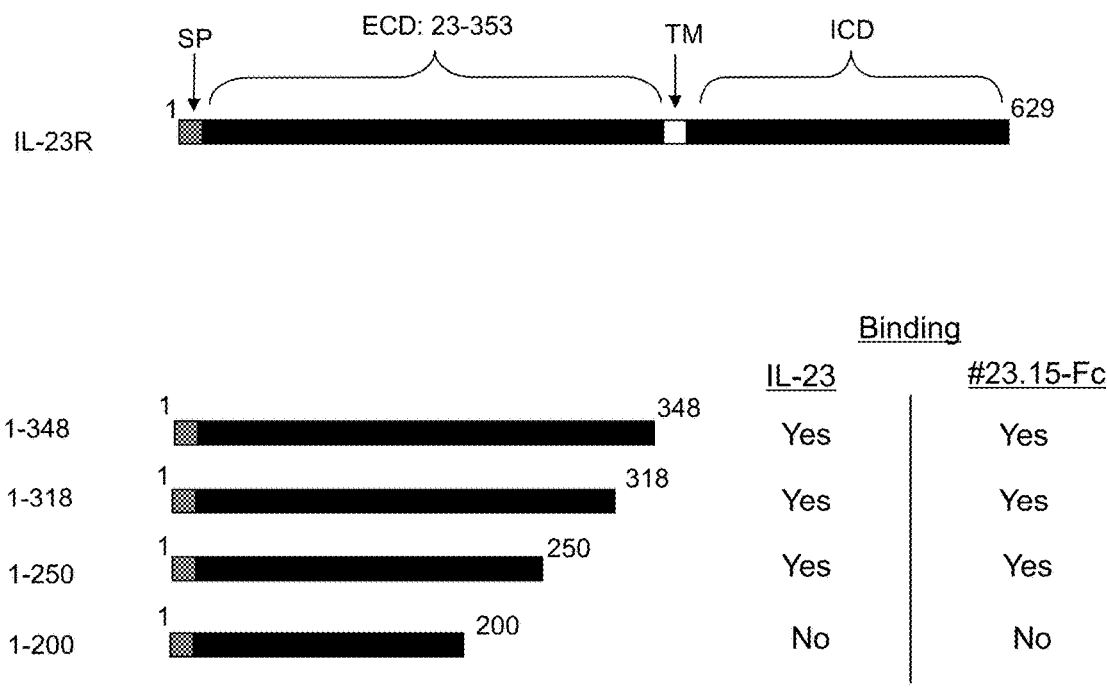
FIG. 48 depicts the immunoprecipitation results of the in vitro assay. A series of deletion mutants is generated as illustrated in the diagram. The assay reveals binding of IL-23 cytokine or polypeptide no. 23.15-Fc fusion protein to soluble recombinant IL-23R and its deletion mutants.
Figure 51:
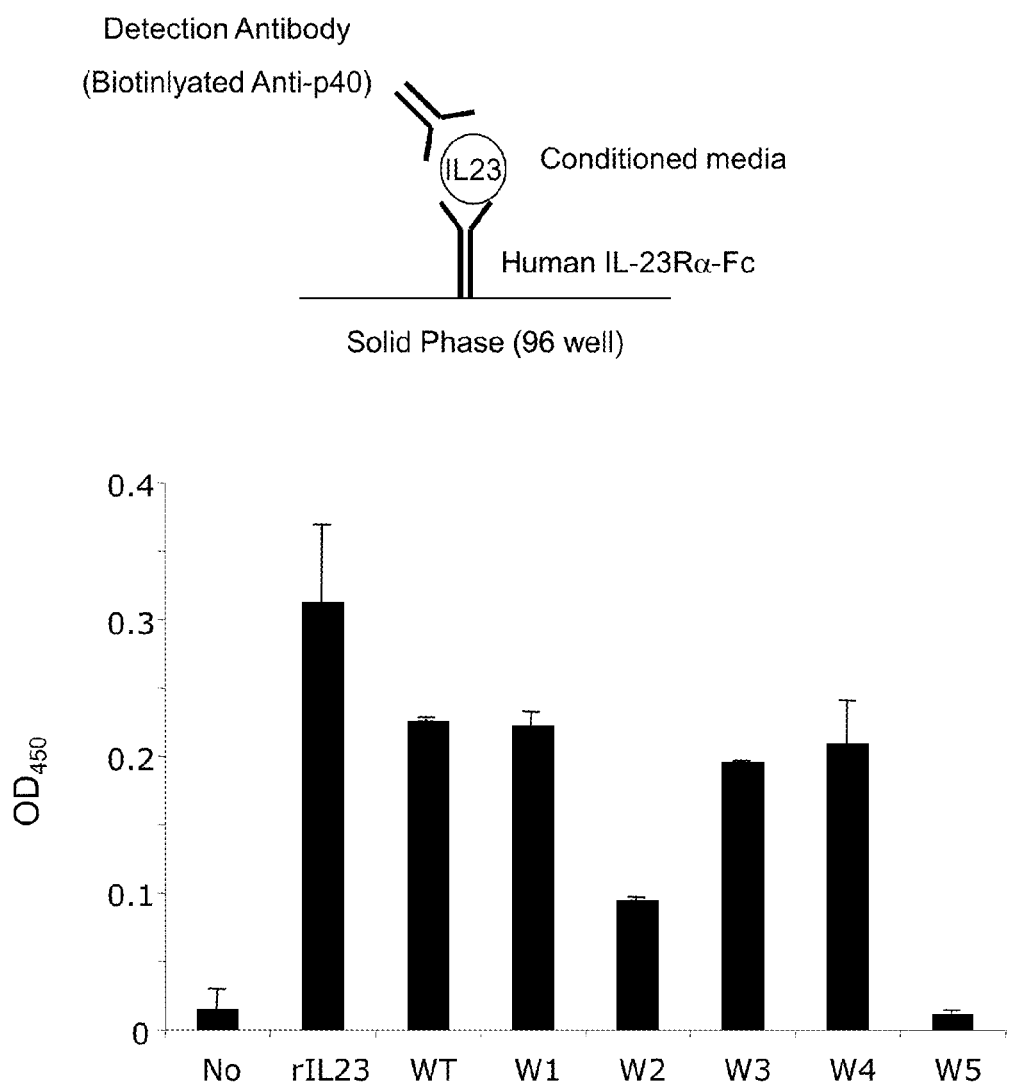
FIG. 51 depicts the ELISA to measure the binding of IL-23 cytokines and its mutant to the IL-23R. Recombinant IL-23 (rIL-23) is used as positive control.
Figure 52:
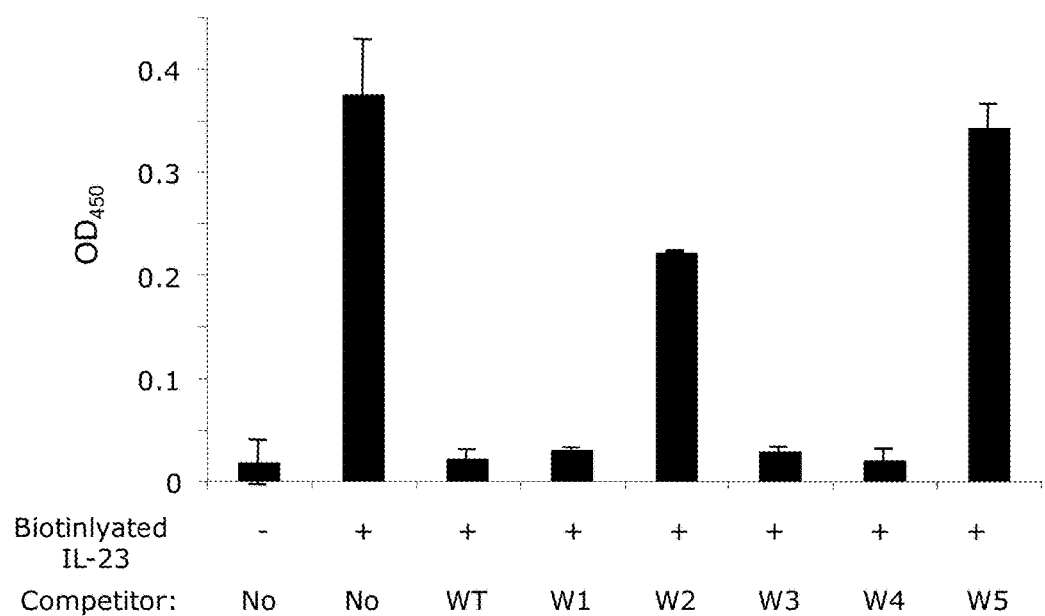
FIG. 52 depicts a Competitive ELISA to examine the competitive inhibitory activity of the IL-23 cytokines and its mutants against biotinylated IL-23 binding towards IL-23R.

Culture media from 293T cells transfected with different FLAG-tagged IL-23R deletion constructs were incubated with 200 ng of either IL-23 or polypeptide no. 23.15-fc fusion protein, then immunoprecipitated with anti-FLAG M2 affinity gel. The immunoprecipitate was subjected to Western blotting and polypeptide no. 23.15-Fc fusion protein or IL-23 was visualized with either anti-mouse IgG or anti-hIL-12/23p40 respectively. IL-23 or polypeptide no. 23.15-fc fusion protein was detected in the precipitate when 1-348, 1-318 or 1-250 protein was present in the precipitation reaction (FIG. 48). In contrast, 1-200 protein was failed to bind to IL-23 or polypeptide no. 23.15-fc fusion protein (FIG. 48).

These experiments confirmed that IL-23 and polypeptide no. 23.15-fc fusion protein bind to the same region of IL-23R.

Example 31

Role of "W" Residues on p19 Subunit of the IL-23 Cytokine

In Example 11 (above), the results clearly indicate an important role of the tryptophan (W) residues in the core structure $WX_1X_2X_3W$ in binding to IL-23R and inhibiting IL-23R activity. In Example 30, the experiments confirmed that IL-23 and polypeptide no. 23.15-fc fusion protein bind to the same region of IL-23R. However, we could not identify the sequence of core structure (i.e. $WX_1X_2X_3W$) on p19 subunit of IL-23 cytokine (See, FIG. 49).

Given the importance of "W" residues on the inhibitory activity of peptides, we examined the role of the five (5) tryptophan residues found on the p19 subunit of IL-23 (See, FIG. 49).

To do so, we performed site-directed mutagenesis to change the "W" residue present on the IL-23 p19 subunit into "G" residue separately one at a time. We created a total of six (6) expression constructs; namely, WT (Wild type—no mutation), W1 (convert W1 into G), W2 (convert W2 into G), W3 (convert W3 into G), W4 (convert W4 into G) and W5 (convert W5 into G) of the p19 subunit of IL-23. The expression construct of p40 subunit of IL-23 was also made.

In order to produce IL-23 cytokines (contains p19 and p40 subunits), expression constructs of p40 and corresponding p19 were co-transfected into the 293T cells. Conditional media were collected 48 hours after transfection. We prepared a total of six (6) different conditional media containing corresponding IL-23 cytokines (WT, W1, W2, W3, W4 and W5). We then examined the expression level of cytokines and their binding to IL-23R by ELISA.

i) Measurement of Expression Levels of IL-23 Cytokines

Figure 53:
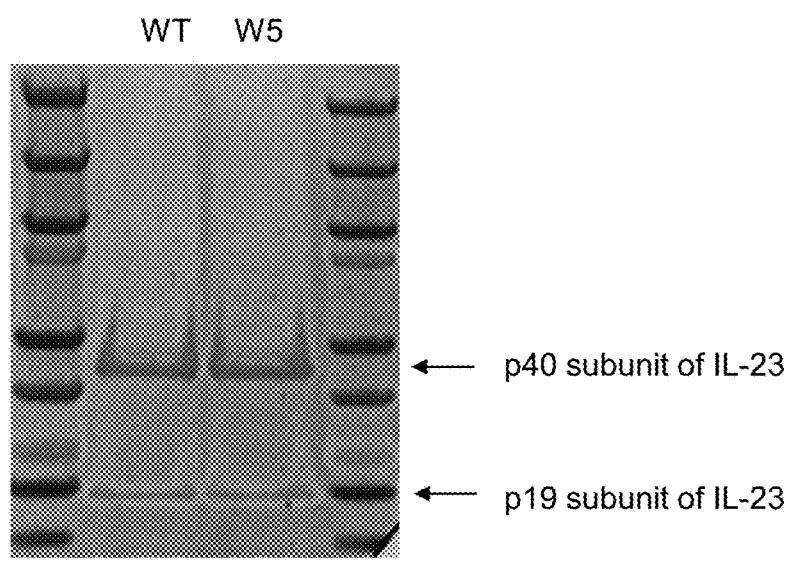
FIG. 53 depicts the isolated IL-23 cytokines (WT and W5) from the secreted source (culture medium) on the SDS-PAGE gel stained with the Coomassie Blue to reveal the purity.

Expression levels of IL-23 cytokines in the conditional media were measured by Human IL-23 ELISA Ready-SET-Go!® Set (eBioscience). FIG. 50 provides a schematic depiction of the IL-23 ELISA and shows the ELISA result.

To prepare the ELISA, microtiter plates were coated with anti-p19 antibody and incubated overnight at 4° C. The plates were blocked for 1 hour at room temperature using the blocking buffer provided in the ELISA kit. After blocking and washing with PBST for three (3) times, recombinant IL-23 or 100 μl of conditional media were added to each well and the plate was incubated overnight at 4° C.

Bound IL-23 cytokines were detected by adding biotinylated anti-p40 antibody. Streptavidin-horseradish peroxidase (HRP) was added to detect anti-p40 antibody bound to IL-23 cytokines Peroxidase activity (representing the level of IL-23 cytokine captured onto plates) was measured by adding 100 μl of a tetramethylbenzidine (TMB) to each well. The color intensity was directly proportional to the amount of the bound IL-23. Optical density was read at $450_{nm}$.

FIG. 50 shows the results of the IL-23 ELISA. All six (6) of the conditional media contained comparable amount of wild type (WT) or mutated IL-23 cytokines (W1, W2, W3, W4 and W5). The $OD_{450}$ data indicates that the amount of IL-23 cytokines being secreted.

ii) Measurement of IL-23 Cytokines Binding to IL-23R

In FIG. 50, the IL-23 ELISA showed that all six (6) conditional media had similar amount of IL-23 cytokines, indicating that the five (5) IL-23 mutants and the wild-type IL-23 released similarly into the media. In this next series of studies, we tested if the "W" residues on p19 subunit of IL-23 cytokine play a role on IL-23 cytokine binding to IL-23R. To do so, we performed the ELISA assay.

FIG. 51 is a schematic depiction of the ELISA to measure IL-23 cytokine binding to its receptor. Recombinant human IL-23R-Fc (2 μg/ml) was coated onto microtiter plates as a capture reagent. Recombinant IL-23 or conditional media containing IL-23 cytokines were added to bind to the immobilized IL-23R-Fc. IL-23 cytokine that bound to IL-23R-Fc was detected using biotinylated anti-p40 antibody (1:250). The bound anti-p40 antibody was detected using streptavidin-horseradish peroxidase (HRP) (1:500) and 100 μl/well of a tetramethylbenzidine (TMB) substrate was added to measure peroxidase activity. The color was measured at optical density (OD) $450_{nm}$. (See, FIG. 51). The color intensity was directly proportional to the amount of the bound IL-23 protein.

Eight (8) ELISAs were performed. Binding of wild type (WT) or mutated IL-23 cytokines (W1, W2, W3, W4 and W5) to IL-23R was examined by ELISA illustrated in FIG. 51. W1, W3 and W4 mutants of p19 subunit of IL-23 cytokine bound to IL-23R as effectively as WT of p19 subunit of IL-23 cytokine did. W2 mutant of p19 subunit of IL-23 cytokine showed 50% reduction when compared to WT of p19 subunit of IL-23 cytokine Intriguingly, W5 mutant of p19 subunit of IL-23 cytokine showed no binding activity to IL-23R. Recombinant IL-23 cytokine (Humanzyme) was run as a positive control. The ELISA data is summarized in FIG. 51.

iii) Measurement of IL-23 Cytokines Binding to IL-23R by Competition Assay

As depicted in FIG. 51, the ELISA indicates that only W2 and W5 mutants of p19 subunit of IL-23 cytokine showed reduction of receptor binding or no receptor binding respectively. In this next series of studies, we used an alternative way to test if the "W" residues on p19 subunit of IL-23 cytokine play a role on IL-23 cytokine binding to IL-23R. To do so, we performed the competitive ELISA assay.

FIG. 52 is a schematic depiction of the Competitive ELISA. Recombinant human IL-23R-Fc (2 μg/ml) was coated onto microtiter plates as a capture reagent. Biotinlyated IL-23 and conditional media were added to compete for binding to the immobilized IL-23R-Fc. Biotinylated IL-23 that bound to IL-23R-Fc was detected using streptavidin-horseradish peroxidase (HRP) (1:500) and 100 μl/well of a tetramethylbenzidine (TMB) substrate was added to measure peroxidase activity. The color was measured at optical density (OD) $450_{nm}$. (See, FIG. 52). The color intensity was directly proportional to the amount of the bound biotinlyated IL-23 protein.

Eight (8) competitive ELISAs were performed. Wild type (WT) or mutated (W1, W2, W3, W4 and W5) IL-23 cytokines in the conditional media were used as competitor in this assay. No signal was detected when there was no biotinlyated IL-23 in the well. In the absence of conditional media, biotinlyated IL-23 cytokine bound effectively to the immobilized IL-23R-Fc. In contrast, biotinlyated IL-23 cytokine failed to bind to IL-23R in the wells of conditional media containing WT, W1, W3 or W4 IL-23 cytokine Only half of the biotinlyated IL-23 cytokine bound to its receptor in the well of conditional medium containing W2 IL-23. Biotinlyated IL-23 cytokine in the well of conditional medium containing W5 IL-23 bound as effectively as biotinlyated IL-23 cytokine in the well with no competitor. The ELISA data is summarized in FIG. 52.

Altogether, these data show that W1, W3 and W4 of p19 subunits of IL-23 cytokine are not essential to IL-23 binding to IL-23R whereas W2 of p19 subunit of IL-23 cytokine plays a limited role on receptor binding. Intriguingly, W5 of p19 subunit of IL-23 cytokine is indispensable to the receptor binding.

Example 33

Isolated WT and W5 IL-23 Cytokines—IL23R Signaling

In Example 32 (above), we showed the indispensable role of the tryptophan residue (W5) in p19 subunit of IL-23 cytokine to bind to IL-23R. We further confirmed the critical role of the W5 residues in the p19 subunit of IL-23 on the receptor binding using cell-based assay developed in the Example 29. To do so, we purified the WT and W5 IL-23 cytokines.

In order to produce IL-23 cytokines (contains p19 and p40 subunits), expression constructs of p40 and corresponding p19 (WT or W5) were co-transfected into the 293T cells. Conditional media were collected 48 hours after transfection. We prepared two (2) different conditional media containing corresponding IL-23 cytokines (WT and W5). The WT and W5 p19 subunits of IL-23 cytokine were tagged with 6×His at the C-terminus. The IL-23 cytokines in the conditional media were purified by using HisTALON Gravity Column (Clontech). The concentration of the purified IL-23 cytokines was measured by absorbance at 280 nm using NanoDrop (Thermo Scientific). The purity of the isolate IL-23 cytokines was examined using SDS PAGE followed by Coomassie Blue staining (See, FIG. 53).

In Example 29 (above), we detailed the development of stably transfected STAT3-Luc reporter clone. IL-23 cytokine stimulates the STAT3 activity in a dose-dependent manner in this cell-based assay. The stably transfected STAT3-Luc reporter DB cells (0.5×10$^6$ cells) were cultured in 100 µl of RPMI+10% FBS. Recombinant IL-23 (Humanzyme) or isolated IL-23 (WT or W5) was added to the cells and incubated at 37° C. for 4 hours. Luciferase activity was measured using Dual-Glo luciferase assay system (Promega).

Figure 54:
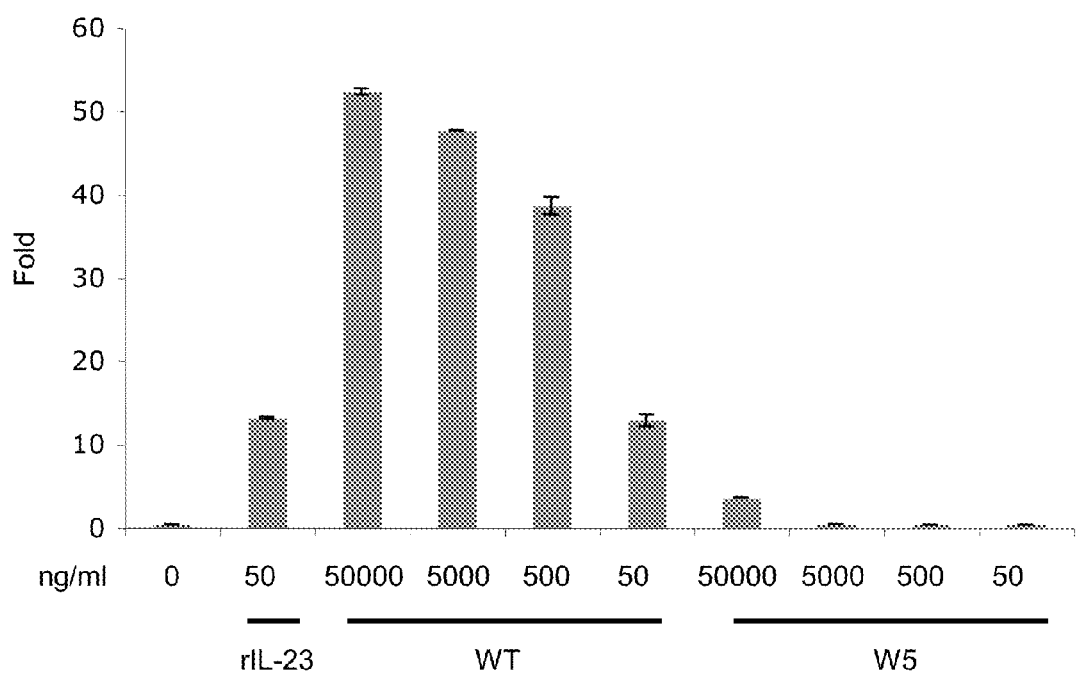
FIG. 54 depicts the effect of recombinant IL-23, isolated WT and W5 IL-23 cytokines, on the DB cells stably transfected with STAT3-Luc reporter construct. Luciferase activity was activated by rIL-23 cytokine IL-23 (WT and W5) binding to its receptor was monitored by cell-based assay using the DB cells stably transfected with STAT3-Luc reporter construct.

As shown in FIG. 54, 50 ng/ml of recombinant IL-23 cytokine was added to the stably transfected DB-STAT-Luc reporter cells. The reporter luciferase activity increased by approximately 10 folds. Isolated WT IL-23 cytokine at different concentrations (50,000, 5,000, 500 and 50 ng/ml) was added to stimulate these stable cells. This isolated WT IL-23 cytokine stimulates the STAT3 activity in a dose-dependent manner. At the concentration of 50 ng/ml, the isolated WT IL-23 cytokine stimulates the IL-23R pathway as good as the recombinant IL-23 cytokine from Humazyme. This observation indicates that our isolated cytokine is biologically active.

In contrast, when we added the isolated W5 IL-23 cytokine at different concentrations (50,000, 5,000, 500 and 50 ng/ml) to the stable cells, none of them showed significant activation of the STAT3 reporter system, indicating that the W5 IL-23 cytokine lacks the ability to stimulate the STAT3 activity.

Altogether, these data show that W5 of p19 subunit of IL-23 cytokine is indispensable to the receptor binding.

Example 34

Design and Generation of Targeted Peptide Library by PCR

In the above-described experiments detailing phage display screening, we have successfully identified a series of peptides that can bound to IL-23 receptor and thus inhibit binding of IL-23 to the IL-23R. The peptides share a property that they contain a core amino acid motif (i.e., "WX$_1$X$_2$YW"). These peptides not only bind to IL-23R but block IL-23 cytokine to its receptor. In our developed biological assays, these peptides are demonstrated to exhibit functional activity of specifically blocking the IL-23/IL-23R cell-signaling pathway.

Among the peptides, peptide no. 23.15 (SEQ ID NO: 126) showed the best inhibitory activity (See, FIG. 55). The peptides, including the peptide no. 23.15 (SEQ ID NO: 126), were identified by phage display screening against 12 amino acid random peptide library. From the perspective of a pure mathematical calculation, it is estimated that 12$^{20}$ independent clones may be required to cover all the possible combinations of 12 amino acid random peptide library. However, our phage display library is known to contain 10$^9$ independent clones (New England BioLabs (Ipswich, Mass.) (Cat. No. E8110S)).

In order to overcome the potential limitation of Phage Display Library and to explore if there may be additional peptide sequences that may show improved inhibitory activities towards binding of IL-23 to IL-23R and its signaling thereof as compared to that of peptide no. 23.15 (SEQ ID NO: 126), we generated a targeted peptide library by PCR for ribosome display screening. The position of tryptophan (W) and tyrosine (Y), and the spacing between them were fixed in this library based on our understanding of their importance in these inhibitory peptides (See, FIG. 55). Using the ribosome display screening, we sought to identify peptides that may potentially show a comparable or better inhibitory activity based on peptide no. 23.15 (SEQ ID NO: 126).

Figure 56:
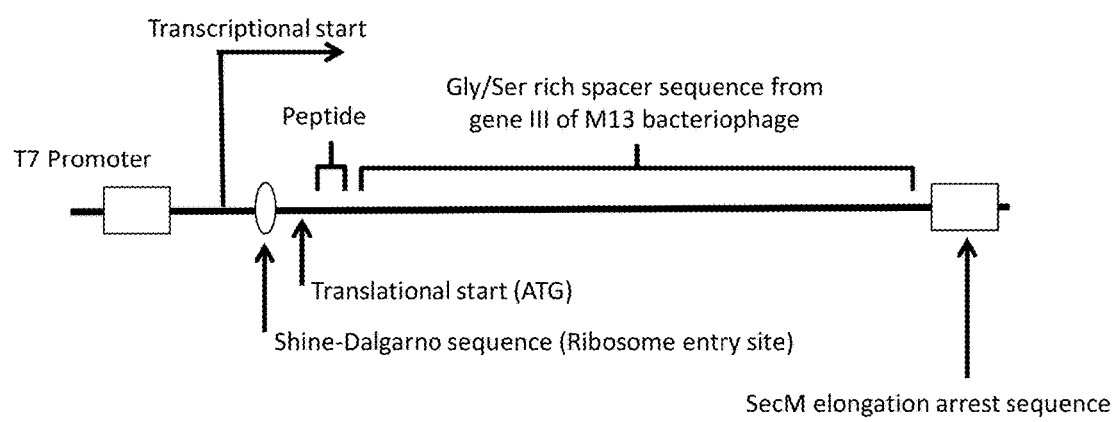
FIG. 56 depicts the schematic diagram of template DNA for in vitro transcription and translation using PURExpress system to generate protein-ribosome-mRNA ternary complex for ribosome display screening. DNA sequence of targeted peptide library was inserted downstream of the T7 promoter and Shine-Dalgarno sequence. A Gly-rich linker (gene III) is located between the gene encoding the targeted peptide library and SecM.

We employed PCR to generate this targeted peptide library which is a double stranded linear DNA library (See, FIG. 56). DNA sequence of targeted peptide library was inserted downstream of the T7 promoter (i.e., a DNA sequence where T7 RNA polymerase binds to and initiates transcription to produce mRNA) and Shine-Dalgarno sequence (i.e., a ribosome binding site). A spacer sequence Gly-rich linker (i.e., gene III of the M13 phage) was located between the gene encoding the targeted peptide library and SecM. The spacer sequence is known to prevent steric hindrance between the displayed peptide sequence and the ribosome. SecM elongation arrest sequence is known to stabilize the mRNA-ribosome-polypeptide ternary complex. The DNA sequence of this targeted peptide library is shown in FIG. 57.

Example 35

Affinity Selection—Ribosome Display Screening

The theory of ribosome display screening is based on the generation of ternary complexes consisting of a nascent polypeptide chain, ribosome, and mRNA, thereby establishing the linkage between genotype and phenotype necessary for affinity selection experiment.

Figure 58:
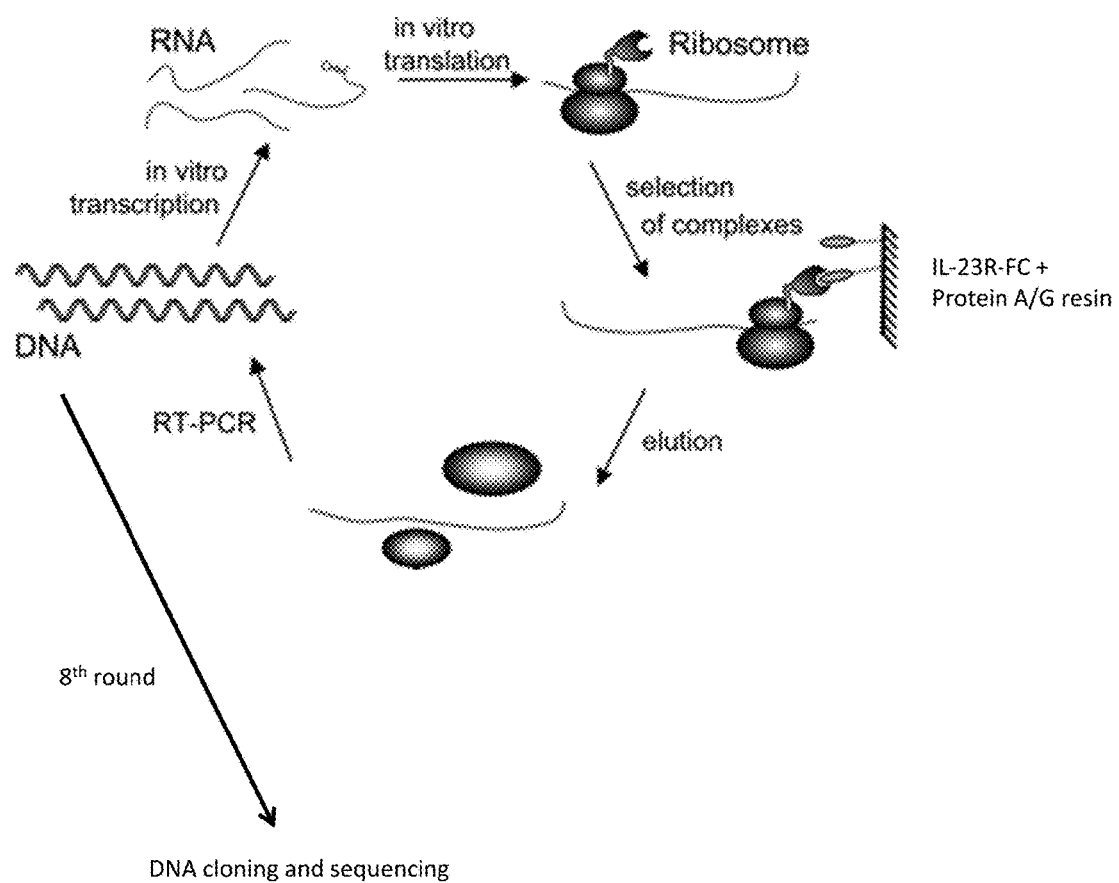
FIG. 58 depicts the schematic diagram of ribosome display screening to identify inhibitory peptides for IL-23R pathway. PCR generated DNA encoding the targeted peptide library was in vitro transcribed and translated into protein-ribosome-mRNA ternary complex using PURExpress system. After each round of affinity selection using IL-23R-Fc fusion protein as bait, mRNA was isolated and subjected to RT-PCR, followed by agarose gel electrophoresis. After $8^{th}$ round of selection, the purified RT-PCR products were subjected to cloning and DNA sequencing.

In this series of study, we used the PURExpress® (NEB), an in vitro transcription and translation system, to generate the protein-ribosome-mRNA ternary complex. Affinity selection of complex bound to IL-23R was performed by incubating 4 µg of IL-23R-Fc fusion protein. The complex binding to IL-23R-Fc protein was then precipitated by protein A-resin (See, FIG. 58).

After 8$^{th}$ round of selection, RT-PCR was cloned using the TOPO cloning kit from Invitrogen. We picked twenty-four (24) clones and performed DNA sequencing to reveal the peptide sequence (See, FIG. 59). The identified peptide sequences are summarized in FIG. 59. The frequency of peptides was illustrated in FIG. 60. We classified these peptides into 3 groups; namely Group A, Group B and Group C, based on the core motif "WX$_1$X$_2$YW" (See, FIG. 61). Group A contains "WVDYW" core (SEQ ID NO: 150) and Group B contains "WQDYW" core (SEQ ID NO: 151), respectively. Group C represents peptides containing other core sequences. The core motif from Group B is the same as the core motif from peptide no. 23.15 (SEQ ID NO: 126), thus confirming the core structure using both Phage Display Screening and Ribosome Display Screening. Because the peptides in Group A, which contains "WVDYW" motif (SEQ ID NO: 150), showed a high frequency, this observation suggested that the Group A peptides may possess a better inhibitory activity when compared to that of peptide no. 23.15 (SEQ ID NO: 126).

Example 36

Figure 62:
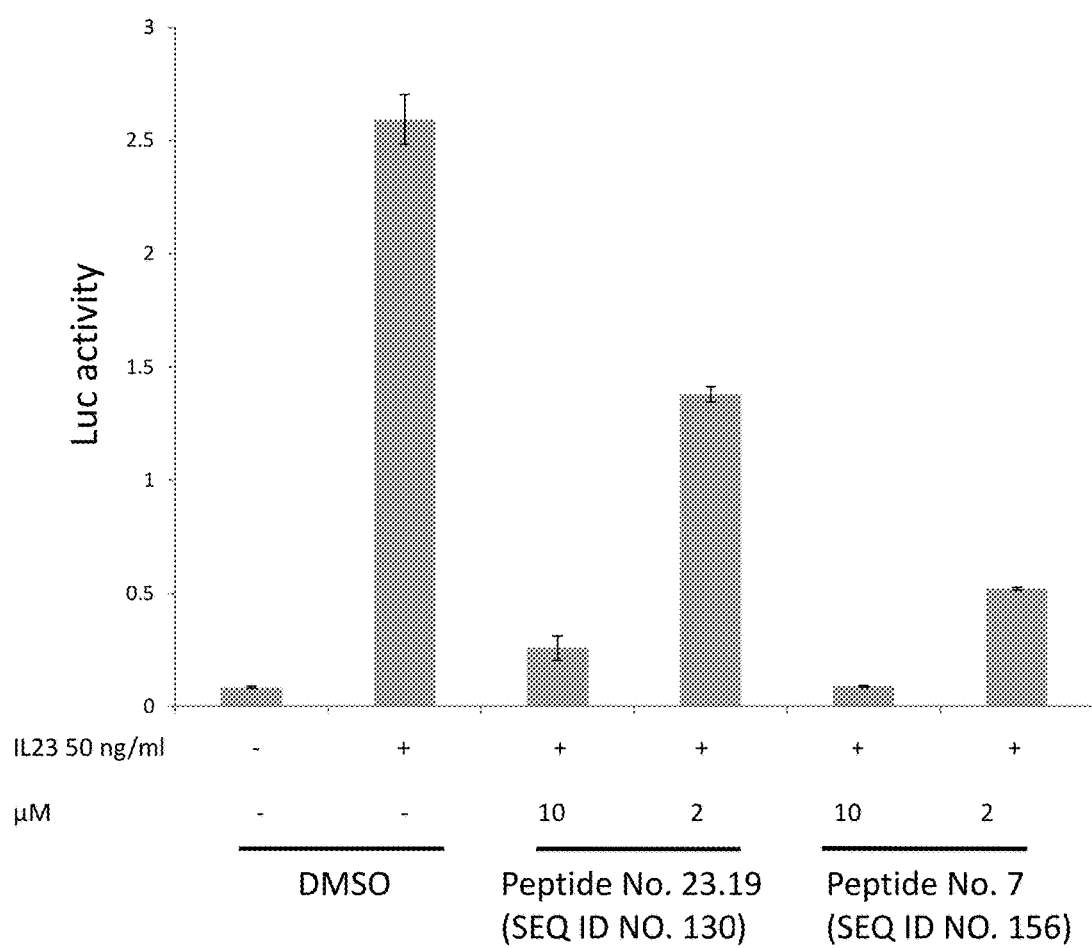
FIG. 62 depicts the result of a cell-based luciferase assay to compare inhibitory activity of cyc23.15 (i.e., peptide no. 23.19 (SEQ ID NO: 130)). In other words, it is the cyclic version of peptide no. 23.15 (SEQ ID NO: 126)) and peptide no. 7 (SEQ ID NO: 156) obtained from the ribosomal display screening.

Comparison of Inhibitory Activity of Peptide No. 23.19 (SEQ ID NO: 130) and Peptide No. 7 (SEQ ID NO: 156) Using Cell Based Assay The isolated peptide no. 7 (SEQ ID NO: 156) and peptide no. 23.19 (SEQ ID NO: 130) (it is a cyclic version of the polypeptide no. 23.15) were used in a cell based assay to compare their inhibitory activity. The stably transfected STAT3-Luc reporter DB cells (0.5×10⁶) were cultured in 100 μl of RPMI+10% FBS. The cells were pre-incubated with two different concentrations (10 μM and 2 μM) of isolated peptides for 30 minutes at 37° C. 50 ng/ml of IL-23 was added to the cells and incubated at 37° C. for an additional 4 hours. Luciferase activity was measured using Dual-Glo luciferase assay system (Promega). The inhibitory activity of isolated peptide no. 7 (SEQ ID NO: 156) is better than that of peptide no. 23.19 (SEQ ID NO: 130) (a cyclic version of polypeptide no. 23.15 (SEQ ID NO: 126) (See, FIG. 62).

This result demonstrates that the ribosome display screening against the targeted peptide library identifies peptides, which unexpectedly show a better inhibitory activity when compared to that of the peptide no. 23.19 (SEQ ID NO: 130) (obtained from phage display screening as described before).

Example 37

Comparison of Inhibitory Activity of Linear Peptide No. 2 (SEQ ID NO: 153), Linear Peptide No. 7 (SEQ ID NO: 156), Cyclic Peptide No. 2HT AA (Head to Tail: Alanine to Alanine) (SEQ ID NO: 177), Cyclic Peptide No. 7CC (SEQ ID NO: 178) (Cysteine to Cysteine) and Cyclic Peptide No. 7HT AA (Head to Tail: Alanine to Alanine) (SEQ ID NO: 179) Using Cell-Free Competitive ELISA The isolated linear peptide no. 2 (SEQ ID NO: 153), linear peptide no. 7 (SEQ ID NO: 156), cyclic peptide no. 2HT AA (SEQ ID NO: 177), cyclic peptide no. 7CC (SEQ ID NO: 178) and cyclic peptide no. 7HT AA (SEQ ID NO: 179) were used in a cell-free competitive ELISA assay, which was performed in accordance with the procedure set forth in Example 6. The $IC_{50}$ values of the polypeptides obtained from the cell-free competitive ELISA were summarized (See, FIG. 63).

We cyclized the isolated linear peptide no. 2 (SEQ ID NO: 153) and linear peptide no. 7 (SEQ ID NO: 156) by either disulphide bond (i.e., peptide no. 7 CC; SEQ ID NO: 178) or head-to-tail amide bond (i.e., peptide no. 2HT AA (SEQ ID NO: 177) and peptide no. 7HT AA (SEQ ID NO: 179)). Cyclization via either disulphide bond or head-to-tail amide bond did not abrogate the polypeptides' ability to inhibit the IL-23 binding to its receptor. Surprisingly, we observed that the cyclic polypeptide no. 2HT AA (SEQ ID NO: 177) indeed performed better than the linear peptide no. 2 (SEQ ID NO: 153). Among the 5 of the tested polypeptides (FIG. 63), we observed that cyclic polypeptide no. 2HT AA (SEQ ID NO: 177) showed the best inhibitory activity. The $IC_{50}$ value of this polypeptide (SEQ ID NO: 177) was 8.1 nM (See, FIG. 63).

Example 38

Comparison of Inhibitory Activity of Linear Peptide No. 2 (SEQ ID NO: 153), Linear Peptide No. 7 (SEQ ID NO: 156), Cyclic Peptide No. 2HT AA (SEQ ID NO: 177) and Cyclic Peptide No. 7HT AA (SEQ ID NO: 179) by Using Cell-Based DB-Luc Assay The isolated linear peptide no. 2 (SEQ ID NO: 153), linear peptide no. 7 (SEQ ID NO: 156), cyclic peptide no. 2HT AA (SEQ ID NO: 177) and cyclic peptide no. 7HT AA (SEQ ID NO: 179) were used in a cell-based DB-Luc assay, which was performed in accordance with the procedure set forth in Example 29. We summarized the $IC_{50}$ value of the various polypeptides in the cell-based DB-Luc assay (See, FIG. 64).

Cyclization of peptide no. 2 (SEQ ID NO: 153) and peptide no. 7 (SEQ ID NO: 156) by head-to-tail amide bond (peptide no. 2HT AA (SEQ ID NO: 177) and peptide no. 7HT AA (SEQ ID NO: 179)) did not eliminate the inhibitory activity of the polypeptides. The cyclic version of both peptide no. 2 and peptide no. 7 were found to be active in this cell-based assay. Consistent with the cell-free competitive ELISA assay, the cyclic peptide no. 2HT AA (SEQ ID NO: 177) performed better than the linear peptide no. 2 (SEQ ID NO: 153). Among the 4 tested polypeptides (FIG. 64), the cyclic peptide no. 2HT AA (SEQ ID NO: 177) showed the best inhibitory activity. The $IC_{50}$ value of this peptide (SEQ ID NO: 177) was 341.8 nM (See, FIG. 64).

Thus, these studies show that cyclic peptide no. 2HT AA (SEQ ID NO: 177) has better inhibitory activity (as compared to the linear counterpart (SEQ ID NO: 153)) in the cell-free and cell-based assays.

Example 39

Cyclic Peptide No. 2HT AA (SEQ ID NO: 177) Inhibits the Production of IL-17F Cytokine Induced by IL-23 in In Vitro Differentiated Human Th17 Cells Th17 cells play a pathological role in autoimmune diseases and IL-23/IL-23R signaling is known to be essential for terminal maturation and function of these cells. In this series of studies, we evaluated if cyclic polypeptides (e.g., SEQ ID NO: 177) are capable of inhibiting the production of IL-17F cytokine by the Th17 cells.

To that end, we designed and performed an in vitro assay using human differentiated Th17 cells. CD4+ naive T cells were negatively enriched using a human CD4+ naive T cells enrichment kit (StemCell Technologies, Catalog #19155). The purity of enriched CD4+ naive T cells was determined by FACS analysis. 1×10⁶ cells/ml of CD4+ naive T cells were differentiated into Th17 cells under Th17 culture condition (CD3/28 beads, 10 ng/ml of IL-1β, 10 ng/ml of IL-6, 10 ng/ml of IL-23 and 1 ng/ml of TGF-β) for 5 days. All cytokines were purchased from Humanzyme. The CD3/28 beads were used according to the manufacturer's instructions (Miltenyi Biotec). Differentiation of Th17 cells was confirmed by the production of IL-17F using ELISA.

Experiments were performed where cyclic peptide no. 2HT AA (SEQ ID NO: 177) was added to the differentiated Th17 cells 30 minutes before the addition of IL-23 cytokine Th17 cells were stimulated for 2 days. Ionomycin (1 μg/ml)/PMA (50 ng/ml) (BD biosciences, San Jose, Calif.) were added to the stimulated cells 4 hours before the collection of media to measure the IL-17F production by ELISA (Catalog #88-7478, eBioscience, San Diego, Calif.).

Figure 65:
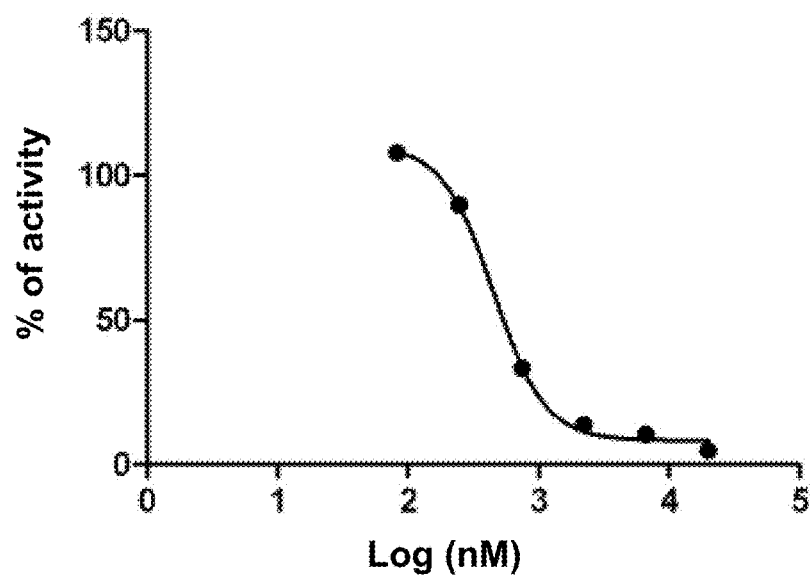
FIG. 65 depicts the dose-response curve of cyclic polypeptide no. 2HT AA (SEQ ID NO: 177) to inhibit IL-17 production upon IL-23 stimulation in the human Th17 cell and a summary of its $IC_{50}$ value.

As shown in FIG. 65, in the absence of cyclic peptide no. 2HT AA (SEQ ID NO: 177), production of IL-17F was induced in a dose-dependent manner (0-2 ng/ml). In order to measure the $IC_{50}$ value of this cyclic peptide, the differentiated Th17 cells were treated with a fixed amount of IL-23 cytokine (1 ng/ml) in the presence of a serial dilution of the cyclic peptide no. 2HT AA (SEQ ID NO: 177) (0-10 μM). The concentrations of the cyclic peptide (SEQ ID NO: 177) were plotted against the percentage of inhibitory activity. The cyclic peptide (SEQ ID NO: 177) was able to inhibit IL-23 cytokine to induce production of IL-17F in Th17 cells in a dose dependent manner. The $IC_{50}$ value of this cyclic peptide (SEQ ID NO: 177) was 338.6 nM (See, FIG. 65).

Thus, these data show that cyclic peptide no. 2HT AA (e.g., SEQ ID NO: 177) provides comparable $IC_{50}$ values in cell-based DB-Luc assay and IL-17F production in differentiated Th17 cells.

Example 40

Cyclic Peptide No. 2HT AA (SEQ ID NO: 177) Inhibits the Production of IL-22 Cytokine Induced by IL-23 in the Human PBMC In this series of studies, we performed an additional cell-based assay to examine whether the cyclic peptide (SEQ ID NO: 177) is capable of inhibiting the production of IL-22 cytokine in human PBMCs induced by IL-23 cytokine Peripheral blood mononuclear cells (PBMCs) were isolated from heparinized venous whole blood from healthy donors by density gradient centrifugation using Ficoll-Paque (Sigma-Aldrich, St Louis, Mo., USA). Human venous blood was purchased as anonymous buffy coats from the New Jersey Blood Transfusion Service. After isolation, the PBMCs were cultured in RPMI-1640 medium (Invitrogen-Gibco, Carlsbad, Calif.) supplemented with 10% heat-inactivated fetal bovine serum (Invitrogen-Gibco) and 1 mM of glutamine (Invitrogen-Gibco) at 37° C.

Figure 66:
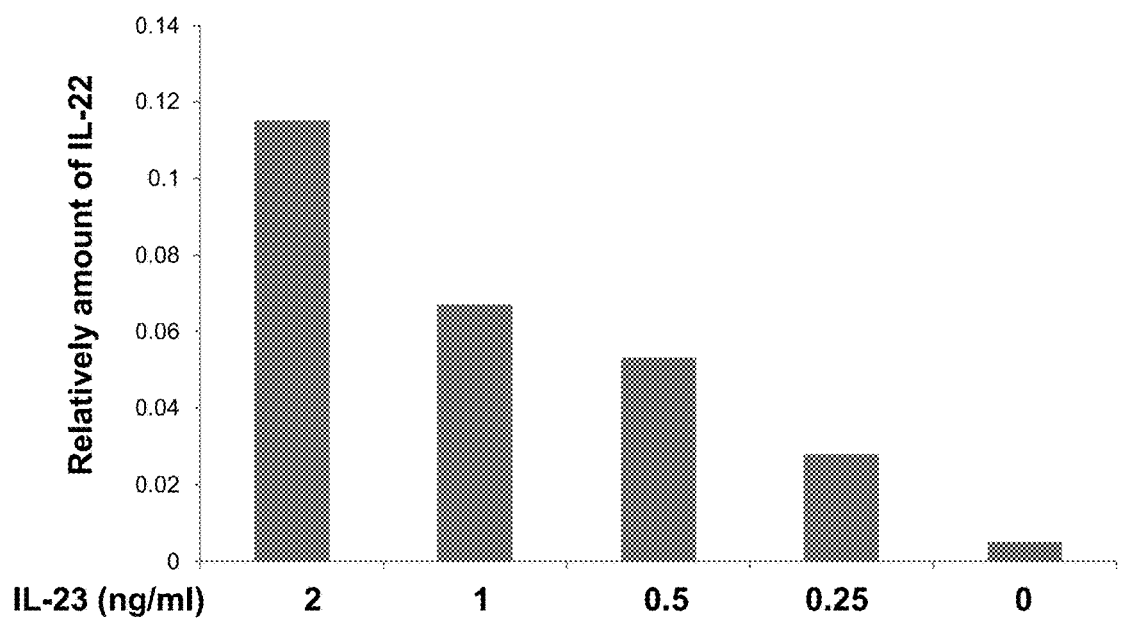
FIG. 66 depicts the dose-response curve of IL-23 to stimulate production of IL-22 in human peripheral blood mononuclear cells (PBMCs). An ELISA was used to measure the amount of IL-22 produced.

Isolated PBMCs ($5 \times 10^6$ cells/ml) were cultured in the presence of IL-22 (5 ng/ml) and IL-18 (20 ng/ml). A serial dilution of IL-23 (from 0-2 ng/ml) was added to the cell culture for 30 hours. We measured the production of IL-22 by ELISA (Catalog #88-7522, eBioscience, San Diego, Calif.) according to manufacturer's protocol). FIG. 66 shows that IL-23 induces the production of IL-22 in a dose-dependent manner between 0-2 ng/ml.

Figure 67:
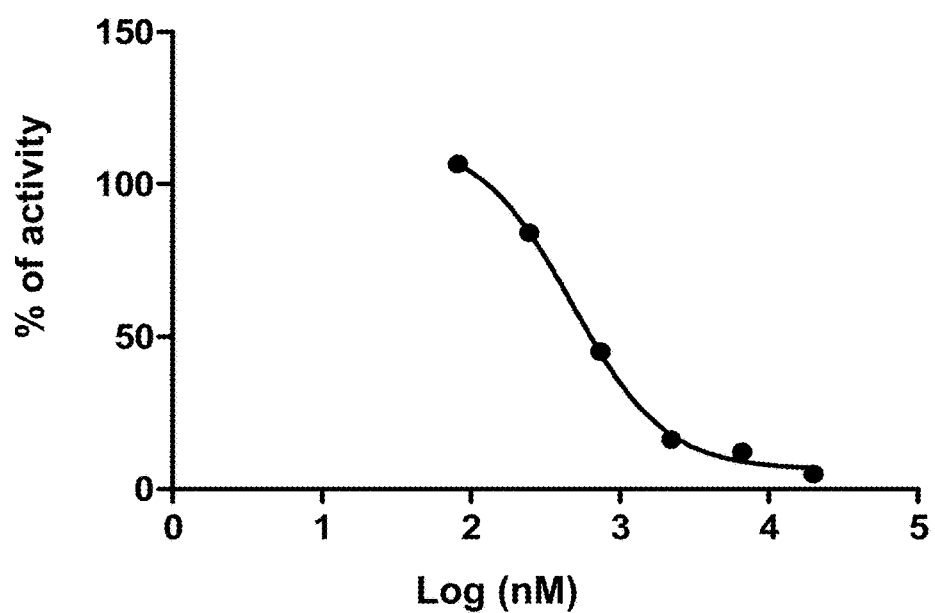
FIG. 67 depicts the dose-response curve of cyclic polypeptide no. 2HT AA (SEQ ID NO: 177) to inhibit IL-22 production upon IL-23 stimulation in the human PBMCs and a summary of its $IC_{50}$ value.

In order to measure the $IC_{50}$ value of cyclic peptide no. 2HT AA (SEQ ID NO: 177), the cells were treated with a fixed amount of IL-23 cytokine (2 ng/ml) in the presence of a serial dilution of cyclic peptide no. 2HT AA (SEQ ID NO: 177). The concentration of peptide was plotted against the percentage of activity as shown in FIG. 67. The cyclic peptide (SEQ ID NO: 177) inhibits IL-23 cytokine in PBMCs in a dose-dependent manner. The $IC_{50}$ value of this cyclic polypeptide (SEQ ID NO: 177) was 337.5 nM (See, FIG. 67). Thus, the cyclic peptide no. 2HT AA (SEQ ID NO: 177) effectively inhibits the IL-23 function in human Th17 cells and human PBMC.

Example 41

Cyclic Peptide No. 2HT AA (SEQ ID NO: 177) Inhibits the mRNA Expression of IL-17F Induced by IL-23 in Rat Splenocytes In addition to the human Th17 cells, we tested whether this cyclic peptide (SEQ ID NO: 177) is capable of inhibiting IL-23 function in splenocytes.

Sprague Dawley (SD) rat spleen was isolated and placed in 3 ml of media (RPMI 1640 with 10% FBS) in a small petri dish (35×10 mm). The rat spleen was placed on a sterile wire mesh screen using sterile forceps. The rat spleen was pushed through the screen with the plunger of a 10 ml syringe into the petri dish. Then, the suspension was mixed by gently pipetting up and down. The cells were spun down at 1,000 rpm for 10 minutes. Red blood cells were lysed by adding a Red Blood Cell lysis buffer. The cell suspension was incubated at room temperature for 5 minutes. The cells were spun down at 1,000 rpm for 10 minutes. The pelleted splenocytes were washed twice with PBS. After washing, the isolated splenocytes were re-suspended in 10 ml of culture media (RPMI 1640 with 10% FBS).

Rat splenocytes ($2.5 \times 10^6$ cells/ml) were prepared and cultured in RPMI-1640 with 10% FBS for 16 hours at 37° C. Cyclic peptide no. 2HT AA (SEQ ID NO: 177) was added to the rat splenocytes 30 minutes before the addition of IL-23 cytokine (200 ng/ml). The stimulation was carried out for an additional 4 hours. mRNA expression of IL-17F was measured by qRT-PCR (rat IL-17F forward primer (GGC-TCC-TGT-GAA-ACA-ACC-AT)(SEQ ID NO: 180) and rat IL-17F reverse primer (ACA-GAA-ATG-CCC-TGG-TTT-TG) (SEQ ID NO: 181). The PCR was performed under the following conditions: 95° C. for 5 minutes, 95° C. for 30 seconds, 60° C. for 30 seconds 72° C. for 30 seconds, times 40 cycles.

In the absence of cyclic peptide no. 2HT AA (SEQ ID NO: 177), mRNA expression of IL-17F was induced in a dose-dependent manner between 0-200 ng/ml (FIG. 68). In order to measure the $IC_{50}$ value of this cyclic peptide, the splenocytes were treated with a fixed amount of IL-23 cytokine (200 ng/ml) in the presence of a serial dilution of cyclic peptide no. 2HT AA (SEQ ID NO: 177) (between 0-10 µm). The cyclic peptide (SEQ ID NO: 177) inhibits IL-23 cytokine to induce production of IL-17F in the rat splenocytes in a dose-dependent manner. The concentration of peptide was plotted against the percentage of activity; the $IC_{50}$ value of this peptide was 269.6 nM (See, FIG. 68).

EXPERIMENTAL METHODS AND PROTOCOLS

1. Phage Display—Negative Selection Assay to Remove Phages that Non-Specifically Bind to Protein a Sepharose 20 µl of Protein A sepharose (GE Healthcare, Waukesha, Wis.) or anti-Flag affinity gel (Sigma, St. Louis, Mo.) was washed with 1 ml of TBST (TBS+0.1% Tween) and re-suspended in 1 ml of blocking buffer (TBST+3% BSA+0.02% sodium azide). The resin was mixed at 4° C. for 1 hour and was washed four times (4×) with 1 ml of 0.1% TBST. $1 \times 10^{11}$ pfu of phage display 12-mer peptide library (Cat. No. E8110S) (New England BioLabs, Ipswich, Mass.) was added to the washed resin and the mixture was incubated at room temperature for 15 minutes. The mixture was centrifuged at 5,000 rpm for 2 minutes to precipitate the bead-bound phages. The non-specifically bound phages were removed. The supernatant containing unbound phages were used in assays to isolate IL-23R binding phages.

2. Selection of Phages Displaying Sequences that Bind to IL-23R

300 µl of the phage-containing supernatant from the negative selection assay was incubated overnight at 4° C. with mixing with 20 µl of protein A sepharose and 10 µg of rhIL23R-Fc (Cat. No. 1400-IR-050) (R&D Systems, Minneapolis, Minn.) or Flag-tagged Δ9 and anti-Flag affinity gel. The mixture was centrifuged at 5,000 rpm for 2 minutes to precipitate the bead-bound phages (i.e., phages displaying sequences that bound IL-23R). The supernatant was removed and the resin was washed ten times (10×) with 1 ml of 0.1% TBST. Phages were eluted from the sepharose beads by adding 1 ml of elution buffer (0.2 M glycine-HCl, pH 2.2, 0.1% BSA) to the resin and incubating the resin-buffer mixture for 10-minutes at room temperature. The beads were separated from the phages by centrifuging the elution mixture at 5,000 rpm for 2 minutes leaving the phages in the supernatant. The supernatant was added to 150 µl of 1 M Tris-HCl, pH 9.1 to neutralize the eluted phages.

3. Amplification of IL-23R Binding Phages

The eluted phages were introduced to an early-log 20 ml culture of E. coli (i.e., ER2738). The mixture was incubated for 4.5 hours at 37° C. with shaking Following incubation, the culture was centrifuged at 12,000 rpm for 10 minutes to remove cell debris and E. coli cells. To precipitate the phages, the upper 80% of the supernatant was incubated overnight at 4° C. with 3 ml of 20% polyethylene glycol (PEG)/2.5 M NaCl. The solution was centrifuged at 12,000 rpm for 30 minutes to collect the precipitated phages. The supernatant was discarded. The pellet was re-suspended in 1 ml of TBS. 200 µl of 20% PEG/2.5 M NaCl was added to the supernatant and the mixture was incubated on ice for 1 hour. The solution was centrifuged at 12,000 rpm for 10 minutes and the pellet re-suspended in 200 µl of TBS.

The phage concentration in the amplified pool was measured by the phage titer on LB/IPTG/Xgal plates. The phage titer was determined by counting blue plaques. Two additional rounds of bio-panning were performed as described above. After 3 rounds of bio-panning, the eluted phages were enumerated by titration before phage amplification.

4. Isolation of Single M13 Plaque for DNA Sequencing and Phage ELISA

Individual plaques (i.e., blue plaques) were randomly selected and amplified by adding the plaques to 1 ml of E. coli ER2738. The mixture was incubated at 37° C. with shaking for 5 hours. The cultures were centrifuged to remove cell debris and the pellets discarded. 500 µl of the supernatant (i.e. LB containing amplified individual phage identified after 3 around of bio-panning) was apportioned for DNA sequencing. The remaining supernatant volume was used in a phage ELISA.

5. DNA Extraction and Sequencing

DNA from the phages that bound to either Δ9-Flag or to IL-23R/Fc chimera was sequenced to determine the amino acid sequence of the polypeptides that bound IL-23R.

Individually amplified phages were precipitated from the 500 µl of supernatant obtained following the phage display assay. 200 µl of 20% PEG/2.5 M NaCl was added to the 500 µl phage-containing supernatant (1:2.5 volume to volume ratio of PEG/NaCl to supernatant). The mixture was incubated for 20 minutes at room temperature. Phages were collected by centrifuging at 12,000 rpm for 10 minutes. The supernatant was discarded and the pellet re-suspended in 100 µl iodide buffer (10 mM Tris-HCl (pH 8.0), 1 mM EDTA, 4 M sodium iodide). 250 µl ethanol was added and the solution incubated at room temperature for 20 minutes. The solution was centrifuged at 12,000 rpm for 10 minutes. The supernatant was discarded and the pellet was washed with 0.5 ml of cold 70% ethanol. After another centrifugation at 12,000 rpm for 10 minutes, the supernatant was discarded and the pellet, containing the phage DNA, was suspended in 20 µl TE buffer.

For DNA sequencing, we used Beckman Coulter GenomeLab DTCS Quick Start Kit (Cat. No. 60812) (Beckman Coulter, Fullerton, Calif.). The concentration of phage DNA was measured by the NanoDrop at $OD_{280}$. (NanoDrop Technologies inc, Wilmington, Del.). Approximately 150 ng of phage DNA was used for each sequencing reaction. 1 pmol of −96 GIII sequencing primer (20-mer), (supplied with New England BioLabs Ph.D.™ 12 Phage Display Peptide Library Kit, Ipswich, Mass.) was used for each reaction. The thermal cycling program was 20 seconds at 96° C., 20 seconds at 50° C., and 4 minutes at 60° C., for 30 cycles. Ethanol precipitation was performed according to the Beckman Coulter kit insert. DNA sequencing was performed using Beckman Coulter CEQ 8000.

6. Phage ELISA

Microtiter plates were coated with 2 µg/ml of recombinant human IL-23R/Fc and incubated overnight at 4° C. The plates were blocked for 2 hours using 10% FBS/TBST at room temperature. 10 µl of 10×PBS was added to each well. 90 µl of M13 phage-containing LB media was also added. To permit phage binding to the IL-23R, the plate was incubated overnight at 4° C.

Bound phage was detected by adding 2 µg/ml of biotinylated anti-M13 antibody (Cat. No.: ab17269) (Abcam, Cambridge, Mass.). Streptavidin-horseradish peroxidase (HRP) was added to detect anti-M13 antibody bound to IL-23R bound phages. Peroxidase activity (representing the level of M13 captured onto plates) was measured by adding 100 µl of a tetramethylbenzidine (TMB) to each well. The color intensity was directly proportional to the amount of the bound M13 phage. Optical density was read at $450_{nm}$.

7. Immuno-Precipitation Assays 1 ml of cell culture media that included polypeptide-Fc fusion protein was incubated with 20 µl of protein A sepharose at room temperature for 1 hour. 1 ml of Δ9 containing culture medium was added to the mixture (i.e., Fc proteins and protein A sepharose) which was incubated at 4° C. overnight with mixing. The mixture was centrifuged, the supernatant removed and the remaining protein A resin washed 5 times with 1 ml PBS to form a precipitate. The precipitated proteins were denatured by addition of sample loading buffer (Bio-Rad, Berkeley, Calif.) and run on 4-12% PAGE and transferred to Immun-Blot PVDF membrane. Membranes were blocked in 5% milk/TPBT at room temperature for 1 hour. Anti-Flag antibody (1:1,000) (Sigma, St. Louis, Mo.) and anti-mouse antibody (1:3,000) were used to detect the Δ9 and Fc proteins, respectively.

8. Competitive ELISA

Recombinant human IL-23R-Fc (2 µg/ml) was coated onto microtiter plates as a capture reagent. IL-23 and polypeptides were added to compete for binding to the immobilized IL-23R-Fc. 50 µg human IL-23 (Cat. No. HZ-1048) (Humanzyme, Chicago, Ill.) in the presence or absence of 100 µM peptides was added to the well and incubated at 4° C. overnight. IL-23 that bound to IL-23R-Fc was detected using biotinylated anti-p40 antibody (1:250). The bound anti-p40 antibody was detected using streptavidin-horseradish peroxidase (HRP) (1:500) and 100 µl/well of a tetramethylbenzidine (TMB) substrate was added to measure peroxidase activity. The color was measured at optical density (OD) $450_{nm}$. The color intensity was directly proportional to the amount of the bound IL-23 protein.

9. Generation of Peptide IL-23R/Fc Fusion Expression Constructs

Polypeptide-Fc fusion proteins were obtained by designing expression constructs (i.e., polypeptide-Fc expression constructs) that expressed the amino acid sequence of interest fused to Fc.

Forward (F) and reverse (R) oligonucleotides corresponding to the desired peptide sequences were designed as set forth in Table 18.

TABLE 18

Oligonucleotide Sequences Used in Generating Polypeptide-Fc Fusion Proteins

| Polypeptide number | Dir | Oligonucleotide Sequence |
|---|---|---|
| 1 | F | C ATG GTT AGT GGT GCT TCG TGG GTT CAG TAT TGG GTT CAG CGG A (SEQ ID NO: 30) |
|  | R | GA TCT CCGCTGAACCCAATACTGAACCCACGAAGCACCACTAAC (SEQ ID NO: 31) |
| 4 | F | C ATG GTT GCT GAG ACG CCT AGT TGG TAT AAT TAT TGG ATG AAT A (SEQ ID NO: 32) |
|  | R | GA TCT ATTCATCCAATAATTATACCAACTAGGCGTCTCAGCAAC (SEQ ID NO: 33) |
| 7 | F | C ATG GTT CAGTCGGATACGTGGATGACGTATTGGAAGCATCATA (SEQ ID NO: 34) |
|  | R | GA TCT ATGATGCTTCCAATACGTCATCCACGTATCCGACTGAAC (SEQ ID NO: 35) |
| 10 | F | C ATG GTT GCGTCTTGGGAGATGTATTGGGCTACGTCGTATAATA (SEQ ID NO: 36) |
|  | R | GA TCT ATTATACGACGTAGCCCAATACATCTCCCAAGACGCAAC (SEQ ID NO: 37) |
| 16 | F | C ATG GTT AATTGGACTAGTCAGCTTCATACGGGGATTTCGACTA (SEQ ID NO: 38) |
|  | R | GA TCT AGTCGAAATCCCCGTATGAAGCTGACTAGTCCAATTAAC (SEQ ID NO: 39) |
| 22 | F | C ATG GTT GCTGTGTGGCAGAATTATTGGAATGAGCAGTTGTAT A (SEQ ID NO: 40) |
|  | R | GA TCT ATACAACTGCTCATTCCAATAATTCTGCCACACAGCAAC (SEQ ID NO: 41) |
| 32 | F | C ATG GTT ACGTCTTGGCAGTCTTTTTGGCATCATCATAATACT A (SEQ ID NO: 42) |
|  | R | GA TCT AGTATTATGATGATGCCAAAAAGACTGCCAAGACGT AAC (SEQ ID NO: 43) |
| 1.1 | F | C ATG GTT AGT GGT GCT TCG Ttt GTT CAG TAT TGG GTT CAG CGG A (SEQ ID NO: 170) |
|  | R | GA TCT CCG CTG AAC CCA ATA CTG AAC AAA CGA AGC ACC ACT AAC (SEQ ID NO: 48) |
| 1.2 | F | C ATG GTT AGT GGT GCT TCG TGG GTT CAG TAT TTT GTT CAG CGG A (SEQ ID NO: 49) |
|  | R | GA TCT CCG CTG AAC AAA ATA CTG AAC CCA CGA AGC ACC ACT AAC (SEQ ID NO: 50) |
| 1.3 | R | C ATG GTT AGT GGT GCT TCG TTT GTT CAG TAT TTT GTT CAG CGG A (SEQ ID NO: 51) |
|  | R | GA TCT CCG CTG AAC AAA ATA CTG AAC AAA CGA AGC ACC ACT AAC (SEQ ID NO: 52) |

The oligonucleotides were re-suspended in TE buffer at 200 μM concentration. Equal amount of forward and reverse oligonucleotides were annealed into double strand form by incubated at 95° C. for 10 minutes. After the mixture cooled down to room temperature, 1 μl of double strand oligonucleotides was used as an insert to ligate with linearized Fc expression construct (Cat. No. ppfc2-mg2ae1) (InvivoGen, San Diego, Calif.). The linearized vector was prepared by treating the DNA with NcoI and BglII restriction enzymes. The ligated DNA was then transformed into Top10 competent cells (Invitrogen, Carlsbad, Calif.). All the Fc expression constructs were verified by DNA sequencing. The ppfc2-mg2ae1 is a plasmid used to construct peptide-Fc Fusion proteins by fusing a sequence encoding a corresponding peptide sequence to the Fc region of an immunoglobulin. These peptide-Fc fusion proteins contain Fc region of mouse IgG2a. The Fc region comprises the CH2 and CH3 domains of the murine IgG2a heavy chain and the hinge region. The hinge serves as a flexible spacer between peptide sequence and the Fc region, allowing each part of the molecule to function independently. Additionally, the plasmid features the IL2 signal sequence for the generation of peptide-Fc fusion proteins secreted into the culture medium.

10. Purification of Fc Proteins

HEK-293T cells cultured in DMEM+10% FBS were transfected with 10 μg of Fc expression constructs using FuGENE® HD (Roche Cat. No. 04709705001). The cells were washed with PBS and the culture medium was replaced by serum free CD293 media (Cat. No. 11913019) (Invitrogen, Carlsbad, Calif.) 16 hours after transfection. The cultured media were collected 72 hours after the transfection and concentrated by using Amicon Ultra-15 Centrifugal Filter Unit with Ultracel-30 membrane (Cat. No. UFC903024) (Millipore, Billerica, Mass.). The Fc proteins were purified using the Protein A IgG purification kit (Cat. No. 44667) (Pierce, Rockford, Ill.). The quantity of purified Fc proteins was measured by $OD_{280}$.

11. Biotinylation of Purified Fc Proteins

Fc proteins were biotinylated using the EZ-Link® Micro Sulfo-NHS-Biotinylation Kit (Cat. No. 21925) (Pierce, Rockford, Ill.). 50 μg of purified Fc proteins in 200 μl of phosphate-buffered saline (PBS pH=7.4) was mixed with 2 μl of sulfo-NHS-biotin solution and incubated on ice for two hours. Excess biotin was removed by centrifuging at 1,000 g for 2 minutes using the Zeba Desalt Spin Column provided in the kit. The collected flow-through solution contained biotinylated Fc protein.

12. Cell Surface Staining for the Flow Cytometry

The cells were first washed twice with ice-cold PBS. 100 μl of blocking buffer (PBS+5% heat inactivated human serum) was added to re-suspend the cell pellet. The mixture was incubated on ice for 30 minutes followed by the addition of staining reagents, such as control isotype-biotinylated goat IgG, biotinylated anti-IL23R, biotinylated Fc protein and biotinylated peptide-Fc fusion proteins. After 30 minutes of incubation on ice, the cells were washed thrice with ice-cold PBS. The washed cells were re-suspended in 100 1 of blocking buffer containing 0.2 µl of detection reagent (Streptavidin-PE, BD Pharmingen, Cat. No. 554061) and were incubated on ice for 30 minutes followed by washing thrice with PBS. The cells were fixed in 1% (v/v) paraformaldehyde/PBS. The fixed cells were then acquired and analyzed.

13. Cell Based Assay—Luciferase Assay

Figure 14:
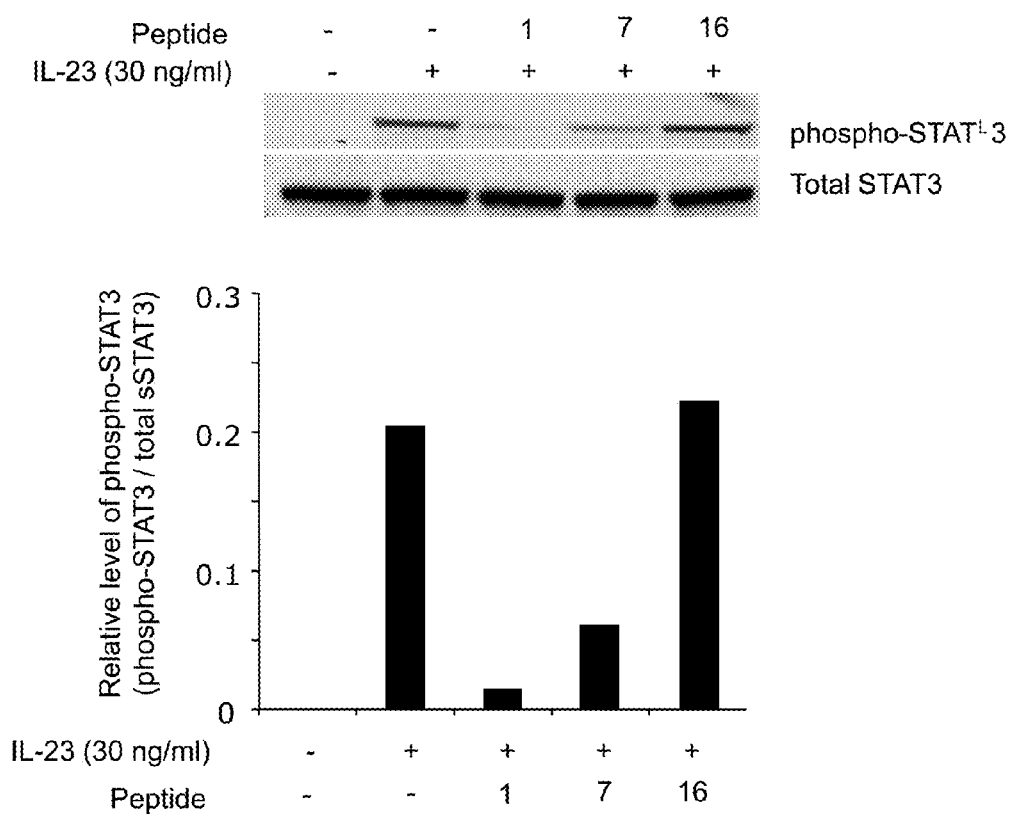
FIG. 14 depicts the results of an in vitro assay in determining the effect of the synthetic polypeptides on cellular signaling mediated by IL-23 and its receptor. An immunoblot was performed to detect the presence of phosphorylated STAT3 (i.e., phospho-STAT3) in cells that had been treated with a synthetic polypeptide (either polypeptide nos. 1, 7 or no. 16) and 30 ng/ml of IL-23. The presence of phospho-STAT3 indicates an IL-23 mediated cellular response. The relative level of phospho-STAT3 to total STAT3 was determined. Notably, the polypeptides that included the $WX_1X_2X_3W$ motif (i.e., polypeptide nos. 1 and 7) inhibited cell signaling as indicated by a decrease in the level of total phospho-STAT3 and in the relative level of phospho-STAT3 to total STAT3.
Figure 15:
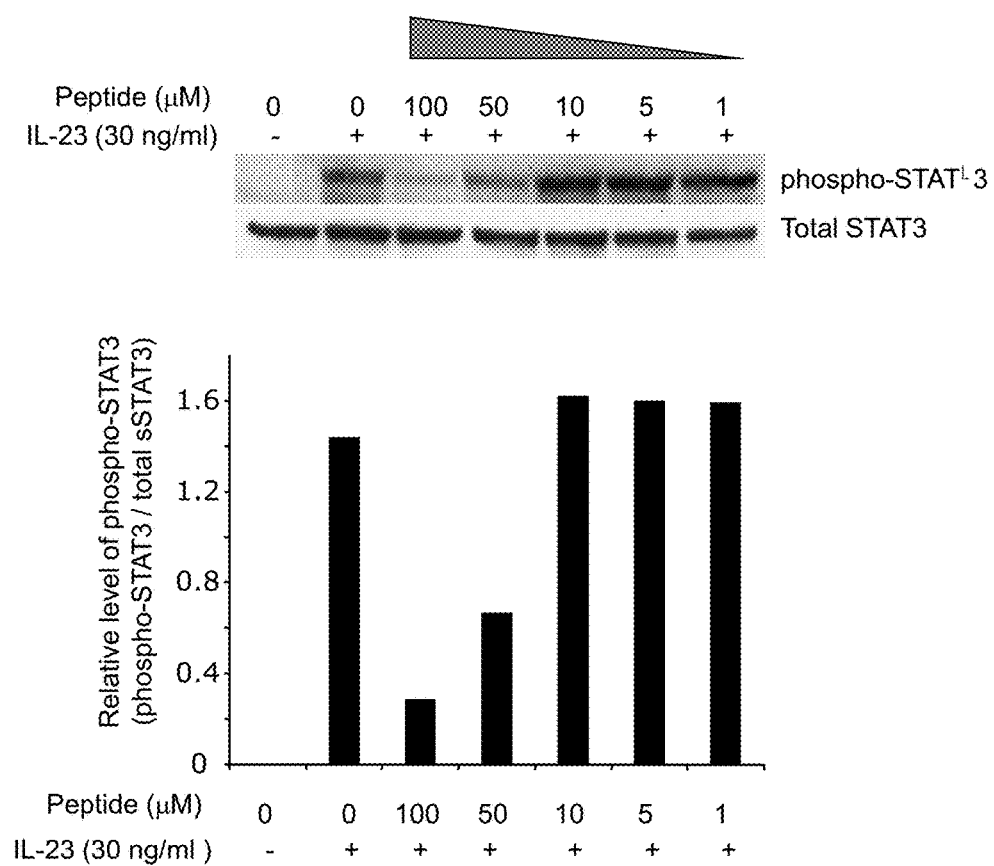
FIG. 15 depicts the results of an in vitro assay in determine the dose-dependent effect of polypeptide no. 1 on cell signaling. DB cells (B lymphoblast cells) were assayed for phospho-STAT3 after exposure to the combination of varying concentrations of polypeptide no. 1-Fc fusion (i.e., 100 mM, 50 μM, 10 μM, 5 μM and 1 μM) and 30 ng/ml of IL-23. The relative level of phospho-STAT3 to total STAT3 was also determined. Polypeptide no. 1 showed a dose-dependent effect on the presence of phospho-STAT3 and on the relative level of level of phospho-STAT3 to total STAT3. Notably, polypeptide no. 1 at concentrations of 100 μM and 50 μM inhibited cellular signaling in DB cells.
Figure 16:
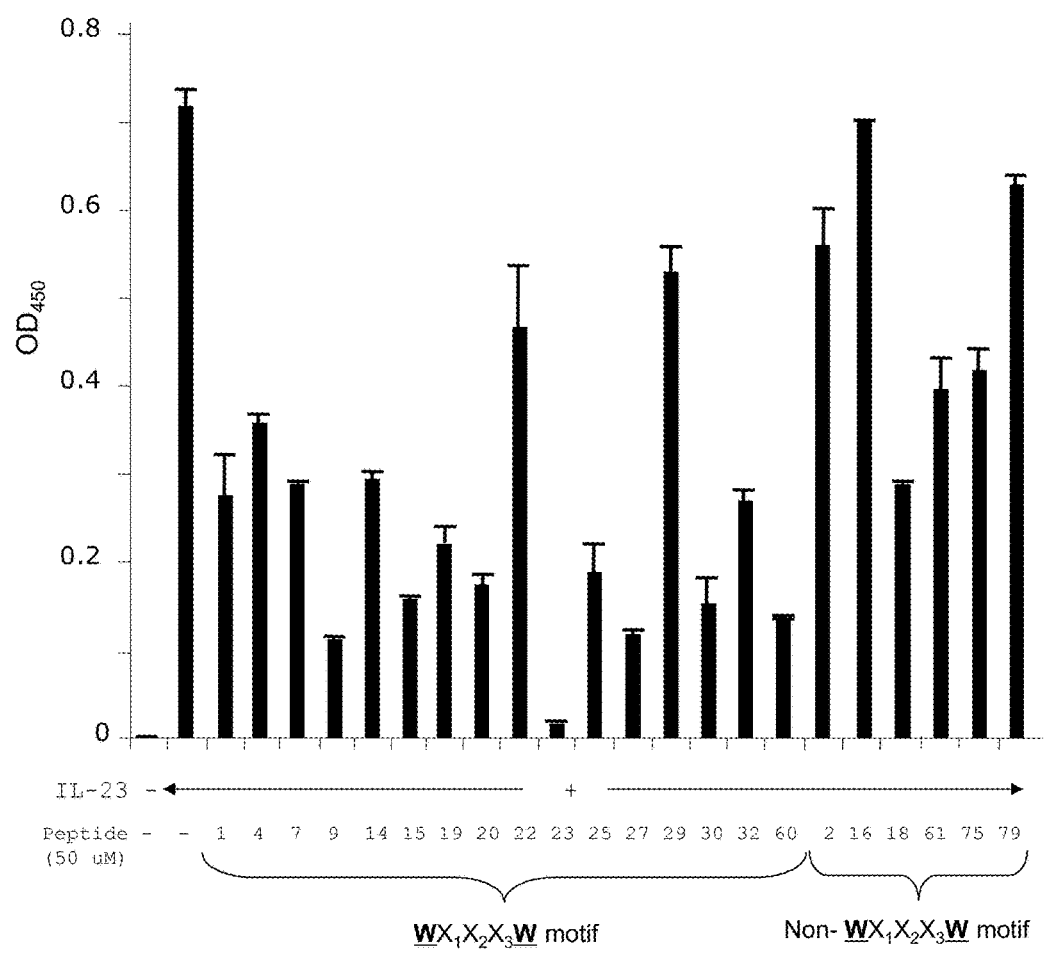
FIG. 16 depicts the results of Competitive ELISA performed to identify polypeptides that inhibit IL-23 binding to IL-23R. 50 μM of polypeptide and 30 ng/ml of IL-23 competed for binding to IL-23R in the Competitive ELISA to determine the inhibitory activity in relation to polypeptide no. 1. Polypeptide nos. 9, 15, 19, 20, 23, 25, 27, 30 and 60 all inhibited IL-23 binding more than polypeptide no. 1. Polypeptide no. 23 had a dramatic inhibitory effect on IL-23 binding to its receptor. All nine (9) of the polypeptides that blocked IL-23 from binding to its receptor greater than polypeptide no. 1 included the core structure $WX_1X_2X_3W$.
Figure 17:
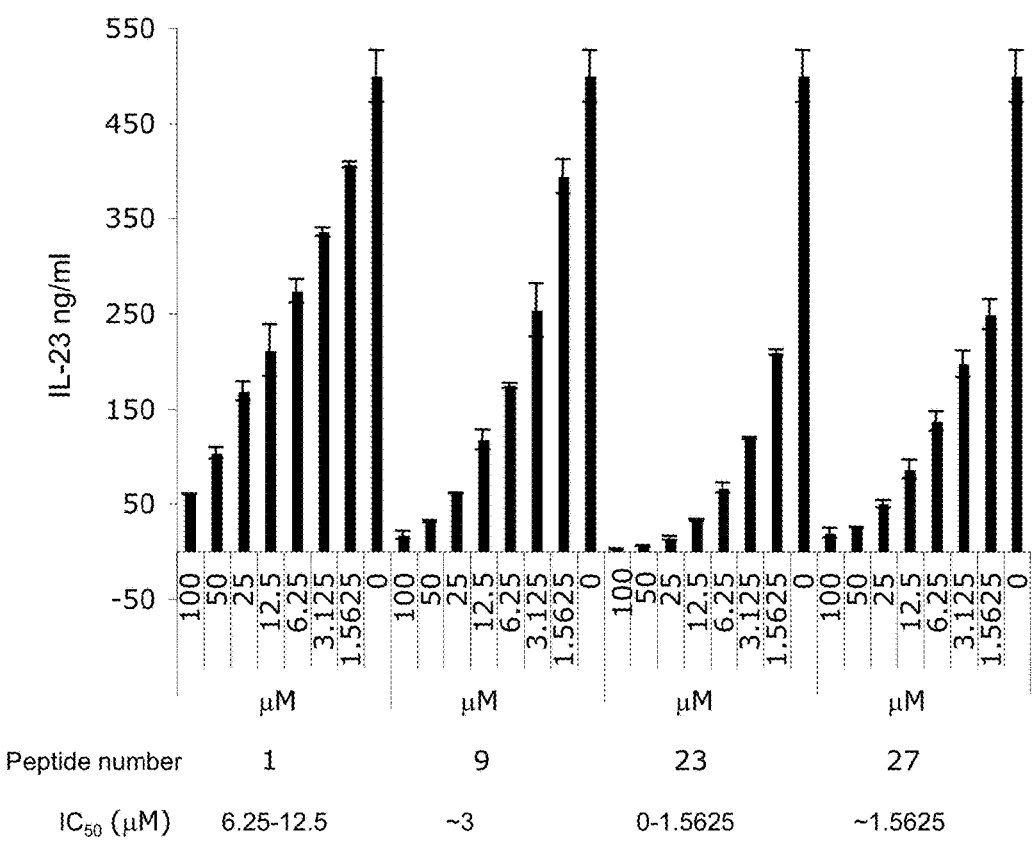
FIG. 17 depicts the results of dose response of polypeptide nos. 1, 9, 23 and 27 in inhibiting IL-23 binding to IL-23R as measured by our Competitive ELISA. Polypeptide no. 23 appears to have the strongest inhibitory activity (i.e., minimal $IC_{50}$) among these polypeptides.

DB cells express IL-23R on the cell surface. In addition, IL-23 stimulated the DB cells through the activation of STAT3 by phosphorylation (p-STAT3) (Example 7 (Figures. 14 and 15)). Based on these observations, DB cells were used to develop a cell-based assay to measure the inhibitory activity of peptide and peptide-Fc fusion protein in the IL-23R pathway.

The Cignal STAT3 reporter (SA Biosciences, CCS-9028L) is designed to measure the transcriptional activity of STAT3 homodimers. STAT3 is activated through phosphorylation in response to various cytokines and growth factors including IL-23. The activation of STAT3 results in formation of STAT3 homodimers, which interact with the sis-inducible element (SIE), a promoter sequence, thereby inducing transcription activity of target genes. The STAT3 reporter is a luciferase construct under the control of multiple SIE. The STAT3-responsive luciferase construct encodes the firefly luciferase reporter gene under the control of a minimal CMV promoter and tandem repeats of the SIE transcriptional response element. The number of response elements and the intervening sequence between these response elements has been experimentally optimized to maximize the signal to noise ratio. This construct monitors both increases and decreases in the transcriptional activity of STAT3 homodimers, and hence the activity of the STAT3 signaling pathway and IL-23R pathway.

The Cignal STAT3 reporter (SA Biosciences, CCS-9028L), which is designed to measure the transcriptional activity of STAT3 homodimers, was transiently transfected into the DB cells. The stably transfected STAT3-Luc reporter clone was selected using 200 ng/ml of Hygromycin B. The activity of IL-23R pathway can be measured by the transcriptional activity of STAT3 homodimers. Phosphorylation of STAT3 induces the formation of homodimer, which results in translocation into nucleus. STAT3 homodimer in the nucleus binds to DNA and activates transcription. Therefore, the Luciferase activity is directly proportional to the activity of IL-23R pathway.

The DB cells stably transfected STAT3-Luc reporter ($0.5 \times 10^6$) were cultured in 100 µl of RPMI+10% FBS. IL-23 was added to the cells and incubated at 37° C. for 4 hours. Luciferase activity was measured using Dual-Glo luciferase assay system (Promega).

14. Cell Based Assay—IL-23/IL-23R Signaling $3 \times 10^6$ DB cells were cultured in 1 ml of RMPI+10% FBS. The cells were pre-incubated with peptides at 4° C. for 30 minutes followed by the addition of 30 ng/ml of IL23 cytokine. After the stimulation for 20 minutes, the cells were washed with ice-cold PBS and lysed in ProteoJET mammalian cell lysis reagent (Fermentas) with protease and phosphatase inhibitors (Sigma). Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (Bio-Rad) per manufacturer's recommendations. Membranes were blocked in 5% milk/TPBT at room temperature for 1 hour. Membranes were first probed with antibodies against p-STAT3 (cell signaling technology), and then stripped and reprobed for STAT3 (cell signaling technology).

15. Site-Directed Mutagenesis—Generation of p19 Mutants

Expression construct of wild-type p19 subunit of IL-23 cytokine (WT) was generated by PCR using Pfx DNA polymerase (Invitrogen). The following primers were used to amplify wild-type p19 subunit of IL-23 cytokine from PBMCs cDNA (WT F: 5' GCCACCATGCTGGGGAGCA-GAGCT 3' (SEQ ID NO: 136)) and (WT R: 5' TCAGT-GATGATGGTGGTGATGTCCGCTGCCGGGACTCA-GGGTTGCTGC 3' (SEQ ID NO: 137)). The amplified PCR product was treated with Taq polymerase to add 3'-A overhang to each end of PCR. The gel-purified product was then subcloning into mammalian expression plasmid using the pcDNA3.3 TOPO TA Cloning kit from Invitrogen. The correct expression construct was subjected to validation by sequencing.

Expression constructs of p19 mutants (W1, W2, W3, W4 and W5) were constructed by site-directed mutagenesis using overlapping PCR. The expression construct of wild-type p19 subunit of IL-23 cytokine was used as PCR template. The following primers were used to mutate the corresponding Tryptophan residue "W" into Glycine residue "G". Generation of p19 mutants was performed by PCR overlap extension. Two fragments, fragment 1: using WT F and W1 R, W2 R, W3 R, W4 R or W5 R; and fragment 2: using WT R and W1 F, W2 F, W3 F, W4 F or W5 F, were amplified using these primer pairs.

```
                                              (SEQ ID NO: 138)
W1 F:    5' CTGTTGCTGCTGCCCGGTACAGCTCAGGGCAGA 3'

(SEQ ID NO: 139)
W1 R:    5' TCTGCCCTGAGCTGTACCGGGCAGCAGCAACAG 3'

(SEQ ID NO: 140)
W2 F:    5' GGCAGCAGCCCTGCCGGTACTCAGTGCCAGCAG 3'

(SEQ ID NO: 141)
W2 R:    5' CTGCTGGCACTGAGTACCGGCAGGGCTGCTGCC 3'

(SEQ ID NO: 142)
W3 F:    5' CTCTGCACACTGGCCGGTAGTGCACATCCACTA 3'

(SEQ ID NO: 143)
W3 R:    5' TAGTGGATGTGCACTACCGGCCAGTGTGCAGAG 3'

(SEQ ID NO: 144)
W4 F:    5' CCTGAGGGTCACCACGGTGAGACTCAGCAGATT 3'

(SEQ ID NO: 145)
W4 R:    5' AATCTGCTGAGTCTCACCGTGGTGACCCTCAGG 3'

(SEQ ID NO: 146)
W5 F:    5' AGTCCCAGCCAGCCAGGTCAGCGTCTCCTTCTC 3'

(SEQ ID NO: 147)
W5 R:    5' GAGAAGGAGACGCTGACCTGGCTGGCTGGGACT 3'
```

Two amplified fragments (1 and 2) for corresponding Tryptophan mutant were then joined together by overlap extension. The final combined fragment was subcloned into pcDNA3.3 TOPO expression vector. The correct expression constructs were subjected to validation by sequencing.

16. Generation of Targeted Peptide Library by PCR

The following primers were used to generate the targeted peptide library:

```
>RBS-LIB-T7
                                        (SEQ ID NO: 167)
TAACTTTAAGAAGGAGATATACCAATGNNKNNKNNKTGGNNKN

NKTACTGGNNKNNKNNKNNK GAGGGTGGCGGTACTAAAC

>T7-RBS F
                                        (SEQ ID NO: 168)
GAAATTAATACGACTCACTATAGGGAGACCACAACGGTTTCCCT

CTAGAAATAATTTTGTTTAACTTTAAGAAGGAGATATACCA

>SECM-M13 R
                                        (SEQ ID NO: 169)
TATTCATCAAGGACCAGCACGAATACCTTGAGCTTGAGAAATCC

AAACAGGAGTAGAAAAATCGATAGCAGCACCGTAA
```

M13 phage DNA was used as a template for the first round of PCR. RBS-LIB-T7 and SECM-M13 R primers were used. DNA gel electrophoresis was performed on the amplified PCR product. The purified product was then used as a template for the second round of PCR using primer set of T7-RBS F and SECM-M13 R. The PCR product was purified and represented the targeted peptide library. DNA concentration of this library was measured by $OD_{260}$ using NanoDrop (Thermo Scientific).

17. In Vitro Transcription and Translation by PURExpress (NEB)

100-250 ng of purified PCR product was used as template for the in vitro transcription and translation. This reaction was performed according to manual provided in the kit (PURExpress® E6850). In general, template DNA was mixed with solution A and B. The reaction was then incubated at 37° C. for 25 minutes followed by the addition of 300 µl stop buffer (50 mM Tris-HCL pH=7.5, 150 mM NaCl, 10 mM MgOAc, 0.1% Tween 20, 2.5 mg/ml Sodium herparin, 1% BSA and 10 µg of yeast RNA). The protein-ribosome-mRNA ternary complex was generated and was ready for ribosome display screening.

18. Affinity Selection—Ribosome Display Screening

Protein A-resin was first blocked in 100 µl wash buffer (50 mM Tris-HCL pH=7.5, 150 mM NaCl, 50 mM MgOAc and 0.1% Tween 20) containing 10 µg of yeast RNA and 3% BSA at room temperature for 30 minutes. Affinity selection of peptides bound to IL-23R was performed by incubating 4 µg of IL-23R-Fc fusion protein with the protein-ribosome-mRNA ternary complex at room temperature for 30 minutes. The complex binding to IL-23R-Fc protein was precipitated by adding with the pre-blocked protein A-resin. The reaction was then incubated at room temperature for 30 minutes followed by washing with the wash buffer for 10 times. The mRNA was eluted by adding 100 µl of elution buffer (50 mM Tris-HCL pH=7.5, 150 mM NaCl, 50 mM EDTA and 10 µg of yeast RNA) and incubating at room temperature for 30 mins. The eluted RNA was then purified using RNeasy MinElute Cleanup kit (Qiagen).

19. Reverse Transcription and PCR

RT-PCR was performed using purified mRNA as a template RNA by

SuperScript III One-Step RT-PCR system with Platinum Taq DNA Polyermase (Invitrogen). Primer set of T7-RBS F and SECM-M13 R was used in the RT-PCR. The PCR product was purified and was used as DNA template for next round of in vitro transcription and translation followed by affinity selection. DNA concentration of purified PCR product was measured by $OD_{260}$ using NanoDrop (Thermo Scientific).

20. Cell Based Assay—Luciferase Assay

DB cells are known to express IL-23R on the cell surface. In addition, it is known that IL-23 stimulates the DB cells through the activation of STAT3 by phosphorylation (p-STAT3). Based on these observations, DB cells were used to develop a cell-based assay to measure the inhibitory activity of peptide in the IL-23R pathway.

The Cignal STAT3 reporter (SA Biosciences, CCS-9028L) was designed to measure the transcriptional activity of STAT3 homodimers. STAT3 is activated through phosphorylation in response to various cytokines and growth factors including IL-23. The activation of STAT3 results in formation of STAT3 homodimers, which interact with the sis-inducible element (SIE), a promoter sequence, thereby inducing transcription activity of target genes. The STAT3 reporter is a luciferase construct under the control of multiple SIE. The STAT3-responsive luciferase construct encodes the firefly luciferase reporter gene under the control of a minimal CMV promoter and tandem repeats of the SIE transcriptional response element. The number of response elements and the intervening sequence between these response elements has been experimentally optimized to maximize the signal to noise ratio. This construct monitors both increases and decreases in the transcriptional activity of STAT3 homodimers, and hence the activity of the STAT3 signaling pathway and IL-23R pathway.

The Cignal STAT3 reporter (SA Biosciences, CCS-9028L), which is designed to measure the transcriptional activity of STAT3 homodimers, was transiently transfected into the DB cells. The stably transfected STAT3-Luc reporter clone was selected using 200 ng/ml of Hygromycin B. The activity of IL-23R pathway can be measured by the transcriptional activity of STAT3 homodimers. Phosphorylation of STAT3 induces the formation of homodimer, which results in translocation into nucleus. STAT3 homodimer in the nucleus binds to DNA and activates transcription. The Luciferase activity is directly proportional to the activity of IL-23R pathway.

The DB cells stably transfected STAT3-Luc reporter ($0.5 \times 10^6$) were cultured in 100 µl of RPMI+10% FBS. IL-23 was added to the cells and incubated at 37° C. for 4 hours. Luciferase activity was measured using Dual-Glo luciferase assay system (Promega).

21. Isolation of Rat Splenocytes

Sprague Dawley (SD) rat spleen was placed in 3 ml of media (RPMI 1640 with 10% FBS) in a small petri dish (35×10 mm). The rat spleen was placed on a sterile wire mesh screen using sterile forceps. The rat spleen was pushed through the screen with the plunger of a 10 ml syringe into the petri dish. Then, the suspension was mixed by gently pipetting up and down. The cells were spun down at 1,000 rpm for 10 minutes. Red Blood Cell lysis buffer was added to the cells to lysate the red blood cells. The suspension was incubated at room temperature for 5 minutes. The cells were spun down at 1,000 rpm for 10 minutes. The pelleted splenocytes were washed twice with the PBS. After the washing, the isolated splenocytes were re-suspended in 10 ml of culture media (RPMI 1640 with 10% FBS).

22. In Vitro TH-17 Cell Differentiation

CD4+ naive T cells were negatively enriched using human CD4+ naive T cells enrichment kit (StemCell Technologies, Catalog #19155). The purity of naive T cells was measured by FACS analysis. 1×10⁶ cells/ml of CD4+ naive T cells were differentiated into TH-17 cells under TH-17 culture condition (CD3/28 beads, 10 ng/ml of IL-1β, 10 ng/ml of IL-6, 10 ng/ml of IL-23 and 1 ng/ml of TGF-β) for 5 days. All cytokines were purchased from Humanzyme. The CD3/28 beads were used according to the manufacturer's instructions (Miltenyi Biotec). The differentiated cells were subjected to RNA extraction and real-time PCR to analyze gene expression.

23. Real-Time PCR (qRT-PCR)

RNA was reverse transcribed into cDNA by AffinityScript QPCR cDNA Synthesis Kit (Stratagene, Catalog #600559) according to the manufacturer's instructions. The real-time PCR was performed using Brilliant II SYBR Green QPCR Master Mix (Stratagene, Catalog #600834).

All referenced gene sequences, non-patent literatures, patent publications and patents cited in this specification are herein incorporated by reference in their entirety. Although the invention has been described in connection with specific preferred embodiments and working examples, it should be understood that the invention as claimed should not be unduly limited to such specific embodiments and examples. Various modifications and variations of the described composition, method, and systems of the invention will be apparent to those skilled in the art without departing from the scope and spirit of the invention.

What is claimed is:

1. An isolated cyclic polypeptide consisting of an amino acid sequence selected from the group consisting of SEQ ID NO: 177, SEQ ID NO: 178 and SEQ ID NO: 179, wherein said isolated cyclic polypeptide inhibits binding of IL-23 to IL-23 receptor and inhibits IL-23-mediated cell signaling.

2. The isolated cyclic polypeptide of claim 1, wherein said isolated cyclic polypeptide consisting of SEQ ID NO: 177.

3. The isolated cyclic polypeptide of claim 1, wherein said isolated cyclic polypeptide consisting of SEQ ID NO: 178.

4. The isolated cyclic polypeptide of claim 1, wherein said isolated cyclic polypeptide consisting of SEQ ID NO: 179.

5. A method of inhibiting production of IL-17F in a Th17 cell in a human, comprising the steps of:
    a) providing a human Th17 cell in need of inhibiting production of IL-17F; and
    b) exposing said Th17 cell to said isolated cyclic polypeptide of claim 1.

6. The method of claim 5, wherein said IL-17F is IL-17F protein.

7. The method of claim 5, wherein said production of IL-17F is assayed by an ELISA.

8. A method of inhibiting production of IL-17F in a splenocyte in a human, comprising the steps of:
    a) providing a human splenocyte in need of inhibiting production of IL-17F from said splenocyte; and
    b) exposing said splenocyte to said isolated cyclic polypeptide of claim 1.

9. The method of claim 8, wherein said IL-17F is IL-17F mRNA.

10. The method of claim 8, wherein said production of IL-17F is assayed by RT-PCR.

11. A method of inhibiting production of IL-22 from a mononuclear cell in a human, comprising the steps of:
    a) providing a human mononuclear cell in need of inhibiting production of IL-22 from said mononuclear cell; and
    b) exposing said mononuclear cell to said isolated cyclic polypeptide of claim 1.

12. The method of claim 11, wherein said IL-22 is IL-22 protein.

13. The method of claim 11, wherein said production of IL-22 is assayed by an ELISA.

* * * * *